United States Patent
Guo et al.

(10) Patent No.: US 11,691,970 B2
(45) Date of Patent: *Jul. 4, 2023

(54) PYRAZOLOPYRIDINONE COMPOUNDS

(71) Applicant: Janssen Pharmaceutica NV, Beerse (BE)

(72) Inventors: Haibing Guo, Shanghai (CN); Zhao-Kui Wan, Shanghai (CN); Luoheng Qin, Shanghai (CN); Qian Liu, Shanghai (CN); Wing Shun Cheung, Shanghai (CN)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/766,477

(22) PCT Filed: Nov. 23, 2018

(86) PCT No.: PCT/CN2018/117295
§ 371 (c)(1),
(2) Date: May 22, 2020

(87) PCT Pub. No.: WO2019/101182
PCT Pub. Date: May 31, 2019

(65) Prior Publication Data
US 2021/0147411 A1    May 20, 2021

(30) Foreign Application Priority Data

Nov. 24, 2017  (WO) ................ PCT/CN2017/112835

(51) Int. Cl.
*C07D 519/00*    (2006.01)
*C07D 471/04*    (2006.01)
*A61P 35/00*     (2006.01)

(52) U.S. Cl.
CPC ......... *C07D 471/04* (2013.01); *C07D 519/00* (2013.01)

(58) Field of Classification Search
CPC ...... C07D 519/00; C07D 471/04; A61P 35/00
USPC ....................................................... 514/403
See application file for complete search history.

(56) References Cited

U.S. PATENT DOCUMENTS

| | | | |
|---|---|---|---|
| 4,666,828 A | 5/1987 | Gusella | |
| 4,801,531 A | 1/1989 | Frossard | |
| 5,192,659 A | 3/1993 | Simons | |
| 5,272,057 A | 12/1993 | Smulson et al. | |
| 5,882,864 A | 3/1999 | An et al. | |
| 6,218,529 B1 | 4/2001 | An et al. | |
| 8,683,202 B2 | 3/2014 | Bücker et al. | |
| 2016/0176896 A1 | 6/2016 | Cortez et al. | |
| 2021/0147446 A1* | 5/2021 | Guo ........................ | A61P 35/00 |

FOREIGN PATENT DOCUMENTS

| | | |
|---|---|---|
| CN | 1659165 A | 8/2005 |
| WO | 02/18383 A2 | 3/2002 |
| WO | 2002/022598 A1 | 3/2002 |
| WO | 2003/087095 A1 | 10/2003 |
| WO | 2004/018419 * | 3/2004 |
| WO | 2004/018419 A2 | 3/2004 |
| WO | 2004/043389 A2 | 5/2004 |
| WO | 2005/046589 A2 | 5/2005 |
| WO | 2007/115947 A1 | 10/2007 |
| WO | 2011/099832 A2 | 8/2011 |
| WO | 2012/018909 A1 | 2/2012 |
| WO | 2012/083170 A1 | 6/2012 |

OTHER PUBLICATIONS

Angerer L.M. et al., "Demonstration of tissue-specific gene expression by in situ hybridization," Meth. Enzymol., vol. 152, 1987, pp. 649-661.
Ausubel, F.M. et al., eds., "Informatics for Molecular Biologists," in Current Protocols in Molecular Biology, Chapter 19, 2004, John Wiley & Sons Inc, pp. 19.0.1-19.0.2.
Bartlett J.M.S., "Fluorescence In Situ Hybridization," Molecular Diagnosis of Cancer. Methods in Molecular Medicine, vol. 97, 2004, pp. 77-87.
Berge et al. (1977) "Pharmaceutically Acceptable Salts," J. Pharm. Sci., vol. 66, pp. 1-19.
Cahn R.S. et al., "Specification of Molecular Chirality," Angew. Chem. Int. Ed. Engl., vol. 5, 1996, pp. 385-415.
Deprimo et al. "Expression profiling of blood samples from an SU5416 Phase III metastatic colorectal cancer clinical trial: a novel strategy for biomarker identification," BMC Cancer, vol. 3, 2003, 3, pp. 1-12.
Innis, M.A., et al., "PCR Protocols: A Guide to Methods and Applications", Academic Press, Inc., (1990), Table of Contents.
Knights et al., "De-regulated FGF receptors as therapeutic targets in cancer," Pharmacology and Therapeutics, vol. 125, Issue 1, Jan. 2010, pp. 105-117.
Korc M. et al., "The Role of Fibroblast Growth Factors in Tumor Growth," Current Cancer Drug Targets, vol. 9, Issue 5, 2009, pp. 639-651.
Malamas, M.S., et al., "Novel triazines as potent and selective phosphodiesterase 10A inhibitors," Bioorganic & Medicinal Chemistry Letters, vol. 22, Issue 18, Sep. 15, 2012, pp. 5876-5884.
March, J., "Stereochemistry," in Advanced Organic Chemistry, Chapter 4, 4th Edition, John Wiley & Sons, New York, 1992, pp. 109-114 & 131-133.
Orre M. et al., "VEGF, VEGFR-1, VEGFR-2, microvessel density and endothelial cell proliferation in tumours of the ovary," Int J Cancer, vol. 84, Issue 2,1999, pp. 101-108.
Rosa S.L. et al., "Fused 3-Hydroxy-3-trifluoromethylpyrazoles Inhibit Mutant Huntingtin Toxicity," ACS Medicinal Chemistry Letters, vol. 4, Issue 10, 2013, pp. 979-984.
Frazier, K., et al., "Design and structure-activity relationship of heterocyclic analogs of 4-amino-3-benzimidazol-2-ylhydroquinolin-2-ones as inhibitors of receptor tyrosine kinases," Bioorganic & Medicinal Chemistry Letters, vol. 16, Issue 8, Apr. 15, 2006, pp. 2247-2251.

* cited by examiner

*Primary Examiner* — Niloofar Rahmani
(74) *Attorney, Agent, or Firm* — BakerHostetler

(57) ABSTRACT

Pyrazolopyridinone compounds, the pharmaceutical compositions comprising said compounds, and the use of said compounds as FGFR (fibroblast growth factor receptor) inhibitors and their use in the treatment of diseases, e.g. cancer.

45 Claims, No Drawings

PYRAZOLOPYRIDINONE COMPOUNDS

CROSS-REFERENCE TO RELATED APPLICATIONS

This application is the National Stage of International Patent Application No. PCT/CN2018/117295, filed Nov. 23, 2018, which claims the benefit of International Patent Application No. PCT/CN2017/112835, filed Nov. 24, 2017, the contents of which are incorporated herein by reference.

FIELD OF THE INVENTION

The invention relates to new pyrazoloypyridinone compounds, to pharmaceutical compositions comprising said compounds, to processes for the preparation of said compounds and to the use of said compounds as FGFR (fibroblast growth factor receptor) inhibitors and to their use in the treatment of diseases, e.g. cancer.

BACKGROUND OF THE INVENTION

The fibroblast growth factor (FGF) signaling pathways have been demonstrated to play critical roles in processes ranging from embryogenesis and wound healing and have also shown strong links to several hallmarks of cancer. Genetic alterations in FGFR family members are associated with tumor growth, metastasis, angiogenesis and survival. A variety of FGFR inhibitors are in clinic trials and have shown clinic response in patients with FGFR aberrations. However, it has been reported that mutations affecting aminoacids in FGFR, e.g. FGFR1, 2 or 3, may cause resistance to FGFR inhibitors or decrease sensitivity to FGFR inhibitors. The development of secondary FGFR kinase domain mutations upon treatment with FGFR inhibitors are an important mechanism of acquired resistance to FGFR inhibition. Equivalent FGFR point mutations exist also de novo in cancers. Gatekeeper mutations have been reported as one of the major mechanism leading to resistance to tyrosine kinase inhibitors. Gatekeeper mutations include FGFR3 V555L/V555M, FGFR1 V561M, FGFR2 V564F/V564I/V564M and FGFR4 V550L. FGFR resistant mutations have been reported in clinic trials and in vitro cellular systems. Therefore new (second generation) FGFR inhibitors are needed for more durable activity in cancers harboring alterations in the FGFR signaling pathway to overcome clinical acquired resistance to first generation FGFR inhibitor therapy. Second generation FGFR inhibitors are needed to overcome the reduced activity observed for first generation FGFR inhibitors against FGFRs harboring the above gatekeeper mutations and hence maintain FGFR inhibiting activity.

It was found that the compounds of the invention show activity against mutated FGFRs, in particular against FGFRs harboring gatekeeper mutations or against mutated FGFR1 or mutated FGFR2 or mutated FGFR3, in particular against FGFR3 V555L, FGFR3 V555M, FGFR1 V561M and FGFR2 V564I, particularly against FGFR3 V555L and FGFR3 V555M.

WO2002/022598, WO2003/087095, WO2004/018419, WO2004/043389, WO2005/046589 each disclose a series of quinolinone derivatives.

DESCRIPTION OF THE INVENTION

The invention provides compounds of formula (I):

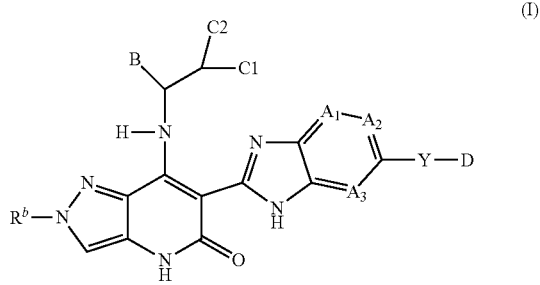

including any tautomeric and stereochemically isomeric form thereof, wherein $A_1$, $A_2$ and $A_3$ each independently represent CH, $CR^a$ or N, provided that maximum two of $A_1$, $A_2$ and $A_3$ may represent $CR^a$;

C1 is hydrogen or $C_{1-4}$alkyl;

C2 is hydrogen, $C_{1-4}$alkyl, hydroxyl or $C_{1-4}$alkoxy;

or C1 and C2 are taken together to form a $C_{3-6}$cycloalkyl together with the carbon atom to which they are attached;

Y is a direct bond, —O—, C(=O), $NR^y$, $S(=O)_2$, or $C_{1-4}$alkyl;

$R^y$ is hydrogen or $C_{1-4}$alkyl;

each $R^a$ independently is $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom selected from N, O or S;

$R^b$ is hydrogen, $C_{1-6}$alkyl, halo$C_{1-6}$alkyl, $C_{1-6}$alkoxy, $C_{1-6}$alkyloxycarbonyl, $C_{2-6}$alkenyl, $C_{2-6}$alkynyl, cyano$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;

D is a 3 to 12 membered heterocyclyl containing at least one heteroatom selected from N, O or S, wherein said heterocyclyl is optionally being substituted with 1 to 5 $R^c$ substituents;

each $R^c$ independently is oxo, halo, $C_{1-6}$alkyl, $C_{1-6}$alkyloxy, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —$SO_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, haloC$_{1-6}$alkyl, oxo, —SO$_2$—NH$_2$, —SO$_2$—NH(C$_{1-4}$alkyl), —SO$_2$—N(C$_{1-4}$alkyl)$_2$, —NH—C(═O)—C$_{2-6}$alkenyl, —C(═O)—C$_{1-6}$alkyl, —C(═O)—C$_{2-6}$alkenyl, C$_{1-6}$alkyl-O—C(═O)—, C$_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

In another aspect, provided is a method for the prophylaxis or treatment of a disease state or condition mediated by a FGFR kinase, which method comprises administering to a subject in need thereof a compound of formula (I) as defined herein, or a pharmaceutically acceptable salt thereof or a solvate thereof.

In a further aspect, provided is a compound of formula (I) as defined herein or a pharmaceutically acceptable salt thereof or a solvate thereof for use in the prophylaxis or treatment of a disease state or condition mediated by a FGFR kinase.

In a still further aspect, provided is use of a compound of formula (I) as defined herein or a pharmaceutically acceptable salt thereof or a solvate thereof for the manufacture of a medicament for the prophylaxis or treatment of a disease state or condition mediated by a FGFR kinase.

In another aspect, provided is a method for the prophylaxis or treatment of cancer, which method comprises administering to a subject in need thereof a compound of formula (I) as defined herein, or a pharmaceutically acceptable salt thereof or a solvate thereof. In particular, the cancer is a cancer mediated by a FGFR kinase.

In a further aspect, provided is a compound of formula (I) as defined herein or a pharmaceutically acceptable salt thereof or a solvate thereof for use in the prophylaxis or treatment of cancer. In particular, the cancer is a cancer mediated by a FGFR kinase.

In still a further aspect, provided is use of a compound of formula (I) as defined herein or a pharmaceutically acceptable salt thereof or a solvate thereof for the manufacture of a medicament for the prophylaxis or treatment of cancer. In particular, the cancer is a cancer mediated by a FGFR kinase.

DETAILED DESCRIPTION OF THE INVENTION

Unless the context indicates otherwise, references to formula (I) in all sections of this document (including the uses, methods and other aspects of the invention) include references to all other sub-formula (e.g. (I-a), (I-A), (I-A-a), (I-B), (I-B-a), (I-C), (I-C-a), (I-D) or (I-D-a)), sub-groups, preferences, embodiments and examples as defined herein.

The prefix "C$_{x-y}$" (where x and y are integers) as used herein refers to the number of carbon atoms in a given group. Thus, a C$_{1-6}$alkyl group contains from 1 to 6 carbon atoms, a C$_{3-6}$cycloalkyl group contains from 3 to 6 carbon atoms, a C$_{1-4}$alkoxy group contains from 1 to 4 carbon atoms, and so on.

The term 'halo' or 'halogen' as used herein refers to a fluorine, chlorine, bromine or iodine atom.

The term 'C$_{1-4}$alkyl', or 'C$_{1-6}$alkyl' as used herein as a group or part of a group refers to a linear or branched saturated hydrocarbon group containing from 1 to 4 or 1 to 6 carbon atoms. Examples of such groups include methyl, ethyl, n-propyl, isopropyl, n-butyl, isobutyl, sec-butyl, tert-butyl, n-pentyl, isopentyl, neopentyl or hexyl and the like.

The term 'C$_{2-4}$alkenyl' or 'C$_{2-6}$alkenyl' as used herein as a group or part of a group refers to a linear or branched hydrocarbon group containing from 2 to 4 or 2 to 6 carbon atoms and containing a carbon carbon double bond.

The term 'C$_{2-4}$alkynyl' or 'C$_{2-6}$alkynyl' as used herein as a group or part of a group refers to a linear or branched hydrocarbon group having from 2 to 4 or 2 to 6 carbon atoms and containing a carbon carbon triple bond.

The term 'C$_{1-4}$alkoxy' or 'C$_{1-6}$alkoxy' as used herein as a group or part of a group refers to an —O—C$_{1-4}$alkyl group or an —O—C$_{1-6}$alkyl group wherein C$_{1-4}$alkyl and C$_{1-6}$alkyl are as defined herein. Examples of such groups include methoxy, ethoxy, propoxy, butoxy, and the like.

The term 'C$_{3-6}$cycloalkyl' as used herein refers to a saturated monocyclic hydrocarbon ring of 3 to 6 carbon atoms. Examples of such groups include cyclopropyl, cyclobutyl, cyclopentyl, or cyclohexyl.

The term 'hydroxyC$_{1-4}$alkyl' or 'hydroxyC$_{1-6}$alkyl' as used herein as a group or part of a group refers to a C$_{1-4}$alkyl or C$_{1-6}$alkyl group as defined herein wherein one or more than one hydrogen atom is replaced with a hydroxyl group. The terms 'hydroxyC$_{1-4}$alkyl' or 'hydroxyC$_{1-6}$alkyl' therefore include monohydroxyC$_{1-4}$alkyl, monohydroxyC$_{1-6}$alkyl and also polyhydroxyC$_{1-4}$alkyl and poly hydroxyC$_{1-6}$alkyl. There may be one, two, three or more hydrogen atoms replaced with a hydroxyl group, so the hydroxyC$_{1-4}$alkyl or hydroxyC$_{1-6}$alkyl may have one, two, three or more hydroxyl groups. Examples of such groups include hydroxymethyl, hydroxyethyl, hydroxypropyl and the like.

The term 'haloC$_{1-4}$alkyl' or 'haloC$_{1-6}$alkyl' as used herein as a group or part of a group refers to a C$_{1-4}$alkyl or C$_{1-6}$alkyl group as defined herein wherein one or more than one hydrogen atom is replaced with a halogen. The term 'haloC$_{1-4}$alkyl' or 'haloC$_{1-6}$alkyl' therefore include monohaloC$_{1-4}$alkyl, monohaloC$_{1-6}$alkyl and also polyhaloC$_{1-4}$alkyl and polyhaloC$_{1-6}$alkyl. There may be one, two, three or more hydrogen atoms replaced with a halogen, so the haloC$_{1-4}$alkyl or haloC$_{1-6}$alkyl may have one, two, three or more halogens. Examples of such groups include fluoroethyl, fluoromethyl, trifluoromethyl or trifluoroethyl and the like.

The term 'haloC$_{1-4}$alkoxy' or 'haloC$_{1-6}$alkoxy' as used herein as a group or part of a group refers to a —O—C$_{1-4}$alkyl group or a —O—C$_{1-6}$ alkyl group as defined herein wherein one or more than one hydrogen atom is replaced with a halogen. The terms 'haloC$_{1-4}$alkoxy' or 'haloC$_{1-6}$alkoxy' therefore include monohaloC$_{1-4}$alkoxy, monohaloC$_{1-6}$alkoxy and also polyhaloC$_{1-4}$alkoxy and polyhaloC$_{1-6}$alkoxy. There may be one, two, three or more hydrogen atoms replaced with a halogen, so the haloC$_{1-4}$alkoxy or haloC$_{1-6}$alkoxy may have one, two, three or more halogens. Examples of such groups include fluoroethyloxy, difluoromethoxy or trifluoromethoxy and the like.

The term cyanoC$_{1-4}$alkyl or cyanoC$_{1-6}$alkyl as used herein refers to a C$_{1-4}$alkyl or C$_{1-6}$alkyl group as defined herein which is substituted with one or two cyano groups, in particular with one cyano group.

The term "heterocyclyl" as used herein shall, unless the context indicates otherwise, include both aromatic and non-aromatic ring systems. Thus, for example, the term "heterocyclyl" includes within its scope aromatic, non-aromatic, unsaturated, partially saturated and fully saturated heterocyclyl ring systems. In general, unless the context indicates otherwise, such ring systems may be monocyclic or bicyclic or bridged and may contain, for example, 3 to 12 ring members, or 4 to 10 ring members, or more usually 5 to 10 ring members. Reference to 4 to 7 ring members include 4, 5, 6 or 7 atoms in the ring, reference to 3 to 6 ring members include 3, 4, 5, or 6 atoms in the ring and reference to 4 to 6 ring members include 4, 5, or 6 atoms in the ring. Examples of monocyclic heterocyclyl ring systems are ring systems containing 3, 4, 5, 6, 7 or 8 ring members, more usually 3 to 7, and preferably 4, 5, 6 or 7 ring members, more preferably 5 or 6 ring members. Examples of bicyclic heterocyclyl ring systems are those containing 8, 9, 10, 11 or 12 ring members, and more usually 9 or 10 ring members. The heterocyclyl ring systems contain at least one heteroatom typically selected from nitrogen, oxygen or sulphur, in particular contain up to 5, up to 4, up to 3, up to 2, or a single heteroatom. Where reference is made herein to a heterocyclyl ring system, the heterocyclyl ring can, unless the context indicates otherwise, be optionally substituted (i.e. unsubstituted or substituted) by one or more substituents as discussed herein.

The heterocyclyl ring systems can be heteroaryl ring systems having from 5 to 12 ring members, more usually from 5 to 10 ring members. The term "heteroaryl" is used herein to denote a heterocyclyl ring system having aromatic character. The term "heteroaryl" embraces polycyclic (e.g. bicyclic) ring systems wherein one or more rings are non-aromatic, provided that at least one ring is aromatic. In such polycyclic systems, the ring system may be attached to the remainder of the compound by an aromatic ring or by a non-aromatic ring.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. The heteroaryl ring system may contain up to about five heteroatoms typically selected from nitrogen, oxygen and sulphur. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrolyl, furanyl, thienyl, imidazolyl, oxazolyl, oxadiazolyl, oxatriazole, isoxazolyl, thiazolyl, thiadiazolyl, isothiazolyl, pyrazolyl, triazolyl and tetrazolyl groups. In particular, examples of five membered heteroaryl groups include but are not limited to pyrrolyl, furanyl, thienyl, imidazolyl, oxazolyl, oxadiazolyl, isoxazolyl, thiazolyl, thiadiazolyl, isothiazolyl, pyrazolyl and triazolyl groups Examples of six membered heteroaryl groups include but are not limited to pyridyl, pyrazinyl, pyridazinyl, pyrimidinyl and triazinyl.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 0, 1, 2 or 3 ring heteroatoms;
c) a pyrimidine ring fused to a 5- or 6-membered ring containing 0, 1 or 2 ring heteroatoms;
d) a pyrrole ring fused to a 5- or 6-membered ring containing 0, 1, 2 or 3 ring heteroatoms;
e) a pyrazole ring fused to a 5- or 6-membered ring containing 0, 1 or 2 ring heteroatoms;
f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms;
i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered aromatic ring containing 1, 2 or 3 ring heteroatoms; and
n) a cyclopentyl ring fused to a 5- or 6-membered aromatic ring containing 1, 2 or 3 ring heteroatoms.

Particular examples of bicyclic heteroaryl groups containing a five membered ring fused to another five membered ring include but are not limited to imidazothiazolyl (e.g. imidazo[2,1-b]thiazole) and imidazoimidazolyl (e.g. imidazo[1,2-a]imidazole).

Particular examples of bicyclic heteroaryl groups containing a six membered ring fused to a five membered ring include but are not limited to benzofuranyl, benzothiophenyl, benzimidazolyl, benzoxazolyl, isobenzoxazolyl, benzisoxazolyl, benzthiazolyl, benzisothiazolyl, isobenzofuranyl, indolyl, isoindolyl, indolizinyl, indolinyl, isoindolinyl, purinyl, indazolyl, pyrazolopyrimidinyl (e.g. pyrazolo[1,5-a]pyrimidine), triazolopyrimidinyl (e.g. [1,2,4]triazolo[1,5-a]pyrimidine), benzodioxolyl, imidazopyrazinyl, imidazopyridazinyl, imidazopyridinyl and pyrazolopyridinyl (e.g. pyrazolo[1,5-a]pyridine) groups.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzthiazolyl, benzisothiazolyl, indolyl, isoindolyl, indolizinyl, indolinyl, isoindolinyl, indazolyl, pyrazolopyrimidinyl (e.g. pyrazolo[1,5-a]pyrimidine), triazolopyrimidinyl (e.g. [1,2,4]triazolo[1,5-a]pyrimidine), imidazopyrazinyl, imidazopyridazinyl, imidazopyridinyl and pyrazolopyridinyl (e.g. pyrazolo[1,5-a]pyridine) groups.

Particular examples of bicyclic heteroaryl groups containing a six membered ring fused to a five membered ring include but are not limited to benzofuranyl, benzothiophenyl, benzimidazolyl, benzthiazolyl, indolyl, isoindolyl, indolizinyl, indolinyl groups.

Particular examples of bicyclic heteroaryl groups containing two fused six membered rings include but are not limited to quinolizinyl, quinolinyl, isoquinolinyl, cinnolinyl, chromanyl, isochromanyl, thiochromanyl, benzopyranyl, benzodioxanyl, benzoxazinyl, pyridopyridinyl, quinoxalinyl, quinazolinyl, phthalazinyl, naphthyridinyl and pteridinyl groups.

Particular examples of bicyclic heteroaryl groups containing two fused six membered rings include but are not limited to quinolizinyl, quinolinyl, isoquinolinyl, benzopyranyl, benzodioxanyl, benzoxazinyl, pyridopyridinyl, quinoxalinyl, quinazolinyl, phthalazinyl, naphthyridinyl and pteridinyl groups.

Particular examples of bicyclic heteroaryl groups containing two fused six membered rings include but are not limited to quinolizinyl, quinolinyl, isoquinolinyl, quinoxalinyl, quinazolinyl, phthalazinyl, naphthyridinyl and pteridinyl groups.

Examples of polycyclic heteroaryl groups containing an aromatic ring and a non-aromatic ring include, tetrahydroisoquinolinyl, tetrahydroquinolinyl, dihydrobenzothienyl, dihydrobenzofuranyl, 2,3-dihydro-benzo[1,4]dioxinyl, benzo[1,3]dioxolyl, 4,5,6,7-tetrahydrobenzofuranyl, tetrahydrotriazolopyrazinyl (e.g. 5,6,7,8-tetrahydro-[1,2,4]triazolo[4,3-a]pyrazinyl), and indolinyl.

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazolyl, benzthiazolyl and benzisothiazole, indolyl, 3H-indolyl, isoindolyl, indolizinyl, isoindolinyl, purinyl, indazolyl, quinolizinyl, benzoxazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic group" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated heterocyclyl groups include piperidine, morpholine, thiomorpholine, piperazine. Partially saturated heterocyclyl groups include pyrazolines, for example 2-pyrazoline and 3-pyrazoline.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), and combinations thereof (e.g. thiomorpholine).

Particular examples include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), azetidinyl, pyranyl (2H-pyranyl or 4H-pyranyl), dihydrothiophenyl, dihydropyranyl, dihydrofuranyl, dihydrothiazolyl, tetrahydrofuranyl, tetrahydrothiophenyl, dioxanyl, dioxolanyl, tetrahydropyranyl, imidazolinyl, oxazolinyl, oxazolidinyl, oxetanyl, thiazolinyl, 2-pyrazolinyl, pyrazolidinyl and piperazinyl. In general, preferred non-aromatic heterocyclyl groups include saturated groups such as piperidinyl, pyrrolidinyl, azetidinyl, morpholinyl and piperazinyl.

Particular examples include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), pyranyl (2H-pyranyl or 4H-pyranyl), dihydrothiophenyl, dihydropyranyl, dihydrofuranyl, dihydrothiazolyl, tetrahydrofuranyl, tetrahydrothiophenyl, dioxanyl, tetrahydropyranyl, imidazolinyl, oxazolinyl, oxazolidinyl, 2-pyrazolinyl, pyrazolidinyl and piperazinyl. In general, preferred non-aromatic heterocyclyl groups include saturated groups such as piperidinyl, pyrrolidinyl, azetidinyl, morpholinyl and piperazinyl.

In a nitrogen-containing non-aromatic heterocyclyl ring the ring must contain at least one ring nitrogen atom.

Particular examples of nitrogen-containing non-aromatic heterocyclyl groups include aziridinyl, morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), dihydrothiazolyl, imidazolinyl, oxazolinyl, thiazolinyl, 2-pyrazolinyl, 3-pyrazolinyl, pyrazolidinyl and piperazinyl.

Particular examples of 3 to 6 membered monocyclic saturated heterocyclyls include morpholinyl, thiomorpholinyl, dioxanyl, piperidinyl (e.g. 1-piperidinyl, 2-piperidinyl, 3-piperidinyl and 4-piperidinyl), piperazinyl, pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, tetrahydrofuranyl, tetrahydrothiophenyl, tetrahydropyranyl (e.g. 4-tetrahydro pyranyl), dithianyl, trioxanyl, trithianyl, aziridinyl, oxiranyl, thiiranyl, diaziridinyl, dioxarinyl, oxetanyl, azetidinyl, thietanyl, dioxetanyl ring systems.

Particular examples of 3 to 6 membered monocyclic saturated heterocyclyls include morpholinyl, thiomorpholinyl, dioxanyl, piperidinyl (e.g. 1-piperidinyl, 2-piperidinyl, 3-piperidinyl and 4-piperidinyl), piperazinyl, pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, tetrahydrofuranyl, tetrahydrothiophenyl, tetrahydropyranyl (e.g. 4-tetrahydro pyranyl), oxiranyl, azetidinyl ring systems.

Particular examples of 3 to 6 membered monocyclic saturated heterocyclyls include morpholinyl, thiomorpholinyl, dioxanyl, piperidinyl (e.g. 1-piperidinyl, 2-piperidinyl, 3-piperidinyl and 4-piperidinyl), piperazinyl, pyrrolidinyl (e.g. 1-pyrrolidinyl, 2-pyrrolidinyl and 3-pyrrolidinyl), imidazolidinyl, pyrazolidinyl, dioxolanyl, tetrahydrofuranyl, tetrahydrothiophenyl, tetrahydropyranyl (e.g. 4-tetrahydro pyranyl) ring systems.

Particular examples of 3 to 6 membered monocyclic heterocyclyls include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, piperazinyl, tetrahydrofuranyl, tetrahydrothiophenyl, dioxanyl, tetrahydropyranyl (e.g. 4-tetrahydro pyranyl), dithianyl, trioxanyl, trithianyl, aziridinyl, oxiranyl, thiiranyl, diaziridinyl, dioxarinyl, oxetanyl, azetidinyl, thietanyl, dioxetanyl, azirinyl, azetyl, 1,2-dithietyl, pyrrolyl, furanyl, thiophenyl, imidazolyl, pyrazolyl, oxazolyl, thiazolyl, isothiazolyl, triazolyl, oxadiazolyl, thiadiazolyl, dithiazolyl, pyridinyl, pyranyl, thiopyranyl, pyrimidinyl, thiazinyl, oxazinyl, triazinyl ring systems.

Particular examples of 3 to 6 membered monocyclic heterocyclyls include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, piperazinyl, tetrahydrofuranyl, tetrahydrothiophenyl, dioxanyl, tetrahydropyranyl (e.g. 4-tetrahydro pyranyl), oxiranyl, oxetanyl, azetidinyl, pyrrolyl, furanyl, thiophenyl, imidazolyl, pyrazolyl, oxazolyl, thiazolyl, isothiazolyl, triazolyl, oxadiazolyl, thiadiazolyl, dithiazolyl, pyridinyl, pyranyl, thiopyranyl, pyrimidinyl, thiazinyl, oxazinyl, triazinyl ring systems.

Particular examples of 3 to 12 membered heterocycles include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, piperazinyl, tetrahydrofuranyl, tetrahydrothiophenyl, dioxanyl, tetrahydropyranyl (e.g. 4-tetrahydropyranyl), dithianyl, trioxanyl, trithianyl, aziridinyl, oxiranyl, thiiranyl, diaziridinyl, dioxarinyl, oxetanyl, azetidinyl, thietanyl, dioxetanyl, azirinyl, azetyl, 1,2-dithietyl, pyrrolyl, furanyl, thiophenyl, imidazolyl, pyrazolyl, oxazolyl, thiazolyl, isothiazolyl, triazolyl, oxadiazolyl, thiadiazolyl, dithiazolyl, pyridinyl, pyranyl, thiopyranyl, pyrimidinyl, thiazinyl, oxazinyl, triazinyl, azepanyl, oxepanyl, thiepanyl, 1,2-diazepanyl, 1,4-diazepanyl, diazepinyl, thiazepinyl, azocanyl, azocinyl, imidazothiazolyl (e.g. imidazo[2,1-b]thiazolyl), imidazoimidazolyl (e.g. imidazo[1,2-a]imidazolyl), benzofuranyl, benzothiophenyl, benzimidazolyl, benzoxazolyl, isobenzoxazolyl, benzisoxazolyl, benzthiazolyl, benzisothiazolyl, isobenzofuranyl, indolyl, isoindolyl, indolizinyl, indolinyl, isoindolinyl, purinyl, indazolyl, pyrazolopyrimidinyl (e.g. pyrazolo[1,5-a]pyrimidinyl), triazolopyrimidinyl (e.g. [1,2,4]triazolo[1,5-a]pyrimidinyl), benzodioxolyl, imidazopyridinyl and pyrazolopyridinyl (e.g. pyrazolo[1,5-a]pyridinyl), quinolinyl, isoquinolinyl, chromanyl, thiochromanyl, isochromanyl, benzodioxanyl, quinolizinyl, benzoxazinyl, pyridopyridinyl, quinoxalinyl, quinazolinyl, cinnolinyl, phthalazinyl, naphthyridinyl, pteridinyl, tetrahydroisoquinolinyl, tetrahydroquinolinyl, dihydrobenzthienyl, dihydrobenzfuranyl, 2,3-dihydro-benzo[1,4]dioxinyl, benzo[1,3]dioxolyl, 4,5,6,7-tetrahydrobenzofuranyl, tetrahydrotriazolopyrazinyl (e.g. 5,6,7,8-tetrahydro-[1,2,4]triazolo[4,3-a]pyrazinyl), 8-oxa-3-azabicyclo-[3.2.1]octanyl, 2-oxa-5-azabicyclo[2.2.1]heptanyl, 3-oxa-8-azabicyclo[3.2.1]octanyl, 3,6-diazabicyclo[3.1.1]heptanyl ring systems.

Particular examples of 3 to 12 membered heterocycles include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, piperazinyl, tetrahydrofuranyl, tetrahydrothiophenyl, dioxanyl, tetrahydropyranyl (e.g. 4-tetrahydropyranyl), oxiranyl, oxetanyl, azetidinyl, pyrrolyl, furanyl, thiophenyl, imidazolyl, pyrazolyl, oxazolyl, thiazolyl, isothiazolyl, triazolyl, oxadiazolyl, thiadiazolyl, dithiazolyl, pyridinyl, pyranyl, thiopyranyl, pyrimidinyl, thiazinyl, oxazinyl, triazinyl, imidazothiazolyl (e.g. imidazo[2,1-b]thiazolyl), imidazoimidazolyl (e.g. imidazo[1,2-a]imidazolyl), benzofuranyl, benzothiophenyl, benzimidazolyl, benzoxazolyl, isobenzoxazolyl, benzisoxazolyl, benzthiazolyl, benzisothiazolyl, isobenzofuranyl, indolyl, isoindolyl, indolizinyl, indolinyl, isoindolinyl, indazolyl, pyrazolopyrimidinyl (e.g. pyrazolo[1,5-a]pyrimidinyl), triazolopyrimidinyl (e.g. [1,2,4]triazolo[1,5-a]pyrimidinyl), benzodioxolyl, imidazopyridinyl and pyrazolopyridinyl (e.g. pyrazolo[1,5-a]pyridinyl), quinolinyl, isoquinolinyl, benzodioxanyl, quinolizinyl, benzoxazinyl, pyridopyridinyl, quinoxalinyl, quinazolinyl, cinnolinyl, phthalazinyl, naphthyridinyl, pteridinyl, tetrahydroisoquinolinyl, tetrahydroquinolinyl, dihydrobenzthienyl, dihydrobenzfuranyl, 2,3-dihydro-benzo[1,4]-dioxinyl, benzo[1,3]dioxolyl, 4,5,6,7-tetrahydrobenzofuranyl, tetrahydrotriazolopyrazinyl (e.g. 5,6,7,8-tetrahydro-[1,2,4]triazolo[4,3-a]pyrazinyl) ring systems.

Particular examples of 5 to 6 membered aromatic heterocycles include but are not limited to pyrrolyl, furanyl, thiophenyl, imidazolyl, furazanyl, oxazolyl, oxadiazolyl, oxatriazolyl, isoxazolyl, thiazolyl, thiadiazolyl, isothiazolyl, pyrazolyl, triazolyl, tetrazolyl, pyridinyl, pyrazinyl, pyridazinyl, pyrimidinyl and triazinyl ring systems.

The heterocyclyl and carbocyclyl rings representing the B or D substituent include bridged ring systems such as for example bridged cycloalkanes, such as for example norbornane (1,4-endo-methylene-cyclohexane), adamantane, oxaadamantane; bridged morpholine rings such as for example 8-oxa-3-azabicyclo[3.2.1]octane, 2-oxa-5-azabicyclo[2.2.1]heptane, 3-oxa-8-azabicyclo[3.2.1]octane; bridged piperazine rings such as for example 3,6-diazabicyclo[3.1.1]heptane; bridged piperidine rings such as for example 1,4-ethylenepiperidine. For an explanation of the distinction between fused and bridged ring systems, see *Advanced Organic Chemistry*, by Jerry March, 4$^{th}$ Edition, Wiley Interscience, pages 131-133, 1992.

The term "carbocyclyl" as used herein shall, unless the context indicates otherwise, include both aromatic and non-aromatic carbon ring systems. Thus, for example, the term "carbocyclyl" includes within its scope aromatic, non-aromatic, unsaturated, partially saturated and fully saturated carbocyclic ring systems. In general, unless the context indicates otherwise, such ring systems may be monocyclic or bicyclic or bridged and may contain, for example, 3 to 12 ring members, or 4 to 10 ring members, or more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic carbocyclyl ring systems are ring systems containing 3, 4, 5, 6, 7 and 8 ring members, more usually 3 to 7, and preferably 4, 5, 6 or 7 ring members, more preferably 5 or 6 ring members. Examples of bicyclic carbocyclyl ring systems are those containing 8, 9, 10, 11 and 12 ring members, and more usually 9 or 10 ring members. Where reference is made herein to a carbocyclyl ring system, the carbocyclyl ring can, unless the context indicates otherwise, be optionally substituted (i.e. unsubstituted or substituted) by one or more substituents as discussed herein.

The carbocyclyl ring systems can be aryl ring systems. The term 'aryl' as used herein refers to carbocyclyl aromatic groups and embraces polycyclic (e.g. bicyclic) ring systems wherein one or more rings are non-aromatic, provided that at least one ring is aromatic. In such polycyclic systems, the ring system may be attached to the remainder of the compound by an aromatic ring or by a non-aromatic ring. The term 'aryl' includes phenyl, naphthyl, indenyl, and tetrahydronaphthyl groups.

Particular examples of 3 to 12 membered carbocycles include cyclopropyl, cyclobutyl, cyclopentyl, cyclohexyl, cycloheptyl, cyclooctyl, phenyl naphthyl, indenyl, tetrahydronaphthyl, azulenyl, norbornane (1,4-endo-methylene-cyclohexane), adamantane ring systems.

Lines drawn into ring systems indicate that the bond may be attached to any of the suitable and available ring atoms.

In an embodiment wherein two or more heteroatoms are involved, these heteroatoms may be the same or part or all of the two or more heteroatoms may be different.

The term "optional" or "optionally" means the event described subsequent thereto may or may not happen. This term encompasses the cases that the event may or may not happen.

As used herein, the expression "one or more" refers to at least one, for example one, two, three, four, five or more, whenever possible and depending on the context.

In the compounds of formula (I) the carbon atom indicated with a "*" in the below formula is a chiral center. The present invention provides compounds of formula (I) wherein said chiral center represents a specific stereochemistry (S or R), in particular compounds of formula (I) wherein said chiral center has S-stereochemistry. Compounds of formula (I) or any subgroup thereof having the S-stereochemistry at the chiral center * exhibit high FGFR inhibitory activity.

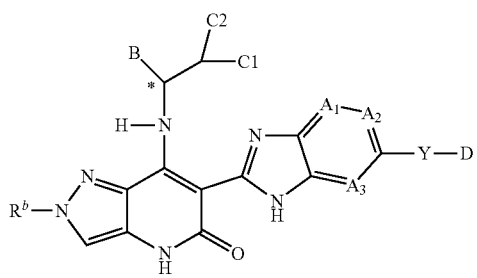

Thus, the present invention provides compounds of formula (I-a)

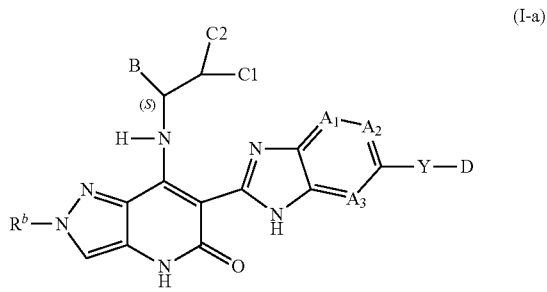

(I-a)

including any tautomeric and stereochemically isomeric form thereof, wherein $A_1$, $A_2$ and $A_3$ each independently represent CH, $CR^a$ or N, provided that maximum two of $A_1$, $A_2$ and $A_3$ may represent $CR^a$;

C1 is hydrogen or $C_{1-4}$alkyl;

C2 is hydrogen, $C_{1-4}$alkyl, hydroxyl or $C_{1-4}$alkoxy;

or C1 and C2 are taken together to form a $C_{3-6}$cycloalkyl together with the carbon atom to which they are attached;

Y is a direct bond, —O—, C(=O), $NR^y$, $S(=O)_2$, or $C_{1-4}$alkyl;

$R^y$ is hydrogen or $C_{1-4}$alkyl;

each $R^a$ independently is $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom selected from N, O or S;

$R^b$ is hydrogen, $C_{1-6}$alkyl, halo$C_{1-6}$alkyl, $C_{1-6}$alkoxy, $C_{1-6}$alkyloxycarbonyl, $C_{2-6}$alkenyl, $C_{2-6}$alkynyl, cyano-$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;

D is a 3 to 12 membered heterocyclyl containing at least one heteroatom selected from N, O or S, wherein said heterocyclyl is optionally being substituted with 1 to 5 $R^c$ substituents;

each $R^c$ independently is oxo, halo, $C_{1-6}$alkyl, $C_{1-6}$alkyloxy, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —SO$_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —SO$_2$—NH$_2$, —SO$_2$—NH($C_{1-4}$alkyl), —SO$_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

The present invention provides compounds of formula (I-A)

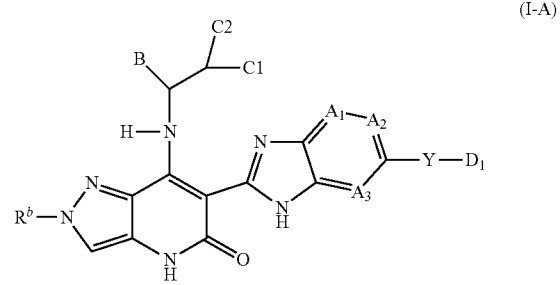

(I-A)

including any tautomeric and stereochemically isomeric form thereof, wherein $A_1$, $A_2$ and $A_3$ each independently represent CH, $CR^a$ or N, provided that maximum two of $A_1$, $A_2$ and $A_3$ may represent $CR^a$;

C1 is hydrogen or $C_{1-4}$alkyl;

C2 is hydrogen, $C_{1-4}$alkyl, hydroxyl or $C_{1-4}$alkoxy;

or C1 and C2 are taken together to form a $C_{3-6}$cycloalkyl together with the carbon atom to which they are attached;

Y is a direct bond, —O—, C(=O), $NR^y$, $S(=O)_2$, or $C_{1-4}$alkyl;

$R^y$ is hydrogen or $C_{1-4}$alkyl;

each $R^a$ independently is $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom selected from N, O or S;

$R^b$ is hydrogen, $C_{1-6}$alkyl, halo$C_{1-6}$alkyl, $C_{1-6}$alkoxy, $C_{1-6}$alkyloxycarbonyl, $C_{2-6}$alkenyl, $C_{2-6}$alkynyl, cyano-$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;

$D_1$ is piperazin-1-yl, wherein said piperazin-1-yl is optionally being substituted with 1 to 5 $R^c$ substituents;

each $R^c$ independently is oxo, halo, $C_{1-6}$alkyl, $C_{1-6}$alkyloxy, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —$SO_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —$SO_2$—$NH_2$, —$SO_2$—NH($C_{1-4}$alkyl), —$SO_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

The present invention provides compounds of formula (I-A) as defined hereinabove having an S stereocenter as in the following formula (I-A-a):

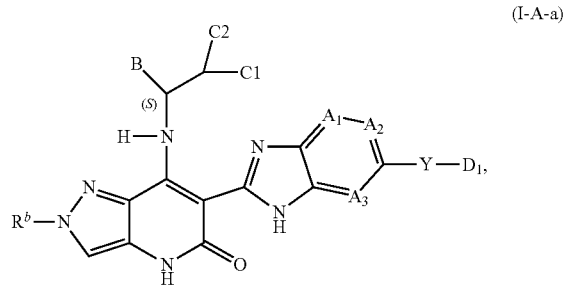

(I-A-a)

including any tautomeric and stereochemically isomeric form thereof, wherein the substituents are as defined above for the compounds of formula (I-A);

or the pharmaceutically acceptable salts thereof or the solvates thereof.

The present invention provides compounds of formula (I-B)

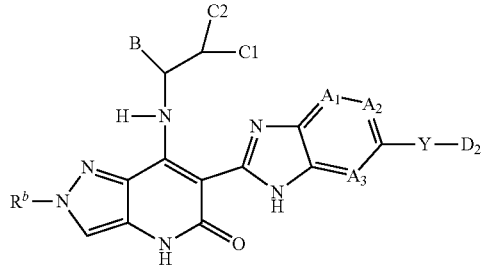

(I-B)

including any tautomeric and stereochemically isomeric form thereof, wherein $A_1$, $A_2$ and $A_3$ each independently represent CH, $CR^a$ or N, provided that maximum two of $A_1$, $A_2$ and $A_3$ may represent $CR^a$;

C1 is hydrogen or $C_{1-4}$alkyl;

C2 is hydrogen, $C_{1-4}$alkyl, hydroxyl or $C_{1-4}$alkoxy;

or C1 and C2 are taken together to form a $C_{3-6}$cycloalkyl together with the carbon atom to which they are attached;

Y is a direct bond, —O—, C(=O), $NR^y$, $S(=O)_2$, or $C_{1-4}$alkyl;

$R^y$ is hydrogen or $C_{1-4}$alkyl;

each $R^a$ independently is $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom selected from N, O or S;

$R^b$ is hydrogen, $C_{1-6}$alkyl, halo$C_{1-6}$alkyl, $C_{1-6}$alkoxy, $C_{1-6}$alkyloxycarbonyl, $C_{2-6}$alkenyl, $C_{2-6}$alkynyl, cyano-$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;

$D_2$ is morpholin-1-yl, wherein said morpholin-1-yl is optionally being substituted with 1 to 5 $R^c$ substituents;

each $R^c$ independently is oxo, halo, $C_{1-6}$alkyl, $C_{1-6}$alkyloxy, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —$SO_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —$SO_2$—$NH_2$, —$SO_2$—NH($C_{1-4}$alkyl), —$SO_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

The present invention provides compounds of formula (I-B) as defined hereinabove having an S stereocenter as in the following formula (I-B-a):

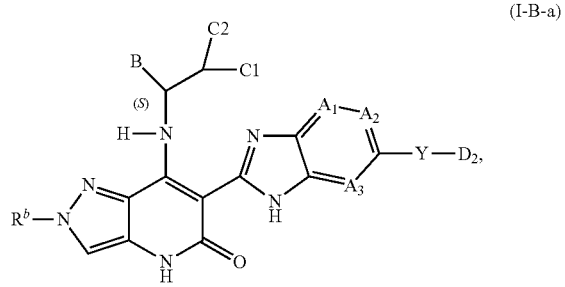

(I-B-a)

including any tautomeric and stereochemically isomeric form thereof, wherein the substituents are as defined above for the compounds of formula (I-B);

or the pharmaceutically acceptable salts thereof or the solvates thereof.

The present invention provides compounds of formula (I-C)

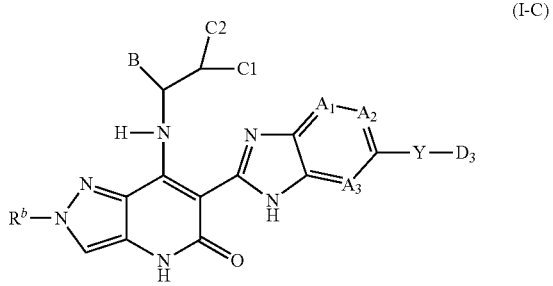

(I-C)

including any tautomeric and stereochemically isomeric form thereof, wherein $A_1$, $A_2$ and $A_3$ each independently represent CH, $CR^a$ or N, provided that maximum two of $A_1$, $A_2$ and $A_3$ may represent $CR^a$;

C1 is hydrogen or $C_{1-4}$alkyl;

C2 is hydrogen, $C_{1-4}$alkyl, hydroxyl or $C_{1-4}$alkoxy;

or C1 and C2 are taken together to form a $C_{3-6}$cycloalkyl together with the carbon atom to which they are attached;

Y is a direct bond, —O—, C(=O), $NR^y$, S(=O)$_2$, or $C_{1-4}$alkyl;

$R^y$ is hydrogen or $C_{1-4}$alkyl;

each $R^a$ independently is $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom selected from N, O or S;

$R^b$ is hydrogen, $C_{1-6}$alkyl, halo$C_{1-6}$alkyl, $C_{1-6}$alkoxy, $C_{1-6}$alkyloxycarbonyl, $C_{2-6}$alkenyl, $C_{2-6}$alkynyl, cyano-$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;

$D_3$ is a 4, 5, 6, or 7 membered monocyclic heterocyclyl, wherein said heterocyclyl is optionally being substituted with 1 to 5 $R^c$ substituents;

each $R^c$ independently is oxo, halo, $C_{1-6}$alkyl, $C_{1-6}$alkyloxy, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —$SO_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —$SO_2$—$NH_2$, —$SO_2$—NH($C_{1-4}$alkyl), —$SO_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

The present invention provides compounds of formula (I-C) as defined hereinabove having an S stereocenter as in the following formula (I-C-a):

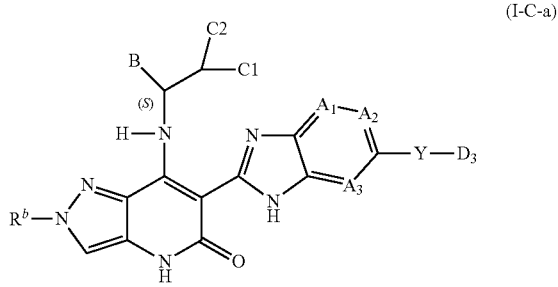

(I-C-a)

including any tautomeric and stereochemically isomeric form thereof, wherein the substituents are as defined above for the compounds of formula (I-C);

or the pharmaceutically acceptable salts thereof or the solvates thereof.

The invention provides compounds of formula (I-D):

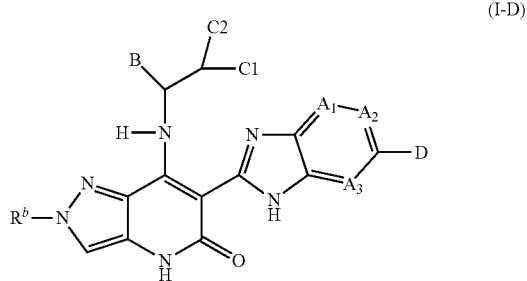

(I-D)

including any tautomeric and stereochemically isomeric form thereof, wherein $A_1$, $A_2$ and $A_3$ each independently represent CH, $CR^a$ or N, provided that maximum two of $A_1$, $A_2$ and $A_3$ may represent $CR^a$;

C1 is hydrogen or $C_{1-4}$alkyl;

C2 is hydrogen, $C_{1-4}$alkyl, hydroxyl or $C_{1-4}$alkoxy;

or C1 and C2 are taken together to form a $C_{3-6}$cycloalkyl together with the carbon atom to which they are attached;

each $R^a$ independently is $C_{1-6}$alkyl, halo$C_{1-6}$alkyl, halo, $C_{1-6}$alkoxy, carboxyl, $C_{1-6}$alkyloxycarbonyl, $C_{2-6}$alkenyl, $C_{2-6}$alkynyl, cyano, cyano$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom selected from N, O or S;

$R^b$ is hydrogen, $C_{1-6}$alkyl, halo$C_{1-6}$alkyl, $C_{1-6}$alkoxy, $C_{1-6}$alkyloxycarbonyl, $C_{2-6}$alkenyl, $C_{2-6}$alkynyl, cyano-$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S;

D is a 3 to 12 membered heterocyclyl containing at least one heteroatom selected from N, O or S, wherein said heterocyclyl is optionally being substituted with 1 to 5 $R^c$ substituents;

each $R^c$ independently is oxo, halo, $C_{1-6}$alkyl, $C_{1-6}$alkyloxy, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —$SO_2$—$C_{1-6}$alkyl, $C_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S;

B is a 3 to 12 membered carbocyclyl or a 3 to 12 membered heterocyclyl containing at least one heteroatom selected from N, O or S, wherein said carbocyclyl and heterocyclyl are each optionally being substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —$SO_2$—$NH_2$, —$SO_2$—NH($C_{1-4}$alkyl), —$SO_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom selected from N, O or S;

or the pharmaceutically acceptable salts thereof or the solvates thereof.

The present invention provides compounds of formula (I-D) as defined hereinabove having an S stereocenter as in the following formula (I-D-a):

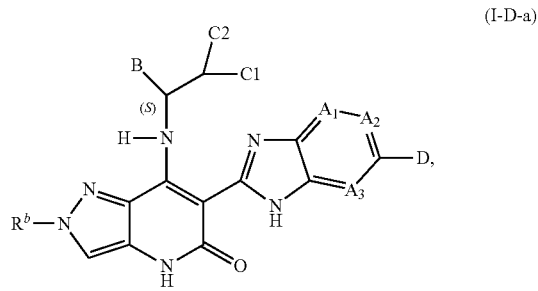

(I-D-a)

including any tautomeric and stereochemically isomeric form thereof, wherein the substituents are as defined above for the compounds of formula (I-D);

or the pharmaceutically acceptable salts thereof or the solvates thereof.

In an embodiment, in the compounds of formula (I), (I-a), (I-A), (I-A-a), (I-B), (I-B-a), (I-C), (I-C-a), (I-D) or (I-D-a), $A_1$, $A_2$ and $A_3$ represent CH or $CR^a$.

In an embodiment, in the compounds of formula (I), (I-a), (I-A), (I-A-a), (I-B), (I-B-a), (I-C), (I-C-a), (I-D) or (I-D-a), $A_1$, $A_2$ and $A_3$ represent CH.

In an embodiment, in the compounds of formula (I), (I-a), (I-A), (I-A-a), (I-B), (I-B-a), (I-C), (I-C-a), (I-D) or (I-D-a), one of $A_1$, $A_2$ and $A_3$ represents $CR^a$.

In an embodiment, in the compounds of formula (I), (I-a), (I-A), (I-A-a), (I-B), (I-B-a), (I-C), (I-C-a), (I-D) or (I-D-a), at least one of $A_1$, $A_2$ and $A_3$ represents $CR^a$.

In an embodiment, in the compounds of formula (I), (I-a), (I-A), (I-A-a), (I-B), (I-B-a), (I-C), (I-C-a), (I-D) or (I-D-a), $A_1$ represents $CR^a$ and $A_2$ and $A_3$ represent CH.

In an embodiment, in the compounds of formula (I), (I-a), (I-A), (I-A-a), (I-B), (I-B-a), (I-C), (I-C-a), (I-D) or (I-D-a), $A_2$ represents $CR^a$ and $A_1$ and $A_3$ represent CH.

In an embodiment, in the compounds of formula (I), (I-a), (I-A), (I-A-a), (I-B), (I-B-a), (I-C), (I-C-a), (I-D) or (I-D-a), $A_1$, $A_2$ and $A_3$ represent N or CH.

In an embodiment, in the compounds of formula (I), (I-a), (I-A), (I-A-a), (I-B), (I-B-a), (I-C), (I-C-a), (I-D) or (I-D-a), one of $A_1$, $A_2$ and $A_3$ represents $CR^a$ and $R^a$ represents $C_{1-6}$alkyl, in particular $C_{1-4}$alkyl, e.g. methyl; halo$C_{1-6}$alkyl, e.g. trifluoromethyl; or halo, e.g. fluoro.

In an embodiment, in the compounds of formula (I), (I-a), (I-A), (I-A-a), (I-B), (I-B-a), (I-C), (I-C-a), (I-D) or (I-D-a), one of $A_1$, $A_2$ and $A_3$ represents $CR^a$ and $R^a$ represents $C_{1-6}$alkyl, in particular $C_{1-4}$alkyl, e.g. methyl; halo$C_{1-6}$alkyl, e.g. trifluoromethyl; halo, e.g. fluoro; or $C_{1-6}$alkoxy, in particular $C_{1-4}$alkoxy, e.g. methoxy.

In an embodiment, in the compounds of formula (I), (I-a), (I-A), (I-A-a), (I-B), (I-B-a), (I-C), (I-C-a), (I-D) or (I-D-a), one of $A_1$, $A_2$ and $A_3$ represents N and the remaining A substituents represent CH or $CR^a$.

In an embodiment, in the compounds of formula (I), (I-a), (I-A), (I-A-a), (I-B), (I-B-a), (I-C), (I-C-a), (I-D) or (I-D-a), $A_2$ represents N and $A_1$ and $A_3$ represent CH or $CR^a$, in particular $A_2$ represents N and $A_1$ and $A_3$ represent CH.

In an embodiment, in the compounds of formula (I), (I-a), (I-A), (I-A-a), (I-B), (I-B-a), (I-C), (I-C-a), (I-D) or (I-D-a), two of $A_1$, $A_2$ and $A_3$ substituents represent N and the remaining A represents CH or $CR^a$.

In an embodiment, in the compounds of formula (I), (I-a), (I-A), (I-A-a), (I-B), (I-B-a), (I-C) or (I-C-a), Y is a direct bond.

In an embodiment, in the compounds of formula (I), (I-a), (I-A), (I-A-a), (I-B), (I-B-a), (I-C) or (I-C-a), Y is —O—, C(=O), $NR^y$, S(=O)$_2$, or $C_{1-4}$alkyl.

In an embodiment, in the compounds of formula (I), (I-a), (I-A), (I-A-a), (I-B), (I-B-a), (I-C) or (I-C-a), Y is a direct bond, C(=O), or $NR^y$, e.g. $NCH_3$.

In an embodiment, in the compounds of formula (I), (I-a), (I-A), (I-A-a), (I-B), (I-B-a), (I-C) or (I-C-a), Y is a direct bond, —O—, or C(=O).

In an embodiment, in the compounds of formula (I), (I-a), (I-A), (I-A-a), (I-B), (I-B-a), (I-C) or (I-C-a), Y is —O—, or C(=O).

In an embodiment, in the compounds of formula (I), (I-a), (I-A), (I-A-a), (I-B), (I-B-a), (I-C), (I-C-a), (I-D) or (I-D-a), $C_1$ is hydrogen.

In an embodiment, in the compounds of formula (I), (I-a), (I-A), (I-A-a), (I-B), (I-B-a), (I-C), (I-C-a), (I-D) or (I-D-a), $C_2$ is hydrogen.

In an embodiment, in the compounds of formula (I), (I-a), (I-A), (I-A-a), (I-B), (I-B-a), (I-C), (I-C-a), (I-D) or (I-D-a), $C_1$ is hydrogen and $C_2$ is $C_{1-4}$alkyl.

In an embodiment, in the compounds of formula (I), (I-a), (I-A), (I-A-a), (I-B), (I-B-a), (I-C), (I-C-a), (I-D) or (I-D-a), $C_1$ and $C_2$ are both hydrogen.

In an embodiment, in the compounds of formula (I), (I-a), (I-A), (I-A-a), (I-B), (I-B-a), (I-C), (I-C-a), (I-D) or (I-D-a), $C_1$ is hydrogen and $C_2$ is hydroxyl.

In an embodiment, in the compounds of formula (I), (I-a), (I-A), (I-A-a), (I-B), (I-B-a), (I-C), (I-C-a), (I-D) or (I-D-a), $C_1$ is hydrogen and $C_2$ is $C_{1-4}$alkoxy.

In an embodiment, in the compounds of formula (I), (I-a), (I-A), (I-A-a), (I-B), (I-B-a), (I-C), (I-C-a), (I-D) or (I-D-a), $C_1$ and $C_2$ are taken together to form $C_{3-6}$cycloalkyl together with the carbon atom to which they are attached, in particular cyclopropyl.

In an embodiment, in the compounds of formula (I), (I-a), (I-A), (I-A-a), (I-B), (I-B-a), (I-C), (I-C-a), (I-D) or (I-D-a),

represents —$CH_3$.

In an embodiment, in the compounds of formula (I), (I-a), (I-A), (I-A-a), (I-B), (I-B-a), (I-C), (I-C-a), (I-D) or (I-D-a),

represents —$CH_2(C_{1-4}$alkyl), in particular —$CH_2CH_3$ or —$CH_2CH_2CH_3$.

In an embodiment, in the compounds of formula (I), (I-a), (I-A), (I-A-a), (I-B), (I-B-a), (I-C), (I-C-a), (I-D) or (I-D-a),

represents —$CH(C_{1-4}$alkyl)$_2$, in particular —$CH(CH_3)_2$.

In an embodiment, in the compounds of formula (I), (I-a), (I-A), (I-A-a), (I-B), (I-B-a), (I-C), (I-C-a), (I-D) or (I-D-a),

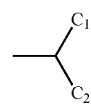

represents -cyclopropyl.

In an embodiment, in the compounds of formula (I), (I-a), (I-A), (I-A-a), (I-B), (I-B-a), (I-C) or (I-C-a), $R^y$ is hydrogen.

In an embodiment, in the compounds of formula (I), (I-a), (I-A), (I-A-a), (I-B), (I-B-a), (I-C) or (I-C-a), $R^y$ is $C_{1-4}$alkyl, in particular methyl.

In an embodiment, in the compounds of formula (I), (I-a), (I-A), (I-A-a), (I-B), (I-B-a), (I-C), (I-C-a), (I-D) or (I-D-a), $R^b$ is hydrogen.

In an embodiment, in the compounds of formula (I), (I-a), (I-A), (I-A-a), (I-B), (I-B-a), (I-C), (I-C-a), (I-D) or (I-D-a), $R^b$ is $C_{1-6}$alkyl, halo$C_{1-6}$alkyl, $C_{1-6}$alkoxy, $C_{1-6}$alkyloxycarbonyl, $C_{2-6}$alkenyl, $C_{2-6}$alkynyl, cyano$C_{1-6}$alkyl, hydroxy$C_{1-6}$alkyl, —C(=O)—$NH_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom selected from N, O or S, or $C_{1-6}$alkyl substituted with $C_{3-6}$cycloalkyl or with phenyl or with a 3 to 6 membered monocyclic heterocyclyl containing at least one heteroatom selected from N, O or S.

In an embodiment, in the compounds of formula (I), (I-a), (I-A), (I-A-a), (I-B), (I-B-a), (I-C), (I-C-a), (I-D) or (I-D-a), $R^b$ is $C_{1-6}$alkyl, halo$C_{1-6}$alkyl, $C_{1-6}$alkoxy, $C_{1-6}$alkyl oxycarbonyl, $C_{2-6}$alkenyl, $C_{2-6}$alkynyl, cyano$C_{1-6}$alkyl, hydroxy$C_{1-6}$alkyl, —C(=O)—$NH_2$, —C(=O)—NH($C_{1-4}$alkyl), or —C(=O)—N($C_{1-4}$alkyl)$_2$.

In an embodiment, in the compounds of formula (I), (I-a), (I-A), (I-A-a), (I-B), (I-B-a), (I-C), (I-C-a), (I-D) or (I-D-a), $R^b$ is $C_{1-6}$alkyl, in particular methyl or ethyl.

In an embodiment, in the compounds of formula (I), (I-a), (I-A), (I-A-a), (I-B), (I-B-a), (I-C), (I-C-a), (I-D) or (I-D-a), D, $D_1$, $D_2$ or $D_3$ is unsubstituted.

In an embodiment, in the compounds of formula (I), (I-a), (I-A), (I-A-a), (I-B), (I-B-a), (I-C), (I-C-a), (I-D) or (I-D-a), D, $D_1$, $D_2$ or $D_3$ is substituted with 1, 2, 3 or 4 $R_c$ substituents.

In an embodiment, in the compounds of formula (I), (I-a), (I-A), (I-A-a), (I-B), (I-B-a), (I-C), (I-C-a), (I-D) or (I-D-a), D, $D_1$, $D_2$ or $D_3$ is substituted with 2 $R_c$ substituents.

In an embodiment, in the compounds of formula (I), (I-a), (I-A), (I-A-a), (I-B), (I-B-a), (I-C), (I-C-a), (I-D) or (I-D-a), D, $D_1$, $D_2$ or $D_3$ is substituted with 1 or 2 $R_c$ substituents.

In an embodiment, in the compounds of formula (I), (I-a), (I-A), (I-A-a), (I-B), (I-B-a), (I-C), (I-C-a), (I-D) or (I-D-a), D, $D_1$, $D_2$ or $D_3$ is substituted with 1 or 2 $R_c$ substituents and each $R_c$ is independently selected from oxo; halo e.g. fluoro; $C_{1-6}$alkyl, in particular $C_{1-4}$alkyl, e.g. methyl; $C_{1-6}$alkyloxy in particular $C_{1-4}$alkyloxy e.g. methoxy; halo$C_{1-6}$alkyl e.g. trifluoromethyl or trifluoroethyl; halo$C_{1-6}$alkyloxy, e.g. trifluoromethoxy; HOOC—$C_{1-6}$alkyl-, e.g. —$CH_2$—COOH; carboxyl; $C_{1-6}$alkyl substituted with —C(=O)—O—$C_{1-6}$ alkyl, e.g. —CH$_2$—C(=O)—O—CH$_2$—CH$_3$; C$_{1-6}$alkyl-O—C(=O)—, e.g. —C(=O)—O—CH$_3$.

In an embodiment, in the compounds of formula (I), (I-a), (I-A), (I-A-a), (I-B), (I-B-a), (I-C), (I-C-a), (I-D) or (I-D-a), D, D$_1$, D$_2$ or D$_3$ is substituted with 1 or 2 R$_c$ substituents and each R$_c$ is independently selected from oxo; halo e.g. fluoro; C$_{1-6}$alkyl, in particular C$_{1-4}$alkyl, e.g. methyl; C$_{1-6}$alkyloxy in particular C$_{1-4}$alkyloxy e.g. methoxy; or haloC$_{1-6}$alkyl e.g. trifluoromethyl or trifluoroethyl.

In an embodiment, in the compounds of formula (I), (I-a), (I-A), (I-A-a), (I-B), (I-B-a), (I-C), (I-C-a), (I-D) or (I-D-a), D, D$_1$, D$_2$ or D$_3$ is substituted with 4 R$_c$ substituents and each R$_c$ substituent independently represents C$_{1-6}$alkyl, in particular C$_{1-4}$alkyl, e.g. methyl.

In an embodiment, in the compounds of formula (I), (I-a), (I-C), (I-C-a), (I-D) or (I-D-a), D or D$_3$ is a bridged heterocyclyl, e.g. 8-oxa-3-azabicyclo[3.2.1]octane.

In an embodiment, in the compounds of formula (I), (I-a), (I-C), (I-C-a), (I-D) or (I-D-a), D or D$_3$ is a bridged heterocyclyl wherein the bridge is —CH$_2$—, —CH$_2$—CH$_2$— or —CH$_2$—CH$_2$—CH$_2$—, in particular —CH$_2$—CH$_2$—, such as for example in 8-oxa-3-azabicyclo[3.2.1]octane.

In an embodiment, in the compounds of formula (I-C) or (I-C-a), D$_3$ is a 4, 5, 6, or 7 membered saturated monocyclic heterocyclyl containing at least one heteroatom selected from N, O or S, wherein said heterocyclyl is optionally being substituted with 1 to 5 R$^c$ substituents, with 1 to 4 R$^c$ substituents, with 1 to 3 R$^c$ substituents, with 1 or 2 R$^c$ substituents or with 1 R$^c$ substituent.

In an embodiment, in the compounds of formula (I-C) or (I-C-a), D$_3$ is a 4, 5, 6, or 7 membered saturated monocyclic heterocyclyl containing at least one heteroatom selected from N, O or S, wherein said heterocyclyl is unsubstituted In an embodiment, in the compounds of formula (I-C) or (I-C-a), D$_3$ is a 5 or 6 membered monocyclic heterocyclyl containing at least one heteroatom selected from N, O or S, wherein said heterocyclyl is optionally being substituted with 1 to 5 R$^c$ substituents, in particular a 6 membered saturated monocyclic heterocyclyl containing at least one heteroatom selected from N, O or S, wherein said heterocyclyl is optionally being substituted with 1 to 5 R$^c$ substituents, with 1 to 4 R$^c$ substituents, with 1 to 3 R$^c$ substituents, with 1 or 2 R$^c$ substituents or with 1 R$^c$ substituent.

In an embodiment, in the compounds of formula (I-C) or (I-C-a), D$_3$ is a 5 or 6 membered saturated monocyclic heterocyclyl containing at least one heteroatom selected from N, O or S, wherein said heterocyclyl is optionally being substituted with 1 to 5 R$^c$ substituents, with 1 to 4 R$^c$ substituents, with 1 to 3 R$^c$ substituents, with 1 or 2 R$^c$ substituents or with 1 R$^c$ substituent. In an embodiment, the heterocyclyl is unsubstituted. In an embodiment, D$_3$ is optionally substituted piperidinyl, morpholinyl, piperazinyl, pyrrolidinyl or tetrahydropyranyl. In an embodiment, D$_3$ is unsubstituted piperidinyl, morpholinyl, piperazinyl, pyrrolidinyl or tetrahydropyranyl.

In an embodiment, in the compounds of formula (I-C) or (I-C-a), D$_3$ is a 4 membered saturated monocyclic heterocyclyl containing at least one heteroatom selected from N, O or S, wherein said heterocyclyl is optionally being substituted with 1 to 5 R$^c$ substituents, with 1 to 4 R$^c$ substituents, with 1 to 3 R$^c$ substituents, with 1 or 2 R$^c$ substituents or with 1 R$^c$ substituent. In an embodiment, the heterocyclyl is unsubstituted. In an embodiment, D$_3$ is unsubstituted azetidinyl.

In an embodiment, in the compounds of formula (I-C) or (I-C-a), D$_3$ is a 5 or 6 membered aromatic monocyclic heterocyclyl containing at least one heteroatom selected from N, O or S, wherein said heterocyclyl is optionally being substituted with 1 to 5 R$^c$ substituents, in particular a 5 membered aromatic monocyclic heterocyclyl containing at least one heteroatom selected from N, O or S, wherein said heterocyclyl is optionally being substituted with 1 to 5 R$^c$ substituents, with 1 to 4 R$^c$ substituents, with 1 to 3 R$^c$ substituents, with 1 or 2 R$^c$ substituents or with 1 R$^c$ substituent, e.g. optionally substituted pyrazole.

In an embodiment, in the compounds of formula (I), (I-a), (I-A), (I-A-a), (I-B), (I-B-a), (I-C), (I-C-a), (I-D) or (I-D-a), each R$^c$ independently is oxo, C$_{1-6}$alkyl, hydroxyC$_{1-6}$alkyl, haloC$_{1-6}$alkyl, haloC$_{1-6}$alkyloxy, carboxyl, HOOC—C$_{1-6}$alkyl-, cyano, cyanoC$_{1-6}$alkyl, C$_{1-6}$alkyl-C(=O)—, —SO$_2$—C$_{1-6}$alkyl, C$_{3-6}$cycloalkyl, phenyl, a 3 to 6 membered monocyclic saturated heterocyclyl containing at least one heteroatom selected from N, O or S, or a 5 or 6 membered monocyclic aromatic heterocyclyl containing at least one heteroatom selected from N, O or S.

In an embodiment, in the compounds of formula (I), (I-a), (I-A), (I-A-a), (I-B), (I-B-a), (I-C), (I-C-a), (I-D) or (I-D-a), each R$^c$ independently is oxo, halo, C$_{1-6}$alkyl, C$_{1-6}$alkoxy or haloC$_{1-6}$alkyl.

In an embodiment, in the compounds of formula (I), (I-a), (I-A), (I-A-a), (I-B), (I-B-a), (I-C), (I-C-a), (I-D) or (I-D-a), B is a 5 or 6 membered carbocyclyl or heterocyclyl containing at least one heteroatom selected from N, O or S, wherein said carbocyclyl and heterocyclyl are each optionally being substituted with 1 to 5, in particular 1 to 4, or 1 to 3, or 1 or 2, or 1 R substituents. In an embodiment, B is unsubstituted.

In an embodiment, in the compounds of formula (I), (I-a), (I-A), (I-A-a), (I-B), (I-B-a), (I-C), (I-C-a), (I-D) or (I-D-a), B is phenyl or a 5 or 6 membered aromatic heterocyclyl containing at least one heteroatom selected from N, O or S, wherein said phenyl and heterocyclyl are each optionally being substituted with 1 to 5, in particular 1 to 4, or 1 to 3, or 1 or 2, or 1 R substituents. In an embodiment, B is unsubstituted.

In an embodiment, in the compounds of formula (I), (I-a), (I-A), (I-A-a), (I-B), (I-B-a), (I-C), (I-C-a), (I-D) or (I-D-a), B is a 3 to 6 membered monocyclic carbocyclyl or heterocyclyl containing at least one heteroatom selected from N, O or S, wherein said carbocyclyl and heterocyclyl are each optionally being substituted with 1 to 5, in particular 1 to 4, or 1 to 3, or 1 or 2, or 1 R substituents. In an embodiment, B is unsubstituted.

In an embodiment, in the compounds of formula (I), (I-a), (I-A), (I-A-a), (I-B), (I-B-a), (I-C), (I-C-a), (I-D) or (I-D-a), B is a 3 to 6 membered monocyclic non-aromatic carbocyclyl or heterocyclyl containing at least one heteroatom selected from N, O or S, wherein said carbocyclyl and heterocyclyl are each optionally being substituted with 1 to 5, in particular 1 to 4, or 1 to 3, or 1 or 2, or 1 R substituents. In an embodiment, B is unsubstituted.

In an embodiment, in the compounds of formula (I), (I-a), (I-A), (I-A-a), (I-B), (I-B-a), (I-C), (I-C-a), (I-D) or (I-D-a), B is a 6 membered aromatic monocyclic heterocyclyl containing at least one heteroatom selected from N, O or S, wherein said heterocyclyl is optionally being substituted with 1 to 4, in particular 1 to 3, or 1 or 2, or 1 R substituents. For example B is optionally substituted pyridyl, pyrimidinyl or pyrazinyl, in particular B is optionally substituted pyridyl or pyrimidinyl. In an embodiment, B is unsubstituted. In an embodiment, B is substituted with 1 R substituent. In an embodiment, the R substituent is selected from $C_{1-6}$alkyl, $C_{1-6}$alkoxy and $C_{3-6}$cycloalkyl. In an embodiment, the R substituent is halo$C_{1-6}$alkyl.

In an embodiment, in the compounds of formula (I), (I-a), (I-A), (I-A-a), (I-B), (I-B-a), (I-C), (I-C-a), (I-D) or (I-D-a), B is a 5 membered aromatic monocyclic heterocyclyl containing at least one heteroatom selected from N, O or S, wherein said heterocyclyl is optionally being substituted with 1 to 3, in particular 1 or 2, or 1 R substituents. For example B is optionally substituted pyrazolyl, oxazolyl or thiazolyl, in particular B is optionally substituted oxazolyl or thiazolyl. In an embodiment, B is unsubstituted. In an embodiment, B is substituted with 1 R substituent. In an embodiment, the R substituent is selected from $C_{1-6}$alkyl, $C_{1-6}$alkoxy and $C_{3-6}$cycloalkyl. In an embodiment, the R substituent is halo$C_{1-6}$alkyl.

In an embodiment, in the compounds of formula (I), (I-a), (I-A), (I-A-a), (I-B), (I-B-a), (I-C), (I-C-a), (I-D) or (I-D-a), B is a 9 to 12 membered bicyclic carbocyclyl or heterocyclyl containing at least one heteroatom selected from N, O or S, wherein said carbocyclyl and heterocyclyl are each optionally being substituted with 1 to 5, in particular 1 to 4, or 1 to 3, or 1 or 2, or 1 R substituents. In an embodiment, B is unsubstituted.

In an embodiment, in the compounds of formula (I), (I-a), (I-A), (I-A-a), (I-B), (I-B-a), (I-C), (I-C-a), (I-D) or (I-D-a), B is pyrimidinyl, optionally being substituted with 1 to 3, in particular 1 or 2, or 1 R substituents; in particular B is unsubstituted pyrimidinyl.

In an embodiment, in the compounds of formula (I), (I-a), (I-A), (I-A-a), (I-B), (I-B-a), (I-C), (I-C-a), (I-D) or (I-D-a), each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —SO$_2$—NH$_2$, —SO$_2$—NH($C_{1-4}$alkyl), —SO$_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, or $C_{1-6}$alkyl-O—C(=O)—.

In an embodiment, in the compounds of formula (I), (I-a), (I-A), (I-A-a), (I-B), (I-B-a), (I-C), (I-C-a), (I-D) or (I-D-a), each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —SO$_2$—NH$_2$, —SO$_2$—NH($C_{1-4}$alkyl), —SO$_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{3-6}$cycloalkyl, phenyl, or a 3 to 6 membered monocyclic heterocyclyl containing at least one heteroatom selected from N, O or S.

In an embodiment, in the compounds of formula (I), (I-a), (I-A), (I-A-a), (I-B), (I-B-a), (I-C), (I-C-a), (I-D) or (I-D-a), there is 1 R substituent, said R being halo$C_{1-6}$alkyl.

In an embodiment, in the compounds of formula (I), (I-a), (I-A), (I-A-a), (I-B), (I-B-a), (I-C), (I-C-a), (I-D) or (I-D-a), B is unsubstituted.

In an embodiment, in the compounds of formula (I), (I-a), (I-A), (I-A-a), (I-B), (I-B-a), (I-C), (I-C-a), (I-D) or (I-D-a), B is substituted with 1 to 5 R substituents, in particular 1 to 4 R substituents, or 1 to 3 R substituents, or 1 or 2 R substituents, or 1 R substituent.

In an embodiment, in the compounds of formula (I), (I-a), (I-A), (I-A-a), (I-B), (I-B-a), (I-C), (I-C-a), (I-D) or (I-D-a), one or more, in particular when possible all of the following conditions apply:

each of $A_1$, $A_2$ and $A_3$ represents CH; or $A_1$ and $A_3$ represent CH and $A_2$ represents N; or at least one of $A_1$, $A_2$ and $A_3$ represents CR$^a$; or $A_1$ represents CR$^a$ and $A_2$ and $A_3$ represent CH;

or $A_2$ represents CR$^a$ and $A_1$ and $A_3$ represent CH;

C1 is hydrogen or $C_{1-4}$alkyl, in particular hydrogen or methyl;

C2 is hydrogen or $C_{1-4}$alkyl or $C_{1-4}$alkoxy, in particular hydrogen, methyl or methoxy;

Y is a direct bond, —O— or C(=O);

each R$^a$ independently is $C_{1-6}$alkyl e.g. methyl, halo$C_{1-6}$alkyl e.g. trifluoromethyl, halo e.g. fluoro, or $C_{1-6}$alkoxy e.g. methoxy;

R$^b$ is $C_{1-6}$alkyl, in particular $C_{1-4}$alkyl e.g. methyl or ethyl;

D is a 4, 5 or 6 membered monocyclic saturated heterocyclyl containing at least one heteroatom selected from N, O or S, wherein said heterocyclyl is optionally being substituted with 1 or 2 R$^c$ substituents; in particular D is piperazinyl, morpholinyl, piperidinyl, tetrahydropyranyl, pyrrolidinyl or azetidinyl, wherein said ring systems are optionally being substituted with 1 or 2 R$^c$ substituents;

each R$^c$ independently is oxo; $C_{1-6}$alkyl e.g. methyl; halo e.g. fluoro; $C_{1-6}$alkoxy e.g. methoxy;

or halo$C_{1-6}$alkyl e.g. trifluoromethyl or trifluoroethyl;

B is a 5 or 6 membered aromatic monocyclic heterocyclyl containing at least one heteroatom selected from N, O or S, wherein said heterocyclyl is optionally being substituted with 1 R substituent; in particular B is pyridyl, pyrimidinyl, pyrazinyl, pyrazolyl, thiazolyl, oxazolyl;

each R independently is $C_{1-6}$alkyl e.g. methyl or isopropyl, $C_{1-6}$alkoxy e.g. methoxy, or $C_{3-6}$cycloalkyl e.g. cyclopropyl.

In an embodiment, the compound is a compound of formula (I-C), (I-C-a), (I-D) or (I-D-a), wherein one or more, in particular when possible all of the following conditions apply: each of $A_1$, $A_2$ and $A_3$ represents CH; or $A_1$ and $A_3$ represent CH and $A_2$ represents N; or at least one of $A_1$, $A_2$ and $A_3$ represents CR$^a$; or $A_1$ represents CR$^a$ and $A_2$ and $A_3$ represent CH;

or $A_2$ represents CR$^a$ and $A_1$ and $A_3$ represent CH;

C1 is hydrogen or $C_{1-4}$alkyl, in particular hydrogen or methyl;

C2 is hydrogen or $C_{1-4}$alkyl or $C_{1-4}$alkoxy, e.g. hydrogen, methyl or methoxy; in particular hydrogen or $C_{1-4}$alkyl, e.g. hydrogen or methyl;

Y is a direct bond, —O— or C(=O), in particular a direct bond or C(=O), more in particular a direct bond;

each R$^a$ independently is $C_{1-6}$alkyl e.g. methyl, halo$C_{1-6}$alkyl e.g. trifluoromethyl, halo e.g. fluoro, or $C_{1-6}$alkoxy e.g. methoxy; in particular hydrogen, halo or $C_{1-6}$alkyl;

R$^b$ is $C_{1-6}$alkyl, in particular $C_{1-4}$alkyl e.g. methyl or ethyl;

D or $D_3$ is a 4, 5 or 6 membered monocyclic saturated heterocyclyl containing at least one heteroatom selected from N, O or S, wherein said heterocyclyl is optionally being substituted with 1 or 2 R$^c$ substituents; in particular D is piperazinyl, morpholinyl, piperidinyl, tetrahydropyranyl, pyrrolidinyl or azetidinyl, wherein said ring systems are optionally being substituted with 1 or 2 R<sup>c</sup> substituents; in particular D is optionally substituted piperazinyl, morpholinyl or pyrrolidinyl;

each $R^c$ independently is oxo, $C_{1-6}$alkyl e.g. methyl, halo e.g. fluoro, $C_{1-6}$alkoxy e.g. methoxy, or halo$C_{1-6}$alkyl e.g. trifluoromethyl or trifluoroethyl; in particular $C_{1-6}$alkyl e.g. methyl;

B is a 5 or 6 membered aromatic monocyclic heterocyclyl containing at least one heteroatom selected from N, O or S, wherein said heterocyclyl is optionally being substituted with 1 R substituent; in particular B is pyridyl, pyrimidinyl, pyrazinyl, pyrazolyl, thiazolyl, oxazolyl; in particular B is unsubstituted pyrimidinyl;

each R independently is $C_{1-6}$alkyl e.g. methyl or isopropyl, $C_{1-6}$alkoxy e.g. methoxy, or $C_{3-6}$cycloalkyl e.g. cyclopropyl.

In an embodiment, the compound of the invention is selected from

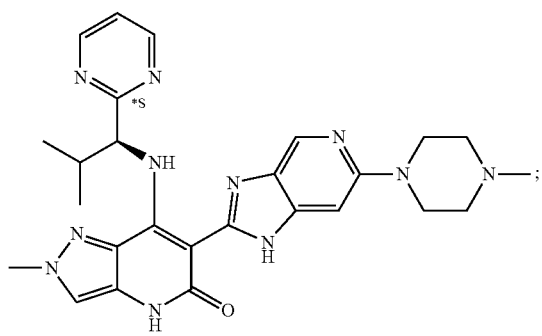

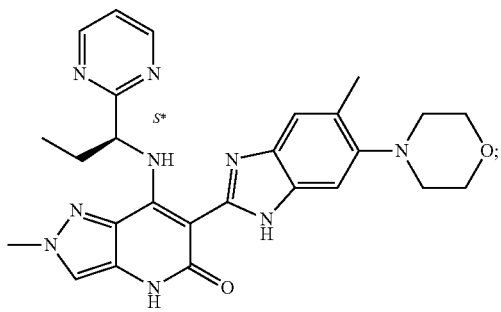 [SMILES: CC[C@H](Nc1c(-c2nc3cc(C)c(N4CCOCC4)cc3[nH]2)c(=O)[nH]c2cn(C)nc12)c1ncccn1]

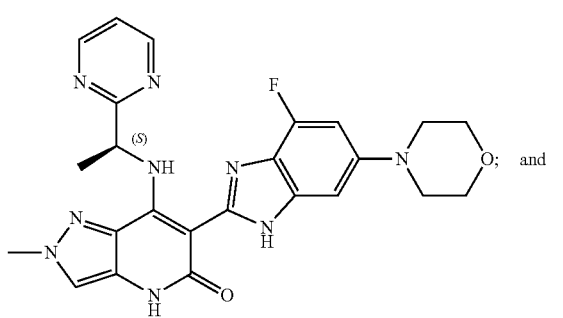

and

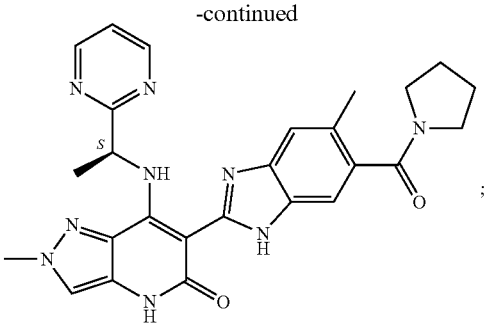

or the pharmaceutically acceptable salts thereof or the solvates thereof.

In an embodiment, the compound of the invention is

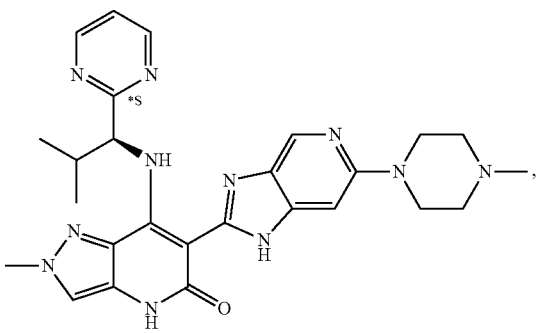

or a pharmaceutically acceptable salt thereof or a solvate thereof.

In an embodiment, the compound of the invention is

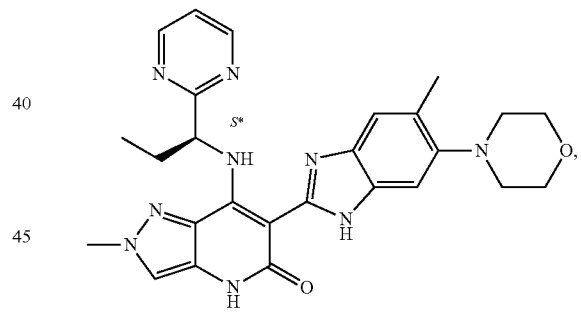

or a pharmaceutically acceptable salt thereof or a solvate thereof.

In an embodiment, the compound of the invention is

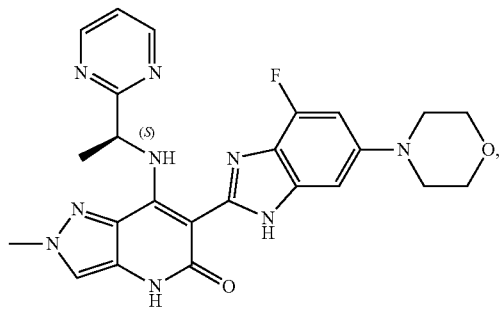

or a pharmaceutically acceptable salt thereof or a solvate thereof.

In an embodiment, the compound of the invention is

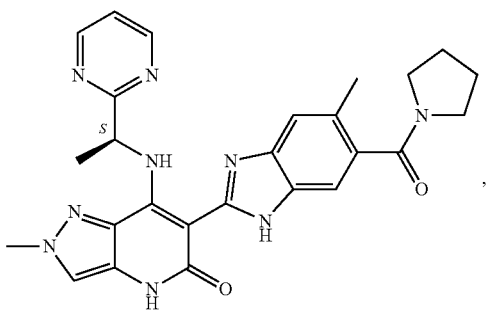

or a pharmaceutically acceptable salt thereof or a solvate thereof.

For the avoidance of doubt, it is to be understood that each general and specific preference, embodiment and example for one substituent may be combined if chemically possible with each general and specific preference, embodiment and example for one or more, preferably, all other substituents as defined herein and that all such embodiments are embraced by this application.

Methods for the Preparation of Compounds of Formula (I)

In this section, as in all other sections of this application unless the context indicates otherwise, references to formula (I) also include all other sub-groups and examples thereof (e.g. (I-a), (I-A), (I-A-a), (I-B), (I-B-a), (I-C), (I-C-a), (I-D) or (I-D-a)) as defined herein.

In general, compounds of formula (I) can be prepared according to the following reaction Scheme 1. In Scheme 1, $W_1$ and $W_2$ represent a suitable leaving group, such as for example halo, e.g. chloro, and P represents a suitable protective group, such as for example 4-methoxybenzyl. All other variables in Scheme 1 are defined according to the present invention.

Scheme 1

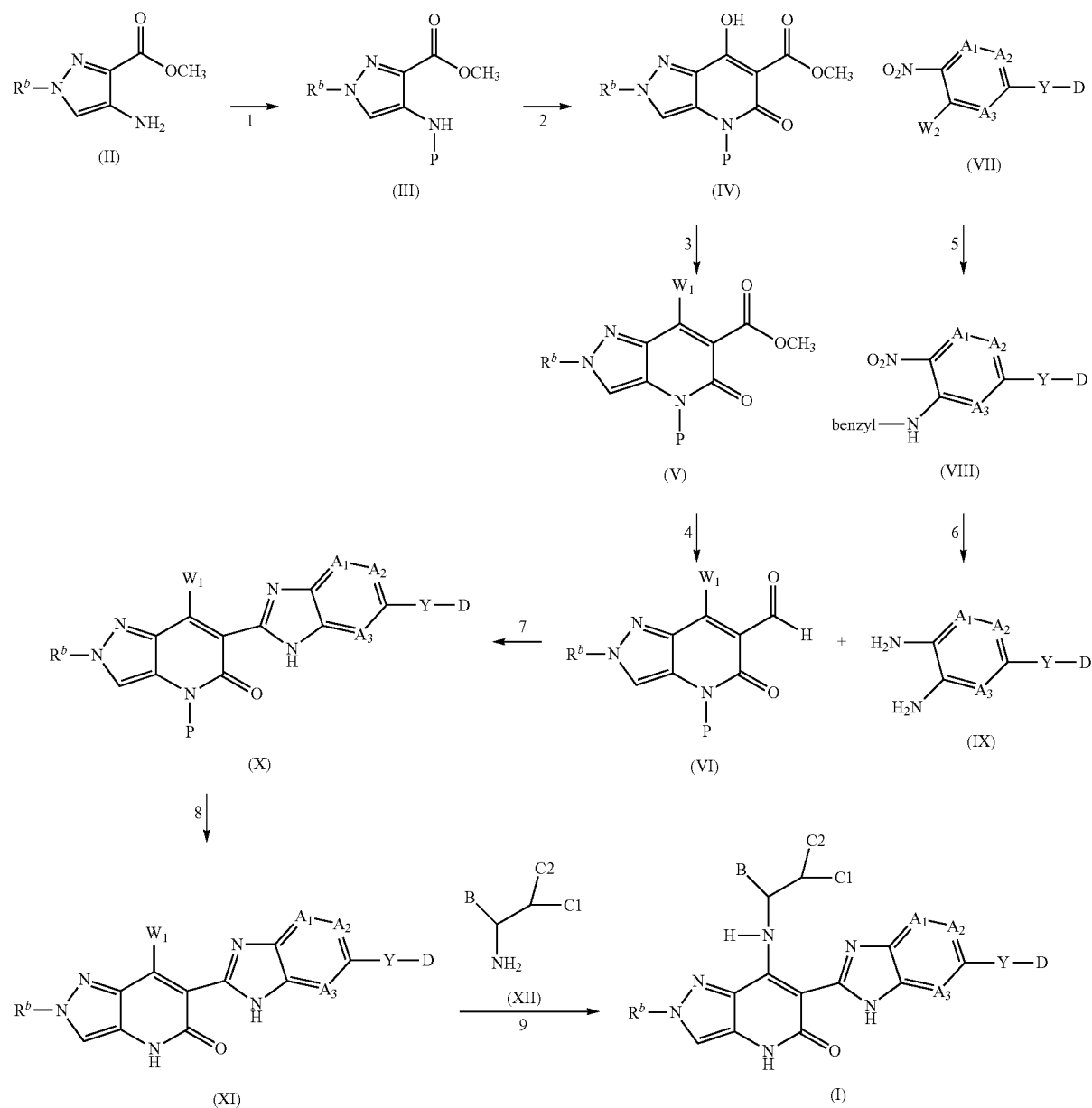

In Scheme 1, the following reaction conditions apply:

1: in the presence of a suitable protective reagent H-P, such as for example 4-methoxybenzaldehyde, and a suitable reducing agent, such as for example NaBH$_4$, a suitable acid, such as for example trifluoroacetic acid, and a suitable solvent, such as for example ethyl acetate, at a suitable temperature, such as for example room temperature;

2: a) in the presence of methyl malonyl chloride, a suitable reducing agent, such as for example sodium hydride, and a suitable solvent, such as for example N,N-dimethylformamide, at a suitable temperature, such as for example room temperature; and b) in the presence of sodium methoxide, at a suitable temperature, such as for example 110° C.;

3: in the presence of a suitable leaving group introducing agent, such as for example oxalyl chloride or phosphoryl chloride, in the presence of a suitable solvent, such as for example N,N-dimethylformamide, and dichloromethane, at a suitable temperature, such as for example room temperature or 15° C.;

4: in the presence of a suitable reducing agent, such as for example diisobutylaluminium hydride and a suitable solvent, such as for example tetrahydrofuran or dichloromethane, at a suitable temperature, such as for example −78° C.;

5: in the presence of phenylmethanamine, a suitable base, such as for example diisopropylethylamine, and a suitable solvent, such as for example acetonitrile, at a suitable temperature, such as for example 70° C.;

6: in the presence of a suitable reducing agent, such as for example H$_2$, and a suitable catalyst, such as for example palladium on charcoal, in a suitable solvent, such as for example an alcohol, e.g. methanol, at a suitable temperature, such as for example 50° C.;

7: in the presence of a suitable oxidant, such as for example FeCl$_3$, and a suitable solvent, such as for example 1,4-dioxane, at a suitable temperature, such as for example 20° C. or 25° C.;

8: in the presence of a suitable deprotecting agent, such as for example trifluoromethanesulfonic acid, and a suitable solvent, such as for example trifluoroacetic acid, at a suitable temperature, such as for example 20° C., 60° C., 80° C. or 85° C.;

9: in the presence of a suitable base, such as for example diisopropylethylamine, potassium bicarbonate or sodium bicarbonate, a suitable phase-transfer catalyst, such as for example tetrabutylammonium iodide or 18-crown-6, and a suitable solvent, such as for example dichloromethane, chloroform, N,N-dimethylacetamide or an alcohol, e.g. ethanol, at a suitable temperature, such as for example 35° C., 40° C., 60° C., 85° C. or 110° C.;

In Scheme 1, the intermediate of formula (XII) can be a specific stereoisomer, e.g. the S enantiomer, resulting in a specific stereoisomer, e.g. the S enantiomer, of formula (I), such as shown below in Scheme 1a for the preparation of compounds of formula (I-a).

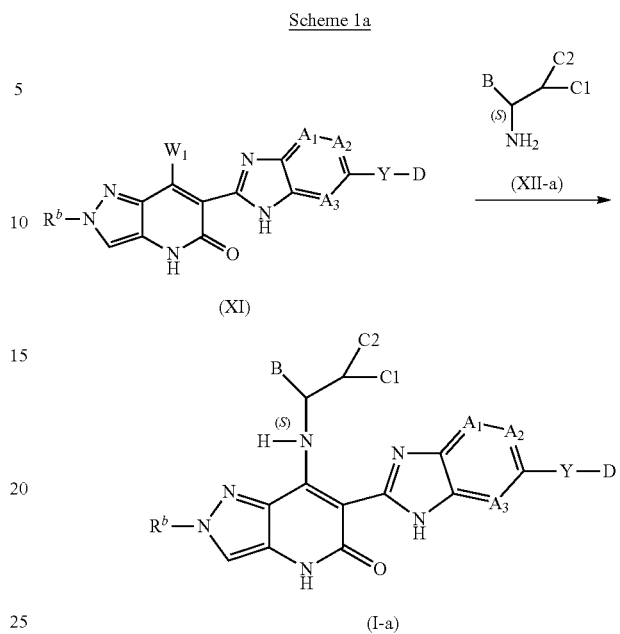

Scheme 1a

Intermediates of formula (IX) wherein Y represents NR$^y$, said intermediates being represented by formula (IX-a), can also be prepared according to the following reaction Scheme 2. In Scheme 2, W$_3$ represents a suitable leaving group, such as for example halo, e.g. bromo. All other variables in Scheme 2 are defined according to the present invention.

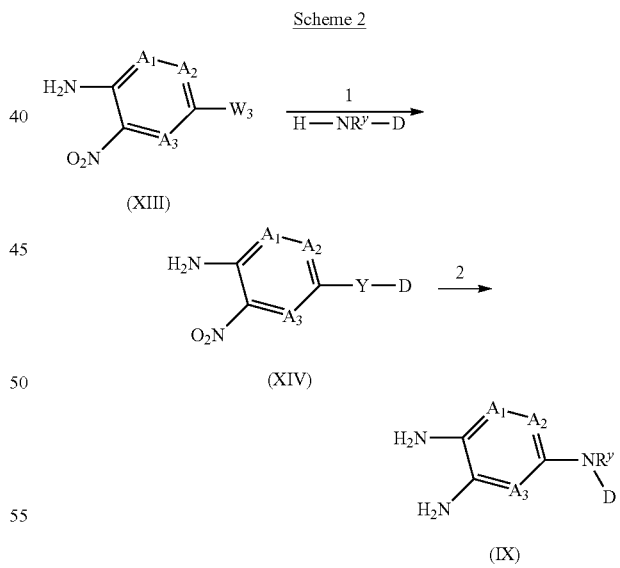

Scheme 2

In Scheme 2, the following reaction conditions apply:

1: in the presence of a suitable catalyst, such as for example tris(dibenzylideneacetone)-dipalladium (0), a suitable ligand, such as for example (2-biphenyl)di-tert-butylphosphine, a suitable base, such as for example sodium tert butoxide, in a suitable solvent, such as for example tetrahydrofuran, at a suitable temperature, such as for example 60° C.;

2: in the presence of a suitable reducing agent, such as H$_2$, a suitable catalyst, such as for example Raney-Nickel, in a suitable solvent, such as for example dioxane, at a suitable temperature, such as for example room temperature;

Intermediates of formula (XIV) wherein Y represents —C(═O)—, said intermediates being represented by formula (XIV-a), can also be prepared according to the following reaction Scheme 3. In Scheme 3, variables are defined according to the present invention.

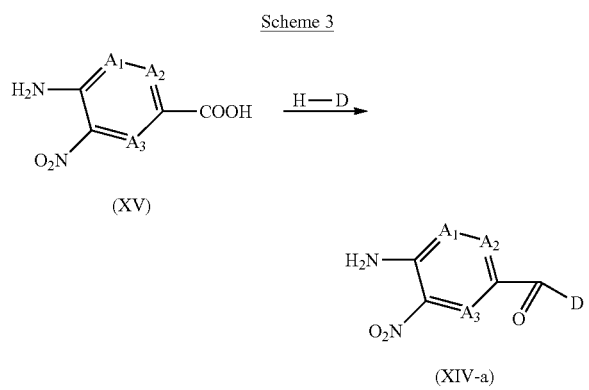

Compounds of formula (I) can also be prepared according to the following reaction Scheme 4. In Scheme 4, W$_4$ represents a suitable leaving group, such as for example halo, e.g. bromo. All other variables in Scheme 4 are defined according to the present invention.

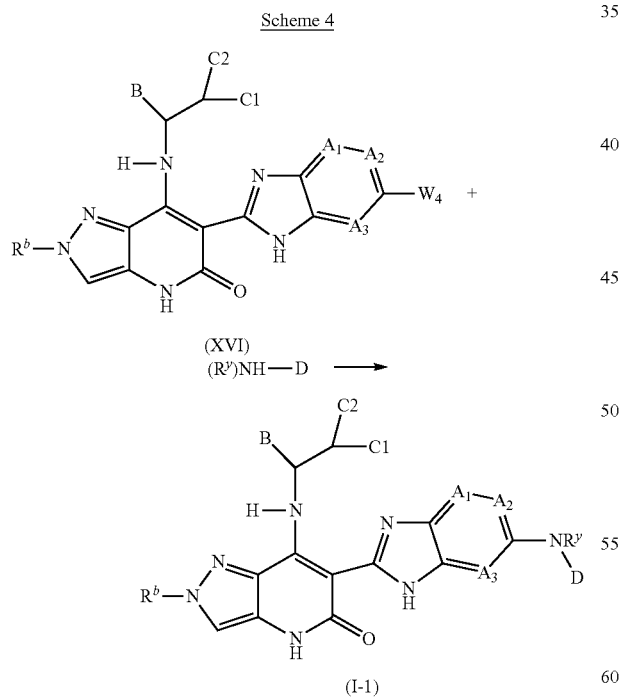

The reaction of Scheme 4 is performed in the presence of a suitable catalyst, such as for example a palladium catalyst, e.g. Pd$_2$(dba)$_3$, a suitable ligand, such as for example davephos (2-dicyclohexylphosphino-2'-(N,N-dimethylamino)biphenyl), a suitable base, such as for example LiHMDS (lithium bis(trimethylsilyl)amide), and a suitable solvent, such as for example tetrahydrofuran.

In Scheme 4, the intermediate of formula (XVI) can be a specific stereoisomer, e.g. the S enantiomer, resulting in a specific stereoisomer, e.g. the S enantiomer, of formula (I), such as shown below in Scheme 4a for the preparation of compounds of formula (I-1-a).

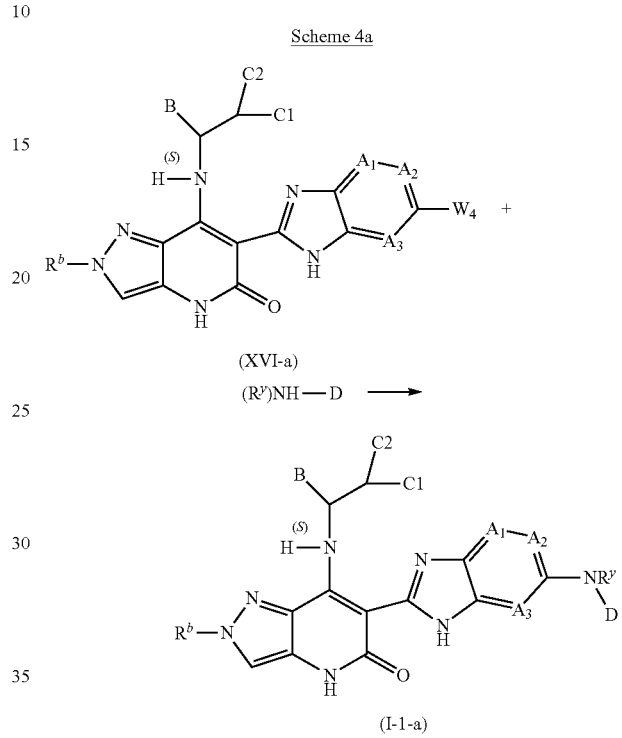

Compounds of formula (I) wherein Y represents a direct bond, said compounds being represented by formula (I-D), can also be prepared according to the following reaction Scheme 5. In Scheme 5, W$_4$ represents a suitable leaving group, such as for example halo, e.g. bromo. All other variables in Scheme 5 are defined according to the present invention.

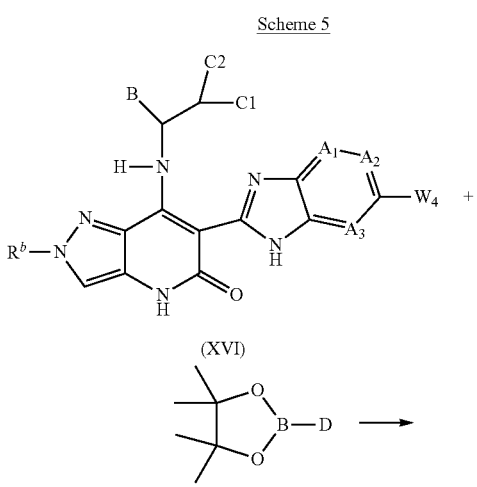

-continued

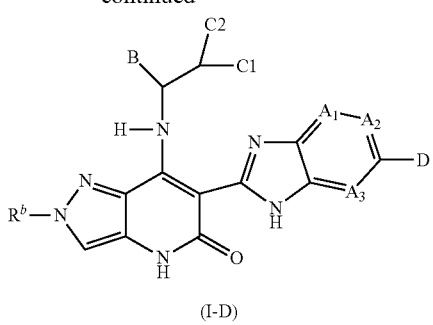

(I-D)

The reaction of Scheme 5 is performed in the presence of a suitable catalyst, such as for example a palladium catalyst, e.g. $Pd_2(dba)_3$, a suitable ligand, such as for example $PCy_3$ (tricyclohexylphosphine), a suitable base, such as for example $K_3PO_4$ (tripotassium phosphate), and a suitable solvent, such as for example dioxane and water.

In Scheme 5, the intermediate of formula (XVI) can be a specific stereoisomer, e.g. the S enantiomer, resulting in a specific stereoisomer, e.g. the S enantiomer, of formula (I-D), such as shown below in Scheme 5a for the preparation of compounds of formula (I-D-a).

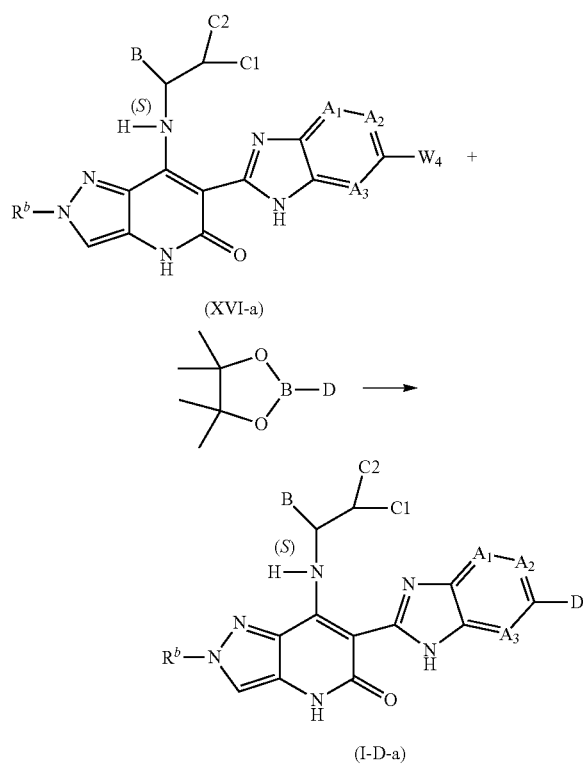

Scheme 5a (XVI-a)

(I-D-a)

Intermediates of formula (XVI) can be prepared according to the following reaction Scheme 6. In Scheme 6, $W_1$ represents a suitable leaving group, such as for example halo, e.g. chloro, and $W_4$ represents a suitable leaving group, such as for example halo, e.g. bromo. All other variables in Scheme 6 are defined according to the present invention.

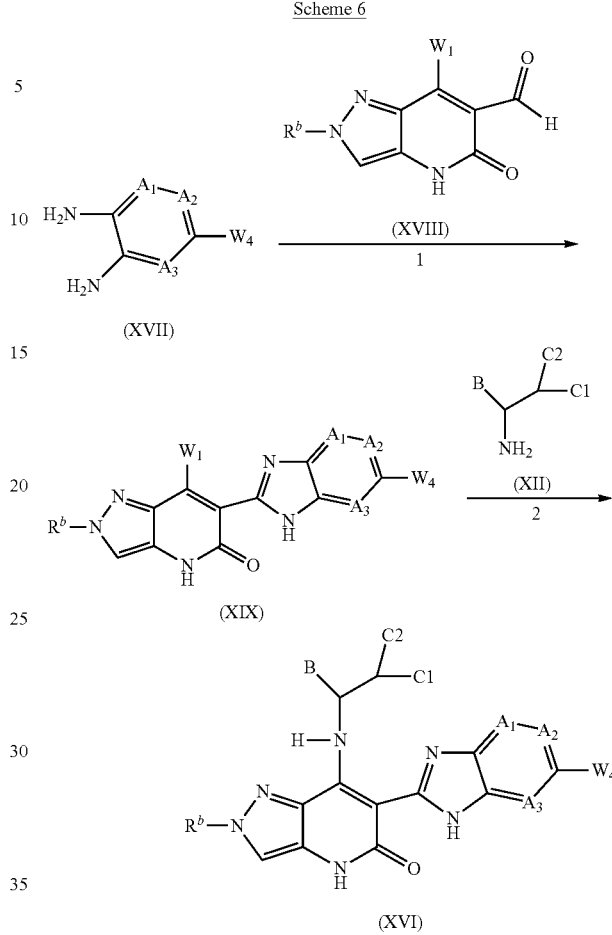

Scheme 6

(XVIII)

(XVII)

(XIX)

(XII)

(XVI)

In Scheme 6, the following reaction conditions apply:
1: in the presence of a suitable solvent, such as for example an alcohol, e.g. ethanol, at a suitable temperature, such as for example 70° C.;
2: in the presence of a suitable base, such as for example $NaHCO_3$, a suitable solvent, such as for example dimethylformamide, at a suitable temperature, such as for example 80° C.

The compounds of formula (I) may also be converted into each other via art-known reactions or functional group transformations.

For instance, compounds of formula (I) wherein $R_c$ represents $C_{1-6}$alkyl substituted with —C(=O)—O—$C_{1-6}$alkyl, or $C_{1-6}$alkyl-O—C(=O)—, can be converted into a compound of formula (I) wherein $R_c$ represents HOOC-C1-6alkyl or carboxyl in the presence of lithium hydroxide, and in the presence of a suitable solvent, such as for example tetrahydrofuran or an alcohol, e.g. methanol.

The compounds of the invention as prepared in the processes described herein may be synthesized in the form of mixtures of enantiomers, in particular racemic mixtures of enantiomers, that can be separated from one another following art-known resolution procedures. Racemic compounds of formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I), and the pharmaceutically acceptable addition salts and solvates thereof, involves liquid chromatography using a chiral stationary phase e.g. by supercritical fluid chromatography. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the preparation of compounds of the present invention, protection of remote functionality (e.g., primary or secondary amine) of intermediates may be necessary. The need for such protection varies depending on the nature of the remote functionality and the conditions of the preparation methods. Suitable amino-protecting groups (NH-PG) include acetyl, trifluoroacetyl, t-butoxycarbonyl (Boc), benzyloxycarbonyl (CBz) and 9-fluorenylmethylene-oxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

In all these preparations, the reaction products may be isolated from the reaction medium and, if necessary, further purified according to methodologies generally known in the art such as, for example, extraction, crystallization, trituration and chromatography. The purity of the reaction products may be determined according to methodologies generally known in the art such as for example LC-MS, TLC, HPLC.

A further aspect of the invention is a process for the preparation of a compound of formula (I) as defined herein, which process comprises:

(i) reacting an intermediate of formula (XI)

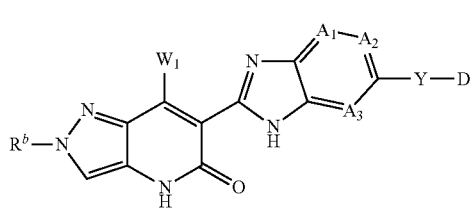

wherein $W_1$ represents a suitable leaving group, such as for example halo, e.g. chloro, with an intermediate of formula (XII)

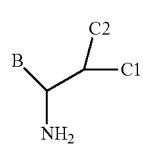

in the presence of a suitable base, such as for example N,N-diisopropylethylamine, potassium bicarbonate or sodium bicarbonate, a suitable phase-transfer catalyst, such as for example tetrabutylammonium iodide or 18-crown-6, and a suitable solvent, such as for example dichloromethane, chloroform, N,N-dimethylacetamide or an alcohol, e.g. ethanol; or (ii) reacting an intermediate of formula (XVI)

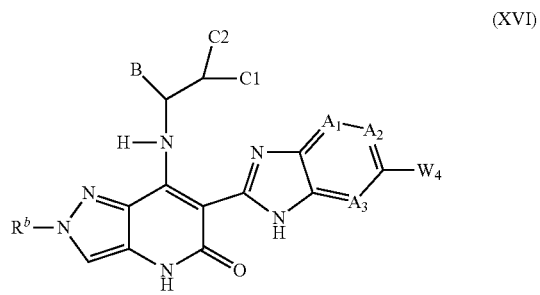

wherein $W_4$ represents a suitable leaving group, such as for example halo, e.g. bromo, with an intermediate of formula $(R^y)HN-D$ in the presence of a suitable catalyst, such as for example a palladium catalyst, e.g. $Pd_2(dba)_3$, a suitable ligand, such as for example davephos (2-dicyclohexylphosphino-2'-(N,N-dimethylamino)biphenyl), a suitable base, such as for example LiHMDS (lithium bis(trimethylsilyl)amide), and a suitable solvent, such as for example tetrahydrofuran; or (iii) reacting an intermediate of formula (XVI)

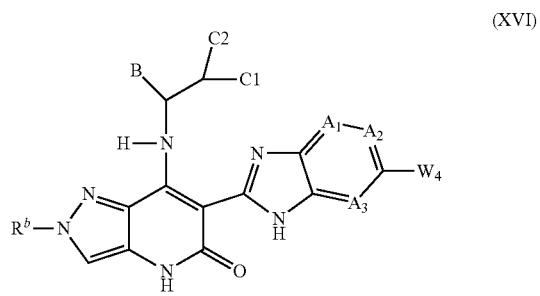

wherein $W_4$ represents a suitable leaving group, such as for example halo, e.g. bromo, with an intermediate of formula

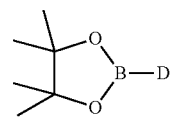

in the presence of a suitable catalyst, such as for example a palladium catalyst, e.g. $Pd_2(dba)_3$, a suitable ligand, such as for example $PCy_3$ (tricyclohexylphosphine), a suitable base, such as for example $K_3PO_4$ (tripotassium phosphate), and a suitable solvent, such as for example dioxane and water; wherein the variables are as defined herein; and optionally thereafter converting one compound of the formula (I) into another compound of the formula (I).

Pharmaceutically Acceptable Salts, Solvates or Derivatives Thereof

In this section, as in all other sections of this application, unless the context indicates otherwise, references to formula (I) include references to all other sub-groups, preferences, embodiments and examples thereof as defined herein.

Unless otherwise specified, a reference to a particular compound also includes ionic forms, salts, solvates, isomers, tautomers, and isotopes, for example, preferably, the salts or isomers or solvates thereof. Compounds of formula (I) can exist in the form of salts, for example acid addition salts or, in certain cases salts of organic and inorganic bases such as carboxylate, sulphonate and phosphate salts. All such salts are within the scope of this invention, and references to compounds of formula (I) include the salt forms of the compounds.

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The salts of the present invention can be synthesized from the parent compound that contains a basic or acidic moiety by conventional chemical methods such as methods described in *Pharmaceutical Salts; Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The compounds of the invention may exist as mono- or di-salts depending upon the pKa of the acid from which the salt is formed.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphorsulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethane-sulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic (e.g., —COOH may be —COO−), then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may form solvates, for example with water (i.e., hydrates) or common organic solvents. As used herein, the term "solvate" means a physical association of the compounds of the present invention with one or more solvent molecules, as well as pharmaceutically acceptable addition salts thereof. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water (hydrate), isopropanol, ethanol, methanol, DMSO, ethyl acetate, acetic acid or ethanolamine and the like. The compounds of the invention may exert their biological effects whilst they are in solution.

Solvates can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed.

Furthermore, the compounds of the present invention may have one or more polymorph (crystalline) or amorphous forms and these forms as such are intended to be included in the scope of the invention.

Compounds of formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I). Examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

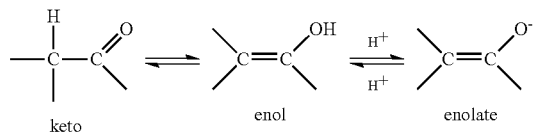

keto     enol     enolate

Such forms in so far as they may exist, are intended to be included within the scope of the present invention. It follows that a single compound may exist in both stereoisomeric and tautomeric form.

Where compounds of formula (I) contain one or more chiral centres, and can exist in the form of two or more optical isomers, references to compounds of formula (I) include all optical isomeric forms thereof (e.g. enantiomers, epimers and diastereoisomers), either as individual optical isomers, or mixtures (e.g. racemic mixtures) of two or more optical isomers, unless the context requires otherwise. When a compound of formula (I) has more than one chiral centre, and one chiral centre is indicated as having an absolute stereoconfiguration, such as in compounds of formula (I-a), (I-A-a), (I-B-a), (I-C-a) or (I-D-a), the other chiral centre(s) include all optical isomeric forms, either as individual optical isomers, or mixtures (e.g. racemic mixtures) of two or more optical isomers, thereof, unless the context requires otherwise. The optical isomers may be characterized and identified by their optical activity (i.e. as + and − isomers depending on the direction in which they rotate plane polarized light, or d and/isomers) or they may be characterized in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog (1966) *Angew. Chem. Int. Ed. Engl*, 5, 385-415. For instance, resolved enantiomers whose absolute configuration is not known can be designated by (+) or (−) depending on the direction in which they rotate plane polarized fight.

Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of formula (I) exist as two or more isomeric forms, one isomeric form, e.g. one enantiomer in a pair of enantiomers, may exhibit advantages over the other isomeric form, e.g. over the other enantiomer, for example, in terms of biological activity. Thus, in certain circumstances, it may be desirable to use as a therapeutic agent only one of a pair of enantiomers, or only one of a plurality of diastereoisomers. It was found that compounds wherein the chiral center indicated with * in the following structure

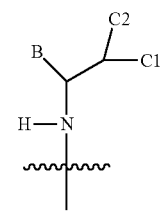

has the S configuration, exhibit higher biological activity than the corresponding R configuration. When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of formula (I) is for instance specified as (S), this means that the compound is substantially free of the (R) isomer; when a compound of formula (I) is for instance specified as E, this means that the compound is substantially free of the Z isomer; when a compound of formula (I) is for instance specified as cis, this means that the compound is substantially free of the trans isomer.

As used herein, any chemical formula with bonds shown only as solid lines and not as solid wedged or hashed wedged bonds, or otherwise not indicated as having a particular configuration (e.g. R, S) around one or more atoms, contemplates each possible stereoisomer, or mixture of two or more stereoisomers.

The terms "stereoisomers", "stereoisomeric forms" or "stereochemically isomeric forms" hereinbefore or hereinafter are used interchangeably.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The compounds of the invention include compounds with one or more isotopic substitutions, and a reference to a particular element includes within its scope all isotopes of the element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context. Radiolabeled compounds of formula (I) may comprise a radioactive isotope selected from the group of $^2H$, $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^2H$, $^3H$, $^{11}C$ and $^{18}F$. More preferably, the radioactive isotope is $^2H$.

In particular, deuterated compounds are intended to be included within the scope of the present invention.

Pharmacology

Protein Tyrosine Kinases (PTK)

The compounds of the invention described herein inhibit or modulate the activity of certain tyrosine kinases, and thus the compounds will be useful in the treatment or prophylaxis, in particular the treatment, of disease states or conditions mediated by those tyrosine kinases, in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signaling molecules which act as autocrine as well as paracrine factors. Autocrine FGF signaling may be particularly important in the progression of steroid hormone-dependent cancers to a hormone independent state. FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Knights et al., Pharmacology and Therapeutics 2010 125:1 (105-117); Korc M. et al Current Cancer Drug Targets 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4).

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signaling pathway. Rhabdomyosarcoma (RMS) is the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2. In addition, mutation screening in patients with syndromic craniosynostoses indicates that a number of recurrent FGFR2 mutations accounts for severe forms of Pfeiffer syndrome. Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene, and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signaling and suggests that the severe phenotypes of these disease syndromes result from ectopic ligand-dependent activation of fibroblast growth factor receptor 2.

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas. Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC). Increased expression was associated with mutation (85% of mutant tumors showed high-level expression) but also 42% of tumors with no detectable mutation showed over-expression, including many muscle-invasive tumors.

Over expression of FGFR4 has been linked to poor prognosis in both prostate and thyroid carcinomas. In addition, a germline polymorphism (Gly388Arg) is associated with increased incidence of lung, breast, colon, liver (HCC) and prostate cancers. In addition, a truncated form of FGFR4 (including the kinase domain) has also been found to be present in 40% of pituitary tumours but not present in normal tissue. FGFR4 overexpression has been observed in liver, colon and lung tumours. FGFR4 has been implicated in colorectal and liver cancer where expression of its ligand FGF19 is frequently elevated.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis. TGFβ1 and PDGF have been reported to be involved in the fibrogenic process and further published work suggests the elevation of FGF's and consequent increase in fibroblast proliferation, may be in response to elevated TGFβ1. The potential therapeutic benefit of targeting the fibrotic mechanism in conditions such as idiopathic pulmonary fibrosis (IPF) is suggested by the reported clinical effect of the anti-fibrotic agent pirfenidone. Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

As indicated hereinabove, a variety of FGFR inhibitors are in clinic trials and have shown clinic response in patients with FGFR aberrations. However, it has been reported that mutations affecting amino acids in FGFR, e.g. FGFR1, 2 or 3, may cause resistance to FGFR inhibitors or decrease sensitivity to FGFR inhibitors. The development of secondary FGFR kinase domain mutations upon treatment with FGFR inhibitors are an important mechanism of acquired resistance to FGFR inhibition. Equivalent FGFR point mutations exist also de novo in cancers. Gatekeeper mutations have been reported as one of the major mechanism leading to resistance to tyrosine kinase inhibitors. Gatekeeper mutations include FGFR3 V555L/V555M, FGFR1 V561M, FGFR2 V564F/V564I/V564M and FGFR4 V550L. FGFR resistant mutations have been reported in clinic trials and in vitro cellular systems. Therefore new (second generation) FGFR inhibitors are needed to overcome clinical acquired resistance to first generation FGFR inhibitor therapy and to maintain the FGFR inhibiting activity against the primary activating FGFR mutations at the same time.

It was found that the compounds of the invention show activity against wild type FGFRs, in particular FGFR1, 2, 3 or 4, more in particular FGFR3, but also against mutated FGFRs, in particular against FGFRs harboring gatekeeper mutations or against mutated FGFR1 or mutated FGFR2 or mutated FGFR3, in particular against FGFR3 V555L, FGFR3 V555M, FGFR1 V561M and FGFR2 V564I, particularly against FGFR3 V555L and FGFR3 V555M.

Biological Activity and Therapeutic Uses

The compounds of the invention, and subgroups thereof, have fibroblast growth factor receptor (FGFR) inhibiting or modulating activity and will be useful in preventing or treating, in particular treating disease states or conditions described herein. In addition, the compounds of the invention, and subgroups thereof, will be useful in preventing or treating, in particular treating diseases or condition mediated by the kinases. References to the preventing or prophylaxis or treatment of a disease state or condition such as cancer include within their scope alleviating or reducing the incidence of cancer.

In an embodiment, compounds of formula (I) are ATP-competitive inhibitors of FGFR kinase.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease state or condition, the biological role played by a kinase may be direct or indirect and may be necessary and/or sufficient for the manifestation of the symptoms of the disease state or condition (or its aetiology or progression). Thus, kinase activity (and in particular aberrant levels of kinase activity, e.g. kinase over-expression) need not necessarily be the proximal cause of the disease state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, the compounds of the invention may be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular against FGFR1, 2 and 3. More in particular compounds of the present invention show activity against wild type FGFRs and/or against mutated FGFRs, in particular FGFRs with point mutations, more in particular against gatekeeper mutations. Gatekeeper mutations include FGFR3 V555L/V555M, FGFR1 V561M, FGFR2 V564F/V564I/V564M and FGFR4 V550L. In particular the compounds of the present invention show activity against gatekeeper mutated FGFR1, FGFR2 and FGFR3, more in particular against FGFR3 V555L, FGFR3 V555M, FGFR1 V561M and FGFR2 V564I, in particular against FGFR3 V555L and FGFR3 V555M.

Diagnosis of tumours with mutations could be performed using techniques known to a person skilled in the art and as described herein such as RT-PCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example small cell lung cancer and non-small cell lung carcinomas (e.g. adenocarcinoma and squamous cell carcinoma)), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma. In particular, squamous lung cancer, breast cancer, colorectal cancer, glioblastoma, astrocytomas, prostate cancer, small cell lung cancer, melanoma, head and neck cancer, thyroid cancer, uterine cancer, gastric cancer, hepatocellular cancer, cervix cancer, multiple myeloma, bladder cancer, endometrial cancer, urothelial cancer, colon cancer, rhabdomyosarcoma, pituitary gland cancer, cholangiocarcinoma.

Examples of cancers which may be treated (or inhibited) include, but are not limited to, bladder cancer, urothelial cancer, metastatic urothelial cancer, surgically unresectable urothelial cancer, breast cancer, glioblastoma, lung cancer, non small cell lung cancer, squamous cell lung cancer, adenocarcinoma of the lung, pulmonary adenocarcinoma, small cell lung cancer, ovarian cancer, endometrial cancer, cervical cancer, soft tissue sarcoma, head and neck squamous cell carcinoma, gastric cancer, oesophageal cancer, squamous cell carcinoma of the oesophagus, adenocarcinoma of the oesophagus, cholangiocarcinoma, hepatocellular carcinoma.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombo-cythemia and primary myelofibrosis. A further haematological disorder is hypereosinophilic syndrome. T-cell lymphoproliferative diseases include those derived from natural Killer cells.

In addition, the compounds of the invention can be used to treat gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate, thyroid, lung, breast, and colon cancers.

A further subset of cancers includes multiple myeloma, bladder, hepatocellular, oral squamous cell carcinoma and cervical carcinomas.

The compounds of the invention, having FGFR such as FGFR1 inhibitory activity, may be particularly useful in the treatment or prevention of breast cancer in particular Classic Lobular Carcinomas (CLC) and lung cancer with FGFR1 amplification or FGFR1 mutations.

As the compounds of the invention have FGFR4 activity they will also be useful in the treatment of prostate or pituitary cancers, or they will be useful in the treatment of breast cancer, lung cancer, prostate cancer, liver cancer (HCC) or lung cancer.

In particular the compounds of the invention as FGFR inhibitors, are useful in the treatment of multiple myeloma, myeloproliferative disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are useful in the treatment of multiple myeloma (in particular multiple myeloma with t(4; 14) translocation or overexpressing FGFR3), prostate cancer (hormone refractory prostate carcinomas), endometrial cancer (in particular endometrial tumours with activating mutations in FGFR2) and breast cancer (in particular lobular breast cancer).

In particular the compounds of the invention are useful in the treatment of cholangiocarcinoma, in particular cholangiocarcinoma with FGFR translocations and mutations, or FGF19 amplifications.

In particular the compounds are useful in the treatment of lobular carcinomas such as CLC (Classic lobular carcinoma).

As the compounds have activity against FGFR3 they will be useful in the treatment of multiple myeloma and bladder cancer.

In particular, the compounds have activity against tumours with FGFR3-TACC3 translocation, in particular bladder or brain tumours with FGFR3-TACC3 translocation.

In particular the compounds are useful for the treatment of t(4; 14) translocation positive multiple myeloma.

In one embodiment the compounds may be useful for the treatment of sarcoma. In one embodiment the compounds may be useful for the treatment of lung cancer, e.g. squamous cell carcinoma.

As the compounds have activity against FGFR2 they will be useful in the treatment of endometrial, ovarian, gastric, hepatocellular, uterine, cervix and colorectal cancers. FGFR2 is also overexpressed in epithelial ovarian cancer, therefore the compounds of the invention may be specifically useful in treating ovarian cancer such as epithelial ovarian cancer.

In one embodiment, the compounds may be useful for the treatment of lung cancer, in particular NSCLC (non small cell lung cancer), squamous cell carcinoma, liver cancer, kidney cancer, breast cancer, colon cancer, colorectal cancer, prostate cancer.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR signaling may be determined by means of a cell growth assay as set out below or by a method as set out in the section headed "Methods of Diagnosis".

The compounds of the invention may be particularly useful in the treatment or prevention of cancers of a type associated with or characterized by the presence of elevated levels of FGFR.

The compounds of the invention may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions that the compounds of the invention may be useful consists of inflammatory diseases, cardiovascular diseases and wound healing.

FGFR is also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

The compound of the invention, having FGFR such as FGFR2 or FGFR3 inhibitory activity, may be particularly useful in the treatment or prevention of the skeletal diseases. Particular skeletal diseases are achondroplasia or thanatophoric dwarfism (also known as thanatophoric dysplasia).

The compound of the invention, having FGFR such as FGFR1, FGFR2 or FGFR3 inhibitory activity, may be particularly useful in the treatment or prevention in pathologies in which progressive fibrosis is a symptom. Fibrotic conditions in which the compounds of the inventions may be useful in the treatment of include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular, the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

The activity of the compounds of the invention as inhibitors of FGFR1-4, in particular point mutated FGFR3, such as for example FGFR3 V555L and FGFR3 V555M, can be measured using the assays set forth in the examples below and the level of activity exhibited by a given compound can be defined in terms of the $IC_{50}$ value. Preferred compounds of the present invention are compounds having an $IC_{50}$ value of less than 1 μM, more preferably less than 0.1 μM, less than 0.01 μM, or less than 0.001 μM.

The invention provides compounds that have FGFR inhibiting or modulating activity, and which may be useful in preventing or treating disease states or conditions mediated by FGFR kinases.

In one embodiment, there is provided a compound as defined herein for use in therapy, for use as a medicine. In a further embodiment, there is provided a compound as defined herein for use in the prophylaxis or treatment, in particular in the treatment, of a disease state or condition mediated by a FGFR kinase.

Thus, for example, the compounds of the invention may be useful in alleviating or reducing the incidence of cancer. Therefore, in a further embodiment, there is provided a compound as defined herein for use in the prophylaxis or treatment, in particular the treatment, of cancer. In one embodiment, the compound as defined herein is for use in the prophylaxis or treatment, in particular the treatment, of FGFR-dependent cancer. In one embodiment, the compound as defined herein is for use in the prophylaxis or treatment, in particular the treatment, of cancer mediated by FGFR kinases.

Accordingly, the invention provides inter alia.

A method for the prophylaxis or treatment of a disease state or condition mediated by a FGFR kinase, which method comprises administering to a subject in need thereof a compound of the formula (I) as defined herein.

A method for the prophylaxis or treatment of a disease state or condition as described herein, which method comprises administering to a subject in need thereof a compound of the formula (I) as defined herein.

A method for the prophylaxis or treatment of cancer, which method comprises administering to a subject in need thereof a compound of the formula (I) as defined herein, in particular a cancer harboring gatekeeper mutated FGFR1, FGFR2 or FGFR3, more in particular a cancer harboring FGFR3 V555L, FGFR3 V555M, FGFR1 V561M or FGFR2 V564I, in particular FGFR3 V555L or FGFR3 V555M. In an embodiment the cancer harbors in addition to a gatekeeper mutated FGFR1, FGFR2 or FGFR3, one or more other FGFR aberrations, such as for instance one or more FGFR mutations or one or more FGFR translocations, such as those defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use in the prophylaxis or treatment of cancer, in particular the treatment of cancer, in particular a cancer harboring gatekeeper mutated FGFR1, FGFR2 or FGFR3, more in particular a cancer harboring FGFR3 V555L, FGFR3 V555M, FGFR1 V561M or FGFR2 V564I, in particular FGFR3 V555L or FGFR3 V555M. In an embodiment the cancer harbors in addition to a gatekeeper mutated FGFR1, FGFR2 or FGFR3, one or more other FGFR aberrations, such as for instance one or more FGFR mutations or one or more FGFR translocations, such as those defined herein.

A compound of formula (I) as defined herein for use as a modulator (e.g. inhibitor) of FGFR.

Use of a compound of formula (I) as defined herein for the manufacture of a medicament for the prophylaxis or treatment, in particular the treatment, of a disease state or condition mediated by a FGFR kinase, the compound having the formula (I) as defined herein.

Use of a compound of formula (I) as defined herein for the manufacture of a medicament for the prophylaxis or treatment of a disease state or condition as described herein.

Use of a compound of formula (I) as defined herein for the manufacture of a medicament for the prophylaxis or treatment, in particular the treatment, of cancer, in particular a cancer harboring gatekeeper mutated FGFR1, FGFR2 or FGFR3, more in particular a cancer harboring FGFR3 V555L, FGFR3 V555M, FGFR1 V561M or FGFR2 V564I, in particular FGFR3 V555L or FGFR3 V555M. In an embodiment the cancer harbors in addition to a gatekeeper mutated FGFR1, FGFR2 or FGFR3, one or more other FGFR aberrations, such as for instance one or more FGFR mutations or one or more FGFR translocations, such as those defined herein.

Use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

Use of a compound of the formula (I) as defined herein for the manufacture of a medicament for prophylaxis or treatment of a disease or condition characterized by up-regulation of a FGFR kinase (e g. FGFR1 or FGFR2 or FGFR3 or FGFR4).

Use of a compound of the formula (I) as defined herein for the manufacture of a medicament for the prophylaxis or treatment of a cancer, the cancer being one which is characterized by up-regulation of a FGFR kinase (e.g. FGFR1 or FGFR2 or FGFR3 or FGFR4).

Use of a compound of the formula (I) as defined herein for the manufacture of a medicament for the prophylaxis or treatment of cancer in a patient selected from a sub-population possessing a genetic aberrations of FGFR3 kinase.

Use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterized by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterized by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterized by up-regulation of an FGFR kinase (e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of a FGFR kinase, thereafter administering to the patient a compound of the formula (I) as defined herein having FGFR kinase inhibiting activity.

In one embodiment, the disease mediated by FGFR kinases is an oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

Mutated Kinases

As indicated hereinabove, drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme.

A study in gastric cancer patient samples showed the presence of two mutations in FGFR2, Ser167Pro in exon IIa and a splice site mutation 940-2A-G in exon IIIc. These mutations are identical to the germline activating mutations that cause craniosynotosis syndromes and were observed in 13% of primary gastric cancer tissues studied. In addition, activating mutations in FGFR3 were observed in 5% of the patient samples tested and overexpression of FGFRs has been correlated with a poor prognosis in this patient group.

In addition, there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR. Diagnosis of tumours with such mutations could be performed using techniques known to a person skilled in the art and as described herein such as RT-PCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561M showed that this mutation conferred resistance to a tyrosine kinase inhibitor compared to that of the wild type. Other mutations that have been found are gatekeeper mutations FGFR3 V555L/V555M, FGFR1 V561M, FGFR2 V564F/V564I/V564M and FGFR4 V550L. The compounds of the invention are specifically active against gatekeeper mutations, in particular against FGFR3 V555L, FGFR3 V555M, FGFR1 V561M and FGFR2 V564I, particularly against FGFR3 V555L and FGFR3 V555M.

The compounds of the present invention may be useful for the treatment of the adult population. The compounds of the present invention may be useful for the treatment of the pediatric population.

Methods of Diagnosis

Prior to administration of a compound of the formula (I), a patient may be screened to determine whether a disease or condition from which the patient is or may be suffering is one which would be susceptible to treatment with a compound having activity against FGFR, in particular FGFR harboring point mutations, in particular FGFR gatekeeper mutations such as for example FGFR3 V555L, FGFR3 V555M, FGFR1 V561M and FGFR2 V564I, in particular FGFR3 V555L and FGFR3 V555M. In an embodiment the cancer harbors in addition to a FGFR gatekeeper mutation, in particular a gatekeeper mutated FGFR1, FGFR2 or FGFR3, such as for example FGFR3 V555L, FGFR3 V555M, FGFR1 V561M and FGFR2 V564I, in particular FGFR3 V555L and FGFR3 V555M, one or more other FGFR aberrations, such as for instance one or more FGFR mutations or one or more FGFR translocations, such as those defined herein.

For example, a biological sample taken from a patient may be analysed to determine whether a condition or disease, such as cancer, that the patient is or may be suffering from is one which is characterized by a genetic abnormality or abnormal protein expression which leads to up-regulation of the levels or activity of FGFR or to sensitisation of a pathway to normal FGFR activity, or to upregulation of these growth factor signaling pathways such as growth factor ligand levels or growth factor ligand activity or to upregulation of a biochemical pathway downstream of FGFR activation.

Examples of such abnormalities that result in activation or sensitisation of the FGFR signal include loss of, or inhibition of apoptotic pathways, up-regulation of the receptors or ligands, or presence of mutant variants of the receptors or ligands e.g PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions. In particular activating mutations in FGFR2 have been identified in 10% of endometrial tumours.

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas. A particular mutation T674I of the PDGF receptor has been identified in imatinib-treated patients. In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway.

Alternatively, a biological sample taken from a patient may be analysed for loss of a negative regulator or suppressor of FGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR. The term diagnosis includes screening. By marker we include genetic markers including, for example, the measurement of DNA composition to identify mutations of FGFR. The term marker also includes markers which are characteristic of up regulation of FGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR may mean that the patient would be particularly suitable for treatment with a FGFR inhibitor. Tumours may preferentially be screened for presence of a FGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer,* 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR or detection of FGFR variants or mutants could be applicable in the present case.

Abnormal levels of proteins such as FGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR including the isoforms thereof, include the measurement of microvessel density. This can for example be measured using methods described by Orre and Rogers (Int J Cancer (1999), 84(2) 101-8).

Therefore, all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcinomas and causes constitutive activation of the kinase activity. Activating mutations of FGFR3 have also been identified in bladder carcinoma cases. These mutations were of 6 kinds with varying degrees of prevalence: R248C, S249C, G372C, S373C, Y375C, K652Q. In addition, a Gly388Arg polymorphism in FGFR4 has been found to be associated with increased incidence and aggressiveness of prostate, colon, lung, liver (HCC) and breast cancer. The compounds of the invention are particularly useful in the treatment of a patient having a FGFR3-TACC3 translocation.

Therefore, in a further aspect the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y373C, K652Q mutations in FGFR3 and Gly388Arg polymorphism in FGFR4, in particular FGFR3 R248C, FGFR3 S249C, FGFR3 G370C, or FGFR3 Y373C.

Particular mutations a patient is screened for include in particular FGFR gatekeeper mutations. Gatekeeper mutations include FGFR3 V555L/V555M, FGFR1 V561M, FGFR2 V564F/V564I/V564M and FGFR4 V550L. Particular mutations a patient is screened for include FGFR3 V555L, FGFR3 V555M, FGFR1 V561M and FGFR2 V564I, in particular FGFR3 V555L and FGFR3 V555M.

In another aspect, the invention includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

The compounds of the invention are particular useful in the treatment of a patient having a FGFR fusion or translocation, in particular FGFR3:TACC3 v1; FGFR3:TACC3 v3; FGFR3:TACC3 Intron; FGFR3:BAIAP2L1; FGFR2:AFF3; FGFR2:BICC1; FGFR2:CASP7; FGFR2:CCDC6; and FGFR2:OFD1. The following abbreviations are used: FGFR (fibroblast growth factor receptor); FGFR3:TACC3 (fusion between genes encoding FGFR3 and transforming acidic coiled-coil containing protein 3); FGFR3:BAIAP2L1 (fusion between genes encoding FGFR3 and brain-specific angiogenesis inhibitor 1-associated protein 2-like protein 1); FGFR2:AFF3 (fusion between genes encoding FGFR2 and AF4/FMR2 family, member 3); FGFR2:BICC1 (fusion between genes encoding FGFR2 and bicaudal C homolog 1); FGFR2:CASP7 (fusion between genes encoding FGFR2 and caspase 7); FGFR2:CCDC6 (fusion between genes encoding FGFR2 and coiled-coil domain containing 6); FGFR2:OFD1 (fusion between genes encoding FGFR2 and oral-facial-digital syndrome 1).

Pharmaceutical Compositions and Combinations

In view of their useful pharmacological properties, the subject compounds may be formulated into various pharmaceutical forms for administration purposes.

In one embodiment the pharmaceutical composition (e.g. formulation) comprises at least one active compound of the invention together with a pharmaceutically acceptable carrier which may include adjuvants, excipients, diluents, fillers, buffers, stabilisers, preservatives, lubricants, or other materials well known to those skilled in the art and optionally other therapeutic or prophylactic agents.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intravaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to exert its anti-tumour activity or to exert its FGFR inhibiting effect.

In an embodiment, the compound of the invention or the pharmaceutical composition of the invention is for oral administration.

Those skilled in the art could determine the effective amount from the test results presented hereinafter. In general, it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

As another aspect of the present invention, a combination of a compound of the present invention with another anticancer agent is envisaged, especially for use as a medicine, more specifically for use in the treatment of cancer or related diseases, in particular a condition or disease mediated by a FGFR kinase.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoids for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and anti angiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors, cmet inhibitors) for example flavoperidol, imatinib mesylate, erlotinib, gefitinib, dasatinib, lapatinib, lapatinib ditosylate, sorafenib, sunitinib, sunitinib maleate, temsirolimus, 6-{difluoro[6-(1-methyl-1H-pyrazol-4-yl)-[1,2,4]triazolo[4,3-b]pyridazin-3-yl]methyl}quinoline or a pharmaceutically acceptable salt thereof, 6-[difluoro(6-pyridin-4-yl[1,2,4]triazolo[4,3-b]pyridazin-3-yl)methyl]quinoline or a pharmaceutically acceptable salt thereof;

famesyltransferase inhibitors for example tipifarnib;

histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat.

Recombinant interleukins for example aldesleukin, denileukin diftitox, interferon alfa 2a, interferon alfa 2b, peginterferon alfa 2b MAPK inhibitors Retinoids for example alitretinoin, bexarotene, tretinoin Arsenic trioxide Asparaginase Steroids for example dromostanolone propionate, megestrol acetate, nandrolone (decanoate, phenpropionate), dexamethasone Gonadotropin releasing hormone agonists or antagonists for example abarelix, goserelin acetate, histrelin acetate, leuprolide acetate Thalidomide, lenalidomide Mercaptopurine, mitotane, pamidronate, pegademase, pegaspargase, rasburicase BH3 mimetics for example ABT-737

MEK inhibitors for example PD98059, AZD6244, CI-1040 colony-stimulating factor analogs for example filgrastim, pegfdgrastim, sargramostim; erythropoietin or analogues thereof (e.g. darbepoetin alfa); interleukin 11; oprelvekin; zoledronate, zoledronic acid; fentanyl; bisphosphonate; palifermin.

a steroidal cytochrome P450 17alpha-hydroxylase-17,20-lyase inhibitor (CYP17), e.g. abiraterone, abiraterone acetate an antibody that blocks the interaction between PD-1 and PD-L1.

In one embodiment, the present invention relates to a combination of a compound of formula (I), a pharmaceutically acceptable salt thereof or a solvate thereof, or any sub-groups and examples thereof, and 6-{difluoro[6-(1-methyl-1H-pyrazol-4-yl)[1,2,4]triazolo[4,3-b]-pyridazin-3-yl]methyl}quinoline or a pharmaceutically acceptable salt thereof.

In one embodiment, the present invention relates to a combination of a compound of formula (I), a pharmaceutically acceptable salt thereof or a solvate thereof, or any sub-groups and examples thereof, and 6-[difluoro(6-pyridin-4-yl[1,2,4]triazolo[4,3-b]pyridazin-3-yl)-methyl]quinoline or a pharmaceutically acceptable salt thereof.

In one embodiment, the present invention relates to a pharmaceutical composition comprising a compound of formula (I), a pharmaceutically acceptable salt thereof or a solvate thereof, or any sub-groups and examples thereof, and 6-{difluoro[6-(1-methyl-1H-pyrazol-4-yl)[1,2,4]-triazolo[4,3-b]pyridazin-3-yl]methyl}quinoline or a pharmaceutically acceptable salt thereof.

In one embodiment, the present invention relates to a pharmaceutical composition comprising a compound of formula (I), a pharmaceutically acceptable salt thereof or a solvate thereof, or any sub-groups and examples thereof, and 6-[difluoro(6-pyridin-4-yl[1,2,4]triazolo[4,3-b]-pyridazin-3-yl)methyl]quinoline or a pharmaceutically acceptable salt thereof.

The compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same. Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the compound according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the compound according to the present invention together with a pharmaceutically acceptable carrier.

The present invention further relates to the use of a combination according to the invention in the manufacture of a pharmaceutical composition for inhibiting the growth of tumour cells.

The present invention further relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

These dosages may be administered for example once, twice or more per course of treatment, which may be repeated for example every 7, 14, 21 or 28 days.

The compounds of formula (I), the pharmaceutically acceptable addition salts, in particular pharmaceutically acceptable acid addition salts, and stereoisomeric forms thereof can have valuable diagnostic properties in that they can be used for detecting or identifying the formation of a complex between a labelled compound and other molecules, peptides, proteins, enzymes or receptors.

The detecting or identifying methods can use compounds that are labelled with labelling agents such as radioisotopes, enzymes, fluorescent substances, luminous substances, etc.

Examples of the radioisotopes include $^{125}I$, $^{131}I$, $^{3}H$ and $^{14}C$. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

EXPERIMENTAL PART

Several methods for preparing the compounds of the invention are illustrated in the following examples. Unless otherwise noted, all starting materials were obtained from commercial suppliers and used without further purification.

When a stereocenter is indicated with 'RS' this means that a mixture of stereoisomers was obtained at the indicated center, unless otherwise indicated. The stereochemical configuration for a stereocenter in some compounds is designated "R" or "S" and/or with a solid wedged or hashed wedged bond indicating the absolute stereoconfiguration is known. For some compounds, the stereochemical configuration at an indicated stereocenter has been designated as "R*" or "S*" with a solid line bond, or a solid wedged or a hashed wedged bond indicating the absolute stereochemistry at the stereocenter is undetermined although it is absolute. So a stereocenter indicated as being S* means it is an absolute stereocenter but it is not determined whether it is S or R.

Hereinafter, the terms: 'RT' or 'rt' means room temperature; 'TFA' means trifluoroacetic acid, 'FA' means formic acid, 'TfOH' means trifluoromethanesulfonic acid, 'DIPEA' means ethyldiisopropylamine or N-ethyl-N-isopropylpropan-2-amine or N,N-diisopropylethylamine, 'R$_T$' or 'R$_t$' means retention time, '18-crown-6' means 1,4,7,10,13,16-Hexaoxacyclo-octadecane, 'SFC' means supercritical fluid chromatography, 'ACN' means acetonitrile, 'DEA' means diethylamine, 'IPA' means isopropyl alcohol, 'DIBAL-H' means diisopropylaluminium hydride, 'PMB' means 4-methoxybenzyl, 'EtOAc' means ethyl acetate, 'DMF' means N,N-dimethylformamide, 'DCM' means dichloromethane, 'DMAc' means N,N-dimethylacetamide, 'THF' means tetrahydrofuran, 'Bn' means benzyl, 'M.P.' or 'm.p.' means melting point, 'HPLC' means High-performance Liquid Chromatography, 'TLC' means Thin Layer chromatography, 'LC-MS' means Liquid Chromatography-mass spectrometry, 'ee' means enantiomeric excess.

Example 1

Preparation of Compound 1

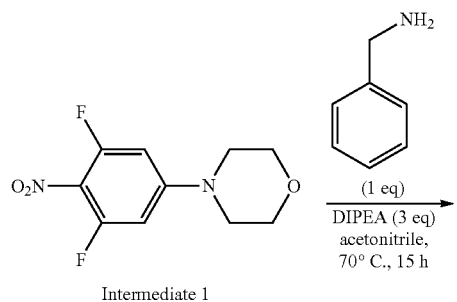

Intermediate 1

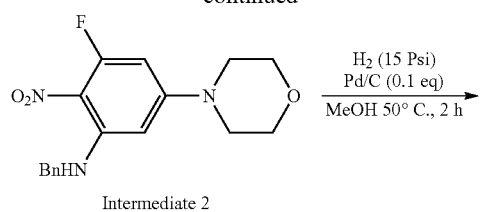

Intermediate 2

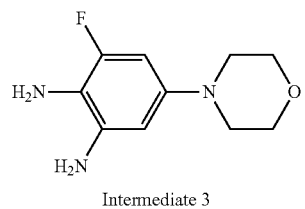

Intermediate 3

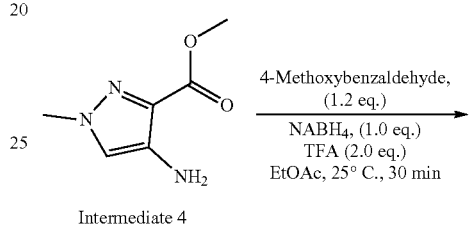

Intermediate 4

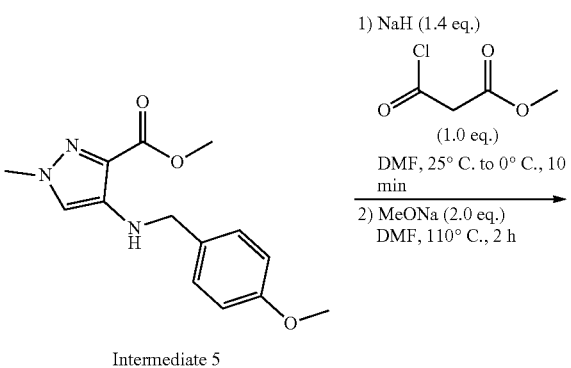

Intermediate 5

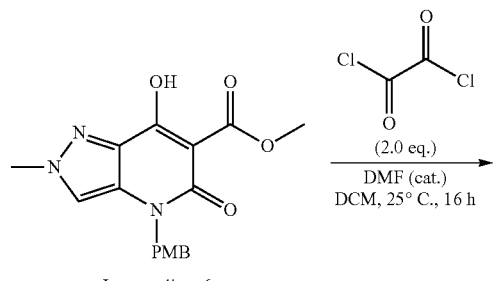

Intermediate 6

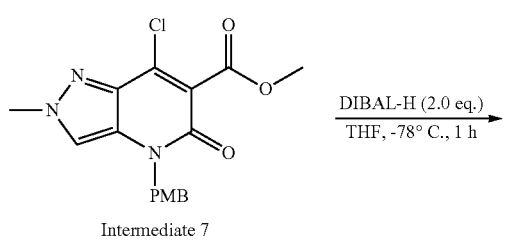

Intermediate 7

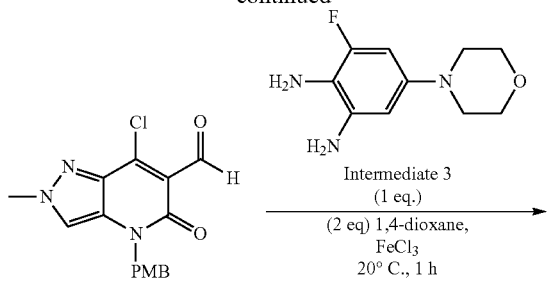

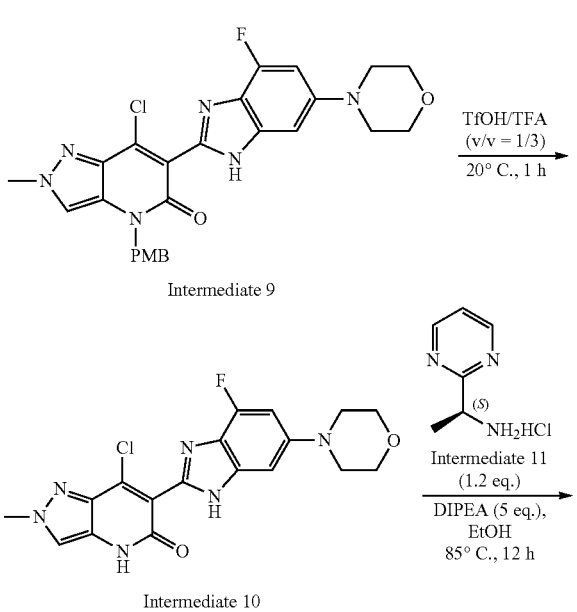

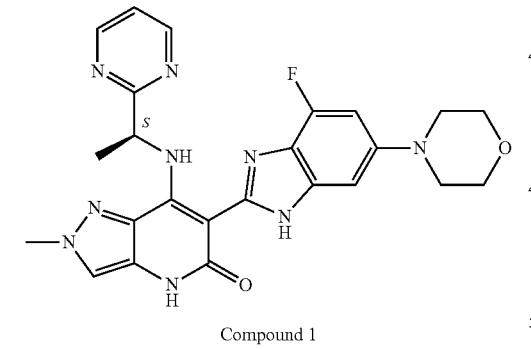

a) Preparation of Intermediate 1

4-(3,5-difluoro-4-nitrophenyl)morpholine

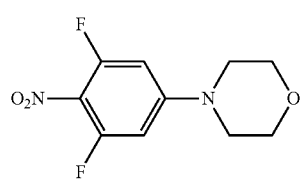

Intermediate 1 was synthesized as described in Bioorganic and Medicinal Chemistry Letters, 2012, vol. 22, #18, 5876-5884.

General procedure A: $^1$H NMR (400 MHz, CHLOROFORMS) (Varian) δ=6.43-6.39 (m, 1H), 6.39-6.34 (m, 1H), 3.93-3.74 (m, 4H), 3.41-3.22 (m, 4H)

b) Preparation of Intermediate 2

N-benzyl-3-fluoro-5-morpholino-2-nitroaniline

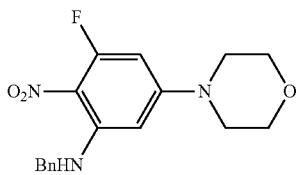

To a solution of intermediate 1 (4-(3,5-difluoro-4-nitrophenyl)morpholine) (5.00 g, 20.5 mmoL) and N-ethyl-N-isopropylpropan-2-amine (7.94 g, 61.4 mmol) in acetonitrile (150 mL) was added phenylmethanamine (2.19 g, 20.5 mmol) dropwise at 20° C. The reaction mixture was heated to 70° C. for 12 hours. Then the mixture was concentrated under reduced pressure to remove most of the solvent and the resulting orange oil was dissolved in ethyl acetate (1 L). The mixture was washed with water (200 mL×3) and brine (300 mL), dried over anhydrous sodium sulfate and filtered. The filtrate was concentrated to give the crude product which was purified by flash column chromatography (eluting with: petroleum ether:ethyl acetate from 1:0 to 1:1) to give intermediate 2 (4.80 g, 70.8% yield) as saffron yellow solids.

General Procedure A: $^1$H NMR (400 MHz, DMSO-d$^6$) (Varian) 8.58-8.47 (m, 1H), 7.44-7.32 (m, 4H), 7.31-7.22 (m, 1H), 6.38-6.26 (m, 1H), 5.80 (d, J=1.5 Hz, 1H), 4.54 (d, J=5.7 Hz, 2H), 3.67-3.57 (m, 4H), 3.30-3.22 (m, 4H).

c) Preparation of Intermediate 3

3-Fluoro-5-morpholinobenzene-1,2-diamine

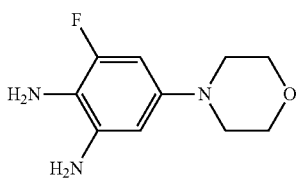 [SMILES: Nc1cc(N2CCOCC2)cc(F)c1N]

Wet palladium on activated carbon (642 mg, 10% on activated carbon) was added to a solution consisting of intermediate 2 (A-benzyl-3-fluoro-5-morpholino-2-nitroaniline) (2.00 g, 6.04 mmol) and methanol (60 mL) in a 250 mL round-bottomed flask. The suspension was degassed under vacuum and purged with hydrogen, then stirred at 50° C. under hydrogen (15 psi) for 2 hours. The mixture was filtered and the filtrate was evaporated under vacuum to afford intermediate 3 (1.10 g, 75.5% purity, 65.1% yield) as black solids.

LC-MS (ESI) (General Procedure B, Method 6): RT=1.26 min, mass calcd. for $C_{10}H_{14}FN_3O$ 211.11, m/z found 212.2 $[M+H]^+$.

d) Preparation of Intermediate 4

Methyl 4-amino-1-methyl-1H-pyrazole-3-carboxylate

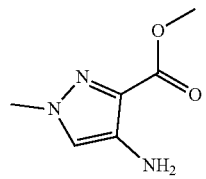

Intermediate 4 was synthesized as described in *ACS Medicinal Chemistry Letters*, 2013, vol. 4, #10, 979-984.

e) Preparation of Intermediate 5

Methyl 4-((4-methoxybenzyl)amino)-1-methyl-1H-pyrazole-3-carboxylate

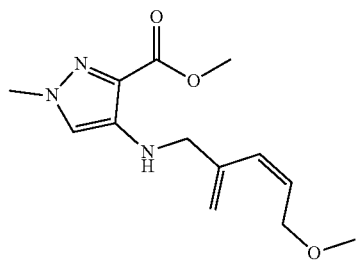

To a solution of intermediate 4 (methyl 4-amino-1-methyl-1H-pyrazole-3-carboxylate) (7.50 g, 48.3 mmol) in ethyl acetate (150 mL) was added 4-methoxybenzaldehyde (7.90 g, 58.0 mmol) and trifluoroacetic acid (7.2 mL, 96.7 mmol). Sodium borohydride (1.83 g, 48.3 mmol) was added to the mixture in portions while keeping the temperature below 35° C. After addition, the mixture was stirred at 25° C. for 30 minutes. The reaction mixture was quenched with water (100 mL) and stirred at 25° C. for 1 hour. Then the mixture was separated and the aqueous layer was extracted with ethyl acetate (50 mL×3). The combined organic layers were washed with brine (100 mL), dried over anhydrous $Na_2SO_4$ and filtered. The filtrate was concentrated to give the crude product which was purified by flash column chromatography (eluting with: petroleum ether:ethyl acetate from 1:0 to 5:4) to give intermediate 5 (7.92 g, 73.9% purity, 73.2% yield) as white solids.

LC-MS (ESI) (General Procedure C, Method 9): RT=0.663 min, mass calcd. for $C_{14}H_{17}N_3O_3$ 275.13, m/z found 275.9 $[M+H]^+$.

f) Preparation of Intermediate 6

Methyl 7-hydroxy-4-(4-methoxybenzyl)-2-methyl-5-oxo-4,5-dihydro-2H-pyrazolo[4,3-b]-pyridine-6-carboxylate

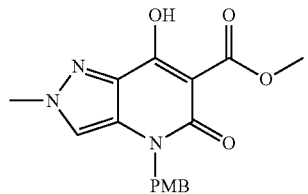

To a solution of intermediate 5 (methyl 4-((4-methoxybenzyl)amino)-1-methyl-1H-pyrazole-3-carboxylate) (13.2 g, 47.9 mmol) in N,N-dimethylformamide (300 mL) was added sodium hydride (2.68 g, 67.1 mmol) in portions. The mixture was stirred at 20° C. for 10 minutes and cooled to 0° C. Methyl malonyl chloride (6.54 g, 47.9 mmol) was dropwise added to the mixture and the mixture was further stirred at 20° C. for 15 minutes. Sodium methoxide (5.18 g, 95.9 mmol) was added to the reaction and the mixture was heated at 110° C. for 2 hours. The reaction mixture was concentrated to give a residue which was dissolved in water (200 mL) and filtered. The filtrate was extracted with tert-butyl methyl ether (100 mL). To the aqueous layer was added concentrated hydrochloric acid to adjust the pH to 3-4 with white solids precipitating out. The collected precipitation was dissolved in dichloromethane (200 mL). The resulting organic solution was washed with brine (300 mL), dried over anhydrous $Na_2SO_4$ and filtered. The filtrate was concentrated to give intermediate 6 (10.0 g, crude) as yellow oil which was used for next step directly.

g) Preparation of Intermediate 7

Methyl 7-chloro-4-(4-methoxybenzyl)-2-methyl-5-oxo-4,5-dihydro-2H-pyrazolo[4,3-b]-pyridine-6-carboxylate

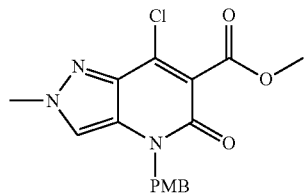

To a solution of intermediate 6 (methyl 7-hydroxy-4-(4-methoxybenzyl)-2-methyl-5-oxo-4,5-dihydro-2H-pyrazolo[4,3-b]pyridine-6-carboxylate) (10.0 g, 29.1 mmol) in dichloromethane (200 mL) was added oxalyl chloride (4.9 mL, 58.2 mmol) and N,N-dimethylformamide (10 drops). The mixture was stirred at 25° C. for 16 hours. Then the mixture was concentrated to give a residue which was dissolved in dichloromethane (200 mL). The resulting solution was washed with water (100 mL×2), brine (100 mL), dried over anhydrous $Na_2SO_4$ and filtered. The filtrate was concentrated to give a residue. The residue was purified by flash column chromatography (eluting with: petroleum ether:ethyl acetate from 1:0 to 5:4) to give intermediate 7 (10.0 g, 94.9% yield) as yellow solids.

General Procedure A: $^1$H NMR (400 MHz, DMSO-d$^6$) (Varian) δ 8.22 (s, 1H), 7.29 (d, J=8.6 Hz, 2H), 6.88 (d, J=8.6 Hz, 2H), 5.06 (s, 2H), 4.07-4.02 (m, 3H), 3.87 (s, 3H), 3.70 (s, 3H).

h) Preparation of Intermediate 8

7-Chloro-4-(4-methoxybenzyl)-2-methyl-5-oxo-4,5-dihydro-2H-pyrazolo[4,3-b]pyridine-6-carbaldehyde

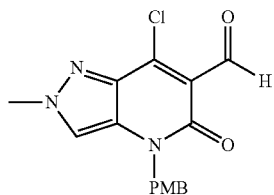

To a solution of intermediate 7 (methyl 7-chloro-4-(4-methoxybenzyl)-2-methyl-5-oxo-4,5-dihydro-2H-pyrazolo [4,3-b]pyridine-6-carboxylate) (7.00 g, 19.3 mmol) in tetrahydrofuran (200 mL) was added diisobutylaluminum hydride in toluene (38.7 mL, 1 M in toluene, 38.7 mmol) dropwise at −78° C. The mixture was stirred at −78° C. for 1 hour. The reaction was quenched with saturated aqueous solution of ammonium chloride (50 mL) at −78° C. and allowed to raise the temperature to 25° C. The mixture was stirred for 1 hour. The mixture was added to 200 mL of CHCl$_3$ and filtered. The filter cake was washed with 200 mL of CHCl$_3$ and filtered for 3 times. The combined organic layers were dried over anhydrous Na$_2$SO$_4$ and filtered. The filtrate was concentrated to give a residue. 30 mL of tert-Butyl methyl ether was added and stirred at 25° C. for 30 minutes. The precipitate was filtered to give intermediate 8 (5.00 g, 73.2% yield) as yellow solids.

LC-MS (ESI) (General Procedure C, Method 9): RT=0.69 min, mass calcd. for C$_{16}$H$_{14}$ClN$_3$O$_3$ 331.07, m/z found 331.9 [M+H]$^+$.

i) Preparation of Intermediate 9

7-Chloro-6-(4-fluoro-6-morpholino-1H-benzo[d] imidazol-2-yl)-4-(4-methoxybenzyl)-2-methyl-2H-pyrazolo[4,3-b]pyridin-5(4H)-one

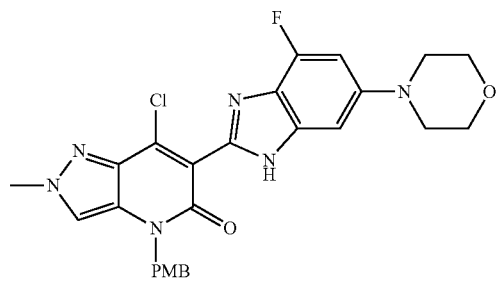

A solution of intermediate 8 (7-Chloro-4-(4-methoxybenzyl)-2-methyl-5-oxo-4,5-dihydro-2H-pyrazolo[4,3-b]pyridine-6-carbaldehyde) (400 mg, 1.21 mmol), intermediate 3 (3-fluoro-5-morpholinobenzene-1,2-diamine) (255 mg, 1.21 mmol) and ferric trichloride (391 mg, 2.41 mmol) in 1,4-dioxane (15 mL) was stirred at room temperature for 1 hour. The mixture was filtered and the filtrate was extracted 3 times with dichloromethane (300 mL in total). The combined organic layer was washed with saturated sodium bicarbonate solution (200 mL) and water (300 mL), dried over anhydrous Na$_2$SO$_4$ and filtered. The filtrate was evaporated under vacuum to afford intermediate 9 (360 mg, 36.8% yield, 64.5% purity) as brown solids. LC-MS (ESI) (General Procedure C, Method 9): RT=0.77 min, mass calcd. for C$_{26}$H$_{24}$ClFN$_6$O$_3$ 522.16, m/z found 523.1 [M+H]$^+$.

j) Preparation of Intermediate 10

7-Chloro-6-(4-fluoro-6-morpholino-1H-benzo[d] imidazol-2-yl)-2-methyl-2H-pyrazolo-[4,3-b]pyridin-5(4H)-one

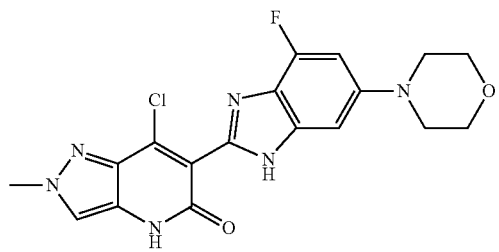 [SMILES: Cn1cc2[nH]c(=O)c(-c3nc4c(F)cc(N5CCOCC5)cc4[nH]3)c(Cl)c2n1]

To a solution of intermediate 9 (7-chloro-6-(4-fluoro-6-morpholino-1H-benzo[d]imidazol-2-yl)-4-(4-methoxybenzyl)-2-methyl-2H-pyrazolo[4,3-b]pyridin-5(4H)-one) (350 mg, 0.432 mmol) in trifluoroacetic acid (6 mL) was added trifluoromethanesulfonic acid (2 mL). The reaction mixture was stirred at 20° C. for 1 hour. Then the mixture evaporated to remove most of the trifluoroacetic acid. The residue was dissolve in dichloromethane (100 mL) and the mixture was alkalized by saturated sodium bicarbonate solution until pH>7. The mixture was separated and the organic layer was washed with brine (50 mL), dried over anhydrous Na$_2$SO$_4$ and filtered. The filtrate was evaporated under vacuum to afford intermediate 10 (160 mg, crude) as brown solids which was used for next step directly.

k) Preparation of Compound 1

(S)-6-(4-fluoro-6-morpholino-1H-benzo[d]imidazol-2-yl)-2-methyl-7-((1-(pyrimidin-2-yl)ethyl)amino)-2H-pyrazolo[4,3-b]pyridin-5(4H)-one

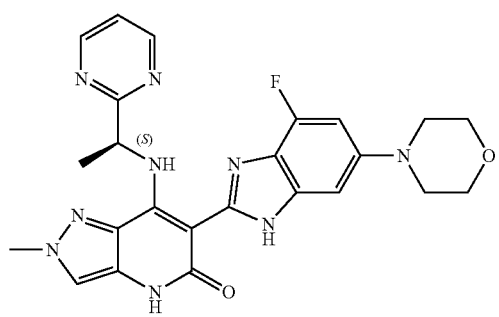

A solution of intermediate 10 (7-chloro-6-(4-fluoro-6-morpholino-1H-benzo[d]imidazol-2-yl)-2-methyl-2H-pyrazolo[4,3-b]pyridin-5(4H)-one) (150 mg, 0.372 mmol), intermediate 11 ((S)-1-(pyrimidin-2-yl)ethanamine hydrochloride) (71.3 mg, 0.447 mmol) and N-ethyl-N-isopropylpropan-2-amine (241 mg, 1.86 mmol) in ethanol (5 mL) was stirred at 85° C. for 1 hour. The mixture was concentrated under reduced pressure to afford the crude product which was purified by prep. HPLC (Column: Phenomenex Gemini C18 250*50 10 u, Mobile Phase A: water (0.225% FA), Mobile Phase B: acetonitrile, Flow rate: 22 mL/min, gradient condition from 28% B to 58%). The pure fractions were collected and the solvent was evaporated under vacuum, and then lyophilized to give the compound, which was further separated by supercritical fluid chromatography (separation condition: AD (250 mm*30 mm, 5 um) column; Mobile phase: A: Supercritical $CO_2$, B: 0.1% $NH_3H_2O$ MeOH, A:B=50:50 at 55 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The pure fraction was collected and the solvent was evaporated under vacuum. The residue was re-suspended in water (10 mL) and the resulting mixture was lyophilized to give compound 1 (15.5 mg, 98.9% purity, 8.41% yield) as a brown powder.

LC-MS (ESI) (General Procedure A, Method 2): RT=4.35 min, mass calcd. for $C_{24}H_{24}FN_9O_2$ 489.20, m/z found 490.0 $[M+H]^+$.

General Procedure A: $^1$H NMR (400 MHz, DMSO-d$^6$) (Varian) 13.26 (d, J=2.0 Hz, 0.1H), 13.00 (d, J=2.0 Hz, 0.9H), 12.53 (d, J=7.9 Hz, 0.9H), 12.43 (d, J=7.9 Hz, 0.1H), 11.05 (s, 1H), 10.90 (s, 0.9H), 8.86 (d, J=4.9 Hz, 0.1H), 8.81 (d, J=4.9 Hz, 1.9H), 7.71 (s, 0.1H), 7.67 (s, 0.9H), 7.41 (t, J=4.9 Hz, 1H), 7.04 (d, J=2.0 Hz, 1H), 6.75 (dd, J=1.9, 13.8 Hz, 1H), 6.41 (quint, J=7.1 Hz, 1H), 3.99-3.94 (m, 3H), 3.80-3.73 (m, 4H), 3.16-3.07 (m, 4H), 1.75-1.67 (m, 3H).

SFC (Method 14): $R_T$=2.63 min, Peak Area: 100%.

Example 2

Preparation of Compound 2

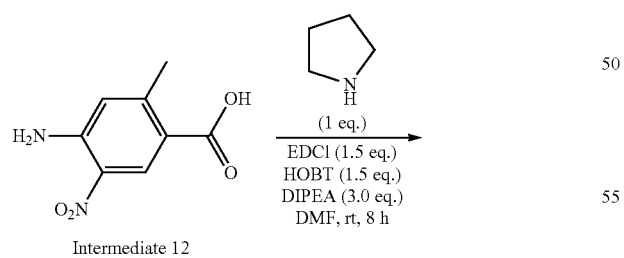

Intermediate 12

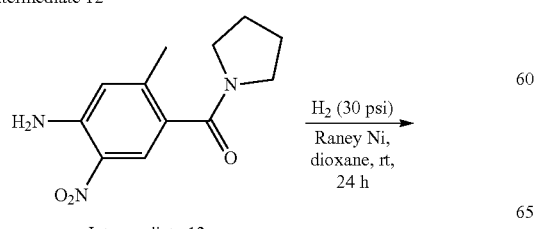

Intermediate 13

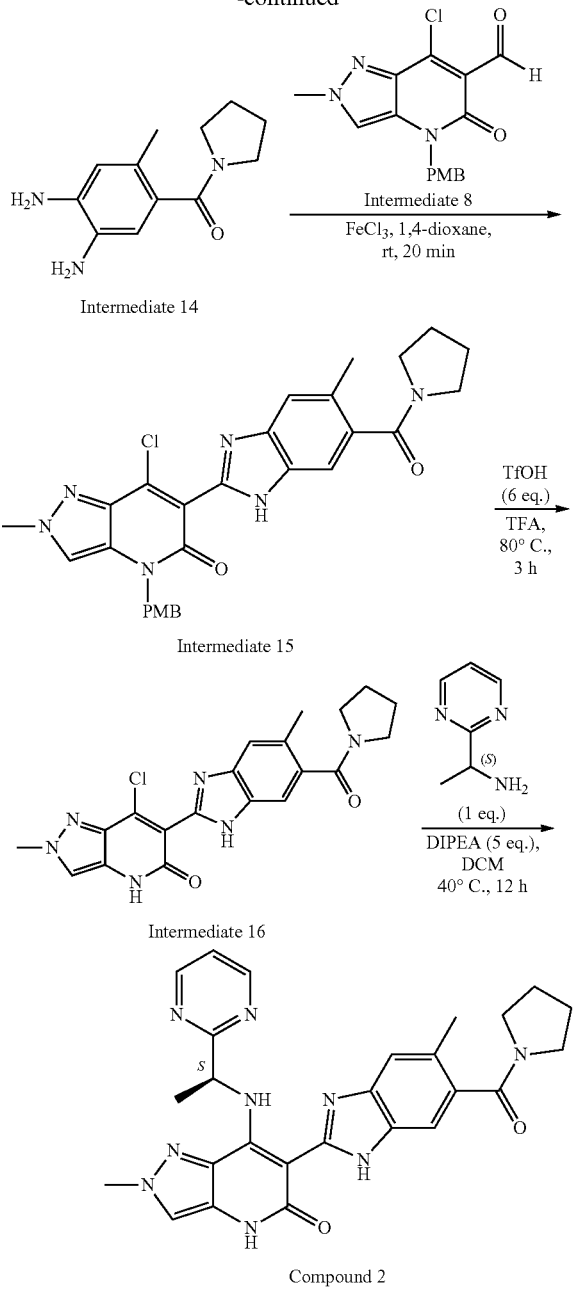

Intermediate 14

Intermediate 15

Intermediate 16

Compound 2 a) Preparation of Intermediate 12

4-Amino-2-methyl-5-nitrobenzoic acid

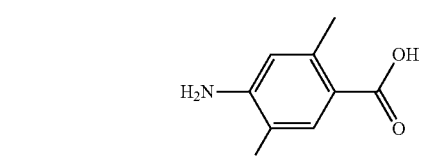

Intermediate 12 was synthesized as described in WO201199832A2.

General Procedure A: $^1$HNMR (400 MHz, DMSO-A) (Varian) δ=8.54 (s, 1H), 7.73 (br. s., 2H), 6.79 (s, 1H), 2.42 (s, 3H)

b) Preparation of Intermediate 13

(4-Amino-2-methyl-5-nitrophenyl)(pyrrolidin-1-yl)methanone

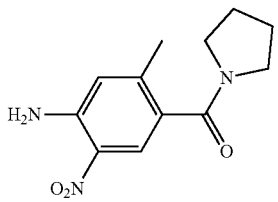 [SMILES: Cc1cc(N)c([N+](=O)[O-])cc1C(=O)N1CCCC1]

1-(3-Dimethylaminopropyl)-3-ethylcarbodiimide hydrochloride (EDCI) (835 mg, 4.36 mmol) was added to a solution of intermediate 12 (4-amino-2-methyl-5-nitrobenzoic acid) (600 mg, 95% purity, 2.91 mmol), pyrrolidine (207 mg, 2.91 mmol), N-ethyl-N-isopropylpropan-2-amine (1.13 g, 8.74 mmol) and 1-hydroxybenzotriazole (HOBT) (588 mg, 4.35 mmol) in anhydrous N,N-dimethylformamide (6 mL). The reaction mixture was stirred at room temperature (rt) for 8 hours. The reaction mixture was poured into ethyl acetate (50 mL) and water (40 mL) carefully. Then the organic layer was separated. The aqueous phase was washed with ethyl acetate (40 mL×3). The combined organic layers were dried over anhydrous $Na_2SO_4$ and filtered. The filtrate was concentrated to dryness under reduced pressure to afford the crude product which was purified by flash column chromatography (petroleum ether:ethyl acetate from 1:0 to 0:1) to give intermediate 13 (700 mg, 95% purity, 91.8% yield) as yellow solids.

General Procedure A: $^1$H NMR (400 MHz, DMSO-d$^5$) (Varian) δ=7.77 (s, 1H), 7.47 (br. s., 2H), 6.81 (s, 1H), 3.39 (t, J=6.8 Hz, 2H), 3.13 (t, J=6.5 Hz, 2H), 2.13 (s, 3H), 1.87-1.69 (m, 4H)

c) Preparation of Intermediate 14

(4,5-diamino-2-methylphenyl)(pyrrolidin-1-yl)methanone

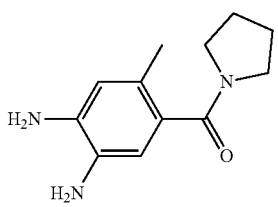 [SMILES: Cc1cc(N)c(N)cc1C(=O)N1CCCC1]

To a solution of intermediate 13 ((4-amino-2-methyl-5-nitrophenyl)(pyrrolidin-1-yl)-methanone) (500 mg, 95% purity, 1.91 mmol) in 1,4-dioxane (10 mL) was added Raney nickel (200 mg) under argon. The suspension was degassed under vacuum and purged with argon for three times, and then purged with hydrogen for three times. The mixture was stirred under hydrogen (30 psi) at 25° C. for 24 hours. The mixture was filtered. Then the filtrate was used in the next step without further work up.

LC-MS (ESI) (General Procedure B, Method 6): RT=0.71 min, mass calcd. for $C_{12}H_{17}N_3O$ 219.14, m/z found 220.2 [M+H]$^+$.

d) Preparation of Intermediate 15

7-chloro-4-(4-methoxybenzyl)-2-methyl-6-(5-methyl-6-(pyrrolidine-1-carbonyl)-1H-benzo[d]imidazol-2-yl)-2H-pyrazolo[4,3-b]pyridin-5(4H)-one

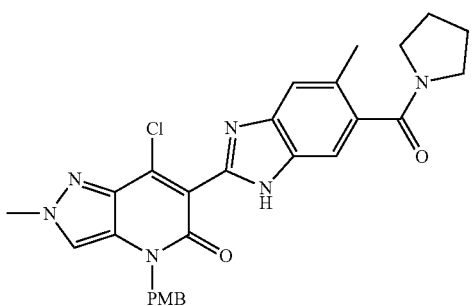

A stir bar, intermediate 8 (7-chloro-4-(4-methoxybenzyl)-2-methyl-5-oxo-4,5-dihydro-2H-pyrazolo[4,3-b]pyridine-6-carbaldehyde) (650 mg, 93.1% purity, 1.82 mmol) and anhydrous 1,4-dioxane (5 mL) were added to a 100 mL round-bottomed flask. Iron (III) chloride (592 mg, 3.65 mmol) was added to the mixture before the mixture was stirred at room temperature for 5 minutes. Intermediate 14 ((4,5-diamino-2-methylphenyl)(pyrrolidin-1-yl)-methanone) (the filtrate) was dropwise added to the mixture. After stirring at room temperature for 20 minutes, the reaction mixture was diluted with water (30 mL) and treated with solid sodium bicarbonate until pH=9. The resultant mixture was extracted with dichloromethane (30 mL). The organic extract was washed with brine (20 mL×3), dried over anhydrous $Na_2SO_4$, filtered, and concentrated to dryness under reduced pressure to afford the crude product, which was purified by flash column chromatography (ethyl acetate:tetrahydrofuran from 1:0 to 1:1) to afford intermediate 15 (677 mg, 87.9% purity, 61.4% yield) as brown solids.

LC-MS (ESI) (General Procedure C, Method 8): RT=2.22 min, mass calcd. for $C_{28}H_{27}ClN_6O_3$ 530.18, m/z found 531.1[M+H]$^+$.

e) Preparation of Intermediate 16

7-Chloro-2-methyl-6-(5-methyl-6-(pyrrolidine-1-carbonyl)-1H-benzo[d]imidazol-2-yl)-2H-pyrazolo[4,3-b]pyridin-5(4H)-one

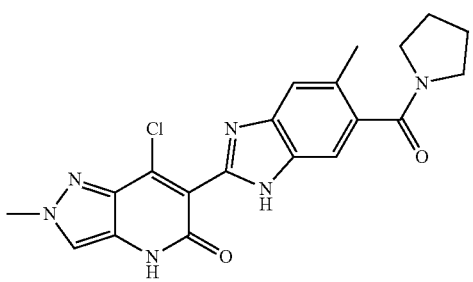 [SMILES: Cc1cc2nc(-c3c(Cl)c4nn(C)cc4[nH]c3=O)[nH]c2cc1C(=O)N1CCCC1]

A stir bar, intermediate 15 (7-chloro-4-(4-methoxybenzyl)-2-methyl-6-(5-methyl-6-(pyrrolidine-1-carbonyl)-1H-benzo[d]imidazol-2-yl)-2H-pyrazolo[4,3-b]pyridin-5(4H)-one) (677 mg, 87.9% purity, 1.12 mmol) and 2,2,2-trifluoroacetic acid (10 mL) were added to a 100 mL round-bottomed flask. Then trifluoromethanesulfonic acid (505 mg, 3.37 mmol) was added to the mixture. The reaction vessel was stirred at 80° C. for 2 hours. Trifluoromethanesulfonic acid (505 mg, 3.37 mmol) was added to the mixture once again. And the mixture was stirred for 1 hour. The mixture was concentrated to dryness under reduced pressure before diluting with water (30 mL) and treating with solid sodium bicarbonate until pH=9. The resultant mixture was extracted with dichloromethane (30 mL×3). The combined organic extracts were dried over anhydrous $Na_2SO_4$, filtered, and concentrated to dryness under reduced pressure to afford intermediate 16. Then intermediate 16 was triturated with tert-butyl methyl ether (15 mL) to give intermediate 16 (400 mg, 97.9% purity, 85.1% yield) as yellow solids.

LC-MS (ESI) (General Procedure C, Method 9): RT=0.53 min, mass calcd. for $C_{20}H_{19}ClN_6O_2$ 410.13, m/z found 411.0 [M+H]$^+$.

f) Preparation of Compound 2

((S)-2-methyl-6-(5-methyl-6-(pyrrolidine-1-carbonyl)-1H-benzo[d]imidazol-2-yl)-7-((1-(pyrimidin-2-yl)ethyl)amino)-2H-pyrazolo[4,3-b]pyridin-5(4H)-one

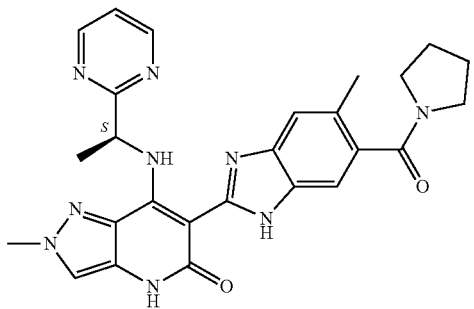

A stir bar, intermediate 16 (7-chloro-2-methyl-6-(5-methyl-6-(pyrrolidine-1-carbonyl)-1H-benzo[d]imidazol-2-yl)-2H-pyrazolo[4,3-b]pyridin-5(4H)-one) (400 mg, 97.9% purity, 0.953 mmol), intermediate 11 ((<S)-1-(pyrimidin-2-yl)ethanamine hydrogen chloride) (152 mg, 0.952 mmol) and N-ethyl-N-isopropylpropan-2-amine (615 mg, 4.76 mmol) in dichloromethane (10 mL) were added to a 25 mL round-bottomed flask. The resultant mixture was stirred at 40° C. for 12 hours. The resultant mixture was poured into dichloromethane (20 mL) and washed with water (10 mL×3). The separated organic layer was dried over anhydrous $Na_2SO_4$, filtered and concentrated to dryness under reduced pressure to afford the crude product which was purified by prep. HPLC (Column: Phenomenex Gemini C18 250×50 10 um, Mobile Phase A: water (0.225% FA), Mobile Phase B: acetonitrile, gradient condition from 22% B to 52%, Gradient Time: 11.2 min, FlowRate: 22 mL/min). The pure fractions were collected and the solvent was evaporated under vacuum, and then lyophilized to give a yellow powder. The product was further purified by supercritical fluid chromatography separation (separation condition: Chiralpak AS-H (150 mm×4.6 mm, 5 um); Mobile phase: A: Supercritical $CO_2$, B: Ethanol (0.05% DEA); Gradient: hold 5% for 0.5 minutes, then from 5% to 40% of B in 3.5 minutes and hold 40% of B for 2.5 minutes, then 5% of B for 1.5 minutes; Flow rate: 3 mL/min; Column Temp: 40° C.; Nozzle Pressure: 100 Bar; Nozzle Temp: 60° C.; Evaporator Temp: 20° C.; Trimmer Temp: 25° C.; Wavelength: 220 nm). The fraction was collected and the solvent was evaporated under vacuum, and then lyophilized to give compound 2 (200 mg, 98.8% purity, 41.6% yield) as a pale yellow powder.

LC-MS (ESI) (General Procedure A, Method 1): mass calcd. for $C_{26}H_{27}N_9O_2$ 497.20, m/z found 498.1[M+H]$^+$.

General Procedure A: $^1$H NMR (400 MHz, DMSO-d$^6$) (Varian) δ=13.01 (d, J=7.3 Hz, 1H), 12.75 (d, J=8.2 Hz, 0.5H), 12.67 (d, J=8.2 Hz, 0.5H), 10.91 (s, 1H), 8.89-8.84 (m, 2H), 7.67 (s, 1H), 7.53-7.38 (m, 3H), 6.53-6.42 (m, 1H), 3.99-3.96 (m, 3H), 3.54-3.47 (m, 2H), 3.14-3.02 (m, 2H), 2.34-2.29 (m, 3H), 1.94-1.85 (m, 2H), 1.84-1.77 (m, 2H), 1.75-1.70 (m, 3H).

SFC (Method 12): RT=4.88 min, Peak area: 99.9%

Example 3

Preparation of Compound 3

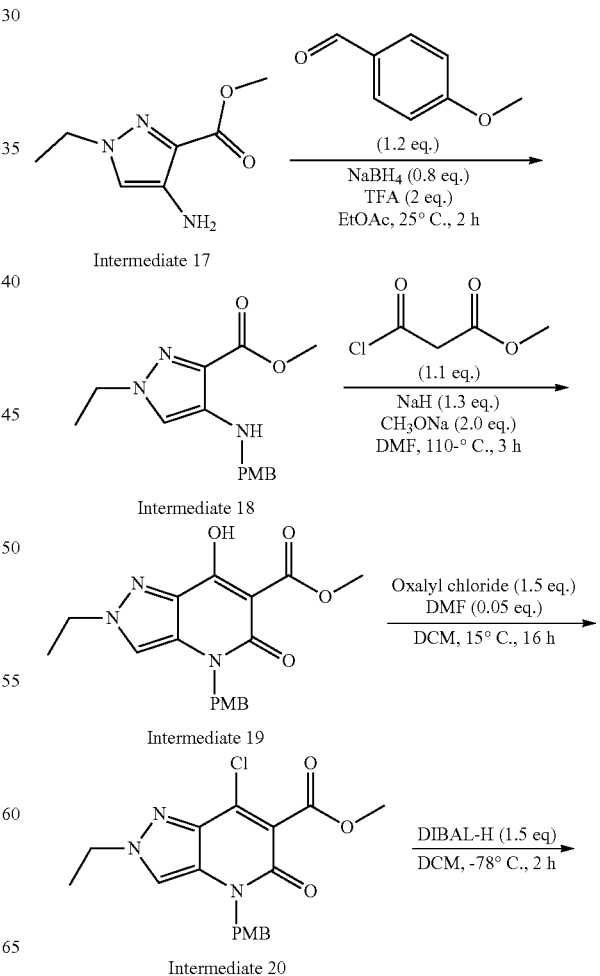

-continued

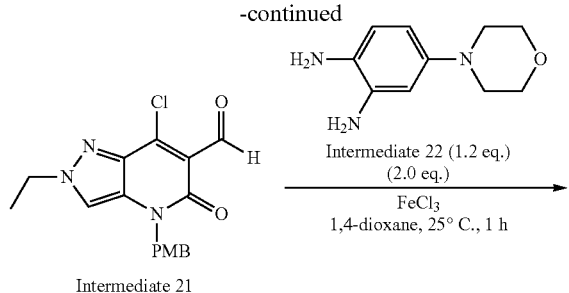

Intermediate 21

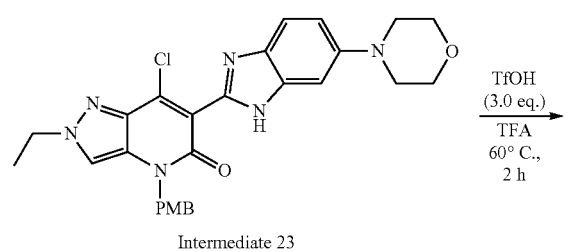

Intermediate 23

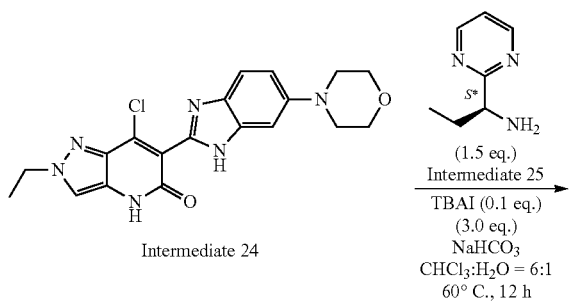

Intermediate 24

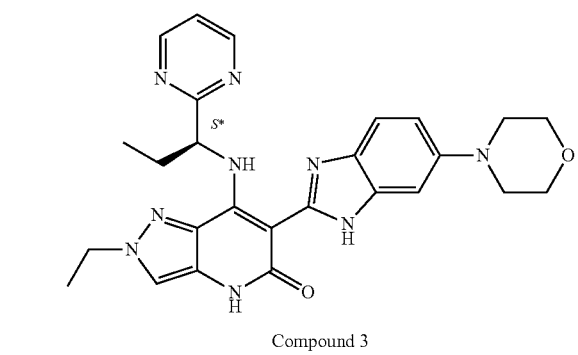 [SMILES: CC[C@H](Nc1c(-c2nc3ccc(N4CCOCC4)cc3[nH]2)c(=O)[nH]c2cn(CC)nc12)c1ncccn1]

Compound 3 a) Preparation of Intermediate 17

Methyl 4-amino-1-ethyl-1H-pyrazole-3-carboxylate

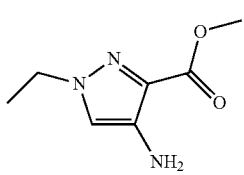

Intermediate 17 was synthesized as described in WO201218909A1.

b) Preparation of Intermediate 18

Methyl 1-ethyl-4-((4-methoxybenzyl)amino)-1H-pyrazole-3-carboxylate

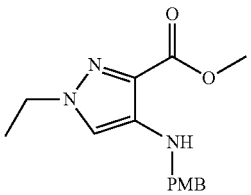

In a beaker (3 L) equipped with a magnetic stirrer, a solution of intermediate 17 (methyl 4-amino-1-ethyl-1H-pyrazole-3-carboxylate) (120 g, 709 mmol), trifluoroacetic acid (162 g, 1.42 mol) and 4-methoxybenzaldehyde (116 g, 852 mmol) in ethyl acetate (1.2 L) was prepared. Sodium borohydride (21.5 g, 568 mmol) was added to the mixture in portions at ice-water bath keeping the temperature below 30° C. Then water (1 L) was added to the mixture to quench the reaction and the mixture was stirred at 25° C. for 2 hours. The mixture was separated and the separated organic layer was washed with water (1 L×3), brine (1 L), dried over $Na_2SO_4$ and filtered. The filtrate was concentrated under reduced pressure to give a crude product which was purified by flash column chromatography (gradient equivalent: petroleum ether:ethyl acetate from 100:0 to 1:1) to afford intermediate 18 (180 g, crude) as light yellow oil.

General Procedure A: $^1$H NMR (400 MHz, DMSO-d$^6$) (Varian) δ 7.34-7.20 (m, 3H), 6.91-6.76 (m, 2H), 4.16-4.03 (m, 2H), 4.03-3.97 (m, 2H), 3.80-3.68 (m, 6H), 1.37-1.21 (m, 3H)

c) Preparation of Intermediate 19

Methyl 2-ethyl-7-hydroxy-4-(4-methoxybenzyl)-5-oxo-4,5-dihydro-2H-pyrazolo[4,3-b]-pyridine-6-carboxylate

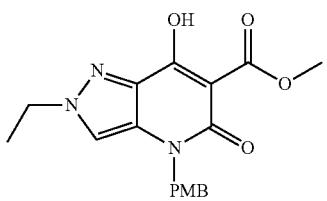

A solution of intermediate 18 (methyl 1-ethyl-4-((4-methoxybenzyl)amino)-1H-pyrazole-3-carboxylate) (90.0 g, 121 mmol) in dry N,N-dimethylformamide (600 mL) was added to a 2 L three-necked flask. Sodium hydride (16.2 g, 60% dispersion in oil, 405 mmol) was added to the mixture at ice-water bath in portions. After addition, the mixture was stirred at 0° C. for 15 minutes and methyl malonyl chloride (44.6 g, 327 mmol) was added to the mixture dropwise at 0° C. The mixture was stirred for another 15 minutes, then sodium methoxide (33.6 g, 622 mmol) was added to the mixture in one portion and the mixture was stirred at 110° C. for 3 hours. The mixture was concentrated under reduced pressure to give a residue. Then the residue was suspended in 300 mL of water and ethyl acetate (400 mL). The separated aqueous phase was acidized by HCl (12 M) until a pH of 6-7. The aqueous phase was extracted with dichloromethane (400 mL×4). The combined dichloromethane extracts were dried over $Na_2SO_4$ and filtered. The filtrate was concentrated to dryness under reduced pressure to afford the crude product which was purified by flash column chromatography (gradient equivalent: petroleum ether:ethyl acetate from 10:0 to 1:9) to afford intermediate 19 (15.0 g, 85.9% purity, 11.6% yield) as yellow sticky solids.

LC-MS (ESI) (General Procedure B, Method 4): RT=1.76 min, mass calcd. for $C_{18}H_{19}N_3O_5$ 357.13, m/z found 358.1 $[M+H]^+$.

d) Preparation of Intermediate 20

Methyl 7-chloro-2-ethyl-4-(4-methoxybenzyl)-5-oxo-4,5-dihydro-2H-pyrazolo-[4,3-b]pyridine-6-carboxylate

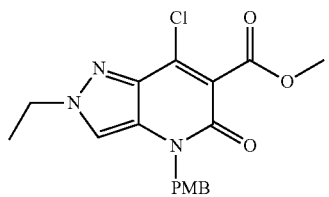

A stir bar, intermediate 19 (methyl 2-ethyl-7-hydroxy-4-(4-methoxybenzyl)-5-oxo-4,5-dihydro-2H-pyrazolo[4,3-d]pyridine-6-carboxylate) (25.0 g, 70.0 mmol) and dichloromethane (150 mL) were added to a 500 mL round-bottomed flask. Oxalyl chloride (8.9 mL, 104 mmol) was added at 0° C. dropwise. Then N,N-dimethylformamide (0.26 g, 3.56 mmol) was added at 0° C., and the resultant mixture was stirred at 15° C. After 16 hours, the reaction mixture was concentrated to dryness under reduced pressure. The residue was suspended in dichloromethane (300 mL) and basified with saturated sodium bicarbonate solution until pH>7. The mixture was separated and the separated organic layer was dried over $Na_2SO_4$ and filtered. The filtrate was concentrated under reduced pressure to give a residue, which was purified by flash column chromatography (gradient equivalent: petroleum ether:ethyl acetate from 1:0 to 1:2) to afford intermediate 20 (7.50 g, 25.7% yield) as light yellow solids.

LC-MS (ESI) (General Procedure C, Method 7): RT=2.93 min, mass calcd. for $C_{18}H_{18}ClN_3O_4$ 375.10, m/z found 375.9 $[M+H]^+$.

General Procedure A: $^1H$ NMR (400 MHz, DMSO-$d^6$) (Bruker) δ=8.31 (s, 1H), 7.30 (d, J=8.5 Hz, 2H), 6.88 (d, J=8.8 Hz, 2H), 5.06 (s, 2H), 4.32 (q, J=7.3 Hz, 2H), 3.89-3.82 (m, 3H), 3.73-3.70 (m, 3H), 1.44 (t, J=7.3 Hz, 3H)

e) Preparation of Intermediate 21

7-chloro-2-ethyl-4-(4-methoxybenzyl)-5-oxo-4,5-dihydro-2H-pyrazolo[4,3-b]pyridine-6-carbaldehyde

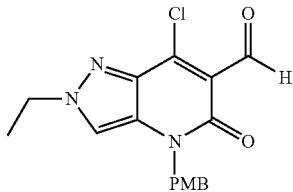

A stir bar, intermediate 20 (methyl 7-chloro-2-ethyl-4-(4-methoxybenzyl)-5-oxo-4,5-dihydro-2H-pyrazolo[4,3-b] pyridine-6-carboxylate) (7.50 g, 20.0 mmol) and dichloromethane (150 mL) were added to a 500 mL three-necked flask under nitrogen. Then diisobutylaluminum hydride (29.9 mL, 1 M in toluene, 29.9 mmol) was dropwise added at −78° C., and the resultant mixture was stirred at −78° C. After 2 hours, the reaction mixture was quenched with saturated ammonium chloride aqueous solution (50 mL) at −78° C. The mixture was stirred at −78° C. for 20 minutes before dichloromethane (100 ml) was added. The reaction mixture was filtered after the mixture was warmed to 25° C. The filter cake was washed with dichloromethane (300 mL×5) and the combined organic layers were dried over $Na_2SO_4$ and filtered. The filtrate was concentrated under reduced pressure to afford the crude product which was purified by flash column chromatography (gradient equivalent: petroleum ether:ethyl acetate from 1:0 to 1:3) to give the product, which was further purified by prep. HPLC (Column: Phenomenex luna C18 250*50 mm*10 um, Mobile Phase A: water (0.1% TFA), Mobile Phase B: acetonitrile, Flow rate: 120 mL/min, gradient condition from 20% B to 50%). The collected pure fractions were neutralized with saturated sodium bicarbonate solution until pH>7. Then the mixture was extracted with dichloromethane (200 mL×3). The combined organic layers were dried over $Na_2SO_4$ and filtered. The filtrate was evaporated to dryness, which was re-suspended in water (10 mL) and the resulting mixture was lyophilized to give intermediate 21 (5.50 g, 90.0% purity, 71.7% yield) as light yellow solids.

LC-MS (ESI) (General Procedure C, Method 9): RT=0.80 min, mass calcd. for $C_{17}H_{16}ClN_3O_3$ 345.09, m/z found 346.0 $[M+H]^+$.

General Procedure A: $^1H$ NMR (400 MHz, DMSO-$d^6$) (Varian) δ=10.28 (s, 1H), 8.31 (s, 1H), 7.38-7.30 (m, 2H), 6.91-6.83 (m, 2H), 5.09 (s, 2H), 4.34 (q, J=13 Hz, 2H), 3.70 (s, 3H), 1.44 (t, J=13 Hz, 3H)

f) Preparation of Intermediate 23

7-chloro-2-ethyl-4-(4-methoxybenzyl)-6-(6-morpholino-1H-benzo[d]imidazol-2-yl)-2H-pyrazolo[4,3-b]pyridin-5(4H)-one

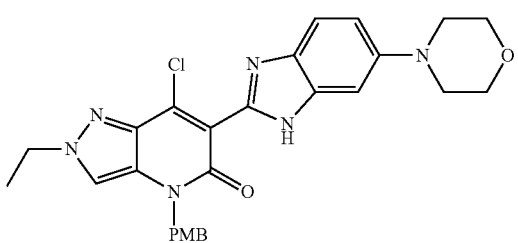

A stir bar, intermediate 21 (7-chloro-2-ethyl-4-(4-methoxybenzyl)-5-oxo-4,5-dihydro-2H-pyrazolo[4,3-b]pyridine-6-carbaldehyde) (800 mg, 2.31 mmol), intermediate 22 (4-morpholinobenzene-1,2-diamine) (537 mg, 2.78 mmol) (synthesized as described in Medicinal Chemistry, 2013, vol. 9, #5 p. 651-659) and dry 1,4-dioxane (10 mL) were added to a 40 mL glass bottle. Then ferric chloride (751 mg, 4.63 mmol) was added to the reaction mixture and the mixture was stirred at 25° C. for 1 hour. The mixture was adjusted to around pH=9.0 by saturated sodium bicarbonate solution (20 mL) and filtered. The filtrate was extracted with dichloromethane (20 mL×3). The combined organic layers were dried over anhydrous $Na_2SO_4$ and filtered. The filtrate was concentrated under reduced pressure to give the product which was purified by flash column chromatography (gradient equivalent: dichloromethane:methanol from 1:0 to 9:1) to give intermediate 23 (800 mg, 68.9% yield, 45.9% yield) as a black powder.

g) Preparation of Intermediate 24

7-chloro-2-ethyl-6-(6-morpholino-1H-benzo[d]imidazol-2-yl)-2H-pyrazolo[4,3-b]-pyridin-5(4H)-one

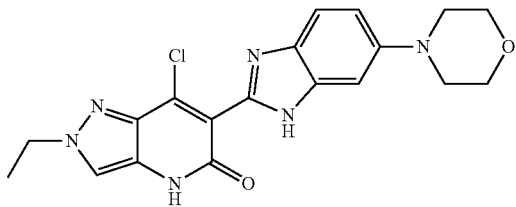 [SMILES: CCn1cc2[nH]c(=O)c(-c3nc4ccc(N5CCOCC5)cc4[nH]3)c(Cl)c2n1]

A stir bar, intermediate 23 (7-chloro-2-ethyl-4-(4-methoxybenzyl)-6-(6-morpholino-1H-benzo[d]imidazol-2-yl)-2H-pyrazolo[4,3-&]pyridin-5(4H)-one) (800 mg, 1.06 mmol) and 2,2,2-trifluoroacetic acid (3 mL) were added to a 50 mL round-bottomed flask. Then trifluoromethanesulfonic acid (0.280 mL) was added to the mixture dropwise and the mixture was stirred at 60° C. for 2 hours. The mixture was concentrated under reduced pressure. The residue was basified by saturated sodium bicarbonate solution until pH=9. The mixture was extracted with chloroform (10 mL×3). The combined organic layers were dried over anhydrous $Na_2SO_4$, filtered and concentrated under reduced pressure to give intermediate 24 (800 mg, crude) as a black powder which was used for next step without further purification.

h) Preparation of Compound 3

(S*)-2-ethyl-6-(6-morpholino-1H-benzo[d]imidazol-2-yl)-7-((1-(pyrimidin-2-yl)propyl)-amino)-2H-pyrazolo[4,3-b]pyridin-5(47f)-one

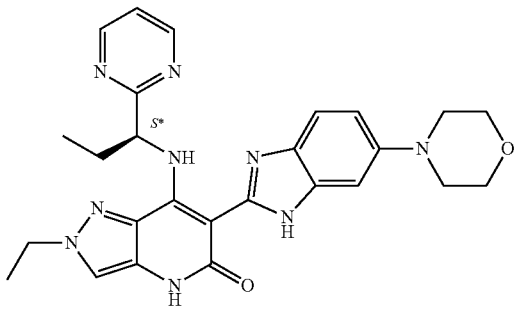

A stir bar, intermediate 24 (7-chloro-2-ethyl-6-(6-morpholino-1H-benzo[d]imidazol-2-yl)-2H-pyrazolo[4,3-b]pyridin-5(4H)-one) (265 mg, 0.664 mmol), intermediate 25 ((S*)-1-(pyrimidin-2-yl)propan-1-amine hydrochloride) (173 mg, 0.996 mmol), tetrabutylammonium iodide (TBAI) (24.5 mg, 0.066 mmol), sodium bicarbonate (167 mg, 1.99 mmol), chloroform (6 mL) and water (1 mL) were added to a 100 mL round-bottomed flask. The resulting mixture was stirred at 60° C. for 12 hours. Then the mixture was extracted with dichloromethane (20 mL). The separated organic layer was washed with water (20 mL×3), dried over anhydrous $Na_2SO_4$ and filtered. The filtrate was concentrated under reduced pressure to give a residue, which was purified by prep. HPLC (Column: Phenomenex Gemini C18 250*50 10 u, Mobile Phase A: water (0.225% FA), Mobile Phase B: acetonitrile, Flow rate: 22 mL/min, gradient condition from 23% B to 53%). The pure fractions were collected and the solvent was evaporated under vacuum. The mixture was lyophilized to dryness to give compound 3 (118 mg, 97.3% purity, 34.7% yield) as yellow solids.

LC-MS (ESI) (General Procedure A, Method 2): RT=4.00 min, mass calcd. for $C_{26}H_{29}N_9O_2$ 499.24, m/z found 500.1 $[M+H]^+$.

General Procedure A: $^1H$ NMR (400 MHz, DMSO-$d^6$) (Varian) δ 12.87 (d, J=5.7 Hz, 1H), 12.64 (d, J=7.9 Hz, 0.4H), 12.57 (d, J=7.9 Hz, 0.6H), 10.89-10.85 (m, 1H), 8.83-8.79 (m, 2H), 7.65 (s, 1H), 7.53 (d, J=8.6 Hz, 0.4H), 7.43 (d, J=8.8 Hz, 0.6H), 7.40-7.35 (m, 1H), 7.23-7.19 (m, 0.6H), 7.06-7.03 (m, 0.4H), 6.95-6.87 (m, 1H), 6.34-6.26 (m, 1H), 4.19 (q, J=7.3 Hz, 2H), 3.82-3.73 (m, 4H), 3.14-3.05 (m, 4H), 2.25-2.09 (m, 2H), 1.30 (t, J=7.3 Hz, 3H), 1.09-0.97 (m, 3H)

SFC (Method 12): RT=2.26 min, Peak Area: 99.0%.

Example 4

Preparation of Compound 4, 4A and 4B

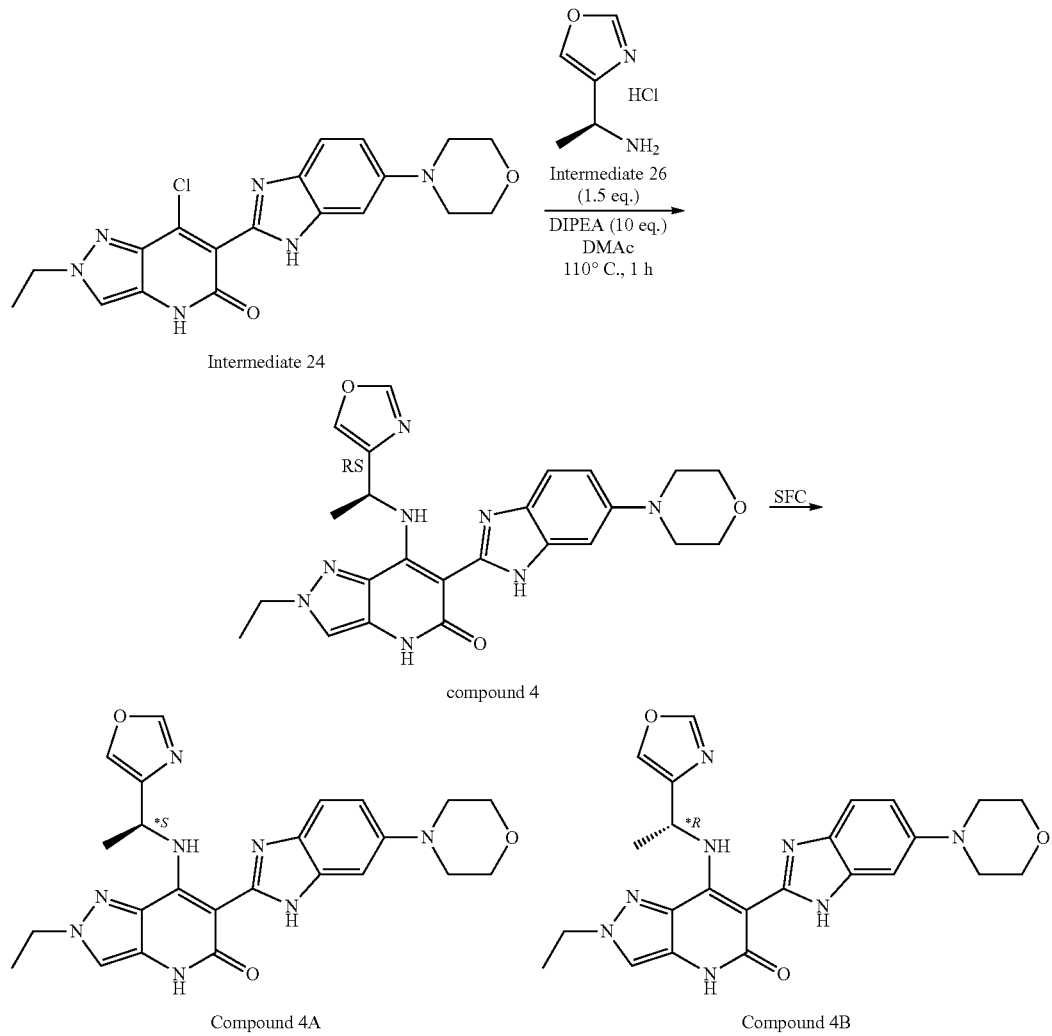

a) Preparation of Compound 4

(Rac)-2-ethyl-6-(6-morpholino-1H-benzo[d]imidazol-2-yl)-7-((1-(oxazol-4-yl)ethyl)-amino)-2H-pyrazolo[4,3-b]pyridin-5(4H)-one

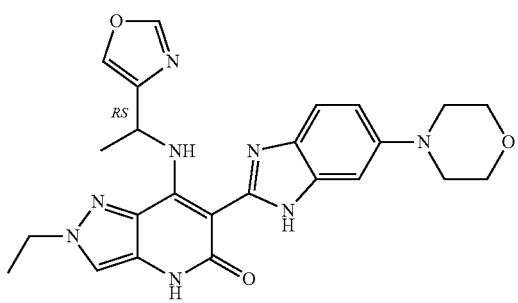 [SMILES: CCn1cc2[nH]c(=O)c(-c3nc4ccc(N5CCOCC5)cc4[nH]3)c(NC(C)c3cocn3)c2n1]

A stir bar, intermediate 24 (7-chloro-2-ethyl-6-(6-morpholino-1H-benzo[d]imidazol-2-yl)-2H-pyrazolo[4,3-b]pyridin-5(4H)-one) (800 mg, 2.01 mmol), intermediate 26 (me)-1-(oxazol-4-yl)ethanamine hydrochloride (447 mg, 3.01 mmol), N,N-diisopropylethylamine (2.61 g, 20.2 mmol) and N,N-dimethylacetamide (10 mL) were added to a 40 mL glass bottle. The mixture was stirred at 110° C. for 1 hour. Then the mixture was cooled to room temperature and diluted with dichloromethane (30 mL) and washed with water (8 mL×5). The separated organic layer was dried over anhydrous $Na_2SO_4$, filtered and concentrated under reduced pressure to give the crude product which was purified by prep. thin layer chromatography (dichloromethane:methanol=10:1) to give compound 4 (350 mg, 95% purity, 35.0% yield) as a yellow powder.

LC-MS (ESI) (General Procedure C, Method 9): RT=0.63 min, mass calcd. $C_{24}H_{26}N_8O_3$ 474.21, m/z found 475.1 $[M+H]^+$.

b) Preparation of Compound 4A (S*)-2-ethyl-6-(6-morpholino-1H-benzo[d]imidazol-2-yl)-7-((1-(oxazol-4-yl)ethyl)amino)-2H-pyrazolo[4,3-b]pyridin-5(4H)-one

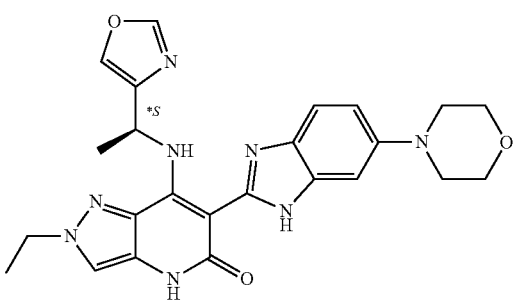 [SMILES: CCn1cc2[nH]c(=O)c(-c3nc4ccc(N5CCOCC5)cc4[nH]3)c(N[C@@H](C)c3cocn3)c2n1]

and compound 4B (R*)-2-ethyl-6-(6-morpholino-1H-benzo[d]imidazol-2-yl)-7-((1-(oxazol-4-yl)ethyl)-amino)-2H-pyrazolo[4,3-b]pyridin-5(4H)-one

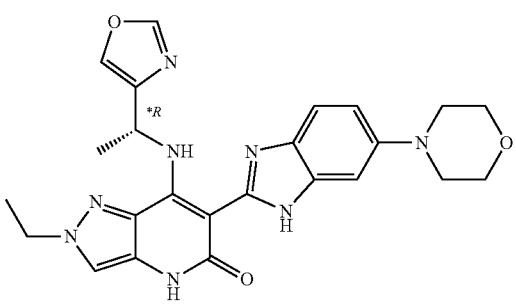 [SMILES: CCn1cc2[nH]c(=O)c(-c3nc4ccc(N5CCOCC5)cc4[nH]3)c(N[C@H](C)c3cocn3)c2n1]

The racemic compound 4 was separated by supercritical fluid chromatography (separation condition: AD (250 mm*30 mm, 10 um); Mobile phase: A: Supercritical $CO_2$, B: 0.1% $NH_3H_2O$ EtOH, A:B=45:55 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The pure fractions were collected and the volatiles were removed under vacuum. The residue was suspended in acetonitrile (2 mL) and water (10 mL). The mixture was lyophilized to dryness to give compound 4A (77.1 mg, 97.4% purity, 21.5% yield) as yellow powder and compound 4B (80.1 mg, 99.1% purity, 22.7% yield) as yellow powder.

Compound 4A:

LC-MS (ESI) (General Procedure A, Method 2): RT=3.86 min, mass calcd. $C_{24}H_{26}N_8O_3$ 474.21, m/z found 475.0 $[M+H]^+$.

General Procedure A: $^1$H NMR (400 MHz, DMSO-d$^6$) (Varian) δ 12.89 (s, 0.4H), 12.87 (s, 0.6H), 12.40 (d, J=8.4 Hz, 0.4H), 12.32 (d, J=8.6 Hz, 0.6H), 10.93 (br. s., 1H), 8.36 (s, 1H), 8.02-7.99 (m, 1H), 7.74 (s, 1H), 7.52 (d, J=8.6 Hz, 0.4H), 7.38 (d, J=8.6 Hz, 0.6H), 7.20 (d, J=2.2 Hz, 0.6H), 7.03 (d, J=2.0 Hz, 0.4H), 6.93-6.86 (m, 1H), 6.44-6.32 (m, 1H), 4.38-4.26 (m, 2H), 3.80-3.72 (m, 4H), 3.12-3.03 (m, 4H), 1.71-1.66 (m, 3H), 1.48-1.41 (m, 3H)

SFC (Method 13): $R_T$=1.77 min, Peak Area: 100%.

Compound 4B:

LC-MS (ESI) (General Procedure A, Method 2): RT=3.86 min, mass calcd. $C_{24}H_{26}N_8O_3$ 474.21, m/z found 475.0 $[M+H]^+$.

General Procedure A: $^1$H NMR (400 MHz, DMSO-d$^6$) (Varian) δ 12.89 (s, 0.4H), 12.87 (s, 0.6H), 12.40 (d, J=8.6 Hz, 0.4H), 12.32 (d, J=8.6 Hz, 0.6H), 10.93 (br. s., 1H), 8.36 (s, 1H), 8.02-7.99 (m, 1H), 7.74 (s, 1H), 7.52 (d, J=8.8 Hz, 0.4H), 7.39 (d, J=8.8 Hz, 0.6H), 7.20 (d, J=2.2 Hz, 0.6H), 7.03 (d, J=2.0 Hz, 0.4H), 6.93-6.88 (m, 1H), 6.44-6.33 (m, 1H), 4.33 (q, J=7.4 Hz, 2H), 3.80-3.73 (m, 4H), 3.12-3.05 (m, 4H), 1.72-7.65 (m, 3H), 1.48-1.42 (m, 3H)

SFC (Method 13): $R_T$=2.07 min, Peak Area: 100%.

Example 5

Preparation of Compound 5

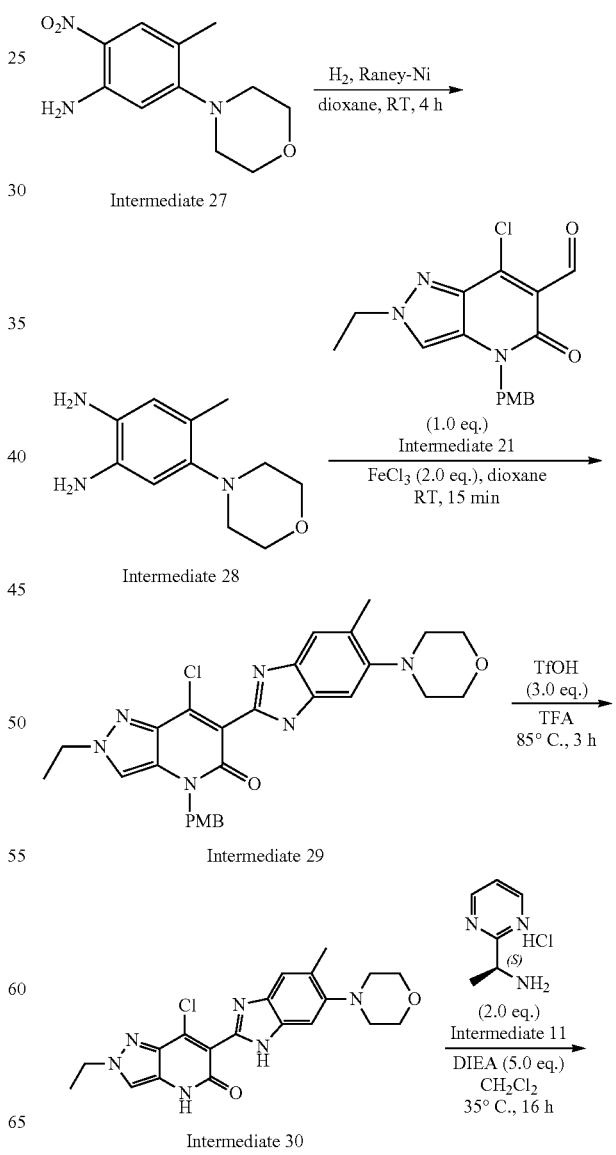

-continued

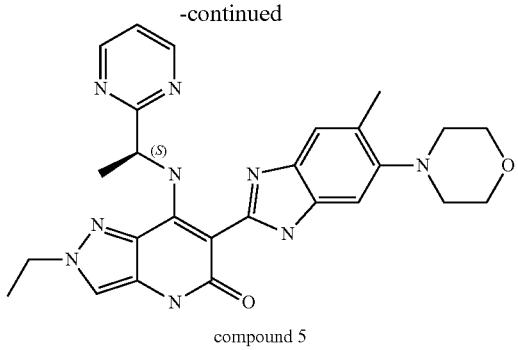

compound 5 a) Preparation of Intermediate 28
4-methyl-5-morpholinobenzene-1,2-diamine

A mixture of intermediate 27 (4-methyl-5-morpholino-2-nitroaniline) (1.0 g, 4.22 mmol) and Raney-Ni (100 mg) in dioxane (40 mL) was stirred at room temperature under balloon pressure of hydrogen gas for 4 hours. Raney-Ni was filtered off and the filtrate was directly used in the next step without further purification.

LC-MS (ESI) (General Procedure B-2, method 2): $R_T$=0.49 min, mass calcd. for $C_{11}H_{17}N_3O$ 207.1, m/z found 208.2 $[M+H]^+$.

b) Preparation of Intermediate 29
7-chloro-2-ethyl-4-(4-methoxybenzyl)-6-(5-methyl-6-morpholino-1H-benzo[d]imidazol-2-yl)-2,4-dihydro-5H-pyrazolo[4,3-b]pyridin-5-one To a mixture of intermediate 28 (4-methyl-5-morpholinobenzene-1,2-diamine) in dioxane (40 mL) was added 4-chloro-2-oxo-1,2-dihydroquinoline-3-carbaldehyde (1.45 g, 4.20 mmol) under an ice-bath. $FeCl_3$ (1.36 g, 8.40 mmol) was added and the resulting mixture was stirred at room temperature for 15 min. The pH of the mixture was adjusted to 8 with saturated $NaHCO_3$. The mixture was extracted with $CH_2Cl_2$ (50 mL*2). The combined organic phase was washed with $H_2O$, brine, dried over $Na_2SO_4$, filtered and concentrated under reduced pressure. The residue was purified by silica gel chromatography (gradient, $CH_2Cl_2$:EtOAc=6:1 to 2:1) to give the title compound (1.59 g, 71.0% yield) as yellow solids.

LC-MS (ESI) (General Procedure B-2, method 4): RT=1.15 min, mass calcd. for $C_{28}H_{29}ClN_6O_3$ 532.2, m/z found 533.3 $[M+H]^+$.

c) Preparation of Intermediate 30
7-chloro-2-ethyl-6-(5-methyl-6-morpholino-1H-benzo[d]imidazol-2-yl)-2,4-dihydro-5H-pyrazolo[4,3-b]pyridin-5-one To a solution of intermediate 29 (7-chloro-2-ethyl-4-(4-methoxybenzyl)-6-(5-methyl-6-morpholino-1H-benzo[d]imidazol-2-yl)-2,4-dihydro-5H-pyrazolo[4,3-b]pyridin-5-one) (1.59 g, 2.99 mmol) in $CF_3COOH$ (20 mL) was added TfOH (1.35 g, 9.00 mmol). The mixture was stirred at 85° C. for 3 hours. Then it was concentrated under reduced pressure. The pH of the residue was adjusted to 8 with saturated $NaHCO_3$. The resulting mixture was extracted with $CH_2Cl_2$ (50 mL*2). The combined organic phase was washed with $H_2O$ and brine, dried over $Na_2SO_4$, filtered and concentrated to give intermediate 30 (1.6 g, crude, yield >100%) as yellow solids which was used in the next step without further purification.

LC-MS (ESI) (General Procedure B-2, method 4): RT=0.93 min, mass calcd. for $C_{20}H_{21}ClN_6O_2$ 412.1, m/z found 413.3 $[M+H]^+$.

d) Preparation of Compound 5
(S)-2-ethyl-6-(5-methyl-6-morpholino-1H-benzo[d]imidazol-2-yl)-7-((1-(pyrimidin-2-yl)-ethyl)amino)-2,4-dihydro-5H-pyrazolo[4,3-b]pyridin-5-one To a solution of intermediate 30 (7-chloro-2-ethyl-6-(5-methyl-6-morpholino-1H-benzo[d]-imidazol-2-yl)-2,4-dihydro-5H-pyrazolo[4,3-b]pyridin-5-one) (300 mg, 0.73 mmol) in $CH_2Cl_2$ (10 mL) was added intermediate 11 ((S)-1-(pyrimidin-2-yl)ethan-1-amine hydrochloride) (232 mg, 1.46 mmol) and DIPEA (471 mg, 3.65 mmol). The mixture was stirred at 35° C. for 16 hours. Then it was concentrated under reduced pressure. The residue was purified by silica gel chromatography (gradient, $CH_2Cl_2$:MeOH=60:1 to 50:1) to give compound 5 (300 mg, 82.3% yield, purity 99.4%, ee: 95.84%) as yellow solids.

LC-MS (ESI) (General Procedure B-2, method 4): RT=1.44 min, mass calcd. for $C_{26}H_{29}N_9O_2$ 499.57, m/z found 500.4 $[M+H]^+$.

General Procedure A-2: $^1H$ NMR (400 MHz, $CD_3OD$) δ 8.78-8.76 (m, 2H), 7.50 (s, 1H), 7.34-7.32 (m, 3H), 6.46-6.41 (m, 1H), 4.23-4.19 (m, 2H), 3.86-3.84 (m, 4H), 2.94-2.92 (m, 4H), 2.42 (s, 3H), 1.85 (d, J=6.8 Hz, 3H), 1.39 (t, J=7.6 Hz, 3H).

Example 6

Preparation of Compound 6

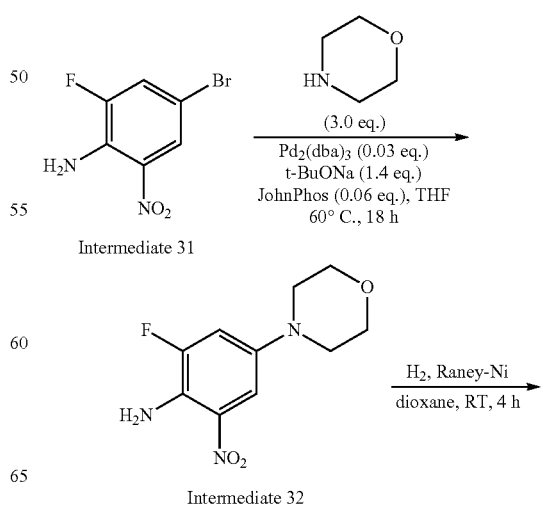

Intermediate 31

Intermediate 32

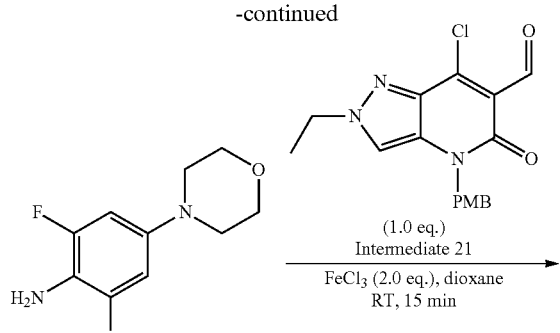

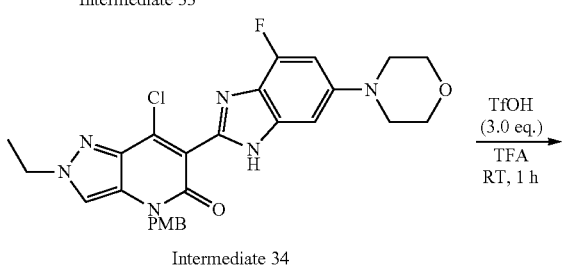

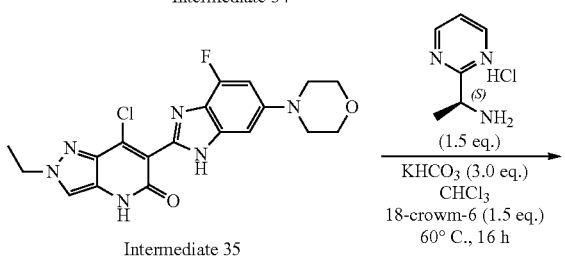

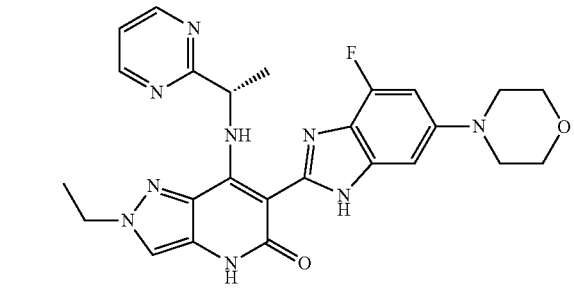

Compound 6 a) Preparation of Intermediate 32

2-fluoro-4-morpholino-6-nitroaniline

To a degassed suspension of intermediate 31 (4-bromo-2-fluoro-6-nitroaniline) (5.0 g, 21.3 mmol), tris(dibenzylideneacetone)dipalladium(0) (586 mg, 0.64 mmol), (2-Biphenyl)di-tert-butylphosphine (JohnPhos) (379 mg, 1.27 mmol) and t-BuONa (2.86 g, 29.78 mmol) in THF (50 mL) was added morpholine (5.55 g, 63.8 mmol). The mixture was stirred at 60° C. for 18 hours. After cooling to room temperature, the mixture was concentrated under reduced pressure to give a residue which was purified by silica gel chromatography (Petrol Ether:EtOAc=5:1) to give intermediate 32 (780 mg, 15.2% yield) as yellow solids.

LC-MS (ESI) (General procedure A-2, method 2): RT=1.60 min, mass calcd. for $C_{10}H_{12}FN_3O_3$ 241.1, m/z found 242.2 [M+H]$^+$.

b) Preparation of Intermediate 33

3-fluoro-5-morpholinobenzene-1,2-diamine

A mixture of intermediate 32 (2-fluoro-4-morpholino-6-nitroaniline) (780 mg, 3.23 mmol) and Raney-Ni (1 g) in dioxane (15 mL) was stirred at room temperature under balloon pressure of hydrogen gas for 4 hours. Raney-Ni was filtered off and the filtrate was directly used in the next step without further purification.

LC-MS (ESI) (General procedure A-2, method 2): RT=1.27 min, mass calcd. for $C_{10}H_{14}FN_3O$ 211.1, m/z found 212.2 [M+H]$^+$.

c) Preparation of Intermediate 34

7-chloro-2-ethyl-6-(4-fluoro-6-morpholino-1H-benzo[d]imidazol-2-yl)-4-(4-methoxy-benzyl)-2,4-dihydro-5H-pyrazolo[4,3-b]pyridin-5-one To a mixture of intermediate 21 (7-chloro-4-(4-methoxybenzyl)-2-ethyl-5-oxo-4,5-dihydro-2H-pyrazolo[4,3-b]pyridine-6-carbaldehyde) (1.11 g, 3.23 mmol) in dioxane (25 mL) was added FeCl$_3$ (1.04 g, 6.46 mmol), followed by a solution of intermediate 33 (3-fluoro-5-morpholinobenzene-1,2-diamine) in dioxane (15 mL). The resulting mixture was stirred at room temperature for 15 minutes, then it was poured into NaHCO$_3$ saturated (50 mL) and extracted with CH$_2$Cl$_2$ (100 mL*2). The combined organic phase was washed with H$_2$O, brine, dried over Na$_2$SO$_4$, filtered and concentrated under reduced pressure. The residue was purified by silica gel chromatography (gradient, CH$_2$Cl$_2$:MeOH=100:0 to 60:1) to give intermediate 35 (650 mg, 37.5% yield) as brown solids.

LC-MS (ESI) (General procedure A-2, method 2): RT=1.62 min, mass calcd. for $C_{27}H_{26}ClFN_6O_3$ 536.2, m/z found 537.3 [M+H]$^+$.

d) Preparation of Intermediate 35

7-chloro-2-ethyl-6-(4-fluoro-6-morpholino-1H-benzo[d]imidazol-2-yl)-2,4-dihydro-5H-pyrazolo[4,3-b]pyridin-5-one To a solution of intermediate 34 (7-chloro-2-ethyl-6-(4-fluoro-6-morpholino-1H-benzo[d]-imidazol-2-yl)-4-(4-methoxybenzyl)-2,4-dihydro-5H-pyrazolo[4,3-b]pyridin-5-one) (650 mg, 1.21 mmol) in CF$_3$COOH (20 mL) was added TfOH (537 mg, 3.63 mmol). The mixture was stirred at room temperature for 1 hour. Then it was concentrated under reduced pressure. The pH of the residue was adjusted to 8 with saturated NaHCO$_3$. The resulting mixture was extracted with CH$_2$Cl$_2$ (50 mL*2). The combined organic phase was washed with H$_2$O and brine, dried over Na$_2$SO$_4$, filtered and concentrated to give intermediate 35 as yellow solids (700 mg, yield >100%) which was used in the next step without further purification.

LC-MS (ESI) (General procedure A-2, method 2): RT=1.32 min, mass calcd. for $C_{19}H_{18}ClFN_6O_2$ 416.1, m/z found 417.3 [M+H]$^+$.

e) Preparation of Compound 6

(S)-2-ethyl-6-(4-fluoro-6-morpholino-1H-benzo[d]imidazol-2-yl)-7-((1-(pyrimidin-2-yl)-ethyl)amino)-2,4-dihydro-5H-pyrazolo[4,3-b]pyridin-5-one To a solution of intermediate 35 (7-chloro-2-ethyl-6-(4-fluoro-6-morpholino-1H-benzo[d]-imidazol-2-yl)-2,4-dihydro-5H-pyrazolo[4,3-b]pyridin-5-one) (700 mg, 1.68 mmol) in CHCl$_3$ (20 mL) was added intermediate 11 ((S)-1-(pyrimidin-2-yl)ethan-1-amine hydrochloride) (402 mg, 2.52 mmol), KHCO$_3$ (504 mg, 5.04 mmol) and 18-crown-6 (665 mg, 2.52 mmol). The mixture was stirred at 60° C. for 16 hours. After cooling to room temperature, the reaction mixture was extracted with CH$_2$Cl$_2$ (50 mL*2). The combined organic phase was washed with KHCO$_3$ saturated (50 mL*3), H$_2$O and brine, dried over Na$_2$SO$_4$, filtered and concentrated under reduced pressure. The residue was purified by silica gel chromatography (CH$_2$Cl$_2$:MeOH=80:1) to afford compound 6 (316.18 mg, 35.7% yield, purity 97.3%, ee: 96.08%) as yellow solids.

LC-MS (ESI) (General Procedure A-2, method 2): R$_T$=1.43 min, mass calcd. for C$_{25}$H$_{26}$FN$_9$O$_2$ 503.5, m/z found 504.4 [M+H]$^+$.

General Procedure A-2: $^1$H NMR (400 MHz, CD$_3$OD) δ 8.77 (d, J=4.0 Hz, 2H), 7.53 (s, 1H), 7.36-7.35 (m, 1H), 6.93-6.922 (m, 1H), 6.74-6.68 (m, 1H), 6.42-6.35 (m, 1H), 4.27-4.19 (m, 2H), 3.88-3.83 (m, 4H), 3.17-3.13 (m, 4H), 1.84 (d, J=6.8 Hz, 3H), 1.41 (t, J=6.8 Hz, 3H).

The following compounds were prepared according to reaction protocols of one of the above Examples using alternative starting materials as appropriate. (In the table 1, Ex. X indicates that the preparation of this compound is described in Example X or is prepared according to Example X).

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

TABLE 1

| Compound ID | Structure | Example |
|---|---|---|
| Compound 7 | 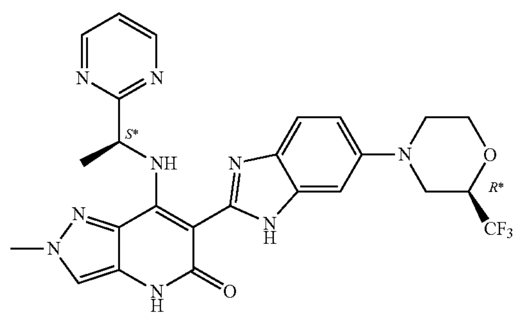 [SMILES: C[C@H](Nc1c(-c2nc3ccc(N4CCO[C@@H](C(F)(F)F)C4)cc3[nH]2)c(=O)[nH]c2cn(C)nc12)c1ncccn1] | Example 1 |
| Compound 8 | 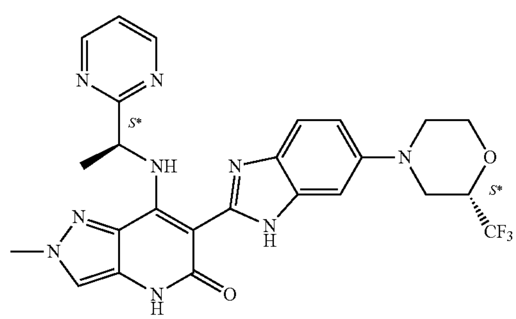 [SMILES: C[C@H](Nc1c(-c2nc3ccc(N4CCO[C@H](C(F)(F)F)C4)cc3[nH]2)c(=O)[nH]c2cn(C)nc12)c1ncccn1] | Example 1 |
| Compound 9 | 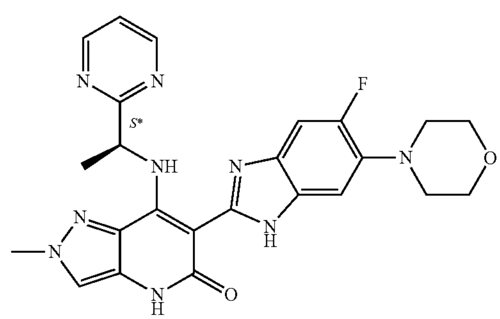 [SMILES: C[C@H](Nc1c(-c2nc3cc(F)c(N4CCOCC4)cc3[nH]2)c(=O)[nH]c2cn(C)nc12)c1ncccn1] | Example 1 |

TABLE 1-continued

| Compound ID | Structure | Example |
|---|---|---|
| Compound 10 | 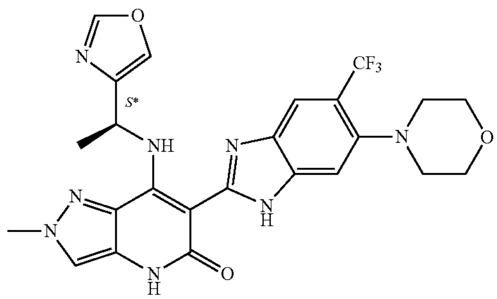 [SMILES: C[C@H](Nc1c(-c2nc3cc(C(F)(F)F)c(N4CCOCC4)cc3[nH]2)c(=O)[nH]c2cn(C)nc12)c1cocn1] | Example 1 |
| Compound 11 | 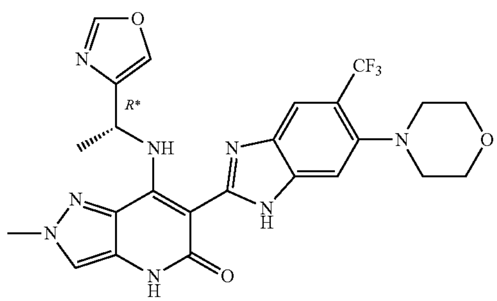 [SMILES: C[C@@H](Nc1c(-c2nc3cc(C(F)(F)F)c(N4CCOCC4)cc3[nH]2)c(=O)[nH]c2cn(C)nc12)c1cocn1] | Example 1 |
| Compound 12 | 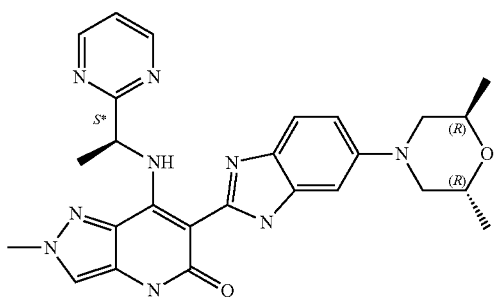 | Example 1 |
| Compound 13 | 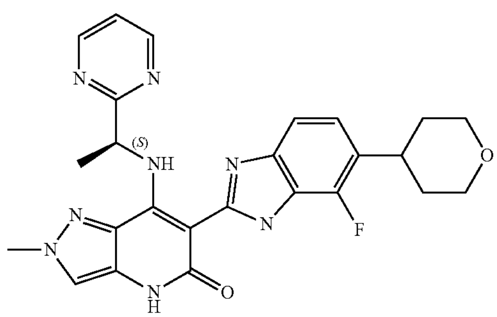 | Example 1 |
| Compound 14 | 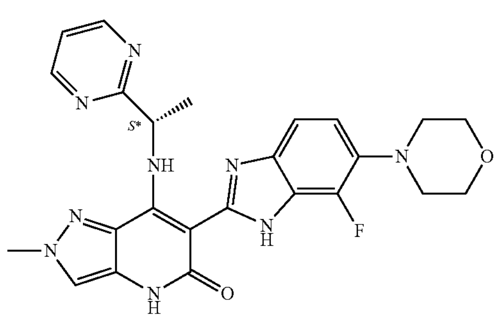 [SMILES: C[C@H](Nc1c(-c2nc3ccc(N4CCOCC4)c(F)c3[nH]2)c(=O)[nH]c2cn(C)nc12)c1ncccn1] | Example 1 |

TABLE 1-continued

| Compound ID | Structure | Example |
|---|---|---|
| Compound 15 | 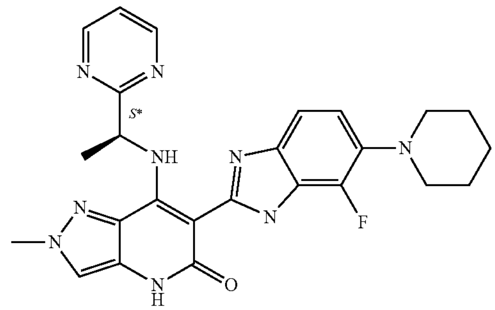 [SMILES: C[C@H](Nc1c(-c2nc3ccc(N4CCCCC4)c(F)c3[nH]2)c(=O)[nH]c2cn(C)nc12)c1ncccn1] | Example 1 |
| Compound 16 | 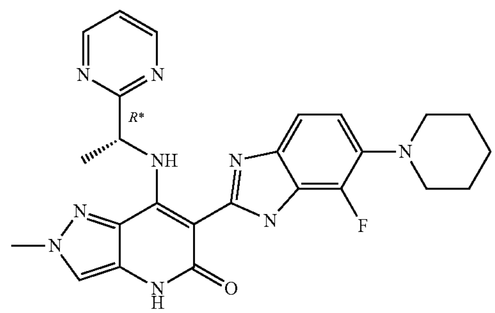 [SMILES: C[C@@H](Nc1c(-c2nc3ccc(N4CCCCC4)c(F)c3[nH]2)c(=O)[nH]c2cn(C)nc12)c1ncccn1] | Example 1 |
| Compound 17 | 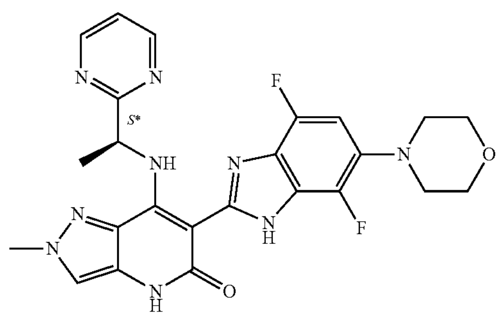 [SMILES: C[C@H](Nc1c(-c2nc3c(F)cc(N4CCOCC4)c(F)c3[nH]2)c(=O)[nH]c2cn(C)nc12)c1ncccn1] | Example 1 |
| Compound 18 | 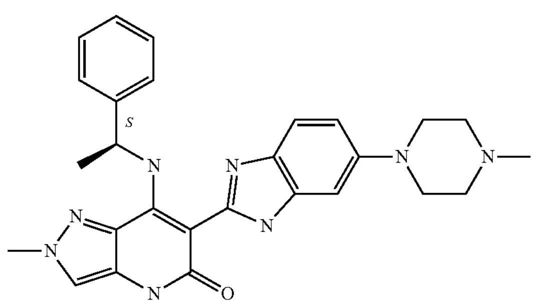 | Example 1 |
| Compound 19 | 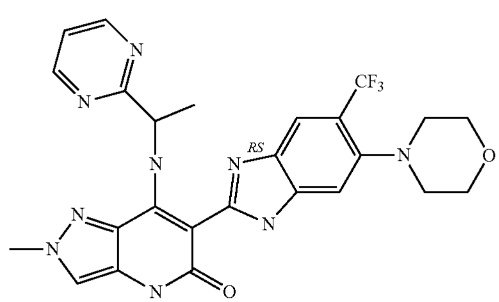 [SMILES: CC(Nc1c(-c2nc3cc(C(F)(F)F)c(N4CCOCC4)cc3[nH]2)c(=O)[nH]c2cn(C)nc12)c1ncccn1] | Example 1 |

TABLE 1-continued

| Compound ID | Structure | Example |
|---|---|---|
| Compound 20 | 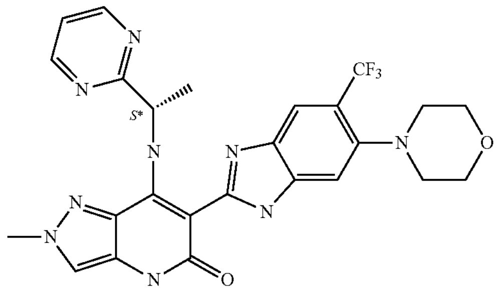 [SMILES: C[C@H](Nc1c(-c2nc3cc(C(F)(F)F)c(N4CCOCC4)cc3[nH]2)c(=O)[nH]c2cn(C)nc12)c1ncccn1] | Example 1 |
| Compound 21 | 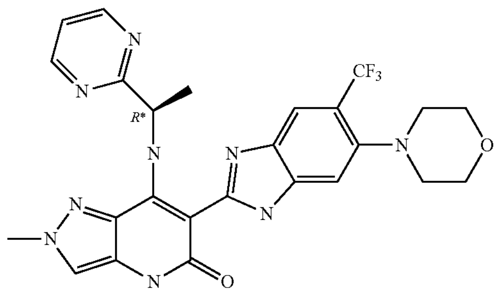 [SMILES: C[C@@H](Nc1c(-c2nc3cc(C(F)(F)F)c(N4CCOCC4)cc3[nH]2)c(=O)[nH]c2cn(C)nc12)c1ncccn1] | Example 1 |
| Compound 22 | 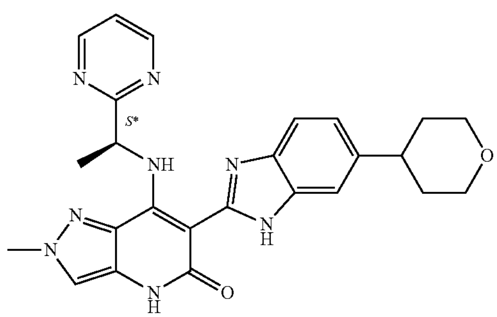 [SMILES: C[C@H](Nc1c(-c2nc3ccc(C4CCOCC4)cc3[nH]2)c(=O)[nH]c2cn(C)nc12)c1ncccn1] | Example 1 |
| Compound 23 | 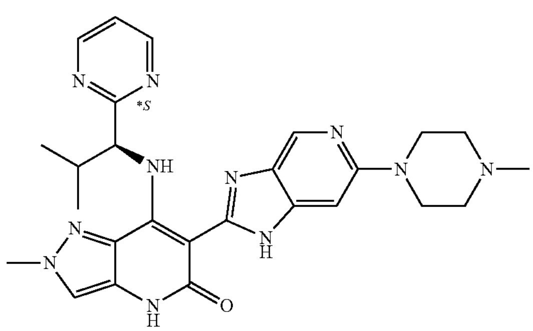 | Example 1 |
| Compound 24 | 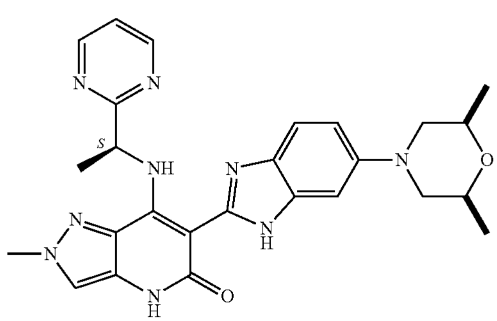 | Example 1 |

TABLE 1-continued

| Compound ID | Structure | Example |
|---|---|---|
| Compound 25 | 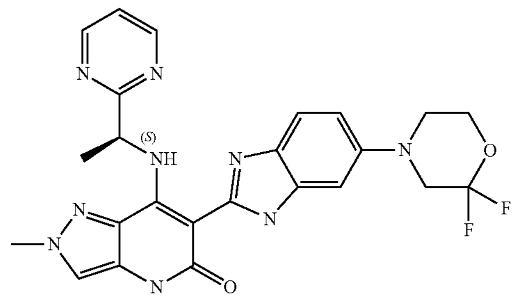 | Example 1 |
| Compound 26 | 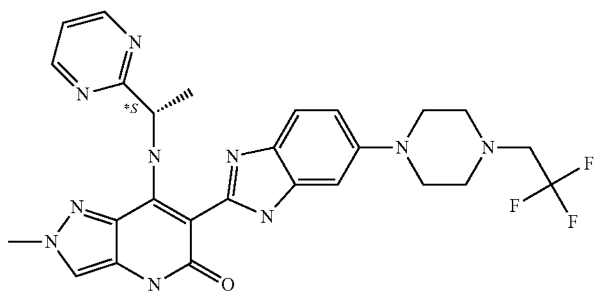 [SMILES: C[C@H](Nc1c(-c2nc3ccc(N4CCN(CC(F)(F)F)CC4)cc3[nH]2)c(=O)[nH]c2cn(C)nc12)c1ncccn1] | Example 1 |
| Compound 27 | 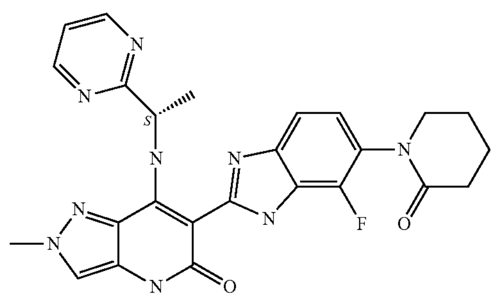 | Example 1 |
| Compound 28 | 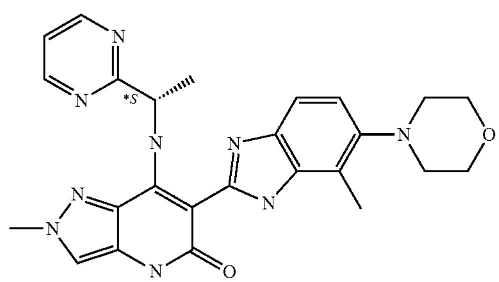 [SMILES: Cc1c(N2CCOCC2)ccc2nc(-c3c(N[C@@H](C)c4ncccn4)c4nn(C)cc4[nH]c3=O)[nH]c12] | Example 1 |
| Compound 29 | 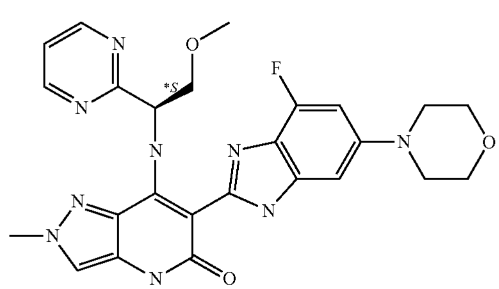 [SMILES: COC[C@@H](Nc1c(-c2nc3c(F)cc(N4CCOCC4)cc3[nH]2)c(=O)[nH]c2cn(C)nc12)c1ncccn1] | Example 1 |

TABLE 1-continued

| Compound ID | Structure | Example |
| --- | --- | --- |
| Compound 30 | 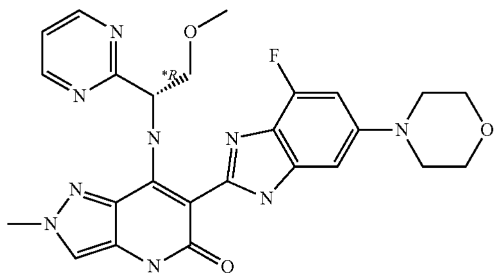 [SMILES: COC[C@H](Nc1c(-c2nc3c(F)cc(N4CCOCC4)cc3[nH]2)c(=O)[nH]c2cn(C)nc12)c1ncccn1] | Example 1 |
| Compound 31 | 0.3HCOOH | Example 1 |
| Compound 32 | 0.2HCOOH | Example 1 |
| Compound 33 | 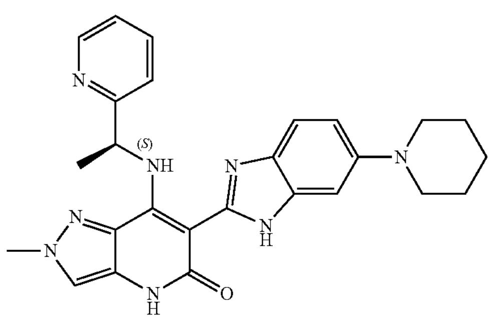 | Example 1 |
| Compound 34 | 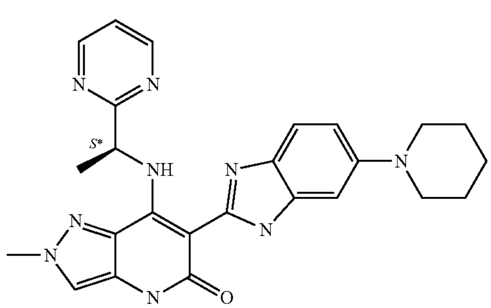 [SMILES: C[C@H](Nc1c(-c2nc3ccc(N4CCCCC4)cc3[nH]2)c(=O)[nH]c2cn(C)nc12)c1ncccn1] | Example 1 |

TABLE 1-continued

| Compound ID | Structure | Example |
| --- | --- | --- |
| Compound 35 | 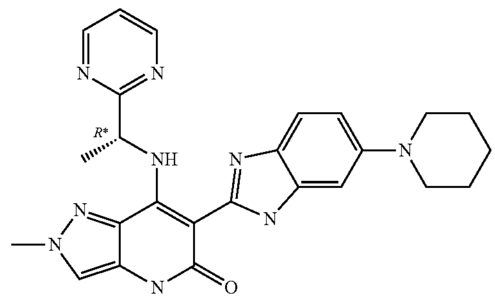 [SMILES: C[C@@H](Nc1c(-c2nc3ccc(N4CCCCC4)cc3[nH]2)c(=O)[nH]c2cn(C)nc12)c1ncccn1] | Example 1 |
| Compound 1 | 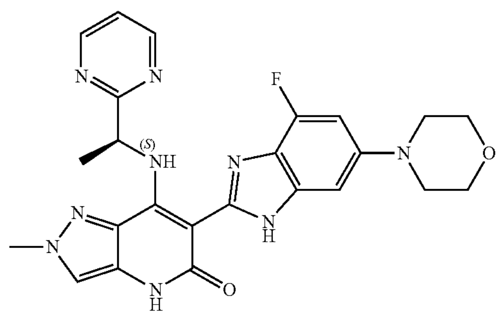 | Example 1 |
| Compound 36 | 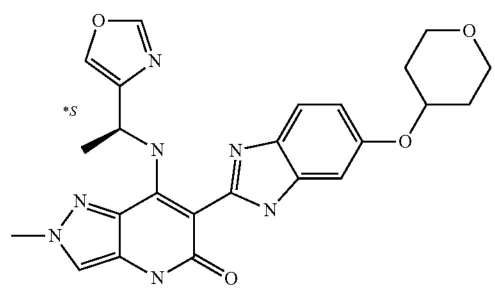 [SMILES: C[C@H](Nc1c(-c2nc3ccc(OC4CCOCC4)cc3[nH]2)c(=O)[nH]c2cn(C)nc12)c1cocn1] | Example 1 |
| Compound 37 | 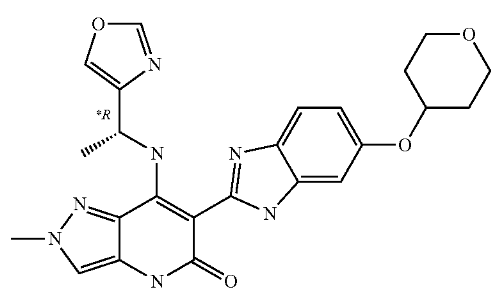 [SMILES: C[C@@H](Nc1c(-c2nc3ccc(OC4CCOCC4)cc3[nH]2)c(=O)[nH]c2cn(C)nc12)c1cocn1] | Example 1 |
| Compound 38 | (0.8 formate) | Example 2 |

TABLE 1-continued

| Compound ID | Structure | Example |
| --- | --- | --- |
| Compound 39 | 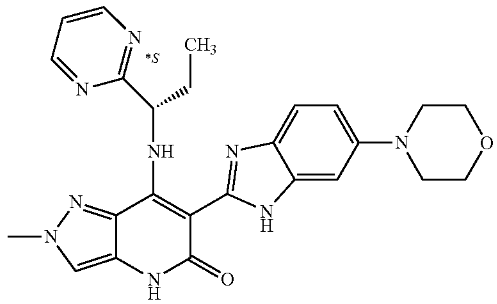 [SMILES: CC[C@H](Nc1c(-c2nc3ccc(N4CCOCC4)cc3[nH]2)c(=O)[nH]c2cn(C)nc12)c1ncccn1] | Example 2 |
| Compound 40 | 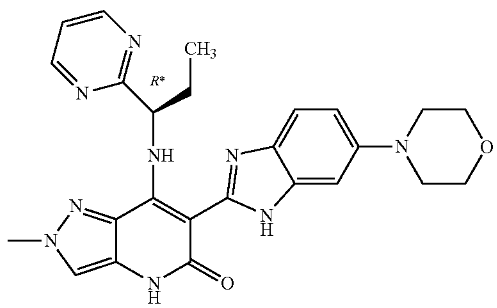 [SMILES: CC[C@@H](Nc1c(-c2nc3ccc(N4CCOCC4)cc3[nH]2)c(=O)[nH]c2cn(C)nc12)c1ncccn1] | Example 2 |
| Compound 41 | 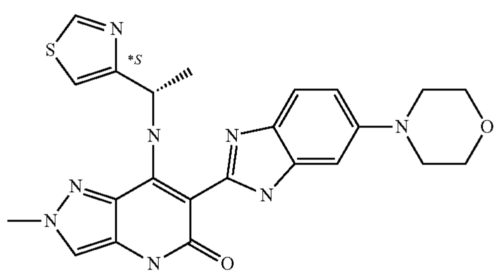 [SMILES: C[C@H](Nc1c(-c2nc3ccc(N4CCOCC4)cc3[nH]2)c(=O)[nH]c2cn(C)nc12)c1cscn1] | Example 2 |
| Compound 42 | 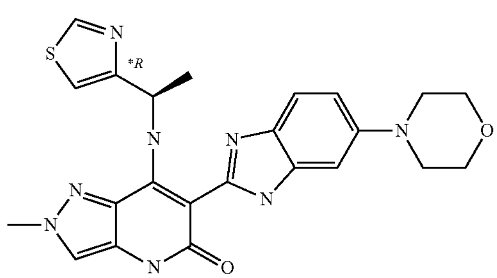 [SMILES: C[C@@H](Nc1c(-c2nc3ccc(N4CCOCC4)cc3[nH]2)c(=O)[nH]c2cn(C)nc12)c1cscn1] | Example 2 |
| Compound 2 | 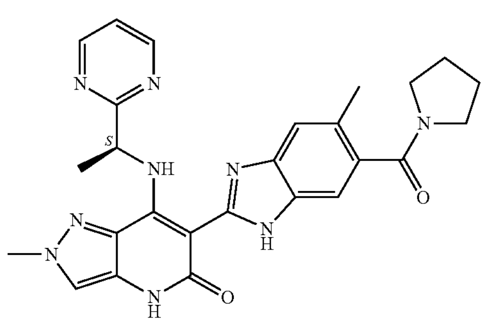 | Example 2 |

TABLE 1-continued

| Compound ID | Structure | Example |
|---|---|---|
| Compound 3 | 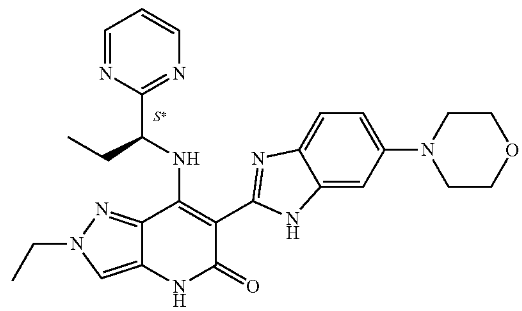 [SMILES: CC[C@H](Nc1c(-c2nc3ccc(N4CCOCC4)cc3[nH]2)c(=O)[nH]c2cn(CC)nc12)c1ncccn1] | Example 3 |
| Compound 43 | 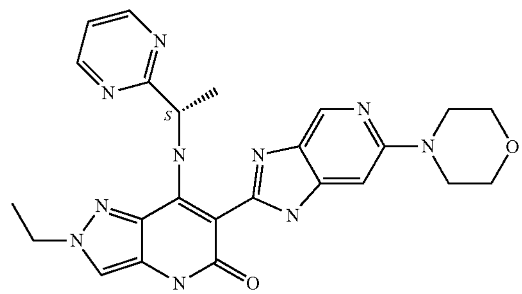 | Example 3 |
| Compound 4A | 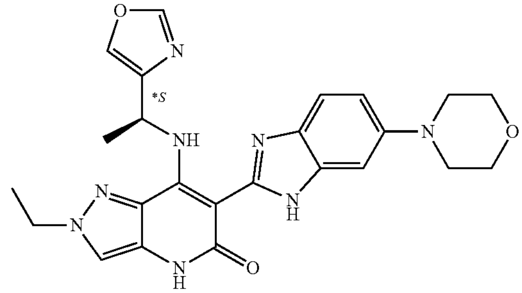 [SMILES: CCn1cc2[nH]c(=O)c(-c3nc4ccc(N5CCOCC5)cc4[nH]3)c(N[C@@H](C)c3cocn3)c2n1] | Example 4 |
| Compound 4B | 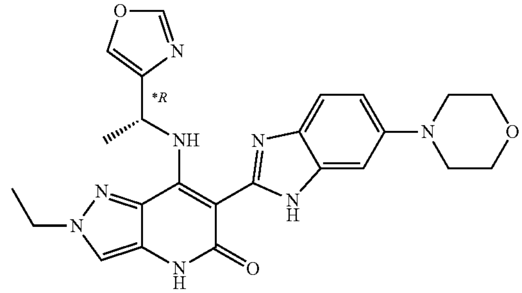 [SMILES: CCn1cc2[nH]c(=O)c(-c3nc4ccc(N5CCOCC5)cc4[nH]3)c(N[C@H](C)c3cocn3)c2n1] | Example 4 |
| Compound 44 | 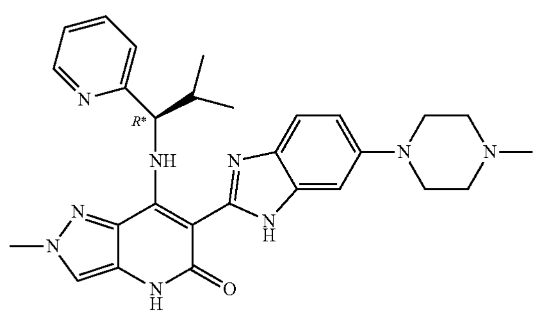 | Example 5 |

TABLE 1-continued

| Compound ID | Structure | Example |
|---|---|---|
| Compound 45 | 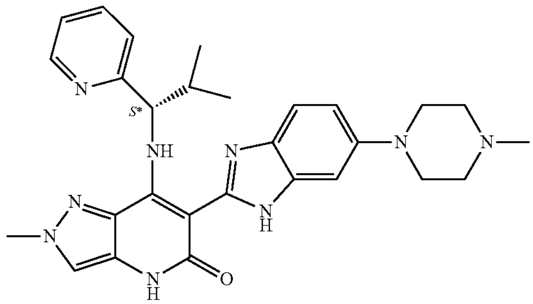 | Example 5 |
| Compound 46 | 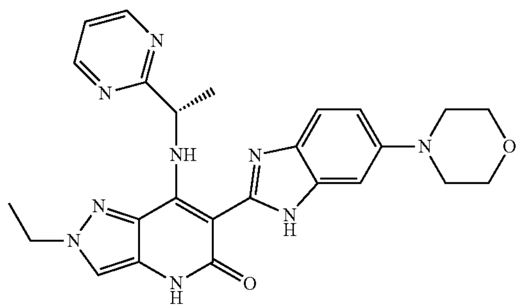 [SMILES: CCn1cc2[nH]c(=O)c(-c3nc4ccc(N5CCOCC5)cc4[nH]3)c(N[C@@H](C)c3ncccn3)c2n1] | Example 5 |
| Compound 47 | 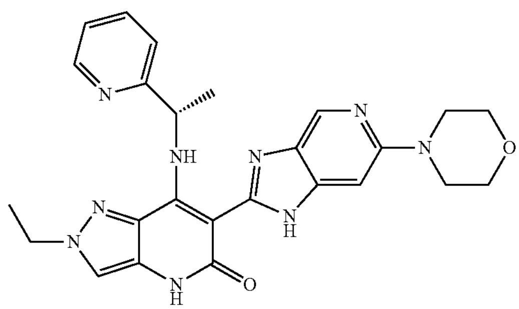 [SMILES: CCn1cc2[nH]c(=O)c(-c3nc4cnc(N5CCOCC5)cc4[nH]3)c(N[C@@H](C)c3ccccn3)c2n1] | Example 5 |
| Compound 48 | 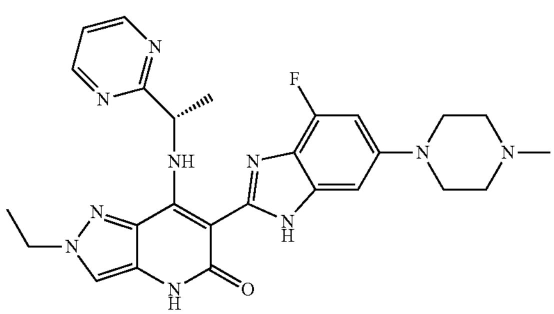 [SMILES: CCn1cc2[nH]c(=O)c(-c3nc4c(F)cc(N5CCN(C)CC5)cc4[nH]3)c(N[C@@H](C)c3ncccn3)c2n1] | Example 5 |
| Compound 49 | 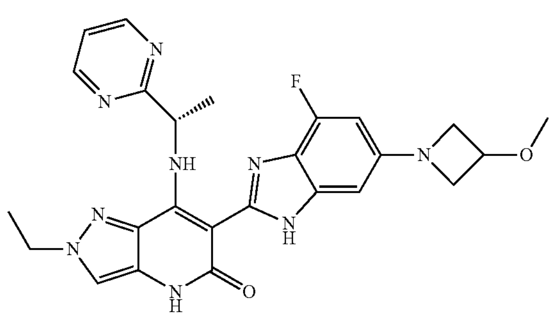 [SMILES: CCn1cc2[nH]c(=O)c(-c3nc4c(F)cc(N5CC(OC)C5)cc4[nH]3)c(N[C@@H](C)c3ncccn3)c2n1] | Example 5 |

TABLE 1-continued
| Compound ID | Structure | Example |
|---|---|---|
| Compound 50 | 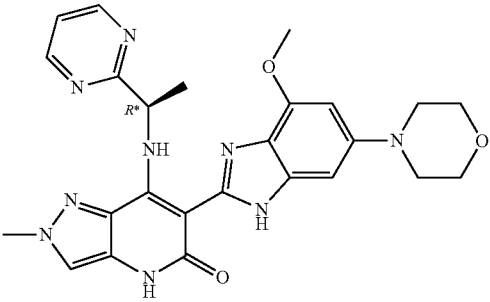 [SMILES: COc1cc(N2CCOCC2)cc2[nH]c(-c3c(N[C@H](C)c4ncccn4)c4nn(C)cc4[nH]c3=O)nc12] | Example 5 |
| Compound 51 | 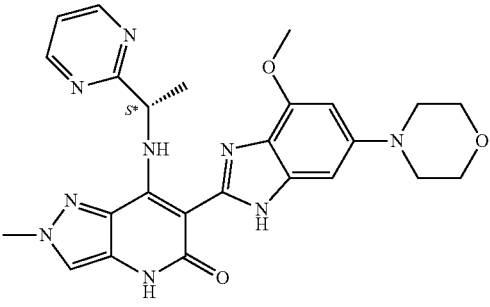 [SMILES: COc1cc(N2CCOCC2)cc2[nH]c(-c3c(N[C@@H](C)c4ncccn4)c4nn(C)cc4[nH]c3=O)nc12] | Example 5 |
| Compound 52 | 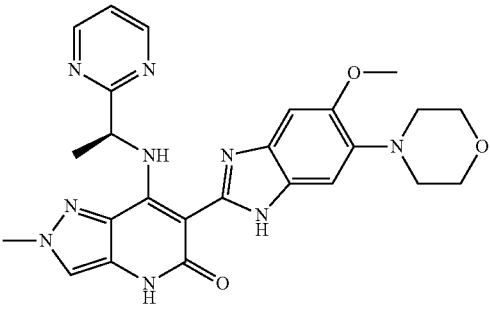 [SMILES: COc1cc2nc(-c3c(N[C@@H](C)c4ncccn4)c4nn(C)cc4[nH]c3=O)[nH]c2cc1N1CCOCC1] | Example 5 |
| Compound 53 | 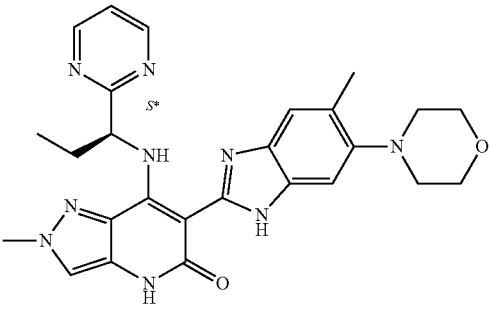 [SMILES: CC[C@H](Nc1c(-c2nc3cc(C)c(N4CCOCC4)cc3[nH]2)c(=O)[nH]c2cn(C)nc12)c1ncccn1] | Example 5 |
| Compound 54 | 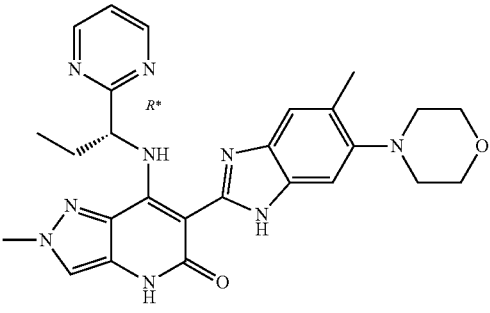 [SMILES: CC[C@@H](Nc1c(-c2nc3cc(C)c(N4CCOCC4)cc3[nH]2)c(=O)[nH]c2cn(C)nc12)c1ncccn1] | Example 5 |

TABLE 1-continued

| Compound ID | Structure | Example |
| --- | --- | --- |
| Compound 5 | 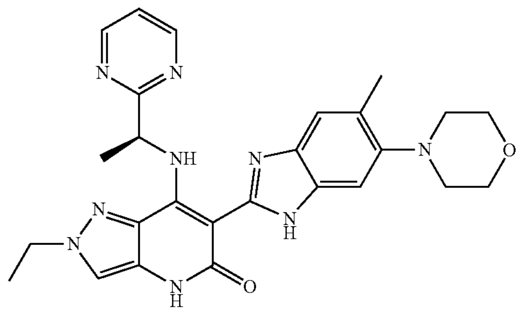 [SMILES: CCn1cc2[nH]c(=O)c(-c3nc4cc(C)c(N5CCOCC5)cc4[nH]3)c(N[C@@H](C)c3ncccn3)c2n1] | Example 5 |
| Compound 6 | 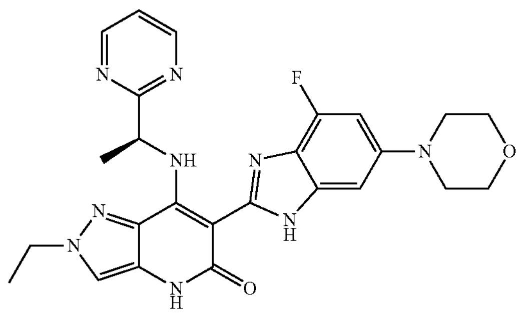 [SMILES: CCn1cc2[nH]c(=O)c(-c3nc4c(F)cc(N5CCOCC5)cc4[nH]3)c(N[C@@H](C)c3ncccn3)c2n1] | Example 6 |
| Compound 55 | 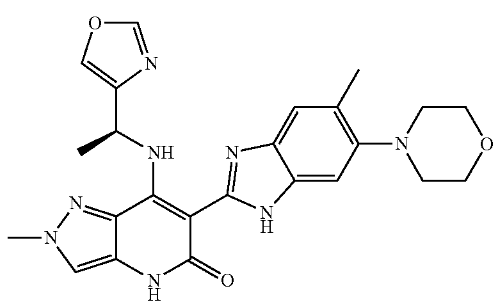 [SMILES: Cc1cc2nc(-c3c(N[C@@H](C)c4cocn4)c4nn(C)cc4[nH]c3=O)[nH]c2cc1N1CCOCC1] | Example 5 |
| Compound 56 | 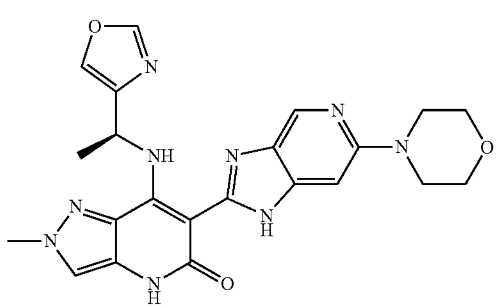 [SMILES: C[C@H](Nc1c(-c2nc3cnc(N4CCOCC4)cc3[nH]2)c(=O)[nH]c2cn(C)nc12)c1cocn1] | Example 5 |

Example 7

Preparation of Intermediates 39 and 41 Used in the Synthesis of Compound 7 and 8 According to Example 1

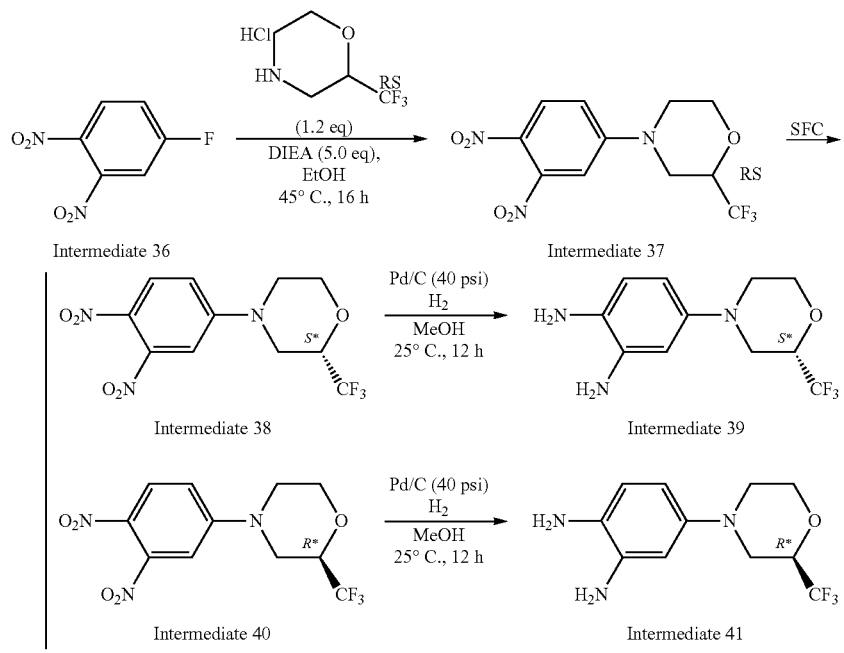

a) Preparation of Intermediate 37

(rac)-4-(3,4-dinitrophenyl)-2-(trifluoromethyl)morpholine

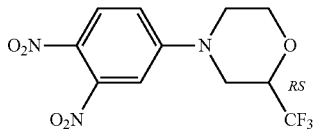

The mixture of intermediate 36 (4-fluoro-1,2-dinitrobenzene) (800 mg, 4.30 mmol), (rac)-2-(trifluoromethyl)morpholine hydrochloride (988 mg, 5.16 mmol) and diisopropylethylamine (2.18 g, 21.5 mmol) in ethanol (10 mL) was stirred at 45° C. for 16 hours. The mixture was concentrated in vacuum to give a residue, which was purified by column chromatography over silica gel (eluent: petroleum ether/ethyl acetate from 100/0 to 85/15). The desired fractions were collected and the solvent was concentrated to dryness under vacuum to give intermediate 37 (1.00 g, 95% purity, 68.8% yield) as yellow solids.

General Procedure A: $^1$H NMR (400 MHz, DMSO-d$^5$) (Varian) δ=8.08 (d, J=9.3 Hz, 1H), 7.63 (d, J=2.6 Hz, 1H), 7.29-7.19 (m, 1H), 4.44-4.29 (m, 1H), 4.20-4.02 (m, 2H), 3.99-3.88 (m, 1H), 3.78-3.65 (m, 1H), 3.19-3.07 (m, 2H).

b) Preparation of Intermediate 38

(S*)-4-(3,4-dinitrophenyl)-2-(trifluoromethyl)morpholine

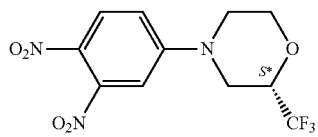 [SMILES: O=[N+]([O-])c1ccc(N2CCO[C@H](C(F)(F)F)C2)cc1[N+](=O)[O-]]

Preparation of Intermediate 40

(R*)-4-(3,4-dinitrophenyl)-2-(trifluoromethyl)morpholine

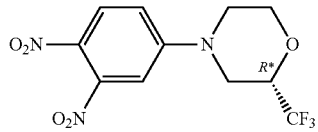

Intermediate 37 ((rac)-4-(3,4-Dinitrophenyl)-2-(trifluoromethyl)morpholine) was separated by supercritical fluid chromatography (separation condition: AS (250 mm*30 mm, 10 um); Mobile phase: A: Supercritical CO$_2$, B: 0.1% NH$_3$H$_2$O EtOH, A:B=50:50 at 60 mL/min; Column Temp:

38° C.; Nozzle Pressure: 100 Bar; Nozzle Temp: 60° C.; Evaporator Temp: 20° C.; Trimmer Temp: 25° C.; Wavelength: 220 nm). The pure fractions were collected and the volatiles were removed under vacuum to give intermediate 38 (480 mg, 99.5% purity, 47.8% yield) as yellow solids. SFC (Method 21): $R_T$=3.42 min, Peak Area: 100%, and to give intermediate 40 which was directly used to synthesize intermediate 41.

c) Preparation of Intermediate 39

(S*)-4-(2-(Trifluoromethyl)morpholino)benzene-1,2-diamine

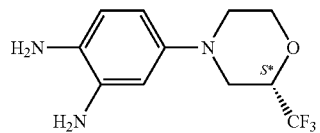 [SMILES: O=[N+]([O-])c1ccc(N2CCO[C@H](C(F)(F)F)C2)cc1[N+](=O)[O-]]

Wet palladium on activated carbon (100 mg, 10% on activated carbon) was added to a solution of intermediate 38 ((S*)-4-(3,4-dinitrophenyl)-2-(trifluoromethyl)morpholine) (480 mg, 1.49 mmol) in methanol (25 mL). The suspension was degassed under vacuum and purged with hydrogen several times and then the mixture was stirred under hydrogen (40 psi) at 25° C. for 12 hours. The suspension was filtered through a pad of Celite and the filter cake was washed with methanol (50 mL×2). The filtrate was concentrated in vacuum to intermediate 39 (450 mg, crude) as brown solids, which was used for next step without further purification.

LC-MS (ESI) (General Procedure B, Method 6): $R_T$=1.75 min, mass calcd. for $C_{11}H_{14}F_3N_3O$ 261.11, m/z found 262.1 $[M+H]^+$.

d) Preparation of Intermediate 41

(R*)-4-(2-(Trifluoromethyl)morpholino)benzene-1,2-diamine

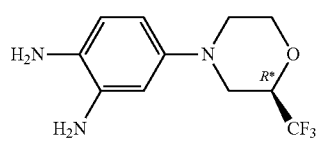

The synthesis of intermediate 41 was similar to the one for intermediate 39 to give intermediate 41 (460 mg, crude) (starting from intermediate 40) as brown solids.

LC-MS (ESI) (General Procedure B, Method 6): $R_T$=1.75 min, mass calcd. for $C_{11}H_{14}F_3N_3O$ 261.11, m/z found 262.1 $[M+H]^+$.

Example 8

Preparation of Intermediate 44 Used in the Synthesis of Compound 12 According to Example 1

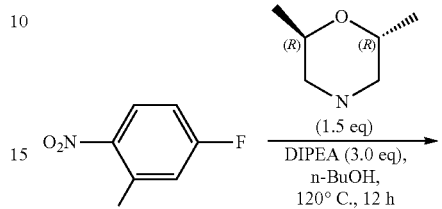

Intermediate 42

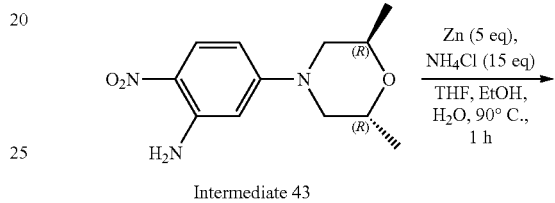

Intermediate 43

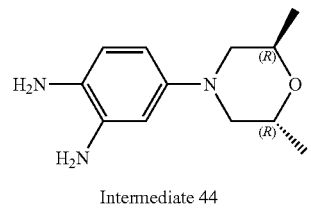

Intermediate 44 a) Preparation of Intermediate 43

5-((2R,6R)-2,6-dimethylmorpholino)-2-nitroaniline

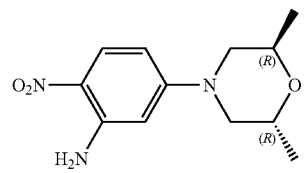

A suspension of intermediate 42 (5-fluoro-2-nitroaniline) (0.904 g, 5.79 mmol), (2R,6R)-2,6-dimethylmorpholine (1.00 g, 8.68 mmol), N,N-diisopropylethylamine (3 mL, 18.2 mmol), and 1-butanol (10 ml) was stirred at 120° C. for 12 hours. Cooling to room-temperature, the reaction mixture was poured into water (50 mL). Then the mixture was extracted with dichloromethane (50 mL×3), and the combined organic layers were washed with water (50 mL×3) and brine (50 mL×3). The separated organic layer was dried over anhydrous $Na_2SO_4$ and filtered. The filtrate was concentrated to dryness under reduced pressure to afford the crude product, which was purified by flash column chromatography (eluent: petroleum ether:ethyl acetate from 1:0 to 1:1) to afford intermediate 43 (0.950 g, 99.7% purity, 65.1% yield) as yellow solids.

LC-MS (ESI) (General Procedure C, Method 9): $R_T$=0.79 min, mass calcd. for $C_{12}H_{17}N_3O_3$ 251.13, m/z found 252.0 [M+H]$^+$.

b) Preparation of Intermediate 44

4-((2R,6R)-2,6-dimethylmorpholino)benzene-1,2-diamine

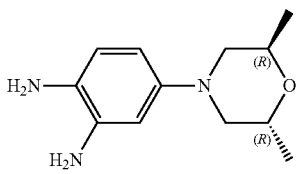

Zinc (1.11 g, 16.9 mmol) was added to a solution consisting of intermediate 43 (5-((2R,6R)-2,6-dimethylmorpholino)-2-nitroaniline) (0.850 g, 3.38 mmol), ammonium chloride (2.71 g, 50.7 mmol) in tetrahydrofuran (25 mL), ethanol (25 mL) and water (10 mL) at 20° C. Then the reaction mixture was stirred at 90° C. for 1 hour. The reaction mixture was cooled to room-temperature, and the suspension was filtered through a pad of Celite® and the pad was washed with water (10 mL). The filtrate was poured into water (100 mL), and extracted with ethyl acetate (100 mL×3). The combined organic extracts were washed with brine, dried over anhydrous Na$_2$SO$_4$ and filtered. The filtrate was concentrated to dryness under reduced pressure to afford the crude product, which was purified by flash column chromatography (eluent: petroleum ether:ethyl acetate from 1:0 to 0:1) to afford intermediate 44 (0.810 g, 87% purity, 94% yield) as a pale yellow solid.

LC-MS (ESI) (General Procedure B, Method 5): $R_T$=0.32 min, mass calcd. for $C_{12}H_{19}N_3O$ 221.15, m/z found 222.0 [M+H]$^+$.

Example 9

Preparation of Intermediate 47 Used in the Synthesis of Compound 13 According to Example 1

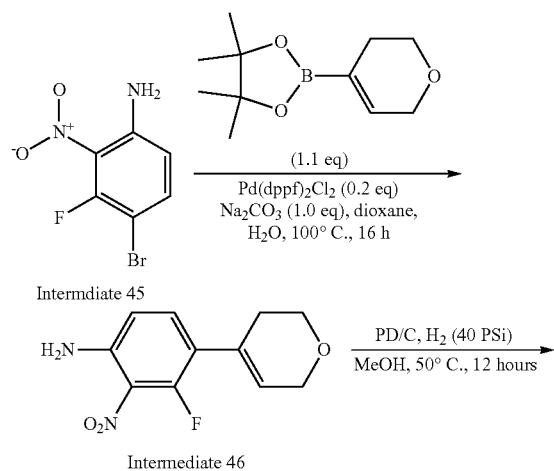

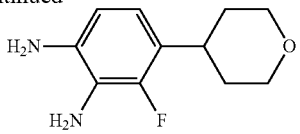

Intermediate 47 a) Preparation of Intermediate 45

4-Bromo-3-fluoro-2-nitroaniline

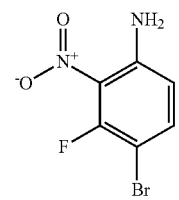

Intermediate 45 was synthesized from 3-fluoro-2-nitroaniline as described in WO2012/83170A1.

b) Preparation of Intermediate 46

4-(3,6-dihydro-2H-pyran-4-yl)-3-fluoro-2-nitroaniline

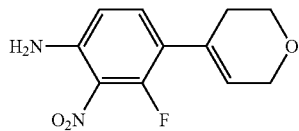

Intermediate 45 (4-bromo-3-fluoro-2-nitroaniline) (2.00 g, 8.51 mmol), 2-(3,6-dihydro-2H-pyran-4-yl)-4,4,5,5-tetramethyl-1,3,2-dioxaborolane (1.97 g, 9.36 mmol), sodium carbonate (0.902 g, 8.51 mmol), 1,4-dioxane (48 mL), and water (12 mL) were added to a round-bottom flask. The mixture was bubbled with nitrogen for 5 minutes and then treated with [1,1'-bis-(diphenylphosphino)ferrocene]dichloropalladium(II) (1.24 g, 1.70 mmol). The mixture was bubbled with nitrogen for another 5 minutes and then heated at 100° C. for 16 hours. The mixture was filtered and the filtrate was concentrated to dryness under reduced pressure to afford the crude product. The residue was extracted with dichloromethane (100 mL×3). The combined organic extracts were dried over Na$_2$SO$_4$(s) and filtered. The filtrate was concentrated to dryness under reduced pressure to afford the crude product, which was purified by flash column chromatography (eluent: petroleum ether:ethyl acetate=3:1) to afford intermediate 46 as yellow solids (1.60 g, 95% purity, 74.98% yield).

General Procedure A: $^1$H NMR (400 MHz, DMSO-d$^6$) (Varian) δ 7.30 (t, J=8.6 Hz, 1H), 6.87 (br. s., 2H), 6.73 (dd, J=0.9, 9.0 Hz, 1H), 5.95 (s, 1H), 4.25-4.12 (m, 2H), 3.76 (t, J=5.4 Hz, 2H), 2.34 (s, 2H).

c) Preparation of Intermediate 47

3-Fluoro-4-(tetrahydro-2H-pyran-4-yl)benzene-1,2-diamine

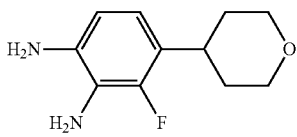

Wet palladium on activated carbon (0.5 g, 10% on activated carbon) was added to a solution consisting of intermediate 46 (4-(3,6-dihydro-2H-pyran-4-yl)-3-fluoro-2-nitroaniline) (1.00 g, 4.20 mmol) and methanol (30 mL). The mixture was bubbled with hydrogen for 5 minutes, and then stirred at 50° C. under hydrogen (40 psi) for 12 hours. The suspension was filtered through a pad of Celite® and the pad was washed with methanol (10 mL). The filtrate was concentrated to dryness under reduced pressure to afford intermediate 47 (0.85 g, 90% purity by TLC, 86.7% yield) as brown oil.

Example 10

Preparation of Intermediate 50 Used to Prepare Compound 15 and 16 According to Example 1

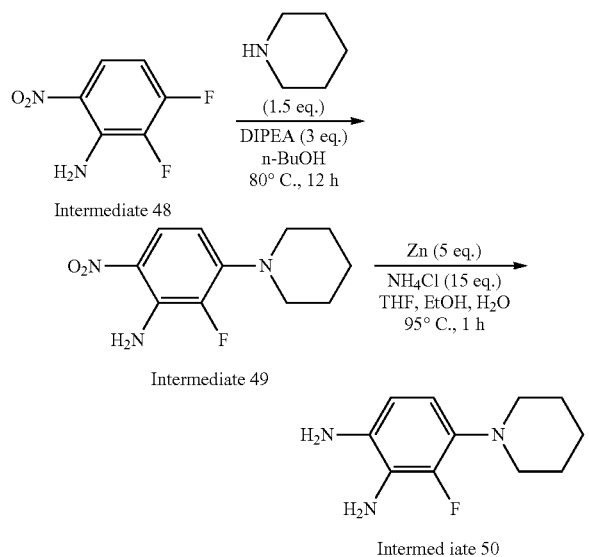

a) Preparation of Intermediate 49

2-Fluoro-6-nitro-3-(piperidin-1-yl)aniline

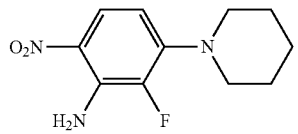

A solution of intermediate 48 (2,3-difluoro-6-nitroaniline) (5.00 g, 28.7 mmol), piperidine (3.67 g, 43.1 mmol) and N,N-diisopropylethylamine (15 mL, 85.9 mmol) in n-butyl alcohol (30 mL) was stirred at 80° C. for 12 hours. The resultant mixture was poured into ethyl acetate (15 mL) and washed with water (30 mL×3). The separated organic layer was dried over anhydrous $Na_2SO_4$ and filtered. The filtrate was concentrated to dryness under reduced pressure to afford the crude intermediate 49 (7.060 g, crude) as yellow solids.

LC-MS (ESI) (General Procedure C, Method 9): $R_T$=0.91 min, mass calcd. for $C_{11}H_{14}FN_3O_2$ 239.11, m/z found 239.9 $[M+H]^+$.

General Procedure A: $^1$H NMR (400 MHz, $CDCl_3$) (Varian) 7.85 (dd, J=1.8, 9.7 Hz, 1H), 6.27 (dd, J=8.8, 9.5 Hz, 1H), 6.10 (s, 2H), 3.32-3.25 (m, 4H), 1.75-1.63 (m, 6H)

b) Preparation of Intermediate 50

3-Fluoro-4-(piperidin-1-yl)benzene-1,2-diamine

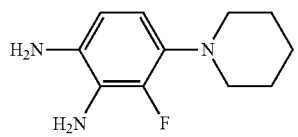 [SMILES: Nc1c([N+](=O)[O-])ccc(N2CCCCC2)c1F]

A solution consisting of intermediate 49 (2-fluoro-6-nitro-3-(piperidin-1-yl)aniline) (1.02 g, 4.28 mmol), Zinc (1.40 g, 21.4 mmol), ammonium chloride (3.40 g, 63.6 mmol), THF (20 mL), ethanol (20 mL) and water (5 mL) were stirred at 95° C. for 1 hour. The reaction mixture was cooled to 25° C. and filtered through a pad of Celite®. The filtrate was poured into water (5 mL), and extracted with ethyl acetate (10 mL×3). The combined organic extracts were washed with brine, dried over anhydrous $Na_2SO_4$ and filtered. The filtrate was concentrated to dryness under reduced pressure to afford intermediate 50 (875 g, crude) as a yellow solid which was used for next step directly.

LC-MS (ESI) (General Procedure C, Method 9): $R_T$=0.151 min, mass calcd. for $C_{11}H_{16}FN_3$ 209.13, m/z found 209.8

General Procedure A: $[M+H]^+$. $^1$H NMR (400 MHz, $CDCl_3$) (Varian) 6.43-6.39 (m, 1H), 6.37-6.31 (m, 1H), 2.91-2.90 (m, 4H), 1.76-1.68 (m, 4H), 1.57-1.50 (m, 2H)

Example 11

Preparation of Intermediate 54 Used in the Synthesis of Compound 17 According to Example 1

-continued

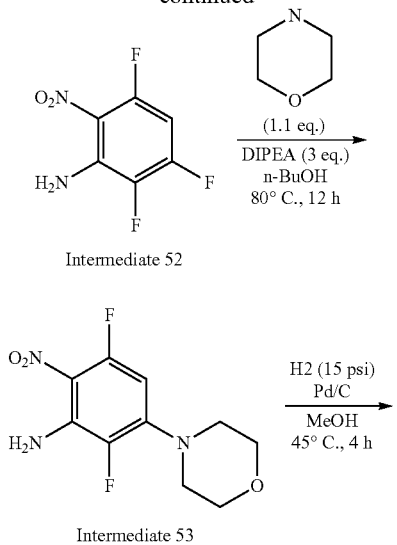

Intermediate 52

Intermediate 53

Intermediate 54 a) Preparation of Intermediate 52

2,3,5-Trifluoro-6-nitroaniline

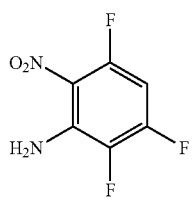 [SMILES: Nc1c(F)c(F)cc(F)c1[N+](=O)[O-]]

A mixture consisting of intermediate 51 (2,3,4,6-tetrafluoronitrobenzene) (2.00 g, 10.3 mmol) and ammonia in dioxane (51 mL) was bubbled with nitrogen for 5 minutes. Then the mixture reaction was stirred at room temperature for 3 hours. The resultant mixture was poured into ethyl acetate (50 mL) and washed with water (30 mL×3). The combined organic extracts were dried over anhydrous $Na_2SO_4$, filtered and concentrated to dryness under reduced pressure to afford the crude intermediate 52, which was purified by flash column chromatography (eluent: petroleum ether:ethyl acetate=8:1 to 4:1) to afford intermediate 52 (1.12 g, 53.9% yield) as a yellow solid.

General Procedure A: $^1$H NMR (400 MHz, CDCl$_3$) (Varian) 6.40-6.25 (m, 1H), 5.91 (br. s., 2H).

b) Preparation of Intermediate 53

2,5-Difluoro-3-morpholino-6-nitroaniline

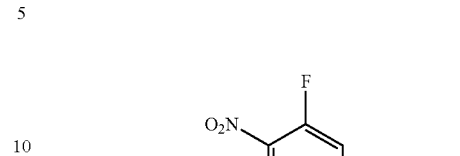

A solution of intermediate 52 (2,3,5-trifluoro-6-nitroaniline) (100 mg, 0.495 mmol), morpholine (47.0 mg, 0.539 mmol) and N,N-diisopropylethylamine (192 mg, 1.49 mmol) in H-butyl alcohol (1 mL) was stirred at 80° C. for 12 hours. The resultant mixture was concentrated to dryness under reduced pressure to afford crude product. The resultant mixture was poured into ethyl acetate (20 mL) and washed with water (10 mL×3). The separated organic layer was dried over anhydrous $Na_2SO_4$ and filtered. The filtrate was concentrated to dryness under reduced pressure to afford the crude product, which was purified by flash column chromatography (eluent: petroleum ether:ethyl acetate=8:1 to 4:1) to afford intermediate 53 (45.0 mg, 31.6% yield) as a yellow solid.

General Procedure A: $^1$H NMR (400 MHz, DMSO-d$^5$) (Varian) 6.52 (dd, J=6.8, 12.3 Hz, 1H), 6.30 (s, 2H), 3.62-3.54 (m, 4H), 2.85-2.74 (m, 4H).

c) Preparation of Intermediate 54

3,6-Difluoro-4-morpholinobenzene-1,2-diamine

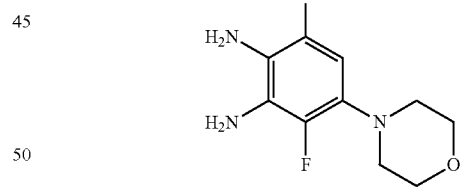

Wet palladium on activated carbon (50 mg) was added to a solution consisting of intermediate 53 (2,5-difluoro-3-morpholino-6-nitroaniline) (45.0 mg, 0.156 mmol) and methanol (10 mL) in a 50 mL round-bottomed flask. The mixture was bubbled with hydrogen (15 psi) for 5 minutes, and then stirred at 45° C. for 4 hours. The reaction mixture was cooled to room temperature and filtered through a pad of Celite®. The filtrate was concentrated to dryness under reduced pressure to afford intermediate 54 (34.4 mg, 53% purity, 50.9% yield) as a purple solid.

General procedure A: $^1$H NMR (400 MHz, DMSO-d$^6$) (Varian) 6.36-6.21 (m, 1H), 4.80 (s, 2H), 4.33 (s, 2H), 3.71-3.66 (m, 4H), 2.69-2.63 (m, 4H).

Example 12

Preparation of Intermediate 58 Used to Synthesize Compound 25 According to Example 1

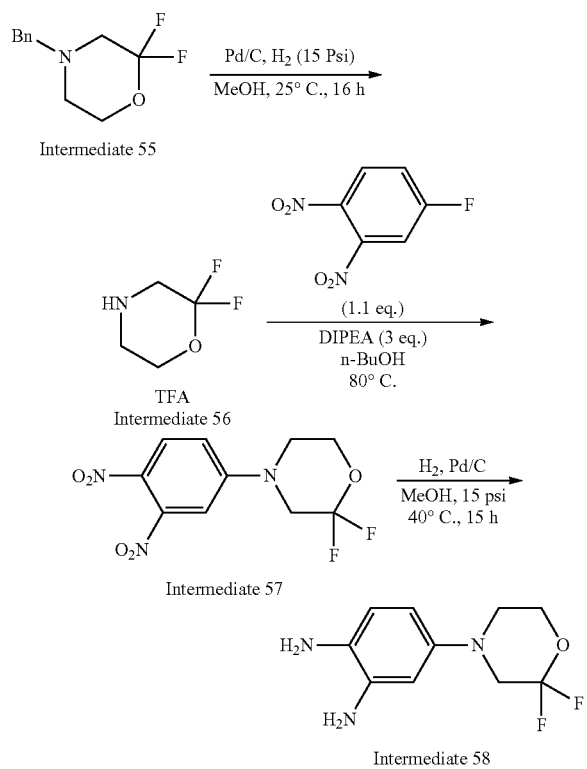

a) Preparation of Intermediate 55

4-Benzyl-2,2-difluoromorpholine

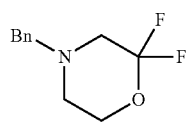

Intermediate 55 was synthesized as described in US2016176896A1.

b) Preparation of Intermediate 56

2,2-difluoromorpholine trifluoroacetate

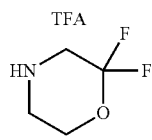

Wet palladium on activated carbon (90 mg, 10% on activated carbon) was added to a solution of intermediate 55 (4-benzyl-2,2-difluoromorpholine) (930 mg, 4.36 mmol) and methanol (10 mL) in a 100 mL round-bottomed flask. The mixture was sparged with hydrogen for 5 minutes, and then stirred at 45° C. under hydrogen (15 psi) for 16 hours. The suspension was filtered through a pad of Celite® and the pad was washed with ethyl acetate (10 mL). The pH of the filtrate was adjusted to 4-6 with trifluoroacetic acid and concentrated to dryness under reduced pressure to afford intermediate 56 (1.0 g, crude) as white solids, which was used for next step without further purification.

c) Preparation of Intermediate 57

4-(3,4-Dinitrophenyl)-2,2-difluoromorpholine

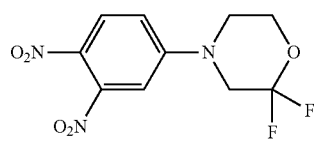 [SMILES: O=[N+]([O-])c1ccc(N2CCOC(F)(F)C2)cc1[N+](=O)[O-]]

A solution consisting of 4-fluoro-1,2-dinitrobenzene (777 mg, 4.18 mmol), intermediate 56 (2,2-difluoromorpholine trifluoroacetate) (900 mg, crude) and N,N-diisopropylethylamine (1.47 g, 11.4 mmol) in w-butanol (20 mL) was stirred at 80° C. for 15 hours before cooling to room-temperature. The reaction mixture was concentrated to dryness under reduced pressure to afford crude product, which was purified by flash column chromatography (eluent: petroleum ether: ethyl acetate from 10:1 to 0:1) to afford intermediate 57 (700 mg, 95% purity) as yellow solids.

General Procedure A: $^1$H NMR (400 MHz, DMSO-d$^5$) (Varian) δ 8.12 (d, J=9.3 Hz, 1H), 7.60 (d, J=2D Hz, 1H), 7.24 (dd, J=2D, 9.5 Hz, 1H), 4.20 (t, J=5.1 Hz, 2H), 4.10 (t, J=8.6 Hz, 2H), 3.68 (t, J=4.9 Hz, 2H)

d) Preparation of Intermediate 58

4-(2,2-difluoromorpholino)benzene-1,2-diamine

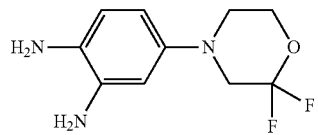

Wet palladium on activated carbon (50 mg, 10% on activated carbon) was added to a solution consisting of intermediate 57 (4-(3,4-dinitrophenyl)-2,2-difluoromorpholine) (500 mg, 1.73 mmol) and methanol (10 mL) in a 100 mL round-bottomed flask. The mixture was sparged with hydrogen for 5 minutes, then stirred at 45° C. under hydrogen (15 psi) for 16 hours before cooling to room-temperature. The suspension was filtered through a pad of Celite® and the pad was washed with ethyl acetate (10 mL). The filtrate was concentrated to dryness under reduced pressure to afford intermediate 58 (390 mg, 95% purity, 93% yield) as brown solids.

General Procedure A: $^1$H NMR (400 MHz, DMSO-d$^6$) (Varian) δ 6.39 (d, J=8.2 Hz, 1H), 6.22 (d, J=2.6 Hz, 1H), 6.04 (dd, J=2.6, 8.4 Hz, 1H), 4.41 (s, 2H), 4.12-4.03 (m, 4H), 3.18 (t, J=8.0 Hz, 2H), 2.98 (t, J=4.5 Hz, 2H).

Example 13

Preparation of Intermediate 61 Used to Synthesize Compound 26 According to Example 1

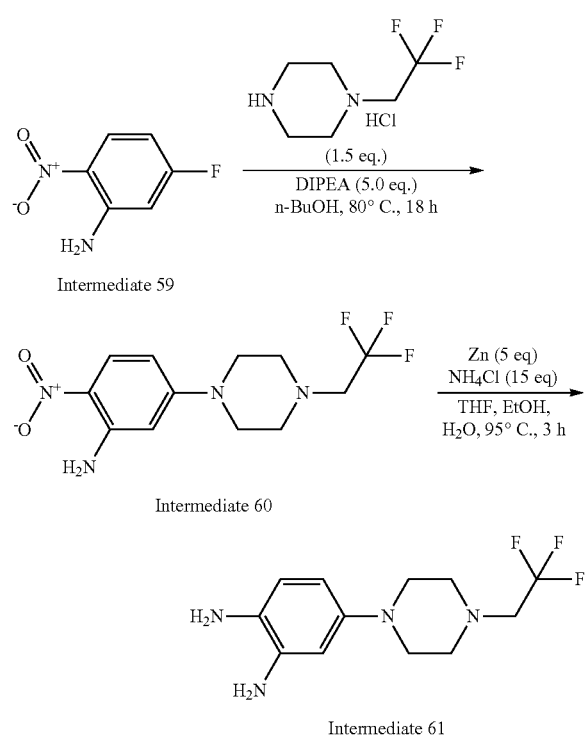

a) Preparation of Intermediate 60

2-nitro-5-(4-(2,2,2-trifluoroethyl)piperazin-1-yl) aniline

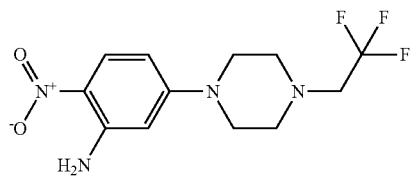

A solution of 1-(2,2,2-trifluoroethyl)piperazine hydrochloride (1.00 g, 4.15 mmol), intermediate 59 (5-fluoro-2-nitroaniline) (0.432 g, 2.77 mmol) and N,N-diisopropylethylamine (2.4 mL, 14 mmol) in n-butanol (5 mL) was stirred at 80° C. for 18 hours. The resultant mixture was poured into ethyl acetate (20 mL). The separated organic layer was washed with water (10 mL×3), dried over anhydrous Na/SO$_2$, filtered and concentrated to dryness under reduced pressure to afford intermediate 60 (836.5 mg, crude) as a yellow solid, which was used for next step directly.

b) Preparation of Intermediate 61

4-(4-(2,2,2-trifluoroethyl)piperazin-1-yl)benzene-1, 2-diamine

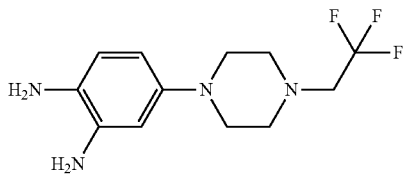

A solution consisting of intermediate 60 (2-nitro-5-(4-(2, 2,2-trifluoroethyl)piperazin-1-yl)-aniline) (1.00 g, 3.29 mmol), zinc (1.08 g, 16.4 mmol), ammonium chloride (2.64 g, 49.3 mmol), THF (20 mL), ethanol (20 mL), and water (10 mL) were stirred at 95° C. for 3 hours. The reaction mixture was cooled to 25° C. and filtered. The filtrate was poured into water (50 mL) and extracted with ethyl acetate (70 mL×3). The combined organic extracts were dried over anhydrous Na/SO$_2$ and filtered. The filtrate was concentrated to dryness under reduced pressure to afford crude product which was purified by flash column chromatography (eluent: ethyl acetate:petroleum ether from 0:1 to 1:1) to give intermediate 61 (390 mg, 86.3% purity, 37.3% yield) as brown solids.

LC-MS (ESI) (General Procedure B, Method 6): R$_T$=1.55 min, mass calcd. for C$_{12}$H$_{17}$F$_3$N$_4$ 274.14, m/z found 275.1 [M+H]$^+$.

Example 14

Preparation of Intermediate 67 Used to Prepare Compound 27 According to Example 1

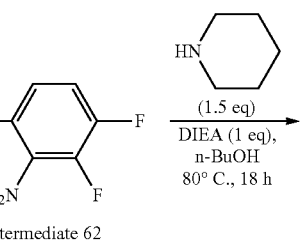

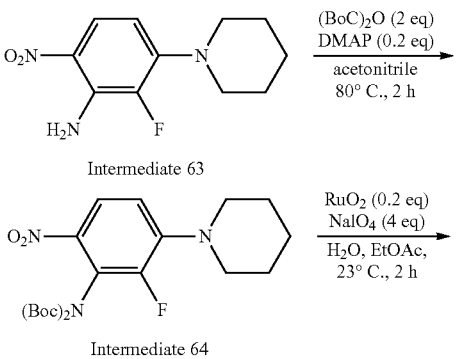

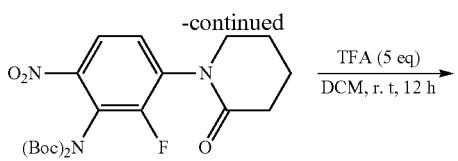

Intermediate 65

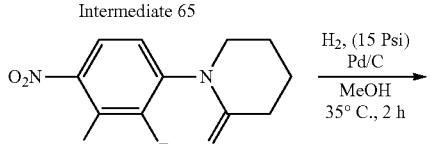

Intermediate 66

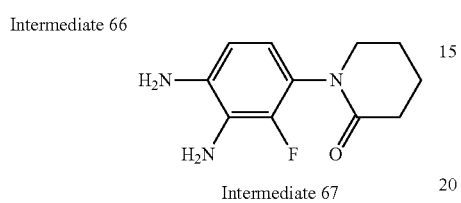

Intermediate 67 a) Preparation of Intermediate 63

2-fluoro-6-nitro-3-(piperidin-1-yl) aniline

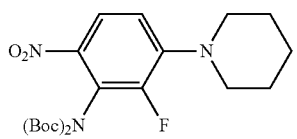

A solution of intermediate 62 (2,3-difluoro-6-nitroaniline) (10.0 g, 57.4 mmol), piperidine (7.34 g, 86.2 mmol) and NA-diisopropylethylamine (7.42 g, 57.4 mmol) in n-butanol (400 mL) was stirred at 80° C. for 18 hours. The resultant mixture was concentrated to dryness under reduced pressure to give crude product which was dissolved in ethyl acetate (800 mL). The organic layer was washed with water (400 mL×3), dried over anhydrous $Na_2SO_4$, and filtered. The filtrate was concentrated to dryness under reduced pressure to afford intermediate 63 (10.02 g, 96.3% purity, 70.2% yield) as yellow solids.

General Procedure A: $^1$H NMR (400 MHz, DMSO-d$^6$) (Varian) 7.74 (dd, J=1.3, 9.7 Hz, 1H), 7.09 (br. s., 2H), 6.38 (t, J=9.2 Hz, 1H), 3.26-3.24 (m, 4H), 1.60-1.58 (m, 6H)

b) Preparation of Intermediate 64 tert-butyl (2-fluoro-6-nitro-3-(piperidin-1-yl)phenyl) carbamate

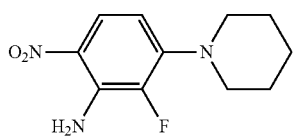

A solution of intermediate 63 (2-fluoro-6-nitro-3-(piperidin-1-yl)aniline) (2.00 g, 8.36 mmol), di-tert-butyl dicarbonate ((Boc)$_2$O) (3.65 g, 16.7 mmol) and 4-dimethylaminopyridine (DMAP) (204 mg, 1.67 mmol) in acetonitrile (50 mL) was stirred at 80° C. for 2 hours. The reaction was poured into dichloromethane (100 mL). The organic layer was washed with water (300 mL), dried with anhydrous $Na_2SO_4$ and filtered. The filtrate was evaporated to afford the crude product which was purified by flash column chromatography (eluent: ethyl acetate:petroleum ether from 0:1 to 1:3) to afford intermediate 64 (2.2 g, 57.8% yield, 96.5% purity) as yellow solids.

General Procedure A: $^1$H NMR (400 MHz, DMSO-d$^5$) (Varian) 8.02-7.95 (m, 1H), 7.16 (t, J=9.2 Hz, 1H), 3.26-3.24 (m, 4H), 1.62-1.60 (m, 6H), 1.33 (s, 18H)

c) Preparation of Intermediate 65 tert-butyl (2-fluoro-6-nitro-3-(2-oxopiperidin-1-yl) phenyl)carbamate

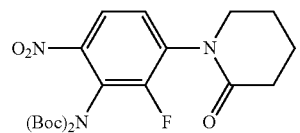

Under air, to a mixture of ruthenium(IV) oxide (115 mg, 0.865 mmol) in water (30 mL) at 23° C. was added sodium periodate (3.70 g, 17.3 mmol). After stirring for 3 minutes at 23° C., ethyl acetate (30 mL) and intermediate 64 (tert-butyl (2-fluoro-6-nitro-3-(piperidin-1-yl) phenyl) carbamate) (1.90 g, 4.32 mmol) were added. The mixture was stirred for 2 hours at 23° C. The reaction mixture was filtered through a pad of Celite® and the filtrate was extracted with ethyl acetate (100 mL×3). The combined organic layers were washed with brine (200 mL), dried over $Na_2SO_4$ and filtered. The filtrate was concentrated to afford intermediate 65 (1.7 g, 86.7% yield) as a brown solid.

General Procedure A: $^1$H NMR (400 MHz, DMSO-d$^6$) (Varian) 8.16-8.03 (m, 1H), 7.80-7.65 (m, 1H), 3.71-3.56 (m, 2H), 2.47-2.41 (m, 2H), 1.90-1.89 (m, 4H), 1.47-1.26 (m, 18H)

d) Preparation of Intermediate 66

1-(3-amino-2-fluoro-4-nitrophenyl)piperidin-2-one

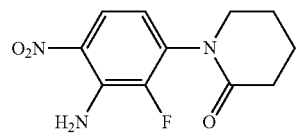

To a solution of intermediate 65 (tert-butyl (2-fluoro-6-nitro-3-(2-oxopiperidin-1-yl) phenyl) carbamate) (1.70 g, 3.75 mmol) in dichloromethane (10 mL) was slowly added trifluoroacetic acid (5 ml) at 20° C. The reaction mixture was stirred at room temperature for 12 hours. The resultant mixture was concentrated to dryness under reduced pressure to give crude product which was suspended in ethyl acetate (500 mL) and water (200 mL), and the pH was adjusted to around 8 by adding saturated sodium bicarbonate solution. The separated organic layer was dried over anhydrous $Na_2SO_4$, filtered and concentrated to dryness under reduced pressure to afford intermediate 66 (1.05 g, 84.5% purity, 93.5 yield) as a yellow solids.

General Procedure A: $^1$H NMR (400 MHz, DMSO-d$^6$) (Varian) 7.92-7.81 (m, 1H), 7.43-7.29 (m, 2H), 6.64 (dd, J=7.1, 9.3 Hz, 1H), 3.55 (t, J=5.4 Hz, 2H), 2.41 (t, J=6.3 Hz, 2H), 1.94-1.77 (m, 4H).

e) Preparation of Intermediate 67

1-(3,4-diamino-2-fluorophenyl) piperidin-2-one

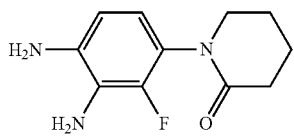

A solution of intermediate 66 (1-(3-amino-2-fluoro-4-nitrophenyl) piperidin-2-one) (1.05 g, 4.15 mmol) and wet palladium on activated carbon (100 mg, 10% on activated carbon) in methanol (50 mL) was stirred at 35° C. under hydrogen (15 psi) for 2 hours. The reaction mixture was cooled to 25° C. and filtered. The filtrate was concentrated to dryness under reduced pressure to afford intermediate 67 (900 mg, 75.5% purity, 73.4% yield) as brown solids.

LC-MS (ESI) (General Procedure B, Method 6): $R_T$=0.69 min, mass calcd. for $C_{11}H_{14}FN_3O$ 223.11, m/z found 224.1 [M+H]$^+$.

Example 15

Preparation of Intermediate 70 Used to Synthesize Compound 28 According to Example 1

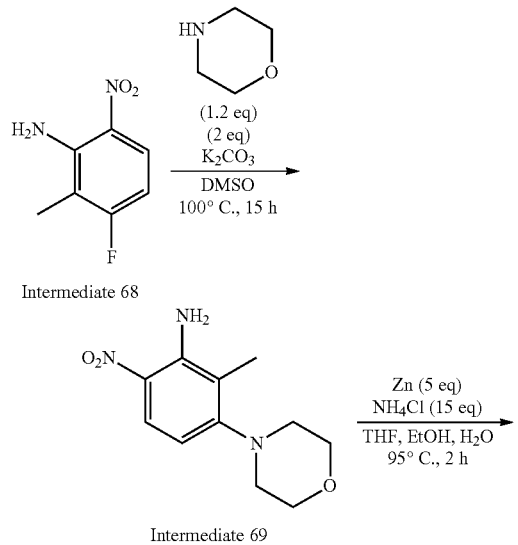

-continued

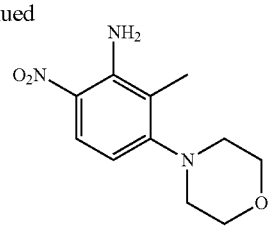

Intermediate 70 a) Preparation of Intermediate 68

3-fluoro-2-methyl-6-nitroaniline

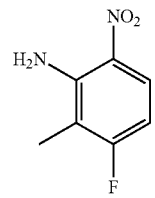

Intermediate 68 was synthesized as described in WO2007115947A1.

General Procedure A: $^1$H NMR (400 MHz, DMSO-d$^6$) (Varian) 7.98 (dd, J=9.6 Hz, 1H), 7.40 (br. s., 2H), 6.54 (t, J=9.0 Hz, 1H), 2.09-2.07 (m, 3H)

b) Preparation of Intermediate 69

2-methyl-3-morpholino-6-nitroaniline

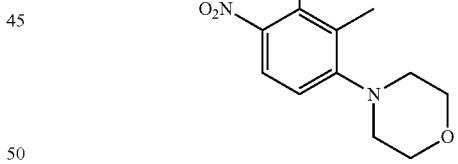

To a solution of intermediate 68 (3-fluoro-2-methyl-6-nitroaniline) (1.50 g, 8.82 mmol) and potassium carbonate (2.44 g, 17.6 mmol) in dimethyl sulfoxide (80 mL) was added morpholine (1.16 mL, 13.2 mmol), and the mixture was stirred at 100° C. for 15 hours. The mixture was poured into water (200 mL). The mixture was extracted with ethyl acetate (150 mL×2). The combined organic layers were dried over Na$_2$SO$_4$ and filtered. The filtrate was evaporated to afford crude product which was purified by flash column chromatography (eluent: ethyl acetate:petroleum ether=0:1 to 1:1) to give intermediate 69 (1.33 g, 97.7% purity, 62.1% yield) as yellow solids.

LC-MS (ESI) (General Procedure B, Method 6): $R_T$=2.13 min, mass calcd. for $C_{11}H_{14}N_3O$ 237.11, m/z found 238.1 [M+H]$^+$.

c) Preparation of Intermediate 70

3-methyl-4-morpholinobenzene-1,2-diamine

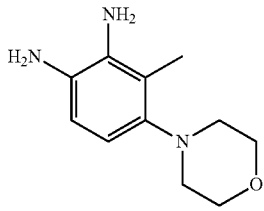 [SMILES: Cc1c(N2CCOCC2)ccc([N+](=O)[O-])c1N]

A solution consisting of intermediate 69 (2-methyl-3-morpholino-6-nitroaniline) (1.00 g, 4.22 mmol), zinc (1.38 g, 21.1 mmol), ammonium chloride (3.38 g, 63.2 mmol), THF (8 mL), ethanol (8 mL) and water (4 mL) was stirred at 95° C. for 2 hours. The reaction mixture was cooled to room temperature and filtered. The filtrate was poured into water (50 mL) and extracted with ethyl acetate (100 mL×3). The combined organic extracts were dried over anhydrous Na$_2$SO$_4$ and filtered. The filtrate was concentrated to dryness under reduced pressure to afford intermediate 70 (870 mg, 96.7% purity, 96.3% yield) as brown solid.

LC-MS (ESI) (General Procedure B, Method 6): R$_T$=1.34 min, mass calcd. for C$_{11}$H$_{17}$N$_3$O 207.14, m/z found 208.2 [M+H]$^+$.

Purification method, LC MS, SFC and NMR for compounds prepared according to the procedures indicated in Table 1

Compound 7

2-Methyl-7-(((S*)-1-(pyrimidin-2-yl)ethyl)amino)-6-(6-((R*)-2-(trifluoromethyl)-morpholino)-1H-benzo[d]imidazol-2-yl)-2H-pyrazolo[4,3-b]pyridin-5(4H)-one

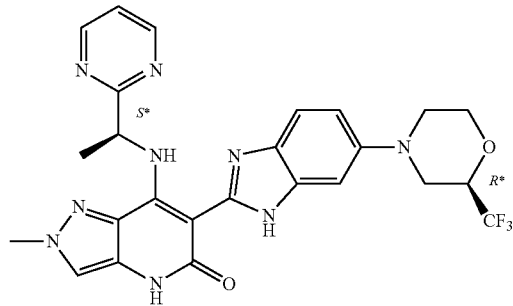 [SMILES: C[C@H](Nc1c(-c2nc3ccc(N4CCO[C@@H](C(F)(F)F)C4)cc3[nH]2)c(=O)[nH]c2cn(C)nc12)c1ncccn1]

After the reaction was completed, the mixture was concentrated in vacuum to give a residue, which was purified by prep. HPLC (Column: Phenomenex Gemini C18 250*50 10 u, Mobile Phase A: water (0.225% FA), Mobile Phase B: acetonitrile, Flow rate: 22 mL/min, gradient condition from 42% B to 72%). The pure fractions were collected and the solvent was evaporated under vacuum to give compound 7 (104 mg, 98.6% purity, 24.6% yield) as yellow solids.

LC-MS (ESI) (General Procedure A, Method 2): R$_T$=4.72 min, mass calcd. for C$_{25}$H$_{24}$F$_3$N$_9$O$_2$ 539.20, m/z found 540.0 [M+H]$^+$.

General Procedure A: $^1$H NMR (400 MHz, DMSO-d$^6$) (Bruker): δ=12.95-12.90 (m, 1H), 12.72-12.62 (m, 1H), 10.88 (br. s., 1H), 8.88-8.82 (m, 2H), 7.68-7.64 (m, 1H), 7.56 (d, J=8.5 Hz, 0.4H), 7.49 (d, J=8.5 Hz, 0.6H), 7.44-7.39 (m, 1H), 7.33-7.29 (m, 0.6H), 7.20-7.16 (m, 0.4H), 7.00-6.95 (m, 1H), 6.53-6.42 (m, 1H), 4.45-4.33 (m, 1H), 4.15-4.07 (m, 1H), 4.02-3.92 (m, 3H), 3.90-3.78 (m, 1H), 3.72-3.62 (m, 1H), 3.55-3.47 (m, 1H), 2.89-2.71 (m, 2H), 1.79-1.69 (m, 3H).

SFC (Method 13): R$_T$=1.32 min, Peak Area: 97.6%.

Compound 8

2-Methyl-7-(((S*)-1-(pyrimidin-2-yl)ethyl)amino)-6-(6-((S*)-2-(trifluoromethyl)-morpholino)-1H-benzo[d]imidazol-2-yl)-2H-pyrazolo[4,3-b]pyridin-5(4H)-one

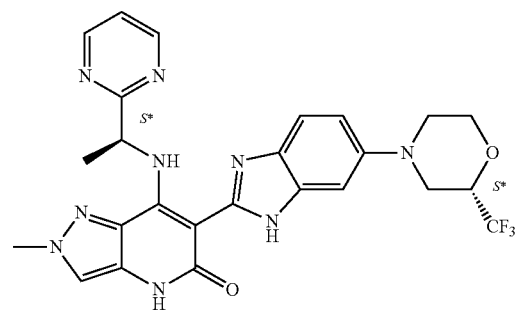 [SMILES: C[C@H](Nc1c(-c2nc3ccc(N4CCO[C@H](C(F)(F)F)C4)cc3[nH]2)c(=O)[nH]c2cn(C)nc12)c1ncccn1]

After the reaction was completed, the mixture was concentrated in vacuum to give a residue, which was purified by prep. HPLC (Column: Phenomenex Gemini C18 250*50 10 u, Mobile Phase A: water (0.225% FA), Mobile Phase B: acetonitrile, Flow rate: 22 mL/min, gradient condition from 42% B to 72%). The pure fractions were collected and the solvent was evaporated under vacuum to give compound 8 (32.0 mg, 99.1% purity, 8.31% yield) as yellow solids.

LC-MS (ESI) (General Procedure A, Method 2): R$_T$=4.77 min, mass calcd. for C$_{25}$H$_{24}$F$_3$N$_9$O$_2$ 539.20, m/z found 540.0 [M+H]$^+$.

General Procedure A: $^1$H NMR (400 MHz, DMSO-de) (Bruker) δ=12.96-12.89 (m, 1H), 12.71-12.62 (m, 1H), 10.87 (br. s., 1H), 8.89-8.81 (m, 2H), 7.69-7.64 (m, 1H), 7.56 (d, J=8.8 Hz, 0.4H), 7.49 (d, J=8.5 Hz, 0.6H), 7.45-7.39 (m, 1H), 7.33-7.29 (m, 0.6H), 7.20-7.16 (m, 0.4H), 7.01-6.94 (m, 1H), 6.53-6.42 (m, 1H), 4.46-4.33 (m, 1H), 4.16-4.07 (m, 1H), 4.01-3.92 (m, 3H), 3.89-3.79 (m, 1H), 3.71-3.62 (m, 1H), 3.55-3.46 (m, 1H), 2.88-2.72 (m, 2H), 1.79-1.70 (m, 3H).

SFC (Method 10): R$_T$=1.02 min, Peak Area: 98.7%.

Compound 9

(S*)-6-(5-Fluoro-6-morpholino-1H-benzo[d]imidazol-2-yl)-2-methyl-7-((1-(pyrimidin-2-yl)ethyl)amino)-2H-pyrazolo[4,3-b]pyridin-5(4H)-one

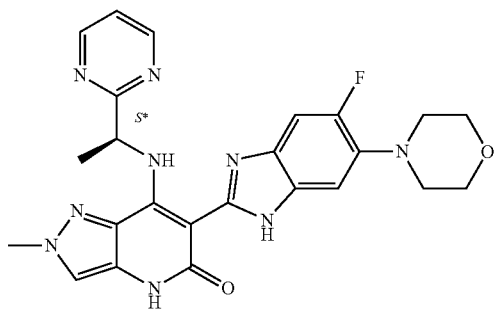 [SMILES: C[C@H](Nc1c(-c2nc3cc(F)c(N4CCOCC4)cc3[nH]2)c(=O)[nH]c2cn(C)nc12)c1ncccn1]

After the reaction was completed, the mixture was concentrated in vacuum to give a residue, which was purified by prep. HPLC (Column: Phenomenex Gemini C18 250*50 10 u, Mobile Phase A: water (0.225% FA), Mobile Phase B: acetonitrile, Flow rate: 22 mL/min, gradient condition from 30% B to 60%). The pure fractions were collected and the solvent was evaporated under vacuum to give compound 9 (16.9 mg, 94.0% purity, 8.71% yields) as yellow solids.

LC-MS (ESI) (General Procedure A, Method 1): $R_T$=4.49 min, mass calcd. for $C_{24}H_{24}FN_9O_2$ 489.20, m/z found 490.0 [M+H]$^+$.

General Procedure A:*H NMR (400 MHz, DMSO-d$^6$) (Varian) δ=12.97 (br. s., 1H), 12.60-12.50 (m, 1H), 10.90-10.83 (m, 1H), 8.89-8.78 (m, 2H), 7.63 (d, J=4.6 Hz, 1H), 7.48-7.30 (m, 2.5H), 7.18 (d, J=7.7 Hz, 0.5H), 6.48-6.36 (m, 1H), 3.93 (d, J=6.4 Hz, 3H), 3.78-3.71 (m, 4H), 3.01-2.92 (m, 4H), 1.74-1.63 (m, 3H).

SFC (Method 14): $R_T$=2.73 min, Peak Area: 98.2%.

Compound 10

(S*)-2-methyl-6-(6-morpholino-5-(trifluoromethyl)-1H-benzo[d]imidazol-2-yl)-7-((1-(oxazol-4-yl)ethyl)amino)-2H-pyrazolo[4,3-b]pyridin-5(4H)-one

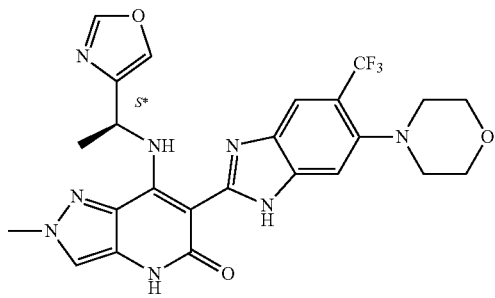 [SMILES: C[C@H](Nc1c(-c2nc3cc(C(F)(F)F)c(N4CCOCC4)cc3[nH]2)c(=O)[nH]c2cn(C)nc12)c1cocn1]

After the reaction was completed, the mixture was purified by prep. HPLC (Column: P Agela Durashell C18 150*25 5 u, Mobile Phase A: water (0.225% FA), Mobile Phase B: acetonitrile, Flow rate: 22 mL/min, gradient condition from 55% B to 85%). The collected pure fractions was evaporated under vacuum to remove most of solvent and then lyophilized to dryness. The residue was further separated by supercritical fluid chromatography (separation condition: Column: AD (250 mm*30 mm, 5 um); Mobile phase: A: Supercritical CO$_2$, B: 0.1% NH$_3$H$_2$O EtOH, A:B=60:40 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The pure fraction was collected and the solvent was evaporated under vacuum to dryness. The residue was re-suspended in water (10 mL) and the resulting mixtures were lyophilized to dryness to give compound 10 (61.8 mg, 100% purity, 5.30% yield) as light yellow solids.

LC-MS (ESI) (General Procedure A, Method 2): $R_T$=5.67 min, mass calcd. for $C_{24}H_{23}F_3N_8O_3$ 528.18, m/z found 529.0 [M+H]$^+$.

General Procedure A: $^1$H NMR (400 MHz, DMSO-d$^5$) (Varian) δ=13.31 (s, 1H), 12.28 (d, J=8.6 Hz, 0.5H), 12.20 (d, J=8.6 Hz, 0.5H), 11.02 (s, 1H), 8.38 (d, J=4.9 Hz, 1H), 8.09-8.02 (m, 1.5H), 7.91 (s, 0.5H), 7.80 (s, 0.5H), 7.74 (d, J=1.8 Hz, 1H), 7.72 (s, 0.5H), 6.44 (qd, J=6.7, 13.8 Hz, 1H), 4.06 (s, 3H), 3.79-3.65 (m, 4H), 2.97-2.79 (m, 4H), 1.70 (t, J=6.6 Hz, 3H).

SFC (Method 18): $R_T$=5.07 min, Peak Area: 100.0%.

Compound 11

(R*)-2-methyl-6-(6-morpholino-5-(trifluoromethyl)-1H-benzo[d]imidazol-2-yl)-7-((1-(oxazol-4-yl)ethyl)amino)-2H-pyrazolo[4,3-b]pyridin-5(4H)-one

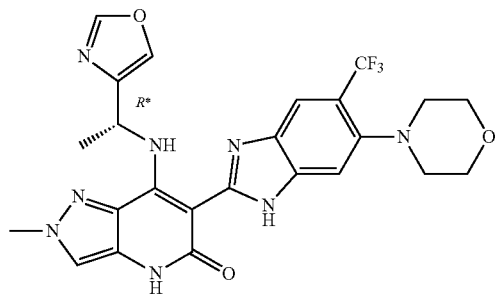 [SMILES: C[C@@H](Nc1c(-c2nc3cc(C(F)(F)F)c(N4CCOCC4)cc3[nH]2)c(=O)[nH]c2cn(C)nc12)c1cocn1]

The mixture was purified by prep. HPLC (Column: P Agela Durashell C18 150*25 5 u, Mobile Phase A: water (0.225% FA), Mobile Phase B: acetonitrile, Flow rate: 22 mL/min, gradient condition from 55% B to 85%). The pure fractions were collected and the solvent was evaporated under vacuum to remove most of solvent and then lyophilized to dryness. The residue was further separated by supercritical fluid chromatography (separation condition: Column: AD (250 mm*30 mm, 5 um); Mobile phase: A: Supercritical CO$_2$, B: 0.1% NH$_3$H$_2$O EtOH, A:B=60:40 at 60 mL/min; Column Temp: 38° C. Nozzle Pressure: 100 Bar; Nozzle Temp: 60° C.; Evaporator Temp: 20° C.; Trimmer Temp: 25° C.; Wavelength: 220 nm). The pure fraction was collected and the solvent was evaporated under vacuum to dryness. The residue was re-suspended in water (10 mL) and the resulting mixtures were lyophilized to dryness to give compound 11 (57.6 mg, 99.5% purity, 4.91% yield) as light yellow solids.

LC-MS (ESI) (General Procedure A, Method 2): $R_T$=5.66 min, mass calcd. for $C_{24}H_{23}F_3N_8O_3$ 528.18, m/z found 529.0 [M+H]$^+$.

General Procedure A: ¹H NMR (400 MHz, DMSO-d⁶) (Varian) δ=13.31 (s, 1H), 12.29 (d, J=8.4 Hz, 0.5H), 12.20 (d, J=8.6 Hz, 0.5H), 11.02 (s, 1H), 8.39 (d, J=4.6 Hz, 1H), 8.08-8.03 (m, 1.5H), 7.91 (s, 0.5H), 7.80 (s, 0.5H), 7.74 (d, J=1.8 Hz, 1H), 7.72 (s, 0.5H), 6.50-6.38 (m, 1H), 4.07 (s, 3H), 3.77-3.66 (m, 4H), 2.96-2.81 (m, 4H), 1.76-1.63 (m, 3H).

SFC (Method 18): $R_T$=5.63 min, Peak Area: 97.6%.

Compound 12

6-(6-((2R,6R)-2,6-dimethylmorpholino)-1H-benzo[d]imidazol-2-yl)-2-methyl-7-(((S*)-1-(pyrimidin-2-yl)ethyl)amino)-2H-pyrazolo[4,3-b]pyridin-5(4H)-one

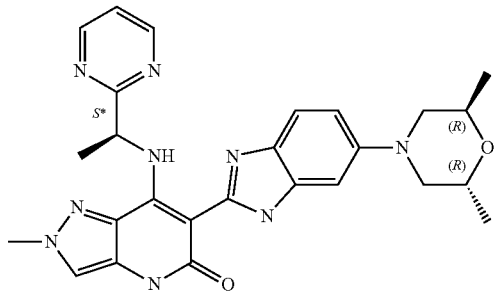

After the reaction was completed, the resultant mixture was concentrated to dryness under reduced pressure to give a residue, which was purified by prep. HPLC (Column: Phenomenex Gemini C18 250*50 10 u, Mobile Phase A: water (0.225% FA), Mobile Phase B: acetonitrile, Flow rate: 22 mL/min, gradient condition from 22% B to 52%). The pure fractions were collected and evaporated to dryness. Then the residue was re-suspended in water (20 mL) and lyophilized to dryness to give the product as red solids. The compound was further purified by supercritical fluid chromatography (separation condition: AD (250 mm*30 mm, 10 um)); Mobile phase: A: Supercritical $CO_2$, B: 0.1% $NH_3H_2O$ IPA, A:B=45:55 at 80 mL/min). The fractions were collected and the solvent was evaporated under vacuum. The residue was re-suspended in water (10 mL) and the resulting mixtures were lyophilized to dryness to give compound 12 (6.5 mg, 99.1% purity, 7.08% yield) as yellow solids.

LC-MS (ESI) (General Procedure A, Method 2): $R_T$=4.17 min, mass calcd. for $C_{26}H_{29}N_9O_2$ 499.24, m/z found 500.1 [M+H]⁺.

General Procedure A: ¹H NMR (400 MHz, DMSO-d⁶) (Bruker) δ 12.87 (s, 0.5H), 12.85 (s, 0.5H), 12.69 (d, J=8.3 Hz, 0.5H), 12.64 (d, J=8.3 Hz, 0.5H), 10.87 (br. s., 0.5H), 10.87 (s, 0.5H), 8.89-8.80 (m, 2H), 7.65 (d, J=3.8 Hz, 1H), 7.51 (d, J=8.8 Hz, 0.5H), 7.45 (d, J=8.5 Hz, 0.5H), 7.41 (t, J=4.8 Hz, 1H), 7.18 (d, J=2.0 Hz, 0.5H), 7.06 (s, 0.5H), 6.89 (d, J=8.8 Hz, 1H), 6.52-6.40 (m, 1H), 4.15-4.04 (m, 2H), 3.98-3.90 (m, 3H), 3.20-3.06 (m, 2H), 2.82 (dd, J=5.8, 11.8 Hz, 2H), 1.77-1.69 (m, 3H), 1.27-1.23 (m, 6H).

SFC (Method 10): $R_T$=1.05 min, Peak Area: 99.5%.

Compound 13

(S)-6-(7-fluoro-6-(tetrahydro-2H-pyran-4-yl)-1H-benzo[d]imidazol-2-yl)-2-methyl-7-((1-(pyrimidin-2-yl)ethyl)amino)-2H-pyrazolo[4,3-b]pyridin-5(4H)-one

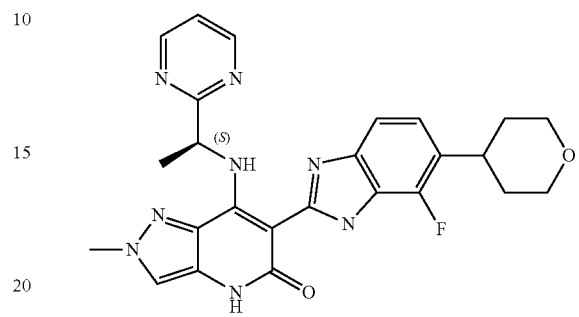

After the reaction was completed, the resultant mixture was concentrated to dryness under reduced pressure to give a residue, which was purified by prep. HPLC (Column: Gemini 150*25 5 um, Mobile Phase A: water (10 mM $NH_4HCO_3$), Mobile Phase B: acetonitrile, Flow rate: 30 mL/min, gradient condition from 45% B to 70%). The pure fractions were collected and the volatiles were removed under vacuum. The residue was re-suspended in water (20 mL) and the resulting mixture was lyophilized to dryness to give compound 13 (20.5 mg, 98.9% purity, 18.6% yield) as pale yellow solids.

LC-MS (ESI) (General Procedure A, Method 1): $R_T$=5.05 min, mass calcd. for $C_{25}H_{25}FN_8O_2$ 488.21, m/z found 489.0 [M+H]⁺.

General Procedure A: ¹H NMR (400 MHz, DMSO-d⁵) (Varian) δ 13.39 (s, 0.1H), 13.11 (s, 0.9H), 12.68 (d, J=7.9 Hz, 0.9H), 12.43 (d, J=8.8 Hz, 0.1H), 11.07 (s, 0.1H), 10.94 (s, 0.9H), 8.87 (d, J=4.9 Hz, 0.3H), 8.83 (d, J=4.9 Hz, 1.7H), 7.72 (s, 0.1H), 7.68 (s, 0.9H), 7.49-7.40 (m, 2H), 7.15 (d, J=6.6 Hz, 0.1H), 7.11-7.04 (m, 0.9H), 6.51-6.37 (m, 1H), 4.02-3.95 (m, 5H), 3.50 (t, J=10.8 Hz, 2H), 3.21 (t, J=12.0 Hz, 1H), 1.90-1.77 (m, 2H), 1.76-1.64 (m, 5H).

SFC (Method 13): $R_T$=1.19 min, Peak Area: 100%.

Compound 14

(S*)-6-(7-fluoro-6-morpholino-1H-benzo[d]imidazol-2-yl)-2-methyl-7-((1-(pyrimidin-2-yl)ethyl)amino)-2H-pyrazolo[4,3-b]pyridin-5(4H)-one

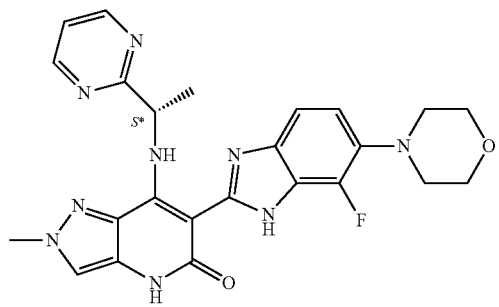 [SMILES: C[C@H](Nc1c(-c2nc3ccc(N4CCOCC4)c(F)c3[nH]2)c(=O)[nH]c2cn(C)nc12)c1ncccn1]

After the reaction was completed, the mixture was concentrated in vacuum to give a residue, which was purified by prep. HPLC (Column: Xtimate C18 150*25 mm*5 um, Mobile Phase A: water (0.225% FA), Mobile Phase B: acetonitrile, Flow rate: 25 mL/min, gradient condition from 27% B to 57%). The pure fractions were collected and the volatiles were removed under vacuum. The residue was re-suspended in water (20 mL) and the resulting mixture was lyophilized to dryness to give compound 14 (20.0 mg, 98.6% purity, 16.1% yield) as pale yellow solids.

LC-MS (ESI) (General Procedure A, Method 1): $R_T$=4.51 min, mass calcd. for $C_{24}H_{24}FN_9O_2$ 489.20, m/z found 490.0 $[M+H]^+$.

General Procedure A: $^1$H NMR (400 MHz, DMSO-d$^6$) (Varian) δ 13.32 (s, 0.2H), 13.05 (s, 0.8H), 12.68 (d, J=7.9 Hz, 0.8H), 12.41 (d, J=8.2 Hz, 0.2H), 11.06 (br. s., 0.2H), 10.92 (s, 0.8H), 8.86 (d, J=4.9 Hz, 0.5H), 8.82 (d, J=4.9 Hz, 1.5H), 7.72 (s, 0.2H), 7.67 (s, 0.8H), 7.46-7.36 (m, 2H), 7.00-6.89 (m, 1H), 6.51-6.37 (m, 1H), 4.01-3.93 (m, 3H), 3.78 (t, J=4.5 Hz, 4H), 3.09-2.95 (m, 4H), 1.75-1.68 (m, 3H).

SFC (Method 13): $R_T$=1.15 min, Peak Area: 100%.

Compound 15

(S*)-6-(7-fluoro-6-(piperidin-1-yl)-1H-benzo[d]imidazol-2-yl)-2-methyl-7-((1-(pyrimidin-2-yl)ethyl)amino)-2H-pyrazolo[4,3-b]pyridin-5(4H)-one

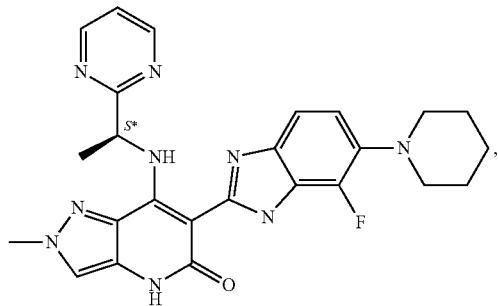

and compound 16

(R*)-6-(7-fluoro-6-(piperidin-1-yl)-1H-benzo[d]imidazol-2-yl)-2-methyl-7-((1-(pyrimidin-2-yl)ethyl)amino)-2H-pyrazolo[4,3-b]pyridin-5(4H)-one

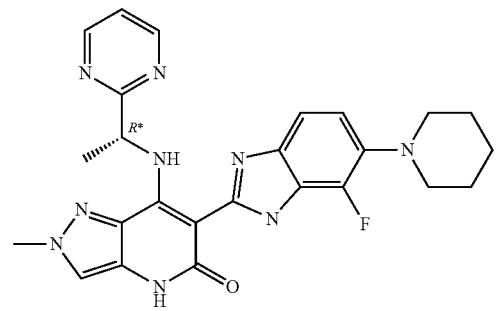

After the reaction was completed, the mixture was concentrated in vacuum to give a residue, which was purified by prep. HPLC (Column: Xtimate C18 150×25 mm×5 um, Mobile Phase A: water (0.225% FA), Mobile Phase B: acetonitrile, Flow rate: 22 mL/min, gradient condition from 22% B to 52%). The pure fractions were collected and the volatiles were removed under vacuum. The residue was re-suspended in water (10 mL) and the resulting mixture was lyophilized to dryness to give the racemic product. The racemic product was separated by supercritical fluid chromatography (separation condition: C2 (250 mm 30 mm, um); Mobile phase: A: Supercritical $CO_2$, B: 0.1% $NH_3H_2O$ MeOH, A:B=60:40 at 55 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The fractions were collected and the solvent was evaporated under vacuum. The residue was re-suspended in water (10 mL) and the resulting mixtures were lyophilized to give compound 15 (10.0 mg, 100% purity, 1.18% yield) as a yellow solid and compound 16 (9.3 mg, 95.4% purity, 1.04% yield) as a yellow solid.

Compound 15

LC-MS (ESI) (General Procedure A, Method 2): $R_T$=3.79 min, mass calcd. for $C_{25}H_{26}FN_9O$ 487.22, m/z found 488.0 $[M+H]^+$.

General Procedure A: $^1$H NMR (400 MHz, DMSO-d$^5$) (Varian) 13.25 (br. s., 0.2H), 13.00 (br. s., 0.8H), 12.66 (d, J=7.9 Hz, 0.8H), 12.40 (d, J=7.7 Hz, 0.2H), 11.05 (br. s., 0.2H), 10.92 (br. s., 0.8H), 8.84 (d, J=4.9 Hz, 0.4H), 8.80 (d, J=4.9 Hz, 1.6H), 7.70 (s, 0.2H), 7.65 (s, 0.8H), 7.41 (t, J=4.9 Hz, 1H), 7.35 (d, J=8.6 Hz, 1H), 6.97-6.87 (m, 1H), 6.47-6.35 (m, 1H), 3.99-3.89 (m, 3H), 3.02-2.87 (m, 4H), 1.78-1.59 (m, 7H), 1.58-1.45 (m, 2H).

SFC (Method 21): $R_T$=8.17 min, peak: 100%.

Compound 16

LC-MS (ESI) (General Procedure A, Method 2): $R_T$=3.78 min, mass calcd. for $C_{25}H_{26}FN_9O$ 487.22, m/z found 488.0 $[M+H]^+$.

General Procedure A: $^1$H NMR (400 MHz, DMSO-d$^6$) (Varian) 13.34-13.26 (br. s., 0.2H), 13.01 (br. s., 0.8H), 12.66 (d, J=7.9 Hz, 0.8H), 12.39 (d, J=8.2 Hz, 0.2H), 10.93 (br. s., 1H), 8.84 (d, J=4.9 Hz, 0.4H), 8.80 (d, J=4.9 Hz, 1.6H), 7.70 (s, 0.2H), 7.65 (s, 0.8H), 7.41 (t, J 20=4.9 Hz, 1H), 7.34 (d, J=8.4 Hz, 1H), 6.96-6.88 (m, 1H), 6.45-6.36 (m, 1H), 3.97-3.92 (m, 3H), 3.00-2.90 (m, 4H), 1.73-1.63 (m, 7H), 1.56-1.47 (m, 2H).

SFC (Method 21): $R_T$=10.4 min, peak: 99.5%.

Compound 17

(S*)-6-(4,7-difluoro-6-morpholino-1H-benzo[d]imidazol-2-yl)-2-methyl-7-((1-(pyrimidin-2-yl)ethyl)amino)-2H-pyrazolo[4,3-b]130pyridine-5(4H)-one

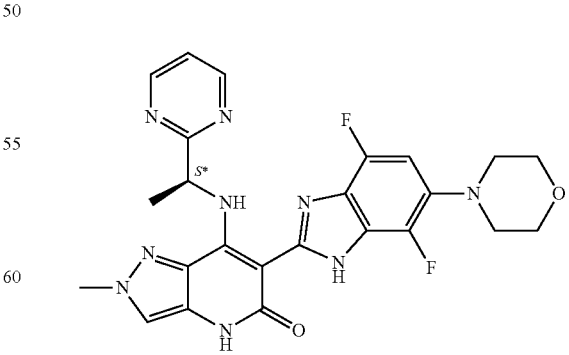

After the reaction was completed, the resultant mixture was extracted with ethyl acetate (20 mL). The separated organic layer was washed with water (10 mL×3), dried over anhydrous $Na_2SO_4$, filtered and concentrated to dryness under reduced pressure. The residue was purified by prep. HPLC (Column: Phenomenex Gemini C18 250*50 10 u, Mobile Phase A: water (0.225% FA), Mobile Phase B: acetonitrile, Flow rate: 22 mL/min, gradient condition from 46% B to 76%). The pure fractions were collected and the volatiles were removed under vacuum. The residue was re-suspended in water (10 mL) and the resulting mixture was lyophilized to dryness to give compound 17 (5.0 mg, 98.3% purity, 10.3% yield) as a purple solid.

LC-MS (ESI) (General Procedure A, Method 1): $R_T$=4.92 min, mass calcd. for $C_{24}H_{23}F_2N_9O_2$ 507.19, m/z found 508.0 $[M+H]^+$.

General Procedure A: $^1H$ NMR (400 MHz, DMSO-$d^5$) (Varian) 13.72 (s, 1H), 11.76 (s, 1H), 11.10 (s, 1H), 8.86-8.71 (m, 2H), 7.73 (s, 1H), 7.39 (s, 1H), 6.89-6.41 (m, 2H), 3.97 (s, 3H), 3.77 (s, 4H), 3.32-2.92 (m, 4H), 1.72 (d, J=6.8 Hz, 3H).

SFC (Method 16): $R_T$=4.87 min, peak: 98.9%.

Compound 18

(S)-2-Methyl-6-(6-(4-methylpiperazin-1-yl)-1H-benzo[d]imidazol-2-yl)-7-((1-phenylethyl)amino)-2H-pyrazolo[4,3-b]pyridin-5(4H)-one

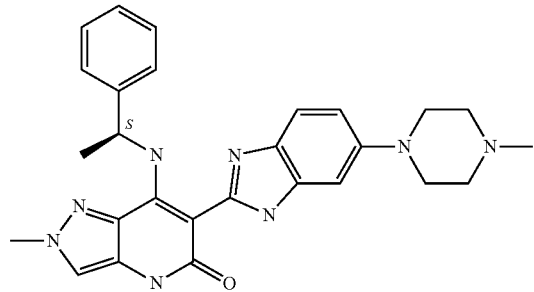

After the reaction was completed, the mixture was filtered and the filtrate was concentrated to dryness under reduced pressure. The residue was extracted with dichloromethane (30 mL×3). The combined organic layers were dried over $Na_2SO_4$(solid), filtered and the filtrate was concentrated to dryness under reduced pressure to give a residue, which was purified by prep. HPLC (Column: Phenomenex Gemini C18 250*50 10 u, Mobile Phase A: water (0.05% ammonia hydroxide v/v), Mobile Phase B: acetonitrile, Flow rate: 22 mL/min, gradient condition from 48% B to 78%). The pure fractions were collected and the solvent was evaporated under vacuum. The residue was re-suspended in water (10 mL) and lyophilized to dryness to afford compound 18 (1.8 mg, 98.6% purity, 0.98% yield) as yellow solids.

LC-MS (ESI) (General Procedure A, Method 2): $R_T$=4.35 min, mass calcd. for $C_{27}H_{30}N_8O$ 482.25, m/z found 483.1 $[M+H]^+$.

General Procedure A: $^1H$ NMR (400 MHz, DMSO-$d^5$) (Varian) δ=12.88 (br. s., 0.4H), 12.86 (br. s., 0.6H), 12.63 (d, J=9.3 Hz, 0.4H), 12.54 (d, J=8.6 Hz, 0.6H), 10.87 (br. s., 1H), 7.67-7.64 (m, 1H), 7.51 (d, J=8.8 Hz, 0.4H), 7.48 (d, J=8.8 Hz, 0.6H), 7.47-7.45 (m, 1.6H), 7.43 (s, 0.4H), 7.34 (dt, J=4.0, 7.6 Hz, 2H), 7.24-7.18 (m, 1.6H), 7.10 (s, 0.4H), 6.95-6.88 (m, 1H), 6.45-6.34 (m, 1H), 4.01 (s, 3H), 3.17-3.09 (m, 4H), 2.60-2.53 (m, 4H), 2.31-2.24 (m, 3H), 1.72-1.64 (m, 3H).

SFC (Method 10): $R_T$=2.71 min, peak area: 100%.

Compound 19

(Rac)-2-Methyl-6-(6-morpholino-5-(trifluoromethyl)-1H-benzo[d]imidazol-2-yl)-7-((1-(pyrimidin-2-yl)ethyl)amino)-2H-pyrazolo[4,3-b]pyridin-5(4H)-one

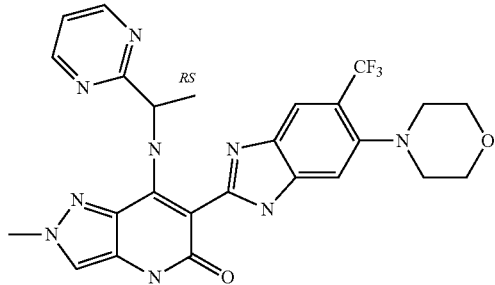 [SMILES: CC(Nc1c(-c2nc3cc(C(F)(F)F)c(N4CCOCC4)cc3[nH]2)c(=O)[nH]c2cn(C)nc12)c1ncccn1]

After the reaction was completed, the mixture was concentrated in vacuum to give a residue, which was purified by prep. HPLC (Column: Phenomenex Gemini C18 250*50 10 u, Mobile Phase A: water (0.225% FA), Mobile Phase B: acetonitrile, Flow rate: 22 mL/min, gradient condition from 40% B to 70%). The pure fractions were collected and the volatiles were removed under vacuum. The residue was suspended in water (15 mL) and lyophilized to give compound 19 (10.0 mg, 5.90% yield, 98.1% purity) as pale yellow solids.

LC-MS (ESI) (General Procedure A, Method 2): $R_T$=5.66 min, mass calcd. for $C_{25}H_{24}F_3N_9O_2$ 539.20, m/z found 540.0 $[M+H]^+$.

General Procedure A: $^1H$ NMR (400 MHz, DMSO-$d^6$) (Bruker) δ 13.30 (s, 0.5H), 13.28 (s, 0.5H), 12.65 (d, J=8.0 Hz, 0.5H), 12.53 (d, J=8.3 Hz, 0.5H), 10.96 (br. s., 0.5H), 10.96 (br. s., 0.5H), 8.89 (d, J=4.8 Hz, 1H), 8.85 (d, J=4.8 Hz, 1H), 8.05 (s, 0.5H), 7.92 (s, 0.5H), 7.83 (s, 0.5H), 7.74 (s, 0.5H), 7.69 (s, 1H), 7.47-7.39 (m, 1H), 6.53-6.44 (m, 1H), 4.00-3.94 (m, 3H), 3.80-3.66 (m, 4H), 2.97-2.90 (m, 2H), 2.89-2.83 (m, 2H), 1.74 (dd, J=3.5, 6.8 Hz, 3H).

SFC (Method 16): $R_T$=1.99 min, peak area: 50.8%; $R_T$=2.15 min, peak area: 49.2%. Compound 20

(S*)2-Methyl-6-(6-morpholino-5-(trifluoromethyl)-1H-benzo[d]imidazol-2-yl)-7-((1-(pyrimidin-2-yl)ethyl)amino)-2H-pyrazolo[4,3-b]pyridin-5(4H)-one

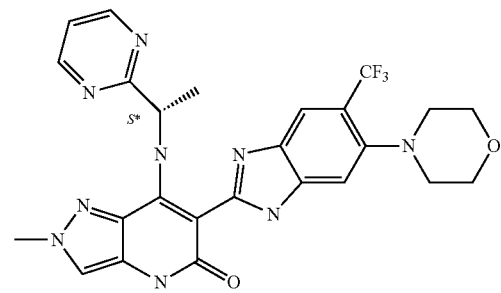 [SMILES: C[C@H](Nc1c(-c2nc3cc(C(F)(F)F)c(N4CCOCC4)cc3[nH]2)c(=O)[nH]c2cn(C)nc12)c1ncccn1]

and

Compound 21

(R*)-2-methyl-6-(6-morpholino-5-(trifluoromethyl)-1H-benzo[d]imidazol-2-yl)-7-((1-(pyrimidin-2-yl)ethyl)amino)-2H-pyrazolo[4,3-b]pyridin-5(4H)-one

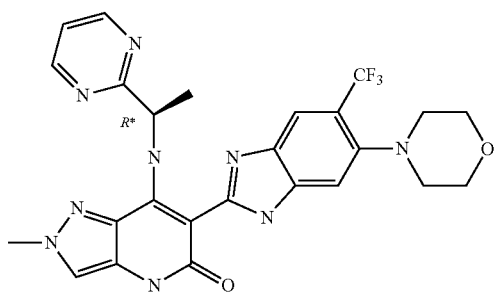 [SMILES: C[C@@H](Nc1c(-c2nc3cc(C(F)(F)F)c(N4CCOCC4)cc3[nH]2)c(=O)[nH]c2cn(C)nc12)c1ncccn1]

Compound 19 was separated by supercritical fluid chromatography (separation condition: AD (250 mm*30 mm, 10 um); Mobile phase: A: Supercritical $CO_2$, B: 0.1% $NH_3H_2O$ EtOH, A:B=55:45 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The pure fractions were collected and the solvent was evaporated under vacuum. The residue was re-suspended in water (10 mL) and the resulting mixtures were lyophilized to dryness to give compound 20 (7.9 mg, 99.2% purity, 4.71% yield) as pale yellow solids and compound 21 (4.5 mg, 99.6% purity, 2.69% yield) as pale yellow solids.

Compound 20

LC-MS (ESI) (General Procedure A, Method 2): $R_T$=5.53 min, mass calcd. for $C_{25}H_{24}F_3N_9O_2$ 539.20, m/z found 540.0 $[M+H]^+$.

General Procedure A: $^1$H NMR (400 MHz, DMSO-$d^6$) (Varian) δ 13.30 (br. s., 0.5H), 13.28 (s, 0.5H), 12.65 (d, J=8.2 Hz, 0.5H), 12.53 (d, J=8.4 Hz, 0.5H), 10.97 (br. s., 1H), 8.89 (d, J 20=4.9 Hz, 1H), 8.85 (d, J=4.9 Hz, 1H), 8.05 (s, 0.5H), 7.92 (s, 0.5H), 7.83 (s, 0.5H), 7.74 (s, 0.5H), 7.69 (s, 1H), 7.49-7.37 (m, 1H), 6.49 (quint, J=7.1 Hz, 1H), 3.98 (s, 3H), 3.81-3.62 (m, 4H), 3.03-2.77 (m, 4H), 1.80-1.68 (m, 3H).

SFC (Method 16): $R_T$=5.34 min, peak area: 100%.

Compound 21

LC-MS (ESI) (General Procedure A, Method 2): $R_T$=5.50 min, mass calcd. for $C_{25}H_{24}F_3N_9O_2$ 539.20, m/z found 540.0 $[M+H]^+$.

General Procedure A: $^1$H NMR (400 MHz, DMSO-$d^6$) (Varian) δ 13.31 (br. s., 0.5H), 13.29 (br. s., 0.5H), 12.65 (d, J=8.2 Hz, 0.5H), 12.52 (d, J=8.4 Hz, 0.5H), 10.97 (br. s., 1H), 8.89 (d, J=4.9 Hz, 1H), 8.85 (d, J=4.9 Hz, 1H), 8.05 (s, 0.5H), 7.92 (s, 0.5H), 7.83 (s, 0.5H), 7.74 (s, 0.5H), 7.69 (s, 1H), 7.48-7.39 (m, 1H), 6.49 (quint, J=7.1 Hz, 1H), 3.98 (s, 3H), 3.86-3.60 (m, 4H), 3.02-2.77 (m, 4H), 1.80-1.67 (m, 3H).

SFC (Method 16): $R_T$=5.82 min, peak area: 99.8%.

Compound 22

(S*)-2-methyl-7-((1-(pyrimidin-2-yl)ethyl)amino)-6-(6-(tetrahydro-2H-pyran-4-yl)-1H-benzo[d]imidazol-2-yl)-2H-pyrazolo[4,3-b]pyridin-5(4H)-one

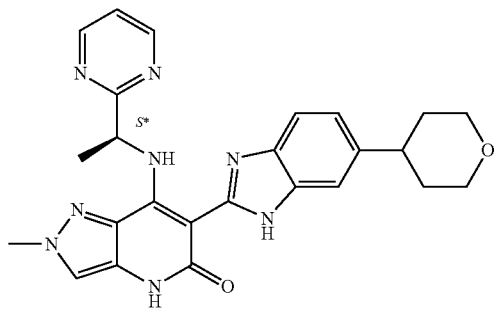 [SMILES: C[C@H](Nc1c(-c2nc3ccc(C4CCOCC4)cc3[nH]2)c(=O)[nH]c2cn(C)nc12)c1ncccn1]

After the reaction was completed, the mixture was concentrated in vacuum to give a residue, which was purified by prep. HPLC (Column: Phenomenex Gemini 150*25 mm*10 um, Mobile Phase A: water (0.05% ammonia hydroxide v/v), Mobile Phase B: acetonitrile, Flow rate: 22 mL/min, gradient condition from 30% B to 60%). The pure fractions were collected and the solvent was evaporated under vacuum to give compound 22 (32.9 mg, 96.3% purity, 9.57% yields) as white solids.

LC-MS (ESI) (General Procedure A, Method 2): $R_T$=4.22 min, mass calcd. for $C_{25}H_{26}N_8O_2$ 470.22, m/z found 471.0 $[M+H]^+$.

General Procedure A: $^1$H NMR (400 MHz, DMSO-de) (Varian) δ 12.97-12.92 (m, 1H), 12.79-12.71 (m, 1H), 10.89 (d, J=5.50 Hz, 1H), 8.86 (t, J=5.20 Hz, 2H), 7.67 (s, 1H), 7.59-7.50 (m, 1.5H), 7.45-7.40 (m, 1.5H), 7.07 (d, J=8.20 Hz, 1H), 6.52-6.43 (m, 1H), 4.01-3.94 (m, 5H), 3.49-3.41 (m, 2H), 2.93-2.81 (m, 1H), 1.80-1.69 (m, 7H)

SFC (Method 10): $R_T$=1.38 min, peak area: 95.8%.

Compound 23

(S*)-2-methyl-7-((2-methyl-1-(pyrimidin-2-yl)propyl)amino)-6-(6-(4-methylpiperazin-1-yl)-1H-imidazo[4,5-c]pyridin-2-yl)-2H-pyrazolo[4,3-b]pyridin-5(4H)-one

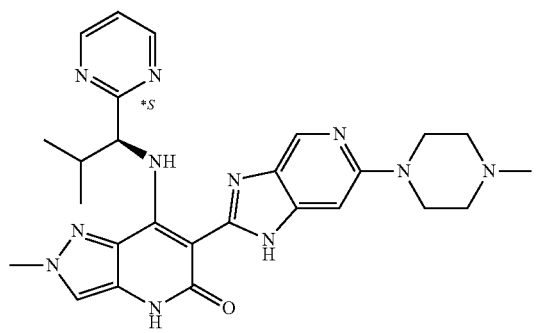

After the reaction was completed, the mixture was extracted with dichloromethane (20 mL). The separated organic layer was washed with water (10 mL×5), dried over anhydrous Na$_2$SO$_4$, filtered and concentrated under reduced pressure to give the crude product which was purified by prep. thin layer chromatography (dichloromethane:methanol=10:1). Then the product was further purified by prep. HPLC (Column: Gemini 150*25 5 u, Mobile Phase A: water (0.05% ammonia hydroxide v/v), Mobile Phase B: acetonitrile, Flow rate: 22 mL/min, gradient condition from 25% B to 55%). The pure fractions were collected and the volatiles were removed under vacuum. The residue was re-suspended in acetonitrile (2 mL) and water (10 mL). The mixture was lyophilized to dryness to give compound 23 (10.1 mg, 97.6% purity, 4.64% yield) as a yellow powder.

LC-MS (ESI) (General Procedure A, Method 1): R$_T$=4.21 min, mass calcd. C$_{26}$H$_{31}$N$_{11}$O 513.27, m/z found 514.1 [M+H]$^+$.

General Procedure A: $^1$H NMR (400 MHz, DMSO-d$^6$) (Varian) δ 13.03 (s, 0.3H), 12.98 (s, 0.7H), 12.57 (d, J=9.0 Hz, 0.3H), 12.42 (d, J=9.0 Hz, 0.7H), 10.89 (br. s., 1H), 8.80 (d, J=5.1 Hz, 2H), 8.55-8.40 (m, 1H), 7.63 (s, 1H), 7.37 (t, J=4.9 Hz, 1H), 6.99 (s, 0.7H), 6.78 (s, 0.3H), 6.47-6.40 (m, 1H), 3.92-3.89 (m, 3H), 3.44-3.38 (m, 4H), 2.65-2.57 (m, 1H), 2.48-2.42 (m, 4H), 2.23 (s, 3H), 1.08-1.00 (m, 6H)

SFC (Method 12): R$_T$=2.11 min, Peak Area: 100%.

Compound 24

6-(6-((cis)-2,6-dimethylmorpholino)-1H-benzo[d]imidazol-2-yl)-2-methyl-7-(((S)-1-(pyrimidin-2-yl)ethyl)amino)-2H-pyrazolo[4,3-b]pyridin-5(4H)-one

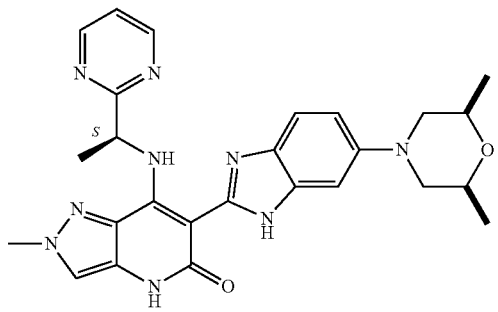

After the reaction was completed, the mixture was extracted with dichloromethane (30 mL×3). The combined organic layers were washed with water (30 mL×3) and brine (30 mL), dried over Na$_2$SO$_4$, filtered and concentrated under reduced pressure to give the crude product which was purified by prep. HPLC (Column: Phenomenex Gemini C18 250*50 10 u, Mobile Phase A: water (0.225% FA), Mobile Phase B: acetonitrile, Flow rate: 22 mL/min, gradient condition from 20% B to 50%). The pure fractions were collected and the solvent was evaporated under vacuum. Then the residue was lyophilized to dryness to give the desired compound as yellow solids. The product was further purified by supercritical fluid chromatography (separation condition: AD (250 mm*30 mm, 10 um); Mobile phase: A: Supercritical CO$_2$, B: 0.1% NH$_3$H$_2$O IPA, A:B=55:45 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give compound 24 (3.20 mg, 98.0% purity, 3.05% yield) as yellow solids.

LC-MS (ESI) (General Procedure A, Method 2): R$_T$=3.93 min, mass calcd. for C$_{26}$H$_{29}$N$_9$O$_2$ 499.24, m/z found 500.1 [M+H]$^+$.

General Procedure A: $^1$H NMR (400 MHz, DMSO-d$^6$) (Varian) δ 12.87 (br. s., 0.4H), 12.85 (br. s., 0.6H), 12.68 (d, J=8.4 Hz, 0.4H), 12.64 (d, J=8.2 Hz, 0.6H), 10.87 (br. s., 1H), 8.84 (dd, J=5.0, 6.3 Hz, 2H), 7.65 (d, J=4.9 Hz, 1H), 7.51 (d, J=8.6 Hz, 0.4H), 7.45 (d, J=8.8 Hz, 0.6H), 7.43-7.38 (m, 1H), 7.20 (d, J=2.0 Hz, 0.6H), 7.06 (s, 0.4H), 6.92 (d, J=8.8 Hz, 1H), 6.54-6.41 (m, 1H), 3.95 (d, J=7.3 Hz, 3H), 3.84-3.68 (m, 2H), 3.61-3.45 (m, 2H), 2.36-2.21 (m, 2H), 1.79-1.66 (m, 3H), 1.17 (d, J=6.2 Hz, 6H)

SFC (Method 10): R$_T$=1.02 min, Peak Area: 100%.

Compound 25

(S)-6-(6-(2,2-difluoromorpholino)-1H-benzo[d]imidazol-2-yl)-2-methyl-7-((1-(pyrimidin-2-yl)ethyl)amino)-2H-pyrazolo[4,3-b]pyridin-5(4H)-one

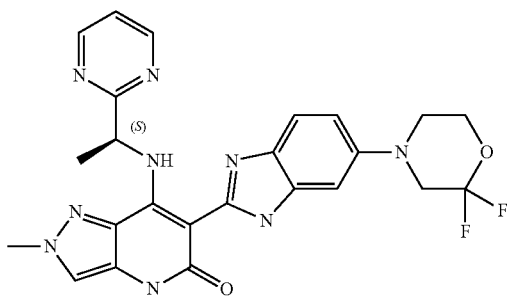

After the reaction was completed, the mixture was extracted with dichloromethane (10 mL×3). The combined organic layers were washed with brine (10 mL), dried over anhydrous Na$_2$SO$_4$, filtered, and concentrated to dryness under reduced pressure to afford the crude product, which was purified by prep. HPLC (Column: Kromasil 150×25 mm×10 µm, Mobile Phase A: water (0.05% ammonia hydroxide), Mobile Phase B: acetonitrile, Flow rate: 22 mL/min, gradient condition from 32% B to 62%). The pure fractions were collected and the volatiles were removed under vacuum. The residue was re-suspended in water (10 mL) and the resulting mixture was lyophilized to give compound 25 (5.00 mg, 95.1% purity, 4.7% yield) as white powder.

LCMS (ESI) (General Procedure A, Method 2): R$_T$=4.49 min, mass calcd. for C$_{24}$H$_{23}$F$_2$N$_9$O$_2$ 507.19 m/z, found 508.0 [M+1]$^+$.

General Procedure A: $^1$H NMR (400 MHz, DMSO-d$^6$) (Bruker) δ 12.94-12.93 (m, 1H), 12.70 (d, J=8.4, 0.5H), 12.64 (d, J=8.4, 0.5H), 10.89 (s, 1H), 8.86 (d, J=4.5 Hz, 2H), 7.66 (d, J=3.8 Hz, 1H), 7.56 (d, J=8.5 Hz, 0.5H), 7.50 (d, J=8.5 Hz, 0.5H), 7.42 (t, J=4.9 Hz, 1H), 7.28 (d, J=2.0 Hz, 0.5H), 7.16 (d, J=1.2 Hz, 0.5H), 7.00-6.93 (m, 1H), 6.55-6.41 (m, 1H), 4.25-4.17 (m, 2H), 3.96 (d, J=4.0 Hz, 3H), 3.60-3.47 (m, 2H), 3.32-3.27 (m, 2H), 1.73 (t, J=6.8 Hz, 3H).

SFC (Method 19): R$_T$=5.06 min, Peak Area: 99.1%.

Compound 26

(S*)-2-methyl-7-((1-(pyrimidin-2-yl)ethyl)amino)-6-(6-(4-(2,2,2-trifluoroethyl)piperazin-1-yl)-1H-benzo[d]imidazol-2-yl)-2H-pyrazolo[4,3-b]pyridin-5(4H)-one

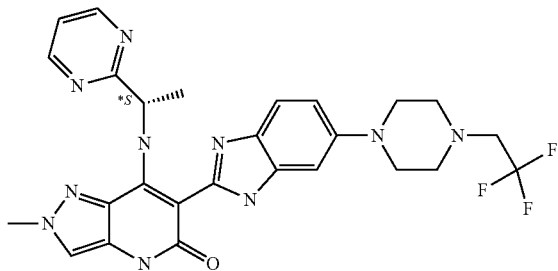 [SMILES: C[C@H](Nc1c(-c2nc3ccc(N4CCN(CC(F)(F)F)CC4)cc3[nH]2)c(=O)[nH]c2cn(C)nc12)c1ncccn1]

After the reaction was completed, the mixture was concentrated under reduced pressure to afford the crude product which was purified by prep. HPLC (Column: Xtimate C18 150*25 mm*5 um, Mobile Phase A: water (0.225% FA), Mobile Phase B: acetonitrile, Flow rate: 22 mL/min, gradient condition from 27% B to 37%). The pure fractions were collected and the solvent was evaporated under vacuum. The residue was suspended in water (50 mL) and lyophilized to dryness to afford the crude compound. The crude compound was separated by supercritical fluid chromatography (separation condition: OJ (250 mm*30 mm, 10 um); Mobile phase: A: Supercritical $CO_2$, B: 0.1% $NH_3H_2O$ MeOH, A:B=65:35 at 50 mL/min;

Column Temp: 38° C.; Nozzle Pressure: 100 Bar; Nozzle Temp: 60° C.; Evaporator Temp: 20° C.; Trimmer Temp: 25° C.; Wavelength: 220 nm). The pure fractions were collected and the solvent was evaporated under vacuum. The residue was re-suspended in water (50 mL) and the resulting mixtures were lyophilized to dryness to compound 26 (1.5 mg, 99.85% purity, 1.684% yield) as yellow solids.

LC-MS (ESI) (General Procedure A, Method 2): $R_T$=4.10 min, mass calcd. for $C_{26}H_{27}F_3N_{10}O$ 552.23 m/z found 553.1 $[M+H]^+$.

General Procedure A: $^1$H NMR (400 MHz, DMSO-d$^6$) (Varian) $^1$H NMR (400 MHz, DMSO-d$^6$) 12.85 (br. s, 1H), 12.73 (d, J=7.9 Hz, 0.4H), 12.64 (d, J=8.2 Hz, 0.6H), 10.86 (br. s, 1H), 8.85 (d, J=3.1 Hz, 1H), 8.84 (d, J=3.1 Hz, 1H), 7.65 (s, 1H), 7.50 (d, J=8.6 Hz, 0.4H), 7.44 (d, J=9.3 Hz, 0.6H), 7.42-7.37 (m, 1H), 7.21-7.17 (m, 0.6H), 7.09-7.05 (m, 0.4H), 6.93-6.86 (m, 1H), 6.51-6.41 (m, 1H), 3.96 (s, 3H), 3.26-3.21 (m, 2H), 3.16-3.09 (m, 4H), 2.85-2.77 (m, 4H), 1.72 (t, J=6.2 Hz, 3H)

SFC (Method 12): $R_T$=2.05 min, Peak Area: 100%.

Compound 27

(S)-6-(7-fluoro-6-(2-oxopiperidin-1-yl)-1H-benzo[d]imidazol-2-yl)-2-methyl-7-((1-(pyrimidin-2-yl)ethyl)amino)-2H-pyrazolo[4,3-b]pyridin-5(4H)-one

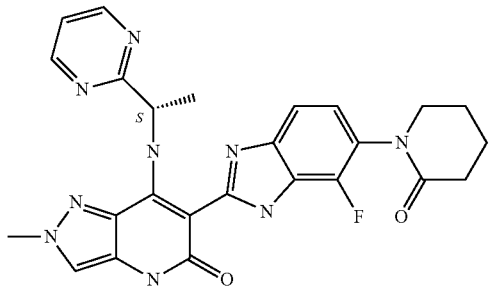

After the reaction was completed, the mixture was extracted with EtOAc (200 mL). The separated organic layer was washed with water (100 mL), dried over $Na_2SO_4$ and concentrated under reduced pressure to afford the crude product which was purified by prep. HPLC (Column: Phenomenex Gemini 150*25 mm*10 um, Mobile Phase A: water (0.05% ammonia hydroxide v/v), Mobile Phase B: acetonitrile, Flow rate: 22 mL/min, gradient condition from 24% B to 54%). The pure fractions were collected and the solvent was evaporated under vacuum. The residue was lyophilized to dryness to afford compound 27 (19.3 mg, 99.1% purity, 7.91% yield) as white solids.

LC-MS (ESI) (General Procedure A, Method 1): $R_T$=4.25 min, mass calcd. for $C_{25}H_{24}FN_9O_2$ 501.20, m/z found 502.0 $[M+H]^+$.

General Procedure A: $^1$H NMR (400 MHz, DMSO-d$^6$) (Varian) 13.22 (br. s., 1H), 12.65-12.59 (m, 1H), 8.84-8.78 (m, 2H), 7.69 (s, 1H), 7.52-7.46 (m, 1H), 7.43 (t, J=4.9 Hz, 1H), 7.07-6.98 (m, 1H), 6.45 (quint, J=7.1 Hz, 1H), 3.98 (s, 3H), 3.66-3.53 (m, 2H), 2.45-2.37 (m, 2H), 1.96-1.83 (m, 4H), 1.70 (d, J=6.8 Hz, 3H)

SFC (Method 13): $R_T$=0.75 min, Peak Area: 100%.

Compound 28

(S*)-2-methyl-6-(7-methyl-6-morpholino-1H-benzo[d]imidazol-2-yl)-7-((1-(pyrimidin-2-yl)ethyl)amino)-2H-pyrazolo[4,3-b]pyridin-5(4H)-one

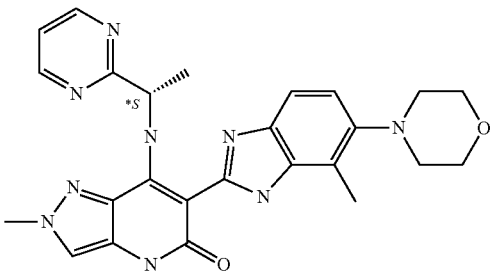

After the reaction was completed, the mixture was concentrated in vacuum to give a residue, which was purified by prep. HPLC (Column: Phenomenex Gemini C18 250*50 10 u, Mobile Phase A: water (0.225% FA), Mobile Phase B:

acetonitrile, Flow rate: 22 mL/min, gradient condition from 30% B to 60%). The pure fractions were collected and the solvent was evaporated under vacuum. The residue was re-suspended in water (50 mL) and the resulting mixtures were lyophilized to dryness, which was separated by supercritical fluid chromatography (separation condition: AD (250 mm*30 mm, 5 um); Mobile phase: A: Supercritical $CO_2$, B: 0.1% $NH_3H_2O$ EtOH, A:B=50:50 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The pure fractions were collected and the solvent was evaporated under vacuum. The residue was re-suspended in water (50 mL) and the resulting mixture was lyophilized to dryness to compound 28 (26.2 mg, 97.7% purity, 10.5% yield) as yellow solids.

LC-MS (ESI) (General Procedure A, Method 1): $R_T$=4.71 min, mass calcd. for $C_{25}H_{27}N_9O_2$ 485.23, m/z found 486.0 $[M+H]^+$.

General Procedure A: $^1H$ NMR (400 MHz, DMSO-$d^6$) (Varian) 13.04-12.90 (m, 1H), 12.87 (br s, 1H), 10.92 (s, 1H), 8.86 (s, 1H), 8.85 (s, 1H), 7.69 (s, 1H), 7.48-7.44 (m, 1H), 7.44-7.40 (m, 1H), 7.03-6.93 (m, 1H), 6.51 (t, J=6.7 Hz, 1H), 4.00 (s, 3H), 3.84-3.72 (m, 4H), 2.96-2.81 (m, 4H), 2.71-2.58 (m, 3H), 1.70 (d, J=6.8 Hz, 3H)

SFC (Method 13): $R_T$=2.47 min, Peak Area: 100%.

Compound 29

(S*)-6-(4-fluoro-6-morpholino-1H-benzo[d]imidazol-2-yl)-7-((2-methoxy-1-(pyrimidin-2-yl)ethyl)amino)-2-methyl-2H-pyrazolo[4,3-b]pyridin-5(4H)-one

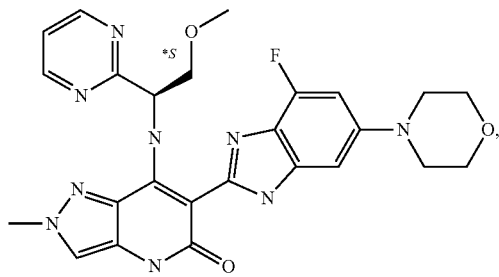

and

Compound 30

(R*)-6-(4-fluoro-6-morpholino-1H-benzo[d]imidazol-2-yl)-7-((2-methoxy-1-(pyrimidin-2-yl)ethyl)amino)-2-methyl-2H-pyrazolo[4,3-b]pyridin-5(4H)-one

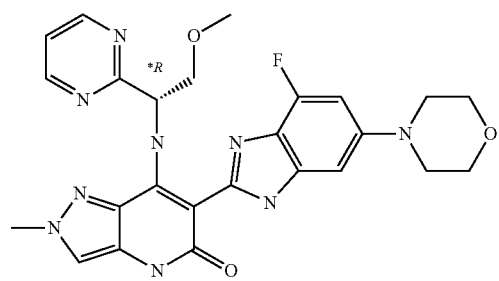

After the reaction was completed, the mixture was extracted with dichloromethane (100 mL). The separated organic layer was washed with water (50 mL×3), dried over $Na_2SO_4$, filtered and concentrated under reduced pressure to afford the crude product which was purified by prep. HPLC (Column: Phenomenex Gemini C18 250*50 10 u, Mobile Phase A: water (0.225% FA), Mobile Phase B: acetonitrile, Flow rate: 22 mL/min, gradient condition from 30% B to 60%). The pure fractions were collected and the solvent was evaporated under vacuum. The residue was lyophilized to dryness to give the racemic product, which was separated by supercritical fluid chromatography (separation condition: AD (250 mm*30 mm, 5 um); Mobile phase: A: Supercritical $CO_2$, B: 0.1% $NH_3H_2O$ IPA, A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The pure fractions were collected and the solvent was evaporated under vacuum. The residue was re-suspended in water (50 mL) and the resulting mixtures were lyophilized to dryness to give compound 29 (26.3 mg, 96.4% purity, 12.8% yield) as white solids, and compound 30 (21.9 mg, 100% purity, 11.1% yield) as white solids.

Compound 29

LC-MS (ESI) (General Procedure A, Method 2): $R_T$=4.07 min, mass calcd. for $C_{25}H_{26}FN_9O_3$ 519.21, m/z found 520.0 $[M+H]^+$.

General Procedure A: $^1H$ NMR (400 MHz, DMSO-$d^6$) (Varian) 13.24-13.21 (m, 0.1H), 13.01-12.95 (m, 0.9H), 12.52-12.46 (m, 0.9H), 12.46-12.42 (m, 0.1H), 11.06 (s, 0.1H), 10.91 (s, 0.9H), 8.83 (d, J=4.9 Hz, 0.2H), 8.77 (d, J=4.9 Hz, 1.8H), 7.69 (s, 0.1H), 7.64 (s, 0.9H), 7.43-7.41 (m, 0.1H), 7.40-7.36 (m, 0.9H), 7.06-7.02 (m, 0.9H), 6.89-6.87 (m, 0.1H), 6.87-6.82 (m, 0.1H), 6.78-6.71 (m, 0.9H), 6.64-6.59 (m, 0.1H), 6.56-6.49 (m, 0.9H), 4.16-4.09 (m, 1H), 4.03-3.96 (m, 1H), 3.92 (s, 0.3H), 3.89 (s, 2.7H), 3.80-3.72 (m, 4H), 3.33-3.30 (m, 3H), 3.15-3.06 (m, 4H)

SFC (Method 20): $R_T$=7.83 min, Peak Area: 100%.

Compound 30

LC-MS (ESI) (General Procedure A, Method 2): $R_T$=4.07 min, mass calcd. for $C_{25}H_{26}FN_9O_3$ 519.21, m/z found 520.0 $[M+H]^+$.

General Procedure A: $^1H$ NMR (400 MHz, DMSO-$d^6$) (Varian) 13.24-13.22 (m, 0.1H), 13.02-12.95 (m, 0.9H), 12.52-12.47 (m, 0.9H), 12.46-12.43 (m, 0.1H), 11.06 (s, 0.1H), 10.91 (s, 0.9H), 8.83 (d, J=4.9 Hz, 0.2H), 8.77 (d, J=4.9 Hz, 1.8H), 7.69 (s, 0.1H), 7.64 (s, 0.9H), 7.43-7.40 (m, 0.1H), 7.40-7.35 (m, 0.9H), 7.07-7.02 (m, 0.9H), 6.89-6.88 (m, 0.1H), 6.87-6.82 (m, 0.1H), 6.78-6.71 (m, 0.9H), 6.64-6.58 (m, 0.1H), 6.55-6.49 (m, 0.9H), 4.16-4.10 (m, 1H), 4.03-3.96 (m, 1H), 3.92 (s, 0.3H), 3.89 (s, 2.7H), 3.80-3.71 (m, 4H), 3.33-3.31 (m, 3H), 3.15-3.06 (m, 4H)

SFC (Method 20): $R_T$=11.76 min, Peak Area: 100%.

Compound 31

(S*)-2-methyl-6-(6-(4-methylpiperazin-1-yl)-1H-benzo[d]imidazol-2-yl)-7-((1-(3-(trifluoromethyl)pyridin-2-yl)ethyl)amino)-2H-pyrazolo[4,3-b]pyridin-5(4H)-one 0.3 formate

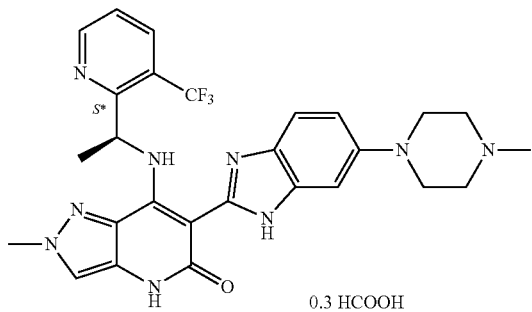

0.3 HCOOH

After the reaction was completed, the mixture was concentrated in vacuum to give a residue, which was extracted with dichloromethane (10 mL×2). The combined organic layers were dried over Na$_2$SO$_4$ and filtered. The filtrate was concentrated to afford the crude product which was purified by prep. HPLC (Column: Phenomenex Gemini C18 250*50 10 u, Mobile Phase A: water (0.225% FA), Mobile Phase B: acetonitrile, Flow rate: 22 mL/min, gradient condition from 2.5% B to 16%). The pure fractions were collected and the solvent was evaporated under vacuum. The residue was re-suspended in water (30 mL) and the resulting mixtures were lyophilized to dryness to give compound 31 (2.2 mg, 97.6% purity, 4.07% yield).

LC-MS (ESI) (General Procedure A, Method 2): R$_T$=4.49 min, mass calcd. for C$_{27}$H$_{28}$F$_3$N$_9$O 551.24, m/z found 552.0 [M+H]$^+$.

General Procedure A: $^1$H NMR (400 MHz, DMSO-d$^6$) (Varian) 12.86-12.82 (m, 0.4H), 12.78-12.76 (m, 0.6H), 12.76-12.73 (m, 1H), 10.88 (br. s, 0.4H), 10.87 (br. s, 0.6H), 9.13-9.07 (m, 1H), 8.37 (br. s, 0.3H), 8.21 (d, J=7.3 Hz, 1H), 7.70 (s, 0.6H), 7.69 (s, 0.4H), 7.65-7.58 (m, 1H), 7.47 (d, J=8.8 Hz, 0.4H), 7.44 (d, J=8.8 Hz, 0.6H), 7.17 (d, J=2.0 Hz, 0.6H), 7.05 (d, J=1.0 Hz, 0.4H), 6.95-6.85 (m, 2H), 4.06-3.99 (m, 3H), 3.15-3.07 (m, 4H), 2.57-2.52 (m, 4H), 2.28-2.20 (m, 3H), 1.69-1.61 (m, 3H)

SFC (Method 17): R$_T$=2.92 min, Peak Area: 100%.

Compound 32

(R*)-2-methyl-6-(6-(4-methylpiperazin-1-yl)-1H-benzo[d]imidazol-2-yl)-7-((1-(3-(trifluoromethyl)pyridin-2-yl)ethyl)amino)-2H-pyrazolo[4,3-b]pyridin-5(4H)-one 0.2 formate

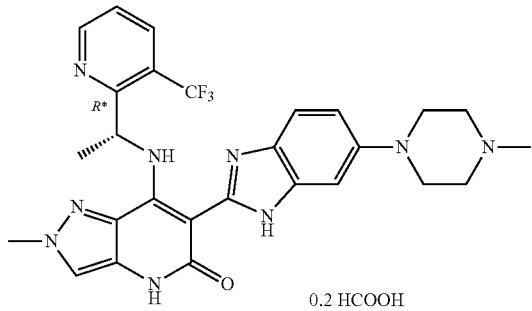

0.2 HCOOH

After the reaction was completed, the mixture was concentrated to remove most of solvent which was extracted with dichloromethane (10 mL×2). The combined organic layers were dried over Na$_2$SO$_4$ and filtered. The filtrate was concentrated to afford the crude product which was purified by prep. HPLC (Column: Phenomenex Gemini C18 250*50 10 u, Mobile Phase A: water (0.225% FA), Mobile Phase B: acetonitrile, Flow rate: 22 mL/min, gradient condition from 2.5% B to 16%). The product was suspended in water (30 mL) and lyophilized to dryness to afford compound 32 (4.2 mg, 97.4% purity, 7.82% yield).

LC-MS (ESI) (General Procedure A, Method 2): R$_T$=4.35 min, mass calcd. for C$_{27}$H$_{28}$F$_3$N$_9$O 551.24, m/z found 552.0 [M+H]$^+$.

General Procedure A: $^1$H NMR (400 MHz, DMSO-d$^6$) (Varian) 12.87-12.73 (m, 2H), 10.89 (br. s, 0.4H), 10.88 (s, 0.6H), 9.14-9.08 (m, 1H), 8.22 (br. d, J=8.2 Hz, 1H), 8.14 (s, 0.2H), 7.71 (s, 0.5H), 7.70 (s, 0.5H), 7.65-7.58 (m, 1H), 7.50 (d, J=8.6 Hz, 0.4H), 7.46 (d, J=8.8 Hz, 0.6H), 7.20 (d, J=1.0 Hz, 0.6H), 7.09 (d, J=1.0 Hz, 0.4H), 6.95-6.87 (m, 2H), 4.06-3.99 (m, J=3.5 Hz, 3H), 3.24-3.18 (m, 3H), 2.95-2.69 (m, 4H), 2.46-2.37 (m, 4H), 1.70-1.62 (m, 3H)

SFC (Method 17): R$_T$=3.98 min, Peak Area: 98.3%.

Compound 33

(S)-2-methyl-6-(6-(piperidin-1-yl)-1H-benzo[d]imidazol-2-yl)-7-((1-(pyridin-2-yl)ethyl)-amino)-2H-pyrazolo[4,3-b]pyridin-5(4H)-one

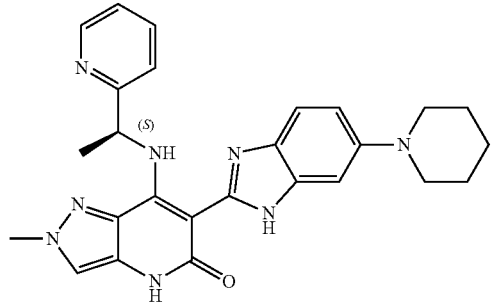

After the reaction was completed, the mixture was concentrated in vacuum to give a residue, which was extracted with dichloromethane:methanol (20 mL, v/v=10:1). The organic layer was separated and collected under vacuum. The crude product was purified by flash column (dichloromethane:methanol from 100:0 to 90:10) to give the product as yellow solids which was further purified by prep. HPLC (Column: Phenomenex Gemini 150 mm*25 mm, 10 μm, Mobile Phase A: water (0.05% ammonia hydroxide), Mobile Phase B: acetonitrile, Flow rate: 25 mL/min, gradient condition from 15% B to 45%). The pure fractions were collected and the solvent was evaporated under vacuum, and then lyophilized to give compound 33 (3.5 mg, 95.1% purity, 5.93% yield) as white powder.

LC-MS (ESI) (General Procedure A, Method 2): R$_T$=3.62 min, mass calcd. for C$_{26}$H$_{28}$N$_8$O 468.24, m/z found 469.1 [M+H]$^+$.

General Procedure A: $^1$H NMR (400 MHz, DMSO-d$^6$) (Varian) 12.86 (s, 0.4H), 12.82 (s, 0.6H), 12.64 (d, J=8.8 Hz, 0.4H), 12.56 (d, J=8.6 Hz, 0.6H), 10.86 (br s, 1H), 8.66-8.56 (m, 1H), 8.41 (br s, 0.2H), 7.81-7.72 (m, 1H), 7.66 (s, 1H), 7.48 (dd, J=3.4, 8.3 Hz, 1.4H), 7.41 (d, J=8.8 Hz, 0.6H), 7.27 (dd, J=4.7, 7.2 Hz, 1H), 7.19 (d, J=2.0 Hz, 0.6H), 7.06 (d, J=2.2 Hz, 0.4H), 6.95-6.84 (m, 1H), 6.49-6.37 (m, 1H), 4.00 (d, J=2.2 Hz, 3H), 3.08 (q, J=5.1 Hz, 4H), 1.75-1.59 (m, 7H), 1.54 (d, J=3.5 Hz, 2H).

SFC (Method 10): R$_T$=1.69 min, Peak Area: 100%.

Compound 34

(S*)-2-methyl-6-(6-(piperidin-1-yl)-1H-benzo[d]imidazol-2-yl)-7-((1-(pyrimidin-2-yl)-ethyl)amino)-2H-pyrazolo[4,3-b]pyridin-5(4H)-one

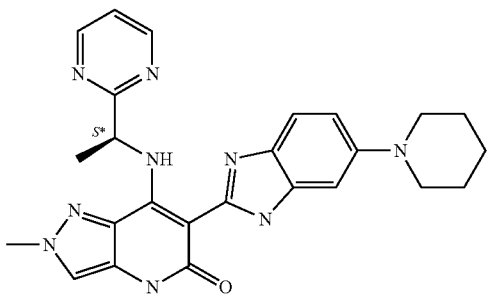 [SMILES: C[C@H](Nc1c(-c2nc3ccc(N4CCCCC4)cc3[nH]2)c(=O)[nH]c2cn(C)nc12)c1ncccn1]

and

Compound 35

(R*)-2-methyl-6-(6-(piperidin-1-yl)-1H-benzo[d]imidazol-2-yl)-7-((1-(pyrimidin-2-yl)-ethyl)amino)-2H-pyrazolo[4,3-b]pyridin-5(4H)-one

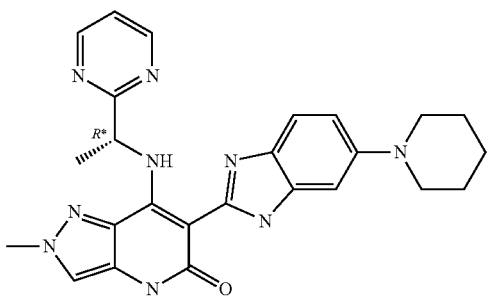 [SMILES: C[C@@H](Nc1c(-c2nc3ccc(N4CCCCC4)cc3[nH]2)c(=O)[nH]c2cn(C)nc12)c1ncccn1]

After the reaction was completed, the mixture was extracted with dichloromethane:methanol (10:1, 20 mL). The separated organic layer was evaporated to dryness. The crude product was purified by flash column (dichloromethane:methanol from 100:0 to 90:10) as yellow solids, which was further separated by supercritical fluid chromatography (separation condition: OD (250 mm×30 mm, 5 um)); Mobile phase: A: Supercritical $CO_2$, B: 0.1% $NH_3H_2O$ EtOH, A:B=55:45 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The pure fractions were collected and the solvent was evaporated under vacuum. The residue was re-suspended in water (10 mL) and the resulting mixtures were lyophilized to dryness to give compound 34 (2.6 mg, 97.5% purity, 14.9% yield) as yellow solids and compound 35 (2.3 mg, 97.7% purity, 13.2% yield) as yellow solids.

Compound 34

LC-MS (ESI) (General Procedure A, Method 2): $R_T$=3.74 min, mass calcd. for $C_{25}H_{27}N_9O$ 469.2, m/z found 470.1 $[M+H]^+$ General Procedure A: $^1$H NMR (400 MHz, DMSO-d$^6$) (Varian) 12.83 (s, 0.4H), 12.80 (s, 0.6H), 12.73 (br d, J=8.2 Hz, 0.4H), 12.66 (br. d., J=8.2 Hz, 0.6H), 10.90-10.81 (m, 1H), 8.84 (dd, J=2.4, 4.9 Hz, 2H), 7.66 (s, 1H), 7.48 (d, J=8.6 Hz, 0.4H), 7.45-7.36 (m, 1.6H), 7.19 (d, J=1.8 Hz, 0.6H), 7.06 (s, 0.4H), 6.93-6.84 (m, 1H), 6.54-6.39 (m, 1H), 3.96 (d, J=3.7 Hz, 3H), 3.14-3.04 (m, 4H), 1.78-1.62 (m, 7H), 1.54 (br. d., J=5.1 Hz, 2H)

SFC (Method 17): $R_T$=5.19 min, Peak Area: 99.2%.

Compound 35

LC-MS (ESI) (General Procedure A, Method 2): $R_T$=3.76 min, mass calcd. for $C_{25}H_{27}N_9O$ 469.23, m/z found 470.1 $[M+H]^+$ General Procedure A: $^1$H NMR (400 MHz, DMSO-d$^6$) (Bruker) 12.83 (s, 0.4H), 12.80 (s, 0.6H), 12.73 (br. d., J=8.2 Hz, 0.4H), 12.66 (br. d., J=7.9 Hz, 0.6H), 10.91-10.82 (m, 1H), 8.84 (dd, J=2.4, 4.9 Hz, 2H), 7.66 (s, 1H), 7.48 (d, J=8.6 Hz, 0.4H), 7.45-7.37 (m, 1.6H), 7.19 (d, J=2.0 Hz, 0.6H), 7.06 (s, 0.4H), 6.93-6.84 (m, 1H), 6.52-6.39 (m, 1H), 3.96 (d, J=3.7 Hz, 3H), 3.16-3.01 (m, 4H), 1.75-1.63 (m, 7H), 1.54 (br. d., J=5.3 Hz, 2H)

SFC (Method 17): $R_T$=6.64 min, Peak Area: 96.8%.

Compound 36

(S*)-2-methyl-7-((1-(oxazol-4-yl)ethyl)amino)-6-(6-((tetrahydro-2H-pyran-4-yl)oxy)-1H-benzo[d]imidazol-2-yl)-2H-pyrazolo[4,3-b]pyridin-5(4H)-one

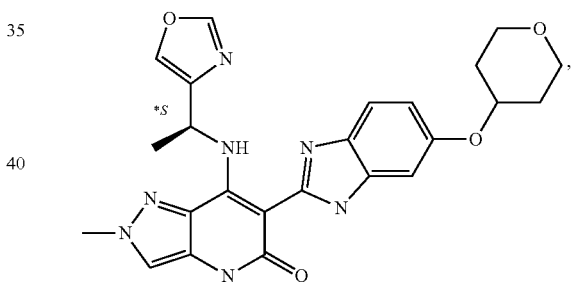

and

Compound 37

(R*)-2-methyl-7-((1-(oxazol-4-yl)ethyl)amino)-6-(6-((tetrahydro-2H-pyran-4-yl)oxy)-1H-benzo[d]imidazol-2-yl)-2H-pyrazolo[4,3-b]pyridin-5(4H)-one

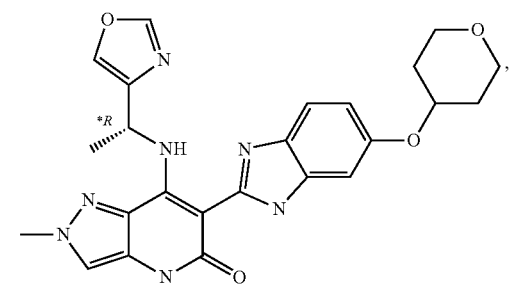 [SMILES: C[C@@H](Nc1c(-c2nc3ccc(OC4CCOCC4)cc3[nH]2)c(=O)[nH]c2cn(C)nc12)c1cocn1]

After the reaction was completed, the mixture was concentrated in vacuum to give a residue, which was purified by flash chromatography column (dichloromethane:methanol from 100:0 to 90:10) to give the product, which was further purified by prep. HPLC (Column: Phenomenex Gemini C18 250*50 10 u, Mobile Phase A: water (0.05% ammonia hydroxide v/v), Mobile Phase B: acetonitrile, Flow rate: 22 mL/min, gradient condition from 48% B to 78%). The pure fractions were collected and the solvent was evaporated under vacuum. The residue was re-suspended in water (10 mL) and lyophilized to dryness to afford compound 36 (2.1 mg, 98.5% purity, 2.32% yield) as white solids, and compound 37 (1.0 mg, 96.0% purity, 1.08% yield) as white solids.

Compound 36

LC-MS (ESI) (General Procedure C, Method 8): $R_T$=3.20 min, mass calcd. for $C_{24}H_{25}N_7O_5$ 475.20, m/z found 476.1 $[M+H]^+$.

General Procedure A: $^1$H NMR (400 MHz, METHANOL-d$^4$) (Bruker) 8.20 (d, J=2.5 Hz, 1H), 7.89 (s, 1H), 7.59 (s, 1H), 7.47 (d, J=8.8 Hz, 0.6H), 7.41 (d, J=8.8 Hz, 0.4H), 7.20 (d, J=2.0 Hz, 0.4H), 7.15 (d, J=2.0 Hz, 0.6H), 6.86 (dt, J=2.3, 8.0 Hz, 1H), 6.61-6.44 (m, 1H), 4.56 (td, J=3.9, 8.0 Hz, 1H), 4.07 (s, 3H), 4.02-3.95 (m, 2H), 3.66-3.51 (m, 2H), 2.12-1.99 (m, 2H), 1.80-1.76 (m, 3H), 1.76-1.70 (m, 2H).

SFC (Method 13): $R_T$=1.66 min, peak area: 100%.

Compound 37

LC-MS (ESI) (General Procedure C, Method 8): $R_T$=3.17 min, mass calcd. for $C_{24}H_{25}N_7O_4$ 475.20, m/z found 476.1 $[M+H]^+$.

General Procedure A: $^1$H NMR (400 MHz, METHANOL-d$^4$) (Bruker) 8.20 (d, J=2.5 Hz, 1H), 7.89 (s, 1H), 7.59 (s, 1H), 7.47 (d, J=8.8 Hz, 0.6H), 7.41 (d, J=8.8 Hz, 0.4H), 7.20 (d, J=2.0 Hz, 0.4H), 7.15 (d, J=2.0 Hz, 0.6H), 6.86 (dt, J=2.3, 8.0 Hz, 1H), 6.61-6.44 (m, 1H), 4.56 (td, J=3.9, 8.0 Hz, 1H), 4.07 (s, 3H), 4.02-3.95 (m, 2H), 3.66-3.51 (m, 2H), 2.12-1.99 (m, 2H), 1.80-1.76 (m, 3H), 1.76-1.70 (m, 2H).

SFC (Method 13): $R_T$=2.55 min, peak area: 99.4%.

Compound 38

(S)-2-methyl-6-(6-morpholino-1H-imidazo[4,5-c]pyridin-2-yl)-7-((1-(pyrimidin-2-yl)-ethyl)amino)-2H-pyrazolo[4,3-b]pyridin-5(4H)-one 0.8 formate

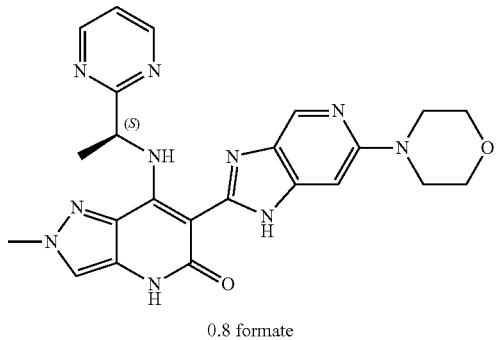

0.8 formate

After the reaction was completed, the mixture was extracted with dichloromethane (20 mL×3). The combined organic layers were washed with brine (20 mL×3), dried over anhydrous $Na_2SO_4$ and filtered. The filtrate was concentrated to dryness under reduced pressure to afford the crude product, which was purified by flash column chromatography (dichloromethane:tetrahydrofuran from 1:0 to 2:3) to afford the product which was triturated with tert-butyl methyl ether (10 mL) to give the crude product. The crude product was further purified by prep. HPLC (Column: Phenomenex Gemini C18 250×50 10 um, Mobile Phase A: water (0.225% FA), Mobile Phase B: acetonitrile, gradient condition from 8% B to 38%). The pure fractions were collected and the solvent was evaporated under vacuum, and then lyophilized to give compound 38 (213 mg, 97.7% purity, 44.6% yield) as a yellow powder.

LC-MS (ESI) (General Procedure A, Method 1): $R_T$=3.87 min, mass calcd. for $C_{23}H_{24}N_{10}O_2$ 472.21, m/z found 473.0 $[M+H]^+$.

General Procedure A: $^1$H NMR (400 MHz, DMSO-d$^6$) (Varian) δ=13.09-12.98 (m, 1H), 12.74 (d, J=8.2 Hz, 0.3H), 12.60 (d, J=7.9 Hz, 0.7H), 11.01-10.92 (m, 1H), 8.92-8.83 (m, 2H), 8.57 (s, 0.3H), 8.54 (s, 0.7H), 8.20 (br. s., 0.8H), 7.70 (s, 1H), 7.46-7.39 (m, 1H), 7.00 (s, 0.7H), 6.91 (s, 0.3H), 6.58-6.36 (m, 1H), 4.02-3.94 (m, 3H), 3.82-3.69 (m, 4H), 3.45-3.30 (m, 4H), 1.78-1.69 (m, 3H)

SFC (Method 14): $R_T$=3.46 min, Peak area: 97.3%

Compound 39

(S*)-2-methyl-6-(6-morpholino-1H-benzo[d]imidazol-2-yl)-7-((1-(pyrimidin-2-yl)-propyl)amino)-2H-pyrazolo[4,3-b]pyridin-5(4H)-one

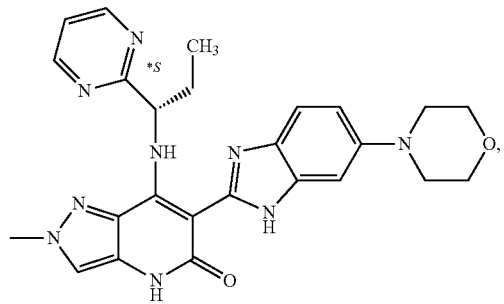 [SMILES: CC[C@H](Nc1c(-c2nc3ccc(N4CCOCC4)cc3[nH]2)c(=O)[nH]c2cn(C)nc12)c1ncccn1]

Compound 40

(R*)-2-methyl-6-(6-morpholino-1H-benzo[d]imidazol-2-yl)-7-((1-(pyrimidin-2-yl)-propyl)amino)-2H-pyrazolo[4,3-b]pyridin-5(4H)-one

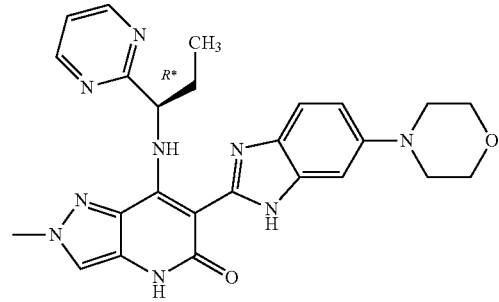 [SMILES: CC[C@@H](Nc1c(-c2nc3ccc(N4CCOCC4)cc3[nH]2)c(=O)[nH]c2cn(C)nc12)c1ncccn1]

After the reaction was completed, the mixture was concentrated to dryness under reduced pressure, which was purified by prep. HPLC (Column: Phenomenex Gemini C18 250*50 mm*10 um, Mobile Phase A: water (0.05% ammonia hydroxide), Mobile Phase B: acetonitrile, Flow rate: 22 mL/min, gradient condition from 30% B to 60%). The pure fractions were collected and the volatiles were removed under vacuum. The residue was re-suspended in water (10 mL) and the resulting mixture was lyophilized to dryness to give the product as brown solids. The product was separated by supercritical fluid chromatography (separation condition: AD (250 mm×30 mm, 10 µm); Mobile phase: A: Supercritical $CO_2$, B: 0.1% $NH_3H_2O$ EtOH, A:B=55:45 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220-nm). The pure fractions were collected and the volatiles were removed under reduced pressure. The residue was re-suspended in water (10 mL) and then lyophilized to dryness to give compound 39 (43.1 mg, 99.8% purity, 17.0% yield) as brown solids, and compound 40 (17.3 mg, 97.3% purity, 6.67% yield) as brown solids.

Compound 39

LC-MS (ESI) (General Procedure A, Method 2): $R_T$=3.64 min, mass calcd. for $C_{25}H_{27}N_9O_2$ 485.23, m/z found 486.1 $[M+H]^+$.

General Procedure A: $^1$H NMR (400 MHz, DMSO-de) (Bruker) δ 12.91-12.82 (m, 1H), 12.72-12.58 (m, 1H), 10.87 (br. s., 1H), 8.88-8.79 (m, 2H), 7.64 (s, 1H), 7.56-7.36 (m, 2H), 7.24-7.01 (m, 1H), 6.95-6.86 (m, 1H), 6.46-6.32 (m, 1H), 3.94 (s, 3H), 3.83-3.73 (m, 4H), 3.16-3.05 (m, 4H), 2.22-2.08 (m, 2H), 1.05-0.93 (m, 3H)

SFC (Method 13): $R_T$=2.26 min, Peak area: 99.7%

Compound 40

LC-MS (ESI) (General Procedure A, Method 2): $R_T$=3.65 min, mass calcd. for $C_{25}H_{27}N_9O_2$ 485.23, m/z found 486.0 $[M+H]^+$.

General Procedure A: $^1$H NMR (400 MHz, DMSO-$d_6$) (Bruker) δ 12.96-12.83 (m, 1H), 12.72-12.57 (m, 1H), 10.87 (br s, 1H), 8.87-8.79 (m, 2H), 7.64 (s, 1H), 7.56-7.36 (m, 2H), 7.24-7.02 (m, 1H), 6.95-6.87 (m, 1H), 6.44-6.33 (m, 1H), 3.94 (s, 3H), 3.83-3.73 (m, 4H), 3.14-3.03 (m, 4H), 2.23-2.08 (m, 2H), 1.09-0.94 (m, 3H)

SFC (Method 13): $R_T$=1.64 min, Peak area: 100%

Compound 41

(S*)-2-methyl-6-(6-morpholino-1H-benzo[d]imidazol-2-yl)-7-((1-(thiazol-4-yl)ethyl)-amino)-2H-pyrazolo[4,3-b]pyridin-5(4H)-one

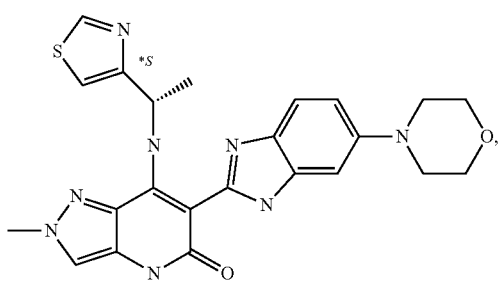 [SMILES: C[C@H](Nc1c(-c2nc3ccc(N4CCOCC4)cc3[nH]2)c(=O)[nH]c2cn(C)nc12)c1cscn1]

and

Compound 42

(R*)-2-methyl-6-(6-morpholino-1H-benzo[d]imidazol-2-yl)-7-((1-(thiazol-4-yl)ethyl)-amino)-2H-pyrazolo[4,3-b]pyridin-5(4H)-one

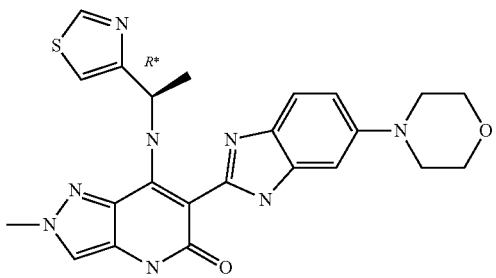 [SMILES: C[C@@H](Nc1c(-c2nc3ccc(N4CCOCC4)cc3[nH]2)c(=O)[nH]c2cn(C)nc12)c1cscn1]

After the reaction was completed, the mixture was concentrated to dryness under reduced pressure which was purified by prep. HPLC (Column: Phenomenex Gemini C18 250*50 mm*10 um, Mobile Phase A: water (0.05% ammonia hydroxide), Mobile Phase B: acetonitrile, Flow rate: 22 mL/min, gradient condition from 40% B to 50%). The pure fractions were collected and the volatiles were removed under vacuum. The residue was re-suspended in water (10 mL) and the resulting mixture was lyophilized to dryness to give the racemic product as brown solids, which was separated by supercritical fluid chromatography (separation condition: AD (250 mm*30 mm, 10 um); Mobile phase: A: Supercritical $CO_2$, B: 0.1% $NH_3H_2O$ IPA, A:B=50:50 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give compound 41 compound (6.5 mg, 99.4% purity, 8.08% yield) as yellow solids, and compound 42 (12.4 mg, 99.8% purity, 15.5% yield) as yellow solids.

Compound 41

LC-MS (ESI) (General Procedure A, Method 2): $R_T$=3.78 min, mass calcd. for $C_{23}H_{24}N_8O_2S$ 476.17, m/z found 477.0 $[M+H]^+$.

General Procedure A: $^1$H NMR (400 MHz, DMSO-$d^6$) (Varian) δ 12.92-12.85 (m, 1H), 12.57 (d, J=9.0 Hz, 0.4H), 12.49 (d, J=8.8 Hz, 0.6H), 10.96-10.88 (m, 1H), 9.11 (d, J=2.0 Hz, 1H), 7.74-7.67 (m, 1H), 7.60-7.49 (m, 1.4H), 7.44-7.39 (m, 0.6H), 7.22-7.18 (m, 0.6H), 7.07-7.02 (m, 0.4H), 6.94-6.87 (m, 1H), 6.69-6.57 (m, 1H), 4.08-4.00 (m, 3H), 3.81-3.73 (m, 4H), 3.13-3.04 (m, 4H), 1.79-1.70 (m, 3H)

SFC (Method 10): $R_T$=2.16 min, Peak Area: 99.4%.

Compound 42

LC-MS (ESI) (General Procedure A, Method 2): $R_T$=3.77 min, mass calcd. for $C_{23}H_{24}N_8O_2S$ 476.2, m/z found 477.0 $[M+H]^+$.

General Procedure A: $^1$H NMR (400 MHz, DMSO-$d^6$) (Varian) δ 12.91-12.85 (m, 1H), 12.56 (d, J=8.8 Hz, 0.4H), 12.48 (d, J=8.8 Hz, 0.6H), 10.93-10.89 (m, 1H), 9.11 (d, J=2.0 Hz, 1H), 7.72-7.68 (m, 1H), 7.59-7.49 (m, 1.4H), 7.42 (d, J=8.8 Hz, 0.6H), 7.22-7.18 (m, 0.6H), 7.06-7.03 (m, 0.4H), 6.94-6.88 (m, 1H), 6.67-6.58 (m, 1H), 4.06-4.01 (m, 3H), 3.80-3.73 (m, 4H), 3.12-3.05 (m, 4H), 1.78-1.70 (m, 3H)

SFC (Method 10): $R_T$=2.79 min, Peak Area: 98.1%.

Compound 43

(S)-2-ethyl-6-(6-morpholino-1H-imidazo[4,5-c]pyridin-2-yl)-7-((1-(pyrimidin-2-yl)ethyl)-amino)-2H-pyrazolo[4,3-b]pyridin-5(4H)-one

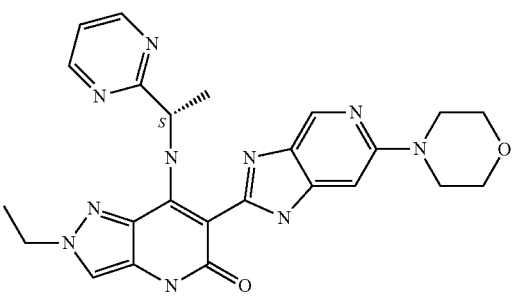

After the reaction was completed, the mixture was extracted by dichloromethane (10 mL×3). The combined organic extracts were washed with brine, dried over anhydrous Na$_2$SO$_4$ and filtered. The filtrate was concentrated to dryness under reduced pressure to afford crude product, which was purified by prep. HPLC (Column: Phenomenex Gemini 150*25 mm*10 um, Mobile Phase A: water (0.05% ammonia hydroxide v/v), Mobile Phase B: acetonitrile, Flow rate: 25 mL/min, gradient condition from 26% B to 56%). The pure fractions were collected and the solvent was evaporated under vacuum. The residue was re-suspended in water (10 mL) and the resulting mixtures were lyophilized to dryness to give compound 43 (116 mg, 95.8% purity, 18.3% yield) as white solids.

LC-MS (ESI) (General Procedure A, Method 1): R$_T$=4.04 min, mass calcd. for C$_{24}$H$_{26}$N$_{10}$O$_2$ 486.22, m/z found 487.0 [M+H]+.

General Procedure A: $^1$H NMR (400 MHz, DMSO-d$^6$) (Varian) δ 13.05-12.97 (m, 1H), 12.66 (d, J=7.9 Hz, 0.3H), 12.51 (d, J=7.9 Hz, 0.7H), 10.98-10.92 (m, 1H), 8.88-8.80 (m, 2H), 8.56 (s, 0.3H), 8.52 (s, 0.7H), 7.69 (s, 1H), 7.44-7.36 (m, 1H), 7.00 (s, 0.7H), 6.89 (s, 0.3H), 6.47-6.31 (m, 1H), 4.39-4.10 (m, 2H), 3.81-3.70 (m, 4H), 3.43-3.36 (m, 4H), 1.82-1.67 (m, 3H), 1.39-1.26 (m, 3H)

SFC (Method 14): R$_T$=2.46 min, Peak Area: 99.2%.

Compound 44

(R*)-2-methyl-7-((2-methyl-1-(pyridin-2-yl)propyl)amino)-6-(6-(4-methylpiperazin-1-yl)-1H-benzo[d]imidazol-2-yl)-2H-pyrazolo[4,3-b]pyridin-5(4H)-one

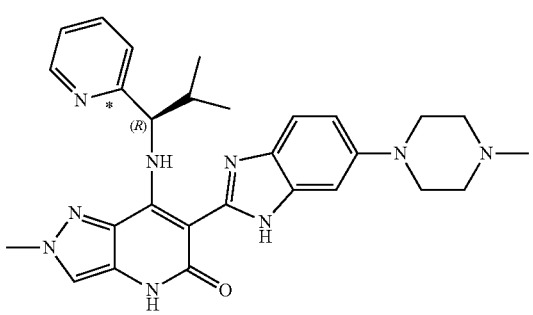

The compound was purified via General Procedure E for HPLC, method 3.

LC-MS (ESI) (General Procedure A-2, method 2): R$_T$=0.95 min, mass calcd. for C$_{28}$H$_{33}$N$_9$O, 511.28, m/z found 512.5 [M+H]+.

General Procedure A-2: $^1$HNMR (400 MHz, CD$_3$OD) δ8.53 (d, J=4.0 Hz, 1H), 7.71 (d, J=6.8 Hz, 1H), 7.52-7.44 (m, 3H), 7.24-7.18 (m, 2H), 7.03-7.00 (m, 1H), 6.42-6.41 (m, 1H), 3.95 (s, 3H), 3.25-3.22 (m, 4H), 2.70-2.68 (m, 4H), 2.58-2.56 (m, 1H), 2.39 (s, 3H), 1.16 (t, J=6.4 Hz, 6H).

Compound 45

(S*)-2-methyl-7-((2-methyl-1-(pyridin-2-yl)propyl)amino)-6-(6-(4-methylpiperazin-1-yl)-1H-benzo[d]imidazol-2-yl)-2H-pyrazolo[4,3-b]pyridin-5(4H)-one

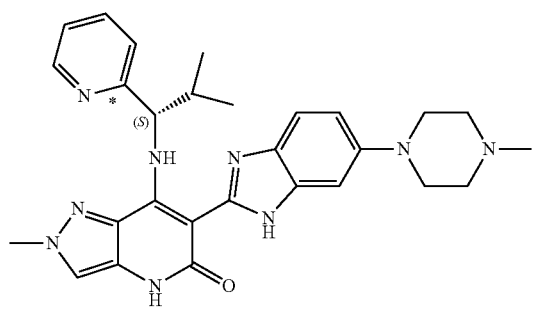

The compound was purified via General Procedure E for HPLC, method 3.

LC-MS (ESI) (General Procedure A-2, method 2): R$_T$=0.95 min, mass calcd. for C$_{28}$H$_{33}$N$_9$O, 511.28, m/z found 512.5 [M+H]+.

General Procedure A-2: $^1$H NMR (400 MHz, CD$_3$OD) δ 8.53 (d, J=4.0 Hz, 1H), 7.71 (d, J=6.8 Hz, 1H), 7.52-7.44 (m, 3H), 7.24-7.18 (m, 2H), 7.03-7.00 (m, 1H), 6.42-6.41 (m, 1H), 3.95 (s, 3H), 3.25-3.22 (m, 4H), 2.70-2.68 (m, 4H), 2.58-2.56 (m, 1H), 2.39 (s, 3H), 1.16 (t, J=6.4 Hz, 6H).

Compound 46

(S)-2-ethyl-6-(6-morpholino-1H-benzo[d]imidazol-2-yl)-7-((1-(pyrimidin-2-yl)ethyl)-amino)-2H-pyrazolo[4,3-b]pyridin-5(4H)-one

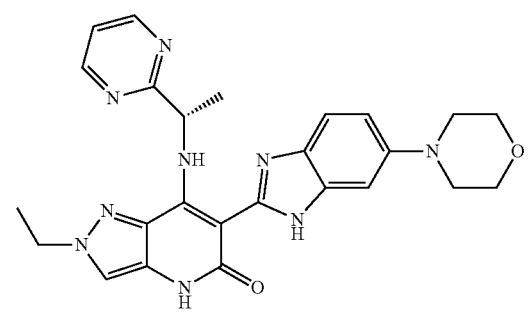 [SMILES: CCn1cc2[nH]c(=O)c(-c3nc4ccc(N5CCOCC5)cc4[nH]3)c(N[C@@H](C)c3ncccn3)c2n1]

The residue was purified by silica gel chromatography (gradient, CH$_2$Cl$_2$: MeOH=150:1 to 50:1) to give crude product (600 mg, 44.8% yield) as yellow solids. The crude compound was further purified by prep. SFC (Separation condition: Instrument: SFC80 (Waters); Column: OD 2.5*25 cm, 10 um; Mobile phase A: Supercritical CO$_2$, Mobile phase B: IPA/ACN/DEA=60/40/0.2, A:B=50/50 at 80 mL/min, Column temperature: 25° C., Back pressure:

100 bar) to afford compound 46 (262.95 mg, 43.8% yield, purity 99.3%, ee: >99%) as yellow solids.

LC-MS (ESI) (General Procedure A-2, method 2): $R_T$=1.20 min, mass calcd. for $C_{25}H_{27}N_9O_2$ 485.54, m/z found 486.4 $[M+H]^+$.

General Procedure A-2: $^1$HNMR (400 MHz, DMSO-d$_6$) δ 12.86 (d, J=2.4 Hz, 1H), 12.63-12.58 (m, 1H), 10.86 (s, 1H), 8.82 (d, J=4.8 Hz, 2H), 7.65 (d, J=1.6 Hz, 1H), 7.54-7.36 (m, 2H), 7.23-7.07 (m, 1H), 6.94-6.87 (m, 1H), 6.40-6.38 (m, 1H), 4.24-4.19 (m, 2H), 3.78-3.76 (m, 4H), 3.11-3.10 (m, 4H), 1.75 (t, J=6.4 Hz, 3H), 1.35-1.30 (m, 3H).

Compound 47

(S)-2-ethyl-6-(6-morpholino-1H-imidazo[4,5-c]pyridin-2-yl)-7-((1-(pyridin-2-yl)ethyl)-amino)-2,4-dihydro-5H-pyrazolo[4,3-b]pyridin-5-one

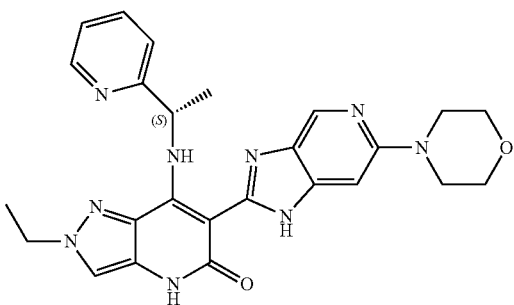

The residue was purified by silica gel column chromatography (CH$_2$Cl$_2$:MeOH=100:1) to give compound 47 (139.8 mg, yield 28.8%, purity 97.8%, ee: >99%) as yellow solids.

LC-MS (ESI) (General Procedure C-2, method 2): $R_T$=1.309 min, mass calcd. for $C_{25}H_{27}N_9O_2$ 485.5, m/z found 486.3 $[M+H]^+$.

General Procedure A-2: $^1$H NMR (400 MHz, CD$_3$OD) δ 8.57-8.45 (m, 2H), 7.78-7.71 (m, 1H), 7.55-7.46 (m, 2H), 7.26-7.25 (m, 1H), 6.99-6.90 (m, 1H), 6.46-6.40 (m, 1H), 4.27-4.20 (m, 2H), 3.89-3.82 (m, 4H), 3.41-3.37 (m, 4H), 1.82 (d, J=6.8 Hz, 3H), 1.39 (t, J=12 Hz, 3H).

Compound 48

(S)-2-ethyl-6-(4-fluoro-6-(4-methylpiperazin-1-yl)-1H-benzo[d]imidazol-2-yl)-7-((1-(pyrimidin-2-yl)ethyl)amino)-2H-pyrazolo[4,3-b]pyridin-5(4H)-one

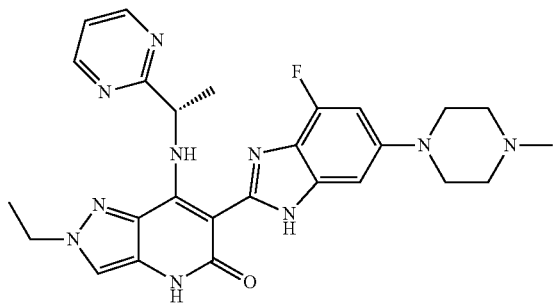 [SMILES: CCn1cc2[nH]c(=O)c(-c3nc4c(F)cc(N5CCN(C)CC5)cc4[nH]3)c(N[C@@H](C)c3ncccn3)c2n1]

The residue was purified by silica gel chromatography (gradient, CH$_2$Cl$_2$: MeOH=50:1 to 20:1) to give crude compound (149 mg, 50% yield) as yellow solids. The crude compound was further purified by prep. SFC (Separation condition: Instrument: SFC80 (Waters); Column: OD 2.5*25 cm, 10 um; Mobile phase A: Supercritical CO$_2$, Mobile phase B: IPA/ACN/DEA=60/40/0.2, A:B=60/40 at 70 mL/min, Column temperature: 25° C., Back pressure: 100 bar) to afford compound 48 (95.9 mg, 32.0% yield, purity 98.4%, ee: >99%) as yellow solids.

LC-MS (ESI) (General Procedure B-2, method 4): $R_T$=0.95 min, mass calcd. for $C_{26}H_{29}FN_{10}O$ 516.57, m/z found 517.4 $[M+H]^+$.

General Procedure A-2: $^1$H NMR (400 MHz, CD$_3$OD) δ 8.78-8.77 (m, 2H), 7.53 (s, 1H), 7.36-7.33 (m, 1H), 6.95 (s, 1H), 6.74-6.71 (m, 1H), 6.40-6.38 (m, 1H), 4.25-4.20 (m, 2H), 3.30-3.28 (m, 4H), 2.88 (m, 4H), 2.54 (s, 3H), 1.83 (d, J=6.8 Hz, 3H), 1.40 (t, J=7.2 Hz, 3H).

Compound 49

(S)-2-ethyl-6-(4-fluoro-6-(3-methoxyazetidin-1-yl)-1H-benzo[d]imidazol-2-yl)-7-((1-(pyrimidin-2-yl)ethyl)amino)-2H-pyrazolo[4,3-b]pyridin-5(4H)-one

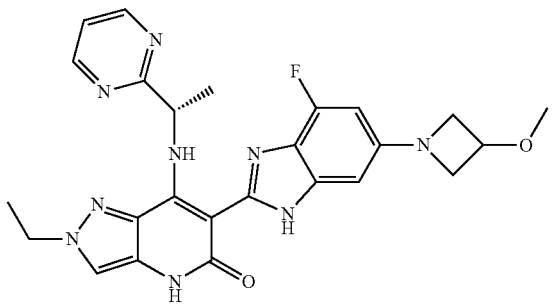 [SMILES: CCn1cc2[nH]c(=O)c(-c3nc4c(F)cc(N5CC(OC)C5)cc4[nH]3)c(N[C@@H](C)c3ncccn3)c2n1]

The residue was purified by silica gel chromatography (gradient, CH$_2$Cl$_2$: MeOH=100:1 to 50:1) to give crude compound (200 mg, 83.0% yield, purity 90.6%). The compound was further purified by prep. SFC (Separation condition: Instrument: SFC80 (Waters); Column: OD 2.5*25 cm, 10 um; Mobile phase A: Supercritical CO$_2$, Mobile phase B:MeOH/DEA=100/0.2, A:B=70/30 at 70 mL/min, Column temperature: 25° C., Back pressure: 100 bar) to afford compound 49 (106.7 mg, 44.0% yield, purity 99.4%, ee: >99%) as yellow solids.

LC-MS (ESI) (General Procedure B-2, method 4): $R_T$=1.56 min, mass calcd. for $C_{25}H_{26}FN_9O_2$ 503.53, m/z found 504.4 $[M+H]^+$.

General Procedure A-2: $^1$HNMR (400 MHz, CD$_3$OD) δ 8.78-8.76 (m, 2H), 7.52 (s, 1H), 7.36-7.33 (m, 1H), 6.44-6.38 (m, 2H), 6.23-6.20 (m, 1H), 4.36-4.33 (m, 1H), 4.26-4.20 (m, 2H), 4.13-4.10 (m, 2H), 3.68-3.66 (m, 2H), 3.35 (s, 3H), 1.84-1.82 (m, 3H), 1.40 (t, J=7.2 Hz, 3H).

Compound 50 and Compound 51

The residue was purified by silica gel chromatography (gradient, CH$_2$Cl$_2$: MeOH=20:1 to 10:1) to give crude product (120 mg, 50% yield) as yellow solids. The crude compound was further purified by prep. SFC (Separation condition: Instrument: SFC80 (Waters); Column: AD 2.5*25 cm, 10 um; Mobile phase A: Supercritical CO₂, Mobile phase B:MeOH/ACN/DEA=60/40/0.2, A:B=50/50 at 80 mL/min, Column temperature: 25° C., Back pressure: 100 bar) to afford compound 50 (12.27 mg, 12.2% yield, purity 95.2%, ee: >99%) and compound 51 (43.28 mg, 36.1% yield, purity 97.3%, ee: >99%).

Compound 50

(R*)-6-(4-methoxy-6-morpholino-1H-benzo[d]imidazol-2-yl)-2-methyl-7-((1-(pyrimidin-2-yl)ethyl)amino)-2,4-dihydro-5H-pyrazolo[4,3-b]pyridin-5-one

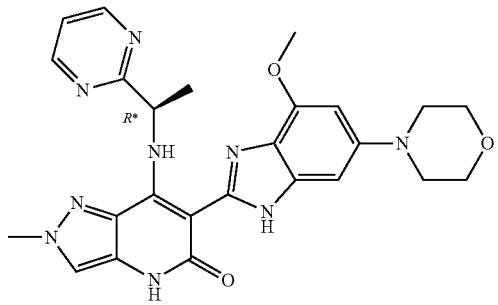 [SMILES: COc1cc(N2CCOCC2)cc2[nH]c(-c3c(N[C@H](C)c4ncccn4)c4nn(C)cc4[nH]c3=O)nc12]

LC-MS (ESI) (General Procedure B-2, method 2): R$_T$=1.35 min, mass calcd. for C$_{25}$H$_{27}$N$_9$O$_3$ 501.55, m/z found 502.3 [M+H]⁺.

General Procedure A-2: ¹H NMR (400 MHz, DMSO-d$_6$) δ 12.99 (s, 1H), 12.83 (s, 1H), 12.50-12.48 (m, 1H), 11.00-10.84 (m, 1H), 8.87-8.80 (m, 2H), 7.68-7.64 (m, 1H), 7.41 (s, 1H), 6.80-6.43 (m, 3H), 4.13-4.12 (m, 2H), 4.07-4.03 (m, 4H), 3.95-3.88 (m, 4H), 3.32-3.05 (m, 4H), 1.72-1.69 (m, 3H).

Compound 51

(S*)-6-(4-methoxy-6-morpholino-1H-benzo[d]imidazol-2-yl)-2-methyl-7-((1-(pyrimidin-2-yl)ethyl)amino)-2,4-dihydro-5H-pyrazolo[4,3-b]pyridin-5-one

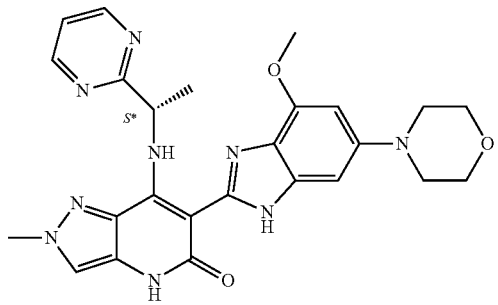 [SMILES: COc1cc(N2CCOCC2)cc2[nH]c(-c3c(N[C@@H](C)c4ncccn4)c4nn(C)cc4[nH]c3=O)nc12]

LC-MS (ESI) (General Procedure B-2, method 2): R$_T$=1.35 min, mass calcd. for C$_{25}$H$_{27}$N$_9$O$_3$ 501.55, m/z found 502.3 [M+H]⁺.

General Procedure A-2: ¹HNMR (400 MHz, DMSO-d$_6$) δ 13.00 (s, 1H), 12.84 (s, 1H), 12.51-12.48 (m, 1H), 11.00-10.86 (m, 1H), 8.85-8.80 (m, 2H), 7.68-7.65 (m, 1H), 7.42-7.40 (m, 1H), 6.80-6.71 (m, 1H), 6.56-6.43 (m, 2H), 4.06 (s, 2H), 3.96 (s, 4H), 3.78-3.75 (m, 4H), 3.14-3.09 (m, 4H), 1.74-1.69 (m, 3H).

Compound 52

(S)-6-(5-methoxy-6-morpholino-1H-benzo[d]imidazol-2-yl)-2-methyl-7-((1-(pyrimidin-2-yl)ethyl)amino)-2H-pyrazolo[4,3-b]pyridin-5(4H)-one

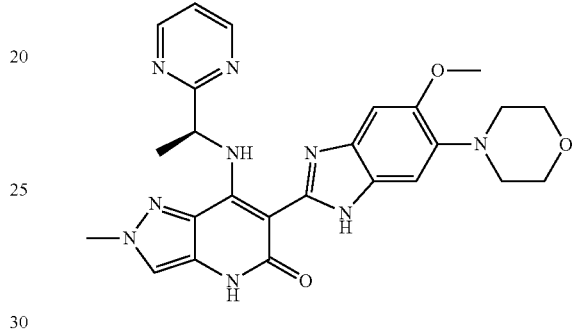

The reaction mixture was purified by silica gel chromatography (CH₂Cl₂: MeOH=25:1) to give crude product (200 mg, yield 70.0%) as a yellow solid. The crude product was further purified by prep. SFC (Separation condition: Instrument: SFC80 (Waters); Column: OD 2.5*25 cm, 10 um; Mobile phase A: Supercritical CO₂, Mobile phase B:IPA/ACN/DEA=60/40/0.2, A:B=60/40 at 80 mL/min, Column temperature: 25° C., Back pressure: 100 bar) to give compound 52 (88.09 mg, 44.0% yield, purity 94.2%, ee: >99%) as yellow solid.

LC-MS (ESI) (General Procedure B-2, method 2): R$_T$=1.29 min, mass calcd. for C$_{25}$H$_{27}$N$_9$O$_3$ 501.54, m/z found 502.3 [M+H]⁺.

General Procedure A-2: ¹H NMR (400 MHz, DMSO-d$_6$) δ 12.88-12.84 (m, 1H), 12.61-21.58 (m, 1H), 12.85-12.81 (m, 1H), 8.85-8.84 (m, 1H), 7.64 (s, 1H), 7.42-7.10 (m, 3H), 6.47-6.45 (m, 1H), 3.95 (s, 3H), 3.86 (s, 3H), 3.76-3.74 (m, 4H), 3.00-2.97 (m, 4H), 1.74-1.72 (m, 3H).

Compound 53 and Compound 54

The residue was purified by silica gel chromatography (CH₂Cl₂: MeOH=150:1 to 50:1) to give crude product (509 mg, 54.8% yield) as yellow solids. The crude product was further purified by prep. SFC (Separation condition: Instrument: SFC80 (Waters); Column: OD 2.5*25 cm, 10 um; Mobile phase A: Supercritical CO₂, Mobile phase B:MeOH/ACN/DEA=60/40/0.2, A:B=50/50 at 80 mL/min, Column temperature: 25° C., Back pressure: 100 bar) to afford compound 53 (153.89 mg, 30.2% yield, purity 99.4%, ee: >99%) and compound 54 (162.32 mg, 31.9% yield, purity 99.6%, ee: >99%).

Compound 53

(S*)-2-methyl-6-(5-methyl-6-morpholino-1H-benzo[d]imidazol-2-yl)-7-((1-(pyrimidin-2-yl)propyl)amino)-2H-pyrazolo[4,3-b]pyridin-5(4H)-one

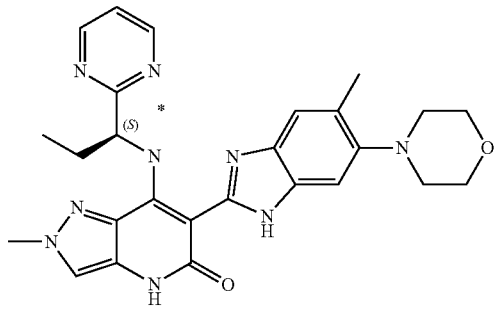

LC-MS (ESI) (General Procedure A-2, method 2): $R_T$=1.44 min, mass calcd. for $C_{26}H_{29}N_9O_2$ 499.57, m/z found 500.4 $[M+H]^+$.

General Procedure A-2: $^1$H NMR (400 MHz, DMSO-$d_6$) δ 12.87 (d, J=5.2 Hz, 1H), 12.65-12.63 (m, 1H), 10.84 (d, J=3.6 Hz, 1H), 8.84-8.82 (m, 2H), 7.63 (s, 1H), 7.46-7.22 (m, 3H), 6.40-6.38 (m, 1H), 3.93 (s, 3H), 3.77-3.76 (m, 4H), 2.88-2.85 (m, 4H), 2.38 (s, 3H), 2.19-2.14 (m, 2H), 1.02-0.97 (m, 3H).

Compound 54

(R*)-2-methyl-6-(5-methyl-6-morpholino-1H-benzo[d]imidazol-2-yl)-7-((1-(pyrimidin-2-yl)propyl)amino)-2H-pyrazolo[4,3-b]pyridin-5(4H)-one

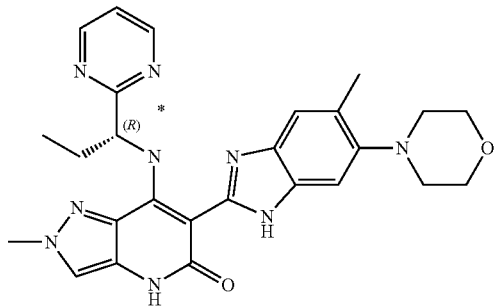

LC-MS (ESI) (General Procedure A-2, method 2): $R_T$=1.43 min, mass calcd. for $C_{26}H_{29}N_9O_2$ 499.57, m/z found 500.4 $[M+H]^+$.

General Procedure A-2: $^1$H NMR (400 MHz, DMSO-r/e) δ 12.87 (d, J=5.2 Hz, 1H), 12.64 (dd, J=8.4, 4.0 Hz, 1H), 10.84 (d, J=4.4 Hz, 1H), 8.83 (dd, J=8.8, 3.2 Hz, 2H), 7.64 (s, 1H), 7.47-7.22 (m, 3H), 6.40-6.39 (m, 1H), 3.93 (s, 3H), 3.79-3.75 (s, 4H), 2.89-2.84 (m, 4H), 2.38 (s, 3H), 2.17-2.14 (m, 2H), 1.00 (t, J=6.8 Hz, 3H).

Compound 55

(S)-2-methyl-6-(5-methyl-6-morpholino-1H-benzo[d]imidazol-2-yl)-7-((1-(oxazol-4-yl)-ethyl)amino)-2H-pyrazolo[4,3-b]pyridin-5(4H)-one

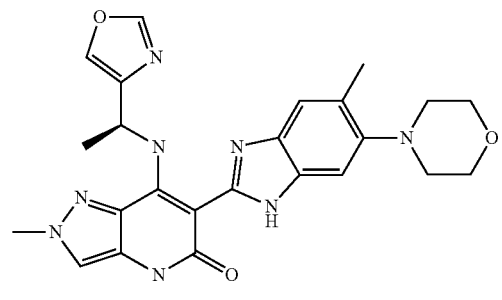 [SMILES: Cc1cc2nc(-c3c(N[C@@H](C)c4cocn4)c4nn(C)cc4[nH]c3=O)[nH]c2cc1N1CCOCC1]

The residue was purified by silica gel chromatography (gradient, $CH_2Cl_2$: MeOH=150:1 to 50:1) to give compound 55 (369.51 mg, 48.5% yield, purity 99.4%, ee: >99%) as yellow solids.

LC-MS (ESI) (General Procedure A-2, method 2): $R_T$=1.46 min, mass calcd. for $C_{24}H_{26}N_8O_3$ 474.52, m/z found 475.4 $[M+H]^+$.

General Procedure A-2: $^1$H NMR (400 MHz, DMSO-de) δ 12.88 (d, J=4.8 Hz, 1H), 12.37-12.35 (m, 1H), 10.90 (d, J=3.6 Hz, 1H), 8.36 (s, 1H), 8.02 (s, 1H), 7.70 (s, 1H), 7.45-7.21 (m, 2H), 6.47-6.35 (m, 1H), 4.05 (s, 3H), 3.77-3.75 (m, 4H), 2.88-2.83 (m, 4H), 2.37 (s, 3H), 1.68 (t, J=6.8 Hz, 3H).

Compound 56

(S)-2-methyl-6-(6-morpholino-1H-imidazo[4,5-c]pyridin-2-yl)-7-((1-(oxazol-4-yl)ethyl)-amino)-2,4-dihydro-5H-pyrazolo[4,3-b]pyridin-5-one

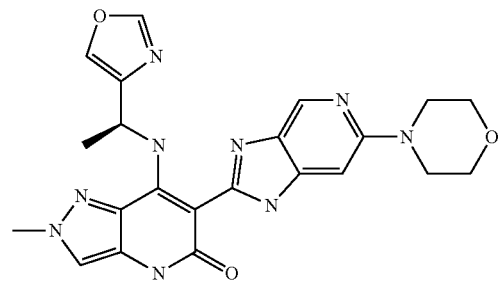 [SMILES: C[C@H](Nc1c(-c2nc3cnc(N4CCOCC4)cc3[nH]2)c(=O)[nH]c2cn(C)nc12)c1cocn1]

The residue was purified by silica gel column chromatography ($CH_2Cl_2$:MeOH=100:1) to give compound 56 (37.15 mg, yield 6.89%, purity 95.4%, ee: >99%) as yellow solids.

LC-MS (ESI) (General Procedure A-2, method 2): $R_T$=1.14 min, mass calcd. for $C_{22}H_{23}N_9O_3$ 461.5, m/z found 462.4 $[M+H]^+$.

General Procedure A-2: $^1$H NMR (400 MHz, DMSO-de) δ 13.13-13.10 (m, 1H), 12.31-12-11 (m, 1H), 11.01-10.97 (m, 1H), 8.53-8.36 (m, 2H), 8.05 (s, 1H), 7.73 (s, 1H), 7.03-6.91 (m, 1H), 6.46-6.40 (m, 1H), 4.06 (s, 3H), 3.77-3.75 (m, 4H), 3.39-3.37 (m, 4H), 1.68 (d, J=4.0 Hz, 3H).

Analytical Part
LCMS
General Procedure A

The LC measurement was performed using an Agilent 1200 HPLC system comprising a degasser, a binary pump, an auto-sampler, a column heater, a diode-array detector (DAD) and a column as specified in the respective methods below. Flow from the DAD was split to a MS spectrometer (Agilent 6110 or 6140) and an ELSD. The MS detector was configured with an electrospray ionization source. Nitrogen was used as the nebulizer gas. The drying gas temperature was maintained at 350° C. Capillary voltage was 2.5 V for positive ionization mode and 3.0 V for negative ionization mode. Mass spectra were acquired by scanning from 100 to 1000 in step size 0.1. The cycle time is 0.89 sec/cycle. Data acquisition was performed with a Chemstation B.04.03

Method 1

In addition to the general procedure A: Reversed phase HPLC was carried out on a Waters XBridge Shield RP18 column (50*2.1 mm 5 μm) with a flow rate of 0.8 mL/min. Two mobile phases (mobile phase A: water with 0.05% $NH_3·H_2O$; mobile phase B: acetonitrile) were used. First, 100% A was hold for 1 minute. Then a gradient was applied to 40% A and 60% B in 4 minutes and then to 5% A and 95% B in 2.5 minutes. Finally return to 100% A in 2 minutes and hold for 0.5 minute. Post Time is 0.5 minute. Oven temperature was 40° C. The injection volume is 2 uL. (MS polarity: positive)

Method 2

In addition to the general procedure A: Reversed phase HPLC was carried out on a Phenomenex Luna-C18 column (5 μm, 2.0×50 mm) with a flow rate of 0.8 mL/min. Two mobile phases (mobile phase A: water with 0.1% TFA; mobile phase B: acetonitrile with 0.05% TFA) were used. 100% A was hold for 1 minute, A gradient from 100% A to 40% A is applied in 4 minutes, and 40% A down to 15% A in 2.5 minutes. And then return to 100% A in 2 minutes and hold for 0.5 minutes. The post time is 0.5 min. Oven temperature was 50° C. The injection volume is 2 uL. (MS polarity: positive)

General Procedure B

The LCMS measurement was performed using an Agilent1200 series system comprising a quaternary pump with degasser, an autosampler, a column oven (set at 50° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 using a cycle time of 0.52 second. The capillary needle voltage was 2.5 kV and the source temperature was maintained at 350° C. Nitrogen was used as the nebulizer gas. Data acquisition was performed with a LC/MSD ChemStation data system.

Method 4

In addition to the general procedure B: Reversed phase HPLC was carried out on an Xtimate C18 column (2.1*30 mm, 3 um) with a flow rate of 1.2 mL/min. Two mobile phases (mobile phase A:water (4 L)+TFA (1.5 mL); mobile phase B:acetonitrile (4 L)+TFA (0.75 mL)) were employed to run a gradient condition from 100% A to 40% A, 60% B in 0.9 minutes, and hold at these conditions for 0.6 minutes, to 40% A and 60% B in 0.01 minutes and reequilibrate with 40% A for 0.49 minutes. An injection volume of 0.1-20 μL was used. Cone voltage was 70 V for positive ionization mode.

Method 5

In addition to the general procedure B: Reversed phase HPLC was carried out on an MERCK C18 column (RP-18e 25-2 mm) with a flow rate of 1.2 mL/min. Two mobile phases (mobile phase A:water (4 L)+TFA (1.5 mL); mobile phase B:acetonitrile (4 L)+TFA (0.75 mL)) were employed to run a gradient condition from 95% A to 5% A, 95% B in 0.7 minutes, and hold at these conditions for 0.4 minutes, to 95% A and 5% B in 0.01 minutes and reequilibrate with 95% A for 0.49 minutes. An injection volume of 0.1-20 μL was used. Cone voltage was 70 V for positive ionization mode.

Method 6

In addition to the general procedure B: Reversed phase HPLC was carried out on an Xbridge Shield RP-18 column (5 um, 2.1*50 mm) with a flow rate of 1.0 mL/min. Two mobile phases (mobile phase A: water (1 L)+$NH_3H_2O$ (0.5 mL); mobile phase B: acetonitrile) were employed to run a gradient condition from 90% A to 20% A, 80% B in 2 minutes, and hold at these conditions for 0.48 minutes, to 90% A and 10% B in 0.01 minutes and reequilibrate with 90% A for 0.11 minutes. An injection volume of 0.1-20 μL was used. Cone voltage was 70 V for positive ionization mode.

General Procedure C

The LCMS measurement was performed using an Shimadzu LCMS-2010 EV series system comprising a quaternary pump with degasser, an autosampler, a column oven (set at 50° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 using a cycle time of 0.25 second. The detector voltage was 1.6 kV and the source temperature was maintained at 250° C. Nitrogen was used as the nebulizer gas. Data acquisition was performed with a LCMS solution data system.

Method 7

In addition to the general procedure C: Reversed phase HPLC was carried out on an Xtimate C18 column (2.1*30 mm, 3 um) with a flow rate of 1.2 mL/min. Two mobile phases (mobile phase A:water (4 L)+TFA (1.5 mL); mobile phase B:acetonitrile (4 L)+TFA (0.75 mL)) were employed to run a gradient condition from 100% A to 40% A, 60% B in 6 minutes, and hold at these conditions for 0.5 minutes, to 40% A and 60% B in 0.01 minutes and reequilibrate with 40% A for 0.49 minutes. An injection volume of 0.1-20 μL was used. Cone voltage was 70 V for positive ionization mode.

Method 8

In addition to the general procedure C: Reversed phase HPLC was carried out on an Xtimate C18 column (2.1*30 mm, 3 um) with a flow rate of 0.8 mL/min. Two mobile phases (mobile phase A:water (4 L)+TFA (1.5 mL); mobile phase B:acetonitrile (4 L)+TFA (0.75 mL)) were employed to run a gradient condition from 90% A to 20% A, 80% B in 6 minutes, and hold at these conditions for 0.5 minutes, to 90% A and 10% B in 0.01 minutes and reequilibrate with 90% A for 0.49 minutes. An injection volume of 0.1-20 μL was used. Cone voltage was 70 V for positive ionization mode.

Method 9

In addition to the general procedure C: Reversed phase HPLC was carried out on an MERCK C18 column (RP-18e 25-2 mm) with a flow rate of 1.2 ml/min. Two mobile phases (mobile phase A:water (4 L)+TFA (1.5 mL); mobile phase B:acetonitrile (4 L)+TFA (0.75 mL)) were employed to run a gradient condition from 95% A to 5% A, 95% B in 0.7 minutes, and hold at these conditions for 0.4 minutes, to 95% A and 5% B in 0.01 minutes and reequilibrate with 95% A for 0.49 minutes. An injection volume of 0.1-20 µl was used. Cone voltage was 70V for positive ionization mode.

General Procedure A-2

The LCMS measurement was performed using a Waters UPLC-QDa system comprising a quaternary pump, an autosampler, a column oven (set at 50° C., unless otherwise indicated), a photo-diode array (PDA) detector and a column as specified in the respective methods below. Flow from the column was split to a MS spectrometer. The MS detector was QDa detector and configured with an electrospray ionization source. Mass spectra were acquired by scanning from 100 to 1000. The capillary needle voltage was 0.8 kV and the source temperature was maintained at 120° C. Nitrogen was used as the nebulizer gas. Data acquisition was performed with a Waters-Micromass MassLynx-Openlynx data system.

Method 2 (90:10)

In addition to the general procedure A-2: Reversed phase HPLC was carried out on an ACQUITY UPLC BEH C18 column (1.7 µm 2.1×50 mm) with a flow rate of 0.6 ml/min. Two mobile phases (mobile phase C: 0.1% formic acid in water; mobile phase D: 0.1% formic acid in acetonitrile) were employed to hold 90% C and 10% D for 1.2 minutes, then hold 5% C and 95% D for 0.8 minutes. An injection volume between 0.3-5 µl was depended on the concentration of sample. Cone voltage was 15 V for positive ionization mode.

General Procedure B-2

The LCMS measurement was performed using a Shimadzu LC-MS2020 system comprising a pump (LC-20AD) with degasser (DGU-20A$_3$), an autosampler (SIL-20AHT), a column oven (CTO-20A) (set at 40° C., unless otherwise indicated), a photo-diode array (PDA) (SPD-M20A) detector, an evaporative light-scattering (ELSD)(Alltech 3300ELSD) detector and a column as specified in the respective methods below. Flow from the column was split to a MS spectrometer. The MS detector was configured with an electrospray ionization source. Mass spectra were acquired by scanning from 80 to 1000. Nitrogen was used as the nebulizer gas. Data acquisition was performed with a Labsolution data system.

Method 2

In addition to the general procedure B-2: Reversed phase UPLC was carried out on a Shimadzu SunFire C18 (5 µm 50*4.6 mm) with a flow rate of 2.0 ml/min. Two mobile phases (mobile phase A: 0.1% formic acid in water; mobile phase B: 0.1% formic acid in acetonitrile) were employed to hold 90% A and 10% B for 1.6 minutes, then hold 5% A and 95% B for 1.0 minute. An injection volume between 0.3-5 µl was depended on the concentration of sample. Cone voltage was 20 V for positive and negative ionization mode. Mass spectra were acquired by scanning from 100 to 1000 in 0.2 seconds using an interscan delay of 0.1 seconds.

Method 4

In addition to the general procedure B-2: Reversed phase UPLC was carried out on a Shimadzu SunFire C18 (5 µm 50*4.6 mm) with a flow rate of 2.0 ml/min. Two mobile phases (mobile phase A: 0.1% formic acid in water; mobile phase B: 0.1% formic acid in acetonitrile) were employed to hold 70% A and 30% B for 1.6 minutes, then hold 5% A and 95% B for 1.0 minute. An injection volume between 0.3-5 µl was depended on the concentration of sample. Cone voltage was 20 V for positive and negative ionization mode. Mass spectra were acquired by scanning from 100 to 1000 in 0.2 seconds using an interscan delay of 0.1 seconds.

General Procedure C-2

The LCMS measurement was performed using an AB system comprising a quaternary pump (G1311A), an autosampler (CTC Analytic HTS), a column oven (G1316A TCC, set at 40° C., unless otherwise indicated), a DAD (G1315B) detector and a column as specified in the respective methods below. Flow from the column was split to a MS spectrometer. The MS (API3000) configured with an electrospray ionization source. Mass spectra were acquired by scanning from 80 to 1000. Nitrogen was used as the nebulizer gas.

Method 2 (90:10)

In addition to the general procedure C-2: Reversed phase HPLC was carried out on a SunFire C18 (5 µm 50*4.6 mm) with a flow rate of 1.0 ml/min. Two mobile phases (mobile phase C: 0.1% $NH_3H_2O$ in water; mobile phase D: 0.1% $NH_3H_2O$ in acetonitrile) were employed to hold 95% C and 5% D for 3 minutes, then hold 5% C and 95% D for 1 minutes. An injection volume was depended on the concentration of sample.

NMR

General Procedure A

The below NMR experiments were carried out using a Bruker Avance III 400 and a Varian 400 spectrometers at ambient temperature, using internal deuterium lock and equipped with BBO 400 MHz probe head for the Bruker Avance III 400 and with Varian 400 ASW PFG 4nuc($^1$H, $^{13}$C,$^{19}$F,$^{31}$P) probe head for the Varian 400. Chemical shifts (δ) are reported in parts per million (ppm).

General Procedure A-2

The below NMR experiments were carried out using a Bruker Avance III400 spectrometers at ambient temperature, using internal deuterium lock and equipped with 5 mm PABBO ($^3$H, $^{13}$C,$^{15}$N,$^{31}$P,$^{19}$F) probe head. Chemical shifts (δ) are reported in parts per million (ppm)

SFC

General Procedure D

The SFC-MS test was performed using a Berger SFC system comprising a binary pump, an auto-sampler, a column heater, a diode-array detector (DAD), a 6-position column switching valve, a solvent switching valve and a back pressure regulator (BPR). Typically the column temperature and the BPR was set at 40 C and 100 bar respectively. Flow from the DAD was split to a MS spectrometer (Agilent 6110). The MS detector was configured with an atmospheric-pressure chemical ionization source. Nitrogen was used as the nebulizer gas. The drying gas temperature was maintained at 250° C. Capillary voltage was 3000 V for positive ionization mode and 3000 V for negative ionization mode. Mass spectra were acquired by scanning from 100 to 1000 in step size 0.1. The cycle time is 1.06 sec/cycle. Data acquisition was performed with a Chemstation B.04.03

Method 10

SFC was carried out on a Chiralpak AD-3 50*4.6 mm I.D., 3 um column with a flow rate of 4 mL/min. Two mobile phases (Mobile phase: A: $CO_2$ B: iso-propanol (0.05% DEA)). The gradient was hold 40%. Column temp was 40° C. (MS polarity: positive)

Method 12

SFC was carried out on a Chiralcel OD-3 50*4.6 mm I.D., 5 um column with a flow rate of 4 mL/min. Two mobile phases (Mobile phase: A: $CO_2$ B: ethanol (0.05% DEA)). The gradient was from 5% to 40% of B in 5 min and hold 40% for 2.5 min, then 5% of B for 2.5 min. Column temp was 40° C. (MS polarity: positive)

Method 13

SFC was carried out on a Chiralpak AD-3 50*4.6 mm I.D., 3 um column with a flow rate of 4 mL/min. Two mobile phases (Mobile phase: A: $CO_2$ B: ethanol (0.05% DEA)). The gradient was hold 40%. Column temp was 40° C. (MS polarity: positive)

Method 14

SFC was carried out on a Chiralpak AD-3 50*4.6 mm I.D., 3 um column with a flow rate of 4 mL/min. Two mobile phases (Mobile phase: A: $CO_2$ B: Methanol (0.05% DEA)). The gradient was hold 40%. Column temp was 40° C. (MS polarity: positive)

General Procedure E

The SFC test was performed using an Agilent 1260 SFC system comprising a degasser, a binary pump, an auto-sampler, a column heater, a diode-array detector (DAD), a 6-position column switching valve, a solvent switching valve and a back pressure regulator (BPR). Typically the column temperature and the BPR was set at 40° C. and 100 bar respectively.

Method 16

SFC was carried out on a Chiralpak AD-3 100×4.6 mm I.D., 3 um column with a flow rate of 2.8 mL/min. Two mobile phases (Mobile phase: A: $CO_2$ B: ethanol (0.05% DEA)). The gradient was from 5% to 40% of B in 4.5 min and hold 40% for 2.5 min, then 5% of B for 1 min. Column temp was 40° C. (MS polarity: positive)

Method 17

SFC was carried out on a Chiralpak AD-3 100×4.6 mm I.D., 3 um with a flow rate of 2.8 mL/min. Two mobile phases (Mobile phase: A: $CO_2$ B: ethanol (0.05% DEA)). The gradient was hold 40% of ethanol (0.05% DEA) in $CO_2$. Column temp was 40° C. (MS polarity: positive)

Method 18

SFC was carried out on a Chiralpak AD-3 100×4.6 mm I.D., 3 um column with a flow rate of 2.8 mL/min. Two mobile phases (Mobile phase: A: $CO_2$ B: iso-propanol (0.05% DEA)). The gradient was from 5% to 40% of B in 4.5 min and hold 40% for 2.5 min, then 5% of B for 1 min. Column temp was 40° C. (MS polarity: positive)

Method 19

SFC was carried out on a Chiralpak AS-3 100×4.6 mm I.D., 3 μm column with a flow rate of 2.5 mL/min. Two mobile phases (Mobile phase: A: $CO_2$ B: ethanol (0.05% DEA). The gradient was from 5% to 40% of B in 4.5 min and hold 40% for 2.5 min, then 5% of B for 1 min. Column temp was 40° C. (MS polarity: positive)

General Procedure F

The SFC test was performed using a Waters UPC^2 system comprising a degasser, a binary pump, an auto-sampler, a column heater, a diode-array detector (PDA), a 6-position column switching valve, a solvent switching valve and a back pressure regulator (BPR). Typically the column temperature and the BPR were set at 35 C and 1500 psi respectively.

Method 20

SFC was carried out on a Chiralpak AS-3 150×4.6 mm I.D., 3 um column with a flow rate of 2.5 mL/min. Two mobile phases (Mobile phase: A: $CO_2$ B: iso-propanol (0.05% DEA)). The gradient was hold 40%. Column temp was 40° C. (MS polarity: positive)

General Procedure G

The SFC test was performed using a Thar SFC system comprising a binary pump, an auto-sampler, a column heater, a diode-array detector (PDA), a 10-position column switching valve, a solvent switching valve and a back pressure regulator (BPR). Typically the column temperature and the BPR was set at 35° C. and 100 bar respectively.

Method 21

SFC was carried out on a Pheno Lux Cellulose-2, 150×4.6 mm I.D., 5 μm column with a flow rate of 2.0 mL/min. Two mobile phases (Mobile phase: A: $CO_2$ B: ethanol (0.05% DEA)). The gradient was hold 50% of ethanol (0.05% DEA) in $CO_2$. Column temp was 40° C. (MS polarity: positive)

HPLC

General Procedure E for HPLC

The HPLC measurement was performed using a LC-20A SHIMADZU system comprising a LC-20AD Quant Pump with DGU-20A degasser, a SIL-20AC autosampler, a CTO-20AC column oven (set at 25° C., unless otherwise indicated), a diode-array detector (SPD-M20A) and a column as specified in the respective methods below.

Method 3

In addition to the general procedure E: Reversed phase HPLC was carried out on a Waters Sunfire C18-5 μm-4.6-150 mm Column (1.7 μm 2.1×50 mm) with a flow rate of 1.0 ml/min. Two mobile phases (mobile phase C: 0.03% TFA in water; mobile phase D: 0.03% TFA in acetonitrile) were employed to hold 95% C and 5% D for 13 minutes, then hold 5% C and 95% D for 3 minutes. An injection volume was depended on the concentration of sample.

Pharmacological Part

Biological Assays

FGFR3 Wild Type Mobility Shift Assay (Enzymatic Assay)

In a final reaction volume of 25 μL, 0.04 ng/μL human FGFR3 wild type enzyme (cytoplasmic domain, from Carna Biosciences) was incubated with 75 μM ATP, 1 μM FL-peptide 30 substrate and 250 nL of testing compound (1% DMSO final) in assay buffer (100 mM HEPES pH 7.4, 10 mM $MgCl_2$, 0.003% Brij35, 1 mM DTT). After incubation for 50 minutes at 30° C. the reaction was stopped with 10 μL of 0.5M EDTA pH 8.0, and then 25 μL of reaction mixture was transferred to reading plate and measured on Caliper EZ reader II. The substrate-product conversion rate was used as raw data for normalization and concentration-response curve (10 dose points with 4× serial dilution, starting with 10 μM) was plotted using Prism to calculate $IC_{50}$ (M), $pIC_{50}$ (–log $IC_{50}$) and HillSlope value.

FGFR3 V555M Mobility Shift Assay (Enzymatic Assay)

In a final reaction volume of 25 μL, 0.04 ng/μL human FGFR3 V555M enzyme (cytoplasmic domain carrying V555M mutation, from Carna Biosciences) was incubated with 30 μM ATP, 1 μM FL-peptide 30 substrate and 250 nL of testing compound (1% DMSO final) in assay buffer (100 mM HEPES pH 7.4, 10 mM $MgCl_2$, 0.003% Brij35, 1 mM DTT). After incubation for 45 minutes at 30° C. the reaction was stopped with 10 μL of 0.5M EDTA pH 8.0, and then 25 μL of reaction mixture was transferred to reading plate and measured on Caliper EZ reader II. The substrate-product conversion rate was used as raw data for normalization and concentration-response curve (10 dose points with 4× serial dilution, starting with 10 μM) was plotted using Prism to calculate $IC_{50}$ (M), $pIC_{50}$ (–log $IC_{50}$) and HillSlope value.

FGFR3 V555L Mobility Shift Assay (Enzymatic Assay)

In a final reaction volume of 25 μL, 0.04 ng/μL human FGFR3 V555L enzyme (cytoplasmic domain carrying V555L mutation, from Carna Biosciences) was incubated with 40 μM ATP, 1 μM FL-peptide 30 substrate and 250 nL of testing compound (1% DMSO final) in assay buffer (100 mM HEPES pH 7.4, 10 mM $MgCl_2$, 0.003% Brij35, 1 mM DTT). After incubation for 50 minutes at 30° C. the reaction was stopped with 10 μL of 0.5M EDTA pH 8.0, and then 25

μL of reaction mixture was transferred to reading plate and measured on Caliper EZ reader II. The substrate-product conversion rate was used as raw data for normalization and concentration-response curve (10 dose points with 4× serial dilution, starting with 10 μM) was plotted using Prism to calculate $IC_{50}$ (M), $pIC_{50}$ ($-\log IC_{50}$) and HillSlope value.

NIH/3T3 FGFR3 WT-TACC3 Cell Proliferation Assay

In day 1, 90 μL of cell suspension (NIH/3T3 cells overexpressing FGFR3 WT-TACC3 fusion protein) (total 30,000 cells per well in growth medium (DMEM containing 1% Glutamax, 10% FBS and 1% Pen/Strep)) was seeded in a 96-well plate and then incubated overnight at 37° C. and 5% $CO_2$. In day 2, 10 μL of growth medium containing 10-fold stock solution of testing compound was added into cell cultures (9 dose points with 4× serial dilution, starting with 10 μM, 0.1% DMSO final). After 72-hr incubation at 37° C. and 5% $CO_2$, in day 5 a volume of 50 μL CellTiter Glo (CTG) reagent was added into cell-containing 96-well plate and the plate was incubated at room temperature for 10 minutes before RLUs (relative light unit) were measured on a microplate reader with luminescence detection module. The RLU value was normalized to survival % and concentration-response curve was plotted using Prism to calculate $IC_{50}$ (M), $pIC_{50}$ ($-\log IC_{50}$) and Hill Slope value.

NIH/3T3 FGFR3 V555M-TACC3 Cell Proliferation Assay

In day 1, 90 μL of cell suspension (NIH/3T3 cells overexpressing FGFR3 V555M-TACC3 fusion protein) (total 30,000 cells per well in growth medium (DMEM containing 1% Glutamax, 10% FBS and 1% Pen/Strep)) was seeded in a 96-well plate and then incubated overnight at 37° C. and 5% $CO_2$. In day 2, 10 μL of growth medium containing 10-fold stock solution of testing compound was added into cell cultures (9 dose points with 4× serial dilution, starting with 10 μM, 0.1% DMSO final). After 72-hr incubation at 37° C. and 5% $CO_2$, in day 5 a volume of 50 μL CellTiter Glo (CTG) reagent was added into cell-containing 96-well plate and the plate was incubated at room temperature for 10 minutes before RLUs (relative light unit) were measured on a microplate reader with luminescence detection module. The RLU value was normalized to survival % and concentration-response curve was plotted using Prism to calculate $IC_{50}$ (M), $pIC_{50}$ ($-\log IC_{50}$) and HillSlope value.

NIH/3T3 Mock Cell Proliferation Assay

In day 1, 90 μL of cell suspension (NIH/3T3 cells transfected with the same control vector as in the above two proliferation assays) (total 30,000 cells per well in growth medium (DMEM containing 1% Glutamax, 10% FBS and 1% Pen/Strep)) was seeded in a 96-well plate and then incubated overnight at 37° C. and 5% $CO_2$. In day 2, 10 μL of growth medium containing 10-fold stock solution of testing compound was added into cell cultures (9 dose points with 3× serial dilution, starting with 30 μM, 0.3% DMSO final). After 72-hr incubation at 37° C. and 5% $CO_2$, in day 5 a volume of 50 μL CellTiter Glo (CTG) reagent was added into cell-containing 96-well plate and the plate was incubated at room temperature for 10 minutes before RLUs (relative light unit) were measured on a microplate reader with luminescence detection module. The RLU value was normalized to survival % and concentration-response curve was plotted using Prism to calculate $IC_{50}$ (M), $pIC_{50}$ ($-\log IC_{50}$) and HillSlope value. This assay served as a counter assay for NIH/3T3 FGFR WT/VM-TACC3 cell proliferation assays to indicate general toxicity of testing compounds caused by off-target effect.

NIH/3T3 FGFR3 WT-TACC3 Cellular Phospho-ERK Assay (In Vitro PD Assay)

50 μL of cell suspension (NIH/3T3 cells overexpressing FGFR3 WT-TACC3 fusion protein) (total 10,000 cells per well in growth medium (DMEM containing 1% Glutamax, 10% FBS and 1% Pen/Strep)) was seeded in a 384-well plate. After overnight incubation at 37° C. and 5% $CO_2$, 5.5 μL of growth medium containing 10× testing compound was added into cell cultures (10 dose points with 4× serial dilution, starting with 10 μM, 0.1% DMSO final). After 1-hr incubation at 37° C. and 5% $CO_2$, the medium was depleted and AlphaLISA SureFire Ultra p-ERK1/2 (Thr202/Tyr204) Assay Kit (from PerkinElmer) was applied for phospho-ERK level detection according to the kit instructions. The RFUs (relative fluorescence units were measured on EnVision microplate reader (ex. 680 nm, em. 615 nm) and concentration-response curve was plotted using Prism to calculate $IC_{50}$ (M), $pIC_{50}$ ($-\log IC_{50}$) and HillSlope value.

NIH/3T3 FGFR3 V555M-TACC3 Cellular Phospho-ERK Assay (In Vitro PD Assay)

50 μL of cell suspension (NIH/3T3 cells overexpressing FGFR3 V555M-TACC3 fusion protein) (total 10,000 cells per well in growth medium (DMEM containing 1% Glutamax, 10% FBS and 1% Pen/Strep)) was seeded in a 384-well plate. After overnight incubation at 37° C. and 5% $CO_2$, 5.5 μL of growth medium containing 10× testing compound was added into cell cultures (10 dose points with 4× serial dilution, starting with 10 μM, 0.1% DMSO final). After 1-hr incubation at 37° C. and 5% $CO_2$, the medium was depleted and AlphaLISA SureFire Ultra p-ERK1/2 (Thr202/Tyr204) Assay Kit (from PerkinElmer) was applied for phospho-ERK level detection according to the kit instructions. The RFUs (relative fluorescence units were measured on EnVision microplate reader (ex. 680 nm, em. 615 nm) and concentration-response curve was plotted using Prism to calculate $IC_{50}$ (M), $pIC_{50}$ ($-\log IC_{50}$) and HillSlope value.

TABLE 2

Pharmacological data ($IC_{50}$; unit nM)

| Compound Number | FGFR3 wild type Caliper | FGFR3 V555M Caliper | FGFR3 V555L Caliper | NIH/3T3 MOCK CTG | NIH/3T3 FGFR3 WT-TACC3 CTG | NIH/3T3 FGFR3 V555M-TACC3 CTG | NIH/3T3 FGFR3 WT-TACC3 pERK | NIH/3T3 FGFR3 V555M-TACC3 pERK |
|---|---|---|---|---|---|---|---|---|
| 7 | 0.3987 | 0.2027 |  | 1080.35 | 10.4715 | 5.77 |  |  |
| 8 | 0.5417 | 0.2354 |  | 444.45 | 6.783 | 6.9105 |  |  |
| 9 | 0.6182 | 0.4832 |  | 690.55 | 17.145 | 7.9825 |  |  |
| 10 | 38.9 | 9.142 |  | 18404 | 129.3 | 167.9 |  |  |
| 11 | 933.4 | 254.3 |  | 27886 | 10000 | 10000 |  |  |
| 12 | 0.8207 | 0.4896 |  | 454.4333 | 9.1045 | 5.244 |  |  |
| 13 | 1.147 | 0.2962 |  | 2101.467 | 22.14 | 11.231 |  |  |
| 14 | 1.903 | 0.8364 |  | 424.3 | 4.0635 | 3.8555 |  |  |
| 15 | 1.062933 | 0.484367 |  | 3695.5 | 16.905 | 6.54425 |  |  |
| 16 | 38.08 | 17.28 |  |  |  |  |  |  |
| 17 | 46.54 | 12.48 |  |  |  |  |  |  |
| 18 | 2.023 | 0.5354 |  | 680.3 | 74.27 | 88.06 |  |  |

TABLE 2-continued

Pharmacological data (IC$_{50}$; unit nM)

| Compound Number | FGFR3 wild type Caliper | FGFR3 V555M Caliper | FGFR3 V555L Caliper | NIH/3T3 MOCK CTG | NIH/3T3 FGFR3 WT-TACC3 CTG | NIH/3T3 FGFR3 V555M-TACC3 CTG | NIH/3T3 FGFR3 WT-TACC3 pERK | NIH/3T3 FGFR3 V555M-TACC3 pERK |
|---|---|---|---|---|---|---|---|---|
| 19 | 8.166 | 4.631 | | 3992.5 | 21.49 | 32.99 | | |
| 20 | 1238 | 667.1 | | | | | | |
| 21 | 3.706 | 1.699 | | 5896 | 17.455 | 27.35 | | |
| 22 | 0.3765 | 0.2272 | | 1076.05 | 18.1035 | 13.92 | | |
| 23 | 0.9789 | 0.3658 | | 265.65 | 34.645 | 27.62 | | |
| 24 | 0.3731 | 0.40805 | 0.4177 | 1831.35 | 11.13575 | 8.38625 | | |
| 25 | 0.4953 | 0.316 | | 1211.5 | 22.31 | 10.225 | | |
| 26 | 0.6367 | 0.4442 | | 768.2 | 5.9625 | 6.09 | | |
| 27 | 0.6099 | 0.1674 | | 1372 | 99.94 | 47.785 | | |
| 28 | 0.9388 | 0.3172 | | 2074.5 | 10.049 | 8.273 | | |
| 29 | 8.561 | 1.659 | | 1534 | 98.34 | 99.35 | | |
| 30 | 469.5 | 106.5 | | | | | | |
| 31 | 120 | 24.97 | | | | | | |
| 32 | 4.292 | 0.9774 | | 4226.5 | 195.05 | 116.025 | | |
| 33 | 17.49 | 10.27 | | 6534.5 | 257.75 | 214.45 | | |
| 34 | 1.219 | 0.7434 | | 733.5 | 23.26 | 27.63 | | |
| 35 | 39.22 | 27.5 | | | | | | |
| 1 | 0.48 | 0.41 | 0.7269 | 1032.58 | 5.9 | 6.96 | 3.45 | 8.04 |
| 36 | 0.8387 | 0.293 | | 753.35 | 49.57 | 48.175 | | |
| 37 | 71.68 | 27.32 | | | | | | |
| 38 | 0.4113 | 0.212 | | 407.95 | 5.896 | 9.538 | | |
| 39 | 0.8807 | 0.2991 | | 457.65 | 16.2755 | 23.82 | | |
| 40 | 530.6 | 225.7 | | | | | | |
| 41 | 23.681 | 12.3604 | 50.82 | 424.6 | 5.57 | 7.1065 | | 210.7 |
| 42 | 18.91465 | 7.8466 | | 305.2 | 8.843 | 7.736 | 2.73 | |
| 2 | 0.9028 | 0.1616 | | 998 | 21.33 | 27.43 | | |
| 3 | 88.3 | 33.52 | | | | | | |
| 43 | 1.037 | 0.6375 | | 415.25 | 12.6235 | 27.505 | | |
| 4A | 3.774 | 1.083 | | 287.9 | 26.125 | 38.08 | | |
| 4B | 656.6 | 231.1 | | | | | | |
| 44 | 395.1 | 80.88 | | | | | | |
| 45 | 1.061 | 0.2885 | | 270.6 | 26.665 | 29.135 | | |
| 46 | 0.8913 | 0.53135 | | 1073.275 | 13.249 | 22.14 | | |
| 47 | 2.032 | 0.5998 | | 1043.25 | 17.39 | 21.12 | | |
| 48 | 0.7383 | 0.5278 | | 352.4 | 9.0415 | 16.955 | | |
| 49 | 2.514 | 1.33 | | 459.7 | 28.15 | 67.45 | | |
| 50 | 95.7 | 44.15 | | | | | | |
| 51 | 0.788 | 0.415 | | 1163 | 44.635 | 54.21 | | |
| 52 | 0.7043 | 0.3803 | | 389.9 | 4.113 | 6.032 | | |
| 53 | 0.9714 | 0.2645 | | 1350.65 | 17.405 | 13.8655 | | |
| 54 | 140.5 | 38.71 | | | | | | |
| 5 | 1.78 | 0.5204 | | 1047.45 | 19.675 | 27.455 | | |
| 6 | 1.162 | 0.4692 | | 1280 | 13.767 | 24.275 | | |
| 55 | 810.8 | 277.3 | | | | | | |
| 56 | 155.6 | 66.39 | | | | | | |

The invention claimed is:

1. A compound of formula (I):

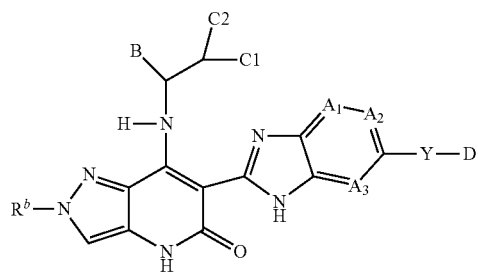

(I)

or a tautomeric or stereochemically isomeric form thereof, wherein:

$A_1$, $A_2$ and $A_3$ each independently are CH, $CR^a$ or N, provided that maximum two of $A_1$, $A_2$ and $A_3$ are $CR^a$;

C1 is hydrogen or $C_{1-4}$alkyl;

C2 is hydrogen, $C_{1-4}$alkyl, hydroxyl or $C_{1-4}$alkoxy;

or C1 and C2 are taken together to form a $C_{3-6}$cycloalkyl together with the carbon atom to which they are attached;

Y is a direct bond, —O—, C(=O), $NR^y$, $S(=O)_2$, or $C_{1-4}$alkyl;

$R^y$ is hydrogen or $C_{1-4}$alkyl;

each $R^a$ independently is $C_{1-6}$alkyl, halo$C_{1-6}$alkyl, halo, $C_{1-6}$alkoxy, carboxyl, $C_{1-6}$alkyl-oxycarbonyl, $C_{2-6}$alkenyl, $C_{2-6}$alkynyl, cyano, cyano$C_{1-6}$alkyl, hydroxy-$C_{1-6}$alkyl, —C(=O)—NH$_2$, —C(=O)—NH($C_{1-4}$alkyl), —C(=O)—N($C_{1-4}$alkyl)$_2$, or a 3 to 6 membered monocyclic saturated heterocyclyl containing at least one heteroatom that is N, O or S;

$R^b$ is hydrogen, $C_{1-6}$alkyl, halo$C_{1-6}$alkyl, $C_{1-6}$alkoxy, $C_{1-6}$alkyloxycarbonyl, $C_{2-6}$alkenyl, $C_{2-6}$alkynyl, cyano$C_{1-6}$alkyl, hydroxy$C_{1-6}$alkyl, —C(=O)—NH$_2$, —C(=O)—NH($C_{1-4}$alkyl), —C(=O)—N($C_{1-4}$alkyl)$_2$, $C_{3-6}$cycloalkyl, phenyl, a 3 to 6 membered monocyclic heterocyclyl containing at least one heteroatom that is N, O or S, or $C_{1-6}$alkyl substituted with $C_{3-6}$cycloalkyl or with phenyl or with a 3 to 6 membered monocyclic heterocyclyl containing at least one heteroatom that is N, O or S;

D is a 3 to 12 membered heterocyclyl containing at least one heteroatom that is N, O or S, wherein said heterocyclyl is optionally substituted with 1 to 5 $R^c$ substituents;

each $R^c$ independently is oxo, halo, $C_{1-6}$alkyl, $C_{1-6}$alkyloxy, hydroxy$C_{1-6}$alkyl, halo$C_{1-6}$alkyl, halo$C_{1-6}$alkyloxy, carboxyl, HOOC—$C_{1-6}$alkyl-, $C_{1-6}$alkyl substituted with —C(=O)—O—$C_{1-6}$alkyl, $C_{1-6}$alkyl-O—C(=O)—, cyano, cyano$C_{1-6}$alkyl, $C_{1-6}$alkyl-C(=O)—, —SO$_2$—$C_{1-6}$alkyl, $C_{3-6}$cycloalkyl, phenyl, a 3 to 6 membered monocyclic saturated heterocyclyl containing at least one heteroatom that is N, O or S, or a 5 or 6 membered monocyclic aromatic heterocyclyl containing at least one heteroatom that is N, O or S;

B is a 3 to 12 membered carbocyclyl or a 3 to 12 membered heterocyclyl containing at least one heteroatom that is N, O or S, wherein said carbocyclyl and heterocyclyl are each optionally substituted with 1 to 5 R substituents;

each R independently is $C_{1-6}$alkyl, cyano, halo, $C_{1-6}$alkoxy, halo$C_{1-6}$alkoxy, hydroxyl, hydroxy$C_{1-6}$alkyl, halo$C_{1-6}$alkyl, oxo, —SO$_2$—NH$_2$, —SO$_2$—NH($C_{1-4}$alkyl), —SO$_2$—N($C_{1-4}$alkyl)$_2$, —NH—C(=O)—$C_{2-6}$alkenyl, —C(=O)—$C_{1-6}$alkyl, —C(=O)—$C_{2-6}$alkenyl, $C_{1-6}$alkyl-O—C(=O)—, $C_{3-6}$cycloalkyl, phenyl, or a 3 to 6 membered monocyclic heterocyclyl containing at least one heteroatom that is N, O or S;

or a pharmaceutically acceptable salt thereof or a solvate thereof.

2. The compound according to claim 1 having the following formula (I-a)

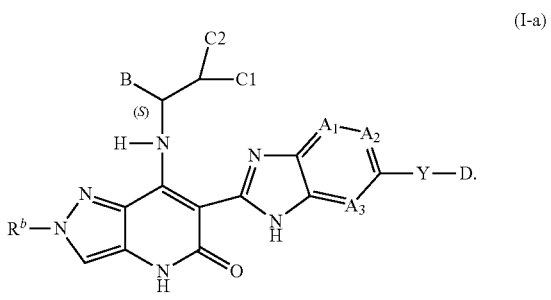

(I-a)

3. The compound according to claim 1, wherein D is piperazin-1-yl, wherein said piperazin-1-yl is optionally substituted with 1 to 5 $R^c$ substituents.

4. The compound according to claim 1, wherein D is morpholin-1-yl, wherein said morpholin-1-yl is optionally substituted with 1 to 5 $R^c$ substituents.

5. The compound according to claim 1, wherein D is a 4, 5, 6, or 7 membered monocyclic heterocyclyl, wherein said heterocyclyl is optionally substituted with 1 to 5 $R^c$ substituents.

6. The compound according to claim 1, wherein $A_1$, $A_2$ and $A_3$ are each CH.

7. The compound according to claim 1, wherein one of $A_1$, $A_2$ and $A_3$ is N and the remaining A substituents are CH or $CR^a$.

8. The compound according to claim 1, wherein $A_1$, $A_2$ and $A_3$ are N or CH.

9. The compound according to claim 1, wherein Y is a direct bond.

10. The compound according to claim 1, wherein Y is —O— or C(=O).

11. The compound according to any claim 1, wherein C1 is hydrogen and C2 is $C_{1-4}$alkyl.

12. The compound according to claim 1, wherein C1 and C2 are hydrogen.

13. The compound according to claim 1, wherein $R^b$ is $C_{1-6}$alkyl.

14. The compound according to claim 1, wherein D is optionally substituted with 1 or 2 $R^c$ substituents and each $R^c$ is independently oxo; $C_{1-6}$alkyl; halo; $C_{1-6}$alkoxy; or halo$C_{1-6}$alkyl.

15. The compound according to claim 1, wherein D is unsubstituted.

16. The compound according to claim 1, wherein B is a 5 or 6 membered heterocyclyl containing at least one heteroatom that is N, O or S, wherein said heterocyclyl is optionally substituted with 1 to 5 R substituents.

17. The compound according to claim 16, wherein B is an aromatic heterocyclyl.

18. The compound according to claim 1, wherein
each of $A_1$, $A_2$ and $A_3$ is CH; or $A_1$ and $A_3$ is CH and $A_2$ is N; or at least one of $A_1$, $A_2$ and $A_3$ is $CR^a$; or $A_1$ is $CR^a$ and $A_2$ and $A_3$ are CH; or $A_2$ is CR' and $A_1$ and $A_3$ are CH;

C1 is hydrogen or $C_{1-4}$alkyl;

C2 is hydrogen, $C_{1-4}$alkyl or $C_{1-4}$alkoxy;

Y is a direct bond, —O— or C(=O);

each $R^a$ independently is $C_{1-6}$alkyl, halo$C_{1-6}$alkyl, halo, or $C_{1-6}$alkoxy;

$R^b$ is $C_{1-6}$alkyl;

D is a 4, 5 or 6 membered monocyclic saturated heterocyclyl containing at least one heteroatom that is N, O or S, wherein said heterocyclyl is optionally substituted with 1 or 2 $R^c$ substituents;

each $R^c$ independently is oxo, $C_{1-6}$alkyl, halo, $C_{1-6}$alkoxy, or halo$C_{1-6}$alkyl;

B is a 5 or 6 membered aromatic monocyclic heterocyclyl containing at least one heteroatom that is N, O or S, wherein said heterocyclyl is optionally substituted with 1 R substituent;

each R independently is $C_{1-6}$alkyl, $C_{1-6}$alkoxy, or $C_{3-6}$cycloalkyl.

19. The compound according to claim 1 wherein the compound is:

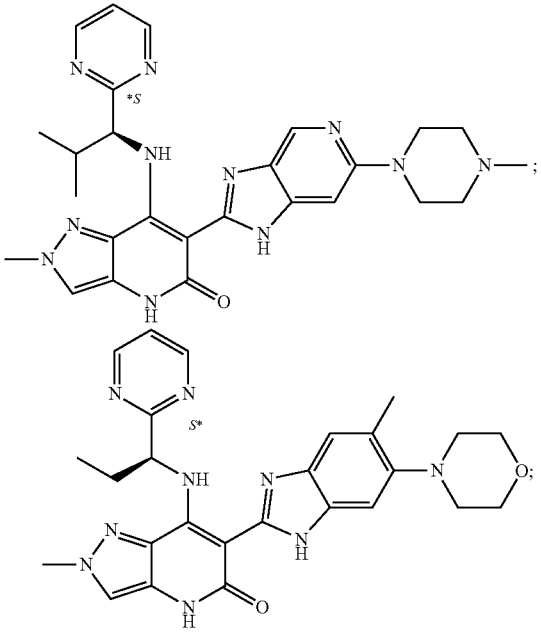

-continued

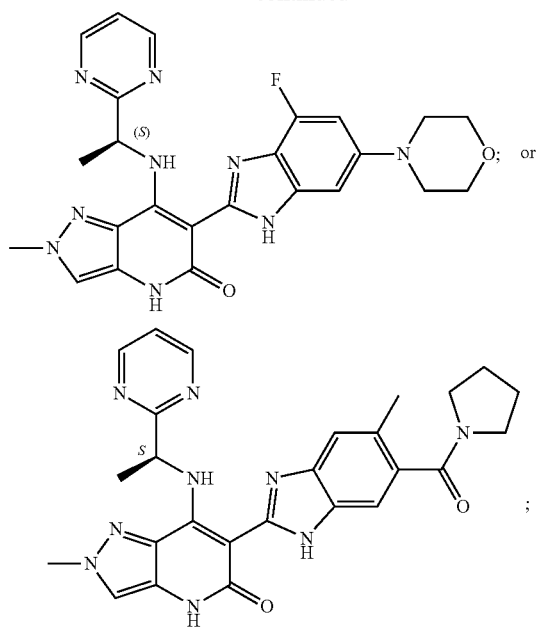

or a pharmaceutically acceptable salt thereof or a solvate thereof.

20. The compound according to claim 19 wherein the compound is

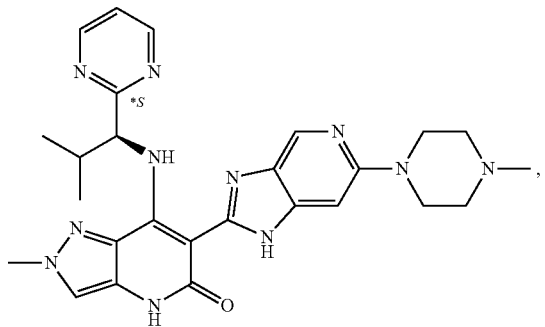

or a pharmaceutically acceptable salt thereof or a solvate thereof.

21. The compound according to claim 19 wherein the compound is

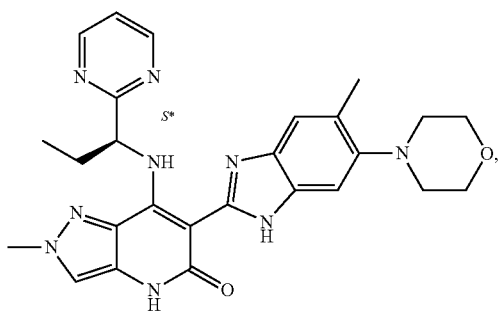 [SMILES: CC[C@H](Nc1c(-c2nc3cc(C)c(N4CCOCC4)cc3[nH]2)c(=O)[nH]c2cn(C)nc12)c1ncccn1]

or a pharmaceutically acceptable salt thereof or a solvate thereof.

22. The compound according to claim 19 wherein the compound is

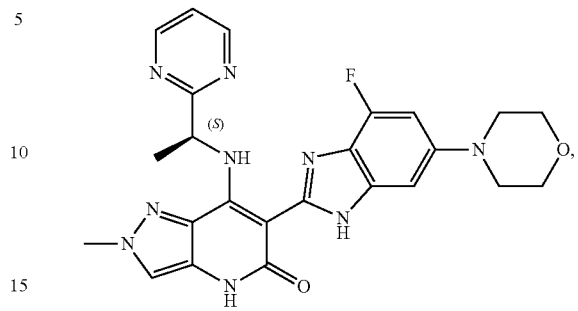

or a pharmaceutically acceptable salt thereof or a solvate thereof.

23. The compound according to claim 19 wherein the compound is

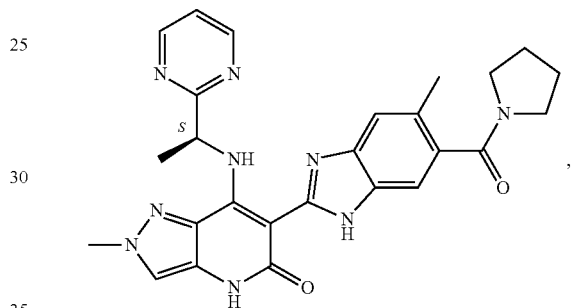

or a pharmaceutically acceptable salt thereof or a solvate thereof.

24. A pharmaceutical composition comprising a compound according to claim 1 and a pharmaceutically acceptable carrier.

25. A method for treating a cancer mediated by a FGFR kinase that is bladder cancer, urothelial cancer, metastatic urothelial cancer, surgically unresectable urothelial cancer, breast cancer, glioblastoma, lung cancer, non small cell lung cancer, squamous cell lung cancer, adenocarcinoma of the lung, pulmonary adenocarcinoma, small cell lung cancer, ovarian cancer, endometrial cancer, cervical cancer, soft tissue sarcoma, head and neck squamous cell carcinoma, gastric cancer, oesophageal cancer, squamous cell carcinoma of the oesophagus, adenocarcinoma of the oesophagus, cholangiocarcinoma, or hepatocellular carcinoma in a subject in need thereof, comprising administering a compound of claim 1 to a subject in need thereof.

26. The method according to claim 25, wherein the cancer is a cancer harboring FGFR3 V555M.

27. A method for inhibiting a FGFR kinase in a subject in need thereof, comprising administering to a subject in need thereof a compound of claim 1.

28. The compound of claim 14, wherein each $R^c$ is independently methyl, fluoro, methoxy, trifluoromethyl or trifluoroethyl.

29. The compound of claim 18, wherein C1 is hydrogen or methyl.

30. The compound of claim 18, wherein C2 is hydrogen, methyl or methoxy.

31. The compound of claim 18, wherein C2 is hydrogen or $C_{1-4}$alkyl.

32. The compound of claim 31, wherein C2 is hydrogen or methyl.

33. The compound of claim 18, wherein Y is a direct bond or C(=O).

34. The compound of claim 33, wherein Y is a direct bond.

35. The compound of claim 18, wherein each $R^a$ independently is methyl, trifluoromethyl, fluoro, or methoxy.

36. The compound of claim 18, wherein each $R^a$ independently is halo or $C_{1-6}$alkyl.

37. The compound of claim 18, wherein $R^b$ is $C_{1-4}$alkyl.

38. The compound of claim 37, wherein $R^b$ is methyl or ethyl.

39. The compound of claim 18, wherein D is piperazinyl, morpholinyl, piperidinyl, tetrahydropyranyl, pyrrolidinyl or azetidinyl, optionally substituted with 1 or 2 substituents.

40. The compound of claim 18, wherein D is piperazinyl, morpholinyl or pyrrolidinyl.

41. The compound of claim 18, wherein each $R^c$ independently is methyl, fluoro, methoxy, trifluoromethyl or trifluoroethyl.

42. The compound of claim 41, wherein each $R^c$ is methyl.

43. The compound of claim 18, wherein B is pyridyl, pyrimidinyl, pyrazinyl, pyrazolyl, thiazolyl, or oxazolyl.

44. The compound of claim 43, wherein B is unsubstituted pyrimidinyl.

45. The compound of claim 18, wherein each R independently is methyl, isopropyl, methoxy, or cyclopropyl.

\* \* \* \* \*